(12) United States Patent
Findlay et al.

(10) Patent No.: US 10,717,733 B2
(45) Date of Patent: Jul. 21, 2020

(54) HALOALLYLAMINE INDOLE AND AZAINDOLE DERIVATIVE INHIBITORS OF LYSYL OXIDASES AND USES THEREOF

(71) Applicant: PHARMAXIS LTD., Frenchs Forest, NSW (AU)

(72) Inventors: Alison Dorothy Findlay, Frenchs Forest (AU); Craig Ivan Turner, Frenchs Forest (AU); Mandar Deodhar, Frenchs Forest (AU); Jonathan Stuart Foot, Frenchs Forest (AU); Wolfgang Jarolimek, Frenchs Forest (AU); Wenbin Zhou, Frenchs Forest (AU); Alan Duncan Robertson, Warrawee (AU)

(73) Assignee: Pharmaxis Ltd., Frenchs Forest, New South Wales (AU)

( * ) Notice: Subject to any disclaimer, the term of this patent is extended or adjusted under 35 U.S.C. 154(b) by 0 days.

(21) Appl. No.: 16/076,979

(22) PCT Filed: Feb. 10, 2017

(86) PCT No.: PCT/AU2017/000039
§ 371 (c)(1),
(2) Date: Aug. 9, 2018

(87) PCT Pub. No.: WO2017/136870
PCT Pub. Date: Aug. 17, 2017

(65) Prior Publication Data
US 2019/0040007 A1    Feb. 7, 2019

(30) Foreign Application Priority Data

Feb. 12, 2016 (AU) ................. 2016900478
Jul. 1, 2016 (AU) ................. 2016902593

(51) Int. Cl.
| | |
|---|---|
| *C07D 471/04* | (2006.01) |
| *C07D 487/04* | (2006.01) |
| *A61K 45/06* | (2006.01) |
| *C07D 209/42* | (2006.01) |
| *A61P 1/16* | (2006.01) |
| *A61P 13/12* | (2006.01) |
| *A61P 11/00* | (2006.01) |
| *A61K 31/4025* | (2006.01) |
| *A61K 31/4045* | (2006.01) |
| *A61K 31/41* | (2006.01) |
| *A61K 31/4245* | (2006.01) |
| *A61K 31/437* | (2006.01) |
| *A61K 31/4439* | (2006.01) |
| *A61K 31/506* | (2006.01) |
| *C07D 209/14* | (2006.01) |
| *C07D 401/04* | (2006.01) |
| *C07D 403/04* | (2006.01) |
| *C07D 403/10* | (2006.01) |
| *C07D 413/10* | (2006.01) |
| *A61K 31/5025* | (2006.01) |
| *A61K 31/519* | (2006.01) |
| *C07D 209/20* | (2006.01) |
| *C07D 209/36* | (2006.01) |

(52) U.S. Cl.
CPC ........ *C07D 471/04* (2013.01); *A61K 31/4025* (2013.01); *A61K 31/4045* (2013.01); *A61K 31/41* (2013.01); *A61K 31/4245* (2013.01); *A61K 31/437* (2013.01); *A61K 31/4439* (2013.01); *A61K 31/506* (2013.01); *A61K 31/5025* (2013.01); *A61K 31/519* (2013.01); *A61K 45/06* (2013.01); *A61P 1/16* (2018.01); *A61P 11/00* (2018.01); *A61P 13/12* (2018.01); *C07D 209/14* (2013.01); *C07D 209/20* (2013.01); *C07D 209/36* (2013.01); *C07D 209/42* (2013.01); *C07D 401/04* (2013.01); *C07D 403/04* (2013.01); *C07D 403/10* (2013.01); *C07D 413/10* (2013.01); *C07D 487/04* (2013.01)

(58) Field of Classification Search
CPC .................... C07D 209/14; A61K 31/4025
See application file for complete search history.

(56) References Cited

U.S. PATENT DOCUMENTS

| | | | |
|---|---|---|---|
| 4,358,603 A | 11/1982 | Yu | |
| 4,522,811 A | 6/1985 | Eppstein et al. | |
| 4,699,928 A | 10/1987 | McDonald | |
| 4,943,593 A | 7/1990 | Palfreyman et al. | |

(Continued)

FOREIGN PATENT DOCUMENTS

| | | |
|---|---|---|
| AU | 2014200520 A1 | 2/2014 |
| WO | WO 2007/120528 | 10/2007 |

(Continued)

OTHER PUBLICATIONS

International Search Report dated Apr. 24, 2017 in connection with PCT International Application No. PCT/AU2017/000039.

(Continued)

*Primary Examiner* — Golam M Shameem
(74) *Attorney, Agent, or Firm* — Gary J. Gershik; Cooper & Dunham LLP

(57) ABSTRACT

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

18 Claims, 4 Drawing Sheets

(56) References Cited

U.S. PATENT DOCUMENTS

| | | | |
|---|---|---|---|
| 4,965,288 | A | 10/1990 | Palfreyman et al. |
| 5,021,456 | A | 6/1991 | Palfreyman et al. |
| 5,059,714 | A | 10/1991 | Palfreyman et al. |
| 5,182,297 | A | 1/1993 | Palfreyman et al. |
| 5,252,608 | A | 10/1993 | Palfreyman et al. |
| 2008/0199933 | A1 | 8/2008 | Sayre |
| 2008/0293936 | A1 | 11/2008 | Burchardt |
| 2009/0053224 | A1 | 2/2009 | Smith et al. |
| 2011/0044907 | A1 | 2/2011 | Marshall et al. |
| 2015/0158813 | A1 | 6/2015 | Deodhar et al. |

FOREIGN PATENT DOCUMENTS

| | | | |
|---|---|---|---|
| WO | WO 2009/017833 | A2 | 2/2009 |
| WO | WO 2009/066152 | | 5/2009 |
| WO | WO 2009/066152 | A2 | 5/2009 |
| WO | WO 2013/163675 | A1 | 11/2013 |

OTHER PUBLICATIONS

Written Opinion of the International Searching Authority dated Apr. 24, 2017 in connection with PCT International Application No. PCT/AU2017/000039.

U.S. Appl. No. 16/076,985, filed Aug. 9, 2018 (Pharmaxis Ltd.), and file history thereof.

PCT International Application Publication No. WO 2007/120528, Wang et al., Oct. 25, 2007 (Exhibit 1).

PCT International Application Publication No. WO 2009/066152, Pharmaxis Ltd., May 28, 2009 (Exhibit 2).

Ashcroft et al., "Simple method of estimating severity, of pulmonary fibrosis on a numerical scale", J Clin Pathol, 1988; 41:467-470 (Exhibit 3).

Chanoki, M., et al., "Increased expression of lysyl oxidase in skin with scleroderma", Br J Dermatol, 1995; 133: 710-715 (Exhibit 4).

Corbel, M., et al., "Inhibition of bleomycin-induced pulmonary fibrosis in mice by the matrix metalloproteinase inhibitor batimastat", J Pathol, Apr. 2001;193(4):538-45 (Exhibit 5).

Counts, D.F., et al., "Collagen lysyl oxidase activity in the lung decreases during bleomycin induced lung fibrosis", J Pharmacol Exp Ther, 1981; 219: 675-678 (Exhibit 6).

Di Donato, A., et al., "Lysyl oxidase expression and collagen cross-linking during chronic adriamycin nephropathy", Nephron, 1997; 76: 192-200 (Exhibit 7).

Halberg et al., "Hypoxia inducible factor 1α induces fibrosis and insulin resistance in white adipose tissue", Cell Biol, 2009; 29: 4467-4483 (Exhibit 8).

Holt A. and Palcic M., "A peroxidase-coupled continuous absorbance plate-reader assay for flavin monoamine oxidases, copper-containing amine oxidases and related enzymes" Nat. Protoc., 2006; 1: 2498-2505 (Exhibit 9).

Huang C et al, "Blockade of KCa3.1 ameliorates renal fibrosis through a TGF-b1/Smad pathway in diabetic mice", Diabetes, 2013 62(8):2923-2934 (Exhibit 10).

Hee-Jung M. et al., "MCF-7 Cells Expressing Nuclear Associated Lysyl Oxidase-like 2(LOXL2) Exhibit an Epithelial-to-Mesenchymal Transition (EMT) Phenotype and are Highly Invasive in Vitro", J Biol Chem., 2013;288: 30000-30008 (Exhibit 11).

Jones et al., "Three-dimensional characterization of fibroblast foci in idiopathic pulmonary fibrosis", AJRCCM 191;2015:1-11 (Exhibit 12).

K. Saito et al. "Characterization of hepatic lipid profiles in a mouse model with nonalcoholic steatohepatitis and subsequent fibrosis", Sci Rep. Aug. 20, 2015;5:1-11 (Exhibit 13).

Kagan H.M. and Li W., "Lysyl oxidase: properties, specificity, and biological roles inside and outside of the cell", J Cell Biochem 2003; 88: 660-672 (Exhibit 14).

Kagan, H.M., "Lysyl, oxidase: Mechanism, regulation and relationship to liver fibrosis", Pathology—Research and Practice, 1994; 190: 910-919 (Exhibit 15).

Kagan, H.M. et al., "Changes in aortic lysyl oxidase activity in diet induced atherosclerosis in the rabbit", Arteriosclerosis, 1981; 1: 287-291 (Exhibit 16).

Kleiner DE. et al., "Design and validation of a histological scoring system for nonalcoholic fatty liver disease", Hepatology, 2005;41:1313 (Exhibit 17).

Lopez, B. et al., "Role of lysyl oxidase in myocardial fibrosis: from basic science to clinical aspects" Am J Physiol Heart Circ Physiol, 2010; 299: H1-H9 (Exhibit 18).

Natsume, M. et al., "Attenuated liver fibrosis and depressed serum albumin levels in carbon tetrachloride-treated IL-6-deficient mice", J. Leukoc. Biol., 1999, 66, 601-608 (Exhibit 19).

Parajuli et al., "Phosphatase PTEN is critically involved in post-myocardial infarction remodeling through the Akt/interleukin-10 signaling pathway", Basic Res Cardiol (2012) 107:248 (Exhibit 20).

S.P. Robins, "Biochemistry and functional significance of collagen cross-linking", Biochem Soc Trans 2007; 35(5): 849-852 (Exhibit 21).

Saito et al, "Single-Column High-Performance Liquid Chromatographic-Fluorescence Detection of Immature, Mature, and Senescent Cross-Links of Collagen", Anal. Biochem., 1997; 253: 26-32 (Exhibit 22).

Siddikiuzzaman et al., "Lysyl oxidase: a potential target for cancer therapy", Inflammapharmacol 2011; 19: 117-129 (Exhibit 23).

Siegel, R.C. et al., "Biochemical and immunochemical study of lysyl oxidase in experimental hepatic fibrosis in the rat", Proc. Natl. Acad. Sci. USA 1978; 75: 2945-2949 (Exhibit 24).

Stewart, G.D. et al., "Analysis of hypoxia-Eissociated gene expression in prostate cancer: lysyl oxidase and glucose transporter-1 expression correlate with Gleason score", Oncol Rep 2008; 20: 1561-1567 (Exhibit 25).

Tang, S.S. et al., "Reaction of aortic lysyl oxidase with beta aminoprophionitrile", J Biol Chem 1983; 258: 4331-4338 (Exhibit 26).

Woznick, A.R. et al., "Lysyl oxidase expression in bronchogenic carcinoma", Am J Surg 2005; 189: 297-301 (Exhibit 27); and.

Yao, Q.Y. et al., "Inhibition by curcumin of multiple sites of the transforming growth factor-beta1 signalling pathway ameliorates the progression of liver fibrosis induced by carbon tetrachloride in rats" BMC Complement Altern Med., Sep. 16, 2012;12(1):156 (Exhibit 28).

U.S. Appl. No. 16/076,985, filed Aug. 9, 2018, Pharmaxis Ltd.

Ashcroft et al., "Simple method of estimating severity of pulmonary fibrosis on a numerical scale", J Clin Pathol, 1988; 41:467-470.

Chanoki, M., et al., "Increased expression of lysyl oxidase in skin with scleroderma", Br J Dermatol, 1995; 133: 710-715.

Corbel, M., et al., "Inhibition of bleomycin-induced pulmonary fibrosis in mice by the matrix metalloproteinase inhibitor batimastat", J Pathol, Apr. 2001;193(4):538-45.

Counts, D.E., et al., "Collagen lysyl oxidase activity in the lung decreases during bleomycin induced lung fibrosis", J Pharmacol Exp Ther, 1981; 219: 675-678.

Di Donato, A., et al., "Lysyl oxidase expression and collagen cross-linking during chronic adriamycin nephropathy", Nephron, 1997; 76: 192-200.

Halberg et al., "Hypoxia inducible factor 1α induces fibrosis and insulin resistance in white adipose tissue", Cell Biol, 2009; 29: 4467-4483.

Holt A. and Palcic M., "A peroxidase-coupled continuous absorbance Plate-reader assay for flavin monoamine oxidases, copper-containing amine oxidases and related enzymes" Nat. Protoc., 2006; 1: 2498-2505.

Huang C et al, "Blockade of KCa3.1 ameliorates renal fibrosis through a TGF-b1/Smad pathway in diabetic mice", Diabetes, 2013 62(8):2923-2934.

Hee-Jung M. et al., "MCF-7 Cells Expressing Nuclear Associated Lysyl Oxidase-like 2(LOXL2) Exhibit an Epithelial-to-Mesenchymal Transition (EMT) Phenotype and are Highly Invasive in Vitro", J Biol Chem., 2013;288: 30000-30008.

Jones et al., "Three-dimensional characterization of fibroblast foci in idiopathic pulmonary fibrosis", AJRCCM 191;2015:1-11.

K. Saito et al. "Characterization of hepatic lipid profiles in a mouse model with nonalcoholic steatohepatitis and subsequent fibrosis", Sci Rep. Aug. 20, 2015;5:1-11.

(56) References Cited

OTHER PUBLICATIONS

Kagan H.M. and Li W., "Lysyl oxidase: properties, specificity, and biological roles inside and outside of the cell", J Cell Biochem 2003; 88: 660-672.

Kagan H.M., "Lysyl oxidase: Mechanism, regulation and relationship to liver fibrosis", Pathology—Research and Practice, 1994; 190: 910-919.

Kagan, H.M. et al., "Changes in aortic lysyl oxidase activity in diet induced atherosclerosis in the rabbit", Arteriosclerosis, 1981; 1: 287-291.

Kleiner DE. et al., "Design and validation of a histological scoring system for nonalcoholic fatty liver disease", Hepatology, 2005;41:1313.

Lopez, B. et al., "Role of lysyl oxidase in myocardial fibrosis: from basic science to clinical aspects" Am J Physiol Heart Circ Physiol, 2010; 299: H1-H9.

Natsume, M. et al., "Attenuated liver fibrosis and depressed serum albumin levels in carbon tetrachloride-treated IL-6-deficient mice", J. Leukoc. Biol., 1999, 66, 601-608.

Parajuli et al., "Phosphatase PTEN is critically involved in postmyocardial infarction remodeling through the Akt/interleukin-10 signaling pathway", Basic Res Cardiol (2012) 107:248.

S.P. Robins, "Biochemistry and functional significance of collagen cross-linking", Biochem Soc Trans 2007; 35(5): 849-852.

Saito et al, "Single-Column High-Performance Liquid Chromatographic-Fluorescence Detection of Immature, Mature, and Senescent Cross-Links of Collagen", Anal. Biochem., 1997; 253: 26-32.

Siddikiuzzaman et al., "Lysyl oxidase: a potential target for cancer therapy", Inflammapharmacol 2011; 19: 117-129.

Siegel, R.C. et al., "Biochemical and immunochemical study of lysyl oxidase in experimental hepatic fibrosis in the rat", Proc. Natl. Acad. Sci. USA 1978; 75: 2945-2949.

Stewart, G.D. et al., "Analysis of hypoxia-associated gene expression in prostate cancer: lysyl oxidase and glucose transporter-1 expression correlate with Gleason score", Oncol Rep 2008; 20: 1561-1567.

Tang, S.S. et al., "Reaction of aortic lysyl oxidase with beta aminoproprionitrile", J Biol Chem 1983; 258: 4331-4338.

Woznick, A.R. et al., "Lysyl oxidase expression in bronchogenic carcinoma", Am J Surg 2005; 189: 297-301.

Q.Y. et al., "Inhibition by curcumin of multiple sites of the transforming growth factor-beta1 signalling pathway ameliorates the progression of liver fibrosis induced by carbon tetrachloride in rats" BMC Complement Altern Med., Sep. 16, 2012;12(1):156.

Oct. 29, 2019 European Search Report issued in connection with European Patent Application No. 17749812.8.

Martínez-Martínez, E. et al. (106) "The lysyl oxidase inhibitor (B-aminopropionitrile) reduces leptin profibrotic effects and ameliorates cardiovascular remodeling in diet-induced obesity in rats", *Journal of Molecular and Cellular Cardiology*, vol. 92, pp. 96-104, 2016.

HALOALLYLAMINE INDOLE AND AZAINDOLE DERIVATIVE INHIBITORS OF LYSYL OXIDASES AND USES THEREOF

CROSS-REFERENCE TO RELATED APPLICATIONS

This application is a § 371 national stage of PCT International Application No. PCT/AU2017/000039, filed Feb. 10, 2017, claiming priority of Australian Patent Applications Nos. 2016902593, filed Jul. 1, 2016 and 2016900478, filed Feb. 12, 2016, the contents of each of which are hereby incorporated by reference into the application.

TECHNICAL FIELD

The present invention relates to novel compounds which are capable of inhibiting certain amine oxidase enzymes. These compounds are useful for treatment of a variety of indications, e.g., fibrosis, cancer and/or angiogenesis in human subjects as well as in pets and livestock. In addition, the present invention relates to pharmaceutical compositions containing these compounds, as well as various uses thereof.

BACKGROUND

A family of five closely relating enzymes have been linked to fibrotic disease and to metastatic cancer. The enzymes are related to lysyl oxidase (LOX), the first family member to be described and four closely related enzymes, LOX-like1 (LOXL1), LOXL2, LOXL3, and LOXL4 (Kagan H. M. and Li W., Lysyl oxidase: properties, specificity, and biological roles inside and outside of the cell. *J Cell Biochem* 2003; 88: 660-672). Lysyl oxidase isoenzymes are copper-dependent amine oxidases which initiate the covalent cross-linking of collagen and elastin. A major function of lysyl oxidase isoenzymes is to facilitate the cross-linking of collagen and elastin by the oxidative deamination of lysine and hydroxylysine amino acid side chains to aldehydes which spontaneously react with neighbouring residues. The resulting cross-linked strands contribute to extracellular matrix (ECM) stability. Lysyl oxidase activity is essential to maintain the tensile and elastic features of connective tissues of skeletal, pulmonary, and cardiovascular systems, among others. The biosynthesis of LOX is well understood; the protein is synthesized as a pre-proLOX that undergoes a series of post-translational modifications to yield a 50 kDa pro-enzyme which is secreted into the extracellular environment. For LOX and LOXL1 proteolysis by bone morphogenetic protein-1 (BMP-1) and other procollagen C-proteinases releases the mature and active form. LOXL2, LOXL3 and LOXL4 contain scavenger receptor cysteine-rich protein domains and are directly secreted as active forms.

Lysyl oxidase isoenzymes belong to a larger group of amine oxidases which include flavin-dependent and copper-dependent oxidases which are described by the nature of the catalytic co-factor. Flavin-dependent enzymes include monoamine oxidase-A (MAO-A), MAO-B, polyamine oxidase and lysine demethylase (LSD1), and the copper-dependent enzymes include semicarbazide sensitive amine oxidase (vascular adhesion protein-1, SSAO/VAP-1), retinal amine oxidase, diamine oxidase and the lysyl oxidase isoenzymes. The copper-dependent amine oxidases have a second co-factor which varies slightly from enzyme to enzyme. In SSAO/VAP-1 it is an oxidized tyrosine residue (TPQ, oxidized to a quinone), whereas in the lysyl oxidase isoenzymes the TPQ has been further processed by addition of a neighboring lysine residue (to form LTQ); see Kagan, H. M. and Li, W., Lysyl oxidase: Properties, specificity, and biological roles inside and outside of the cell. *J Cell Biochem* 2003; 88: 660-672.

Since lysyl oxidase isoenzymes exhibit different in vivo expression patterns it is likely that specific isoenzymes will have specific biological roles. Catalytically active forms of LOX have been identified in the cytosolic and nuclear compartments which suggest the existence of undefined roles of LOX in cellular homeostasis. Significant research is currently underway to define these roles. LOX itself, for example, plays a major role in epithelial-to-mesenchymal transition (EMT), cell migration, adhesion, transformation and gene regulation. Different patterns of LOX expression/activity have been associated with distinct pathological processes including fibrotic diseases, Alzheimer's disease and other neurodegenerative processes, as well as tumour progression and metastasis. See, for example, Woznick, A. R., et al. Lysyl oxidase expression in bronchogenic carcinoma. *Am J Surg* 2005; 189: 297-301. Catalytically active forms of LOXL2 can be also found in the nucleus (J Biol Chem. 2013; 288: 30000-30008) and can deaminate lysine 4 in histone H3 (*Mol Cell* 2012 46: 369-376).

Directed replacement of dead or damaged cells with connective tissue after injury represents a survival mechanism that is conserved throughout evolution and appears to be most pronounced in humans serving a valuable role following traumatic injury, infection or diseases. Progressive scarring can occur following more chronic and/or repeated injuries that causes impaired function to parts or all of the affected organ. A variety of causes, such as chronic infections, chronic exposure to alcohol and other toxins, autoimmune and allergic reactions or radio- and chemotherapy can all lead to fibrosis. This pathological process, therefore, can occur in almost any organ or tissue of the body and, typically, results from situations persisting for several weeks or months in which inflammation, tissue destruction and repair occur simultaneously. In this setting, fibrosis most frequently affects the lungs, liver, skin and kidneys.

Liver fibrosis occurs as a complication of haemochromatosis, Wilson's disease, alcoholism, schistosomiasis, viral hepatitis, bile duct obstruction, exposure to toxins and metabolic disorders. Liver fibrosis is characterized by the accumulation of extracellular matrix that can be distinguished qualitatively from that in normal liver. This fibrosis can progress to cirrhosis, liver failure, cancer and eventually death. This is reviewed in Kagan, H. M. Lysyl oxidase: Mechanism, regulation and relationship to liver fibrosis. *Pathology—Research and Practice* 1994; 190: 910-919.

Fibrotic tissues can accumulate in the heart and blood vessels as a result of hypertension, hypertensive heart disease, atherosclerosis and myocardial infarction where the accumulation of extracellular matrix or fibrotic deposition results in stiffening of the vasculature and stiffening of the cardiac tissue itself. See Lopez, B., et al. Role of lysyl oxidase in myocardial fibrosis: from basic science to clinical aspects. *Am J Physiol Heart Circ Physiol* 2010; 299: H1-H9.

A strong association between fibrosis and increased lysyl oxidase activity has been demonstrated. For example, in experimental hepatic fibrosis in rat (Siegel, R. C., Chen, K. H. and Acquiar, J. M, Biochemical and immunochemical study of lysyl oxidase in experimental hepatic fibrosis in the rat. *Proc. Natl. Acad. Sci. USA* 1978; 75: 2945-2949), in models of lung fibrosis (Counts, D. F., et al., Collagen lysyl oxidase activity in the lung decreases during bleomycin-induced lung fibrosis. *J Pharmacol Exp Ther* 1981; 219:

675-678) in arterial fibrosis (Kagan, H. M., Raghavan, J. and Hollander, W., Changes in aortic lysyl oxidase activity in diet-induced atherosclerosis in the rabbit. *Arteriosclerosis* 1981; 1: 287-291.), in dermal fibrosis (Chanoki, M., et al., Increased expression of lysyl oxidase in skin with scleroderma. *Br J Dermatol* 1995; 133: 710-715) and in adriamycin-induced kidney fibrosis in rat (Di Donato, A., et al., Lysyl oxidase expression and collagen cross-linking during chronic adriamycin nephropathy. *Nephron* 1997; 76: 192-200). Of these experimental models of human disease, the most striking increases in enzyme activity are seen in the rat model of $CCl_4$-induced liver fibrosis. In these studies, the low level of enzyme activity in the healthy liver increased 15- to 30-fold in fibrotic livers. The rationale for the consistent and strong inhibition of fibrosis by lysyl oxidase isoenzyme blockers is that the lack of cross-linking activity renders the collagen susceptible to matrix metalloproteinases and causes degradation. Hence, any type of fibrosis should be reversed by treatment with lysyl oxidase isoenzyme inhibitors. In humans, there is also a significant association between lysyl oxidase activity measured in the plasma and liver fibrosis progression. Lysyl oxidase activity level is normally negligible in the serum of healthy subjects, but significantly increased in chronic active hepatitis and even more in cirrhosis, therefore lysyl oxidase might serve as a marker of internal fibrosis.

BAPN (β-aminopropionitrile) is a widely used, nonselective lysyl oxidase inhibitor. Since the 1960s BAPN has been used in animal studies (mainly rat, mouse and hamster) and has been efficacious in reducing collagen content in various models (eg. $CCl_4$, bleomycin, quartz) and tissues (eg. liver, lung and dermis). See Kagan, H. M. and Li, W., Lysyl oxidase: Properties, specificity and biological roles inside and outside of the cell. *J Cell Biochem* 2003; 88: 660-672.

Lysyl oxidase isoenzymes are highly regulated by Hypoxia-Induced Factor 1α (HIF-1α) and TGF-β, the two most prominent growth factor that cause fibrosis (Halberg et al., Hypoxia-inducible factor 1α induces fibrosis and insulin resistance in white adipose tissue. *Cell Biol* 2009; 29: 4467-4483). Collagen cross linking occurs in every type of fibrosis, hence a lysyl oxidase isoenzyme inhibitor could be used in idiopathic pulmonary fibrosis, scleroderma, kidney or liver fibrosis. Lysyl oxidase isoenzymes are not only involved in the cross-linking of elastin and collagen during wound healing and fibrosis but also regulate cell movement and signal transduction. Its intracellular and intranuclear function is associated with gene regulation and can lead to tumorgenesis and tumor progression (Siddikiuzzaman, Grace, V. M and Guruvayoorappan, C., Lysyl oxidase: a potential target for cancer therapy. *Inflammapharmacol* 2011; 19: 117-129). Both down and upregulation of lysyl oxidase isoenzymes in tumour tissues and cancer cell lines have been described, suggesting a dual role for lysyl oxidase isoenzymes and LOX pro-peptide as a metastasis promoter gene as well as a tumour suppressor gene.

To date, an increase in lysyl oxidase isoenzymes mRNA and/or protein has been observed in breast, CNS cancer cell lines, head and neck squamous cell, prostatic, clear cell renal cell and lung carcinomas, and in melanoma and osteosarcoma cell lines. Statistically significant clinical correlations between lysyl oxidase isoenzymes expression and tumor progression have been observed in breast, head and neck squamous cell, prostatic and clear cell renal cell carcinomas. The role of lysyl oxidase isoenzymes in tumor progression has been most extensively studied in breast cancer using in vitro models of migration/invasion and in in vivo tumorgenesis and metastasis mouse models. Increased lysyl oxidase isoenzymes expression was found in hypoxic patients, and was associated with negative estrogen receptor status (ER-), decreased overall survival in ER-patients and node-negative patients who did not receive adjuvant systemic treatment, as well as shorter metastasis-free survival in ER-patients and node negative patients. Lysyl oxidase isoenzymes mRNA was demonstrated to be up-regulated in invasive and metastatic cell lines (MDA-MB-231 and Hs578T), as well as in more aggressive breast cancer cell lines and distant metastatic tissues compared with primary cancer tissues.

In head and neck squamous cell carcinomas, increased lysyl oxidase isoenzyme expression was found in association with CA-IX, a marker of hypoxia, and was associated with decreased cancer specific survival, decreased overall survival and lower metastasis-free survival. In oral squamous cell carcinoma, lysyl oxidase isoenzyme mRNA expression was upregulated compared to normal mucosa.

Gene expression profiling of gliomas identified overexpressed lysyl oxidase isoenzyme as part of a molecular signature indicative of invasion, and associated with higher-grade tumors that are strongly correlated with poor patient survival. Lysyl oxidase isoenzyme protein expression was increased in glioblastoma and astrocytoma tissues, and in invasive U343 and U251 cultured astrocytoma cells.

In tissues, lysyl oxidase isoenzyme mRNA was upregulated in prostate cancer compared to benign prostatic hypertrophy, correlated with Gleason score, and associated with both high grade and short time to recurrence (Stewart, G. D., et al., Analysis of hypoxia-associated gene expression in prostate cancer: lysyl oxidase and glucose transporter-1 expression correlate with Gleason score. *Oncol Rep* 2008; 20: 1561-1567).

Up-regulation of lysyl oxidase isoenzyme mRNA expression was detected in renal cell carcinoma (RCC) cell lines and tissues. Clear cell RCC also demonstrated lysyl oxidase isoenzyme up-regulation. Indeed, LOX over expression appeared preferentially in clear cell RCC compared to mixed clear and granular, granular, oxyphil, tubulopapillary and chromophobe RCC/ontocytomas. In clear cell RCC, smoking was associated with allelic imbalances at chromosome 5q23.1, where the LOX gene is localized, and may involve duplication of the gene.

SiHa cervical cancer cells demonstrated increased invasion in vitro under hypoxic/anoxic conditions; this was repressed by inhibition of extracellular catalytically active lysyl oxidase activity by treatment with BAPN as well as LOX antisense oligos, LOX antibody, LOX shRNA or an extracellular copper chelator.

The scientific and patent literature describes small molecule inhibitors of lysyl oxidase isoenzymes and antibodies of LOX and LOXL2 with therapeutic effects in animal models of fibrosis and cancer metastasis. Some known MAO inhibitors also are reported to inhibit lysyl oxidase isoenzyme (e.g., the MAO-B inhibitor Mofegiline illustrated below). This inhibitor is a member of the haloallylamine family of MAO inhibitors; the halogen in Mofegiline is fluorine. Fluoroallylamine inhibitors are described in U.S. Pat. No. 4,454,158. There are issued patents claiming fluoroallylamines and chloroallylamines, for example MDL72274 (illustrated below) as inhibitors of lysyl oxidase (U.S. Pat. Nos. 4,943,593; 4,965,288; 5,021,456; 5,059,714; 5,182,297; 5,252,608). Many of the compounds claimed in these patents are also reported to be potent MAO-B and SSAO/VAP-1 inhibitors.

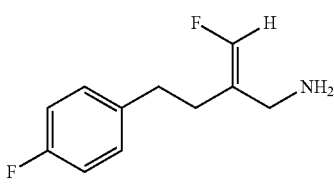

Mofegiline

MDL72274

Additional fluoroallylamine inhibitors are described U.S. Pat. No. 4,699,928. Other examples structurally related to Mofegiline can be found in WO 2007/120528.

WO 2009/066152 discloses a family of 3-substituted 3-haloallylamines that are inhibitors of SSAO/VAP-1 useful as treatment for a variety of indications, including inflammatory disease. None of these documents specifically disclose the fluoroallylamine compounds of formula (I) according to the present invention.

Antibodies to LOX and LOXL2 have been disclosed in US 2009/0053224 with methods to diagnostic and therapeutic applications. Anti-LOX and anti-LOXL2 antibodies can be used to identify and treat conditions such as a fibrotic condition, angiogenesis, or to prevent a transition from an epithelial cell state to a mesenchymal cell state: US 2011/0044907.

SUMMARY

The present invention provides substituted fluoroallylamine compounds that inhibit lysyl oxidase (LOX), lysyl oxidase-like2 (LOXL2) and other lysyl oxidase isoenzymes. Surprisingly, modification of 3-substituted-3-fluoroallylamine structures described previously has led to the discovery of novel compounds that are potent inhibitors of the human LOX and LOXL isoenzymes. Furthermore, certain of these novel compounds also selectively inhibit certain LOX and LOXL isoenzymes with respect to the other enzymes in the amine oxidase family.

A first aspect of the invention provides for a compound of Formula I:

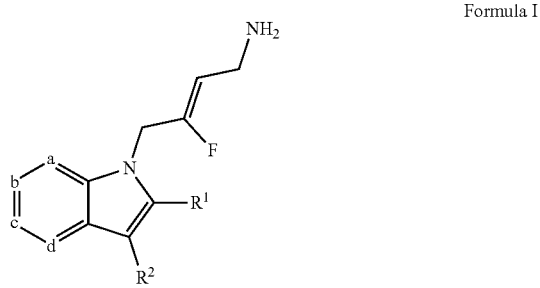

Formula I or a stereoisomer, pharmaceutically acceptable salt, polymorphic form, solvate, tautomeric form or prodrug thereof; wherein:

a is N or $CR^3$;
b is N or $CR^4$;
c is N or $CR^5$;
d is N or $CR^6$;
and from 0 to 2 of a, b, c and d are N;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

A second aspect of the invention provides for a pharmaceutical composition comprising a compound according to the first aspect of the invention, or a pharmaceutically acceptable salt, solvate or prodrug thereof, and at least one pharmaceutically acceptable excipient, carrier or diluent.

A third aspect of the invention provides for a method of inhibiting the amine oxidase activity of LOX, LOXL1, LOXL2, LOXL3 and LOXL4 in a subject in need thereof, comprising administering to the subject an effective amount of a compound according to the first aspect of the invention, or a pharmaceutically acceptable salt, solvate or prodrug thereof, or a pharmaceutical composition according to the second aspect of the invention.

A fourth aspect of the invention provides for a method of treating a condition associated with LOX, LOXL1, LOXL2, LOXL3 and LOXL4 protein, comprising administering to a subject in need thereof a therapeutically effective amount of compound according to the first aspect of the invention, or a pharmaceutically acceptable salt, solvate or prodrug thereof, or a pharmaceutical composition according to the second aspect of the invention.

A fifth aspect of the invention provides for use of a compound according to the first aspect of the invention, or a pharmaceutically acceptable salt, solvate or prodrug thereof, for the manufacture of a medicament for treating a condition associated with LOX, LOXL1, LOXL2, LOXL3 and LOXL4 protein.

A sixth aspect of the invention provides for a compound according to the first aspect of the invention, or a pharmaceutically acceptable salt, solvate or prodrug thereof, for use in treating a condition associated with LOX, LOXL1, LOXL2, LOXL3 and LOXL4 protein.

In one embodiment of the methods and uses of the present invention the condition is selected from a liver disorder, kidney disorder, cardiovascular disease, fibrosis, cancer and angiogenesis.

Contemplated herein is combination therapy in which the methods further comprise co-administering additional therapeutic agents that are used for the treatment of liver disorders, kidney disorders, cardiovascular diseases, cancer, fibrosis, angiogenesis and inflammation.

Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically states to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl" includes within its meaning monovalent ("alkyl") and divalent ("alkylene") straight chain or branched chain saturated hydrocarbon radicals having from 1 to 6 carbon atoms, e.g., 1, 2, 3, 4, 5 or 6 carbon atoms. The straight chain or branched alkyl group is attached at any available point to produce a stable compound. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

The term "alkoxy" or "alkyloxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "cycloalkyl" as used herein includes within its meaning monovalent ("cycloalkyl") and divalent ("cycloalkylene") saturated, monocyclic, bicyclic, polycyclic or fused analogs. In the context of the present disclosure the cycloalkyl group may have from 3 to 10 carbon atoms. In the context of the present disclosure the cycloalkyl group may also have from 3 to 7 carbon atoms. A fused analog of a cycloalkyl means a monocyclic ring fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, adamantyl and the like.

The term "aryl" or variants such as "arylene" as used herein refers to monovalent ("aryl") and divalent ("arylene") single, polynuclear, conjugated and fused analogs of aromatic hydrocarbons having from 6 to 10 carbon atoms. A fused analog of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,3-benzodioxolyl, 1,4-benzodioxanyl, and the like. A "substituted aryl" is an aryl that is independently substituted, with one or more, preferably 1, 2 or 3 substituents, attached at any available atom to produce a stable compound.

The term "alkylaryl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of alkylaryl groups include benzyl.

The term "heteroaryl" and variants such as "heteroaromatic group" or "heteroarylene" as used herein, includes within its meaning monovalent ("heteroaryl") and divalent ("heteroarylene"), single, polynuclear, conjugated and fused heteroaromatic radicals having from 5 to 10 atoms, wherein 1 to 4 ring atoms, or 1 to 2 ring atoms are heteroatoms independently selected from O, N, NH and S. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. The heteroaromatic group may be $C_{5-8}$ heteroaromatic. A fused analog of heteroaryl means a heteroaryl group fused to a monocyclic cycloalkyl or monocyclic heterocyclyl group in which the point of attachment is on the aromatic portion. Examples of heteroaryl groups and fused analogs thereof include pyrazolyl, pyridyl, oxazolyl, oxadiazolyl, thiadiazolyl, tetrazolyl, triazinyl, thienyl, benzoxazolyl, benzothiazolyl, benzimidazolyl, benzofuranyl, benzothiophenyl, furo (2,3-b)pyridyl, quinolyl, indolyl, isoquinolyl, pyrimidinyl, pyridazinyl, pyrazinyl, 2,2'-bipyridyl, phenanthrolinyl, quinolinyl, isoquinolinyl, imidazolinyl, thiazolinyl, pyrrolyl, furanyl, thiophenyl, oxazolyl, isoxazolyl, isothiazolyl, triazolyl, and the like. "Nitrogen containing heteroaryl" refers to heteroaryl wherein any heteroatoms are N. A "substituted heteroaryl" is a heteroaryl that is independently substituted, with one or more, preferably 1, 2 or 3 substituents, attached at any available atom to produce a stable compound.

The term "heterocyclyl" and variants such as "heterocycloalkyl" as used herein, includes within its meaning monovalent ("heterocyclyl") and divalent ("heterocyclylene"), saturated, monocyclic, bicyclic, polycyclic or fused hydrocarbon radicals having from 3 to 10 ring atoms, wherein from 1 to 5, or from 1 to 3, ring atoms are heteroatoms independently selected from O, N, NH, or S, in which the point of attachment may be carbon or nitrogen. A fused analog of heterocyclyl means a monocyclic heterocycle fused to an aryl or heteroaryl group in which the point of attachment is on the non-aromatic portion. The heterocyclyl group may be $C_{3-8}$ heterocyclyl. The heterocycloalkyl group may be $C_{3-6}$ heterocyclyl. The heterocyclyl group may be $C_{3-5}$ heterocyclyl. Examples of heterocyclyl groups and fused analogs thereof include aziridinyl, pyrrolidinyl, thiazolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, quinuclidinyl, azetidinyl, morpholinyl, tetrahydrothiophenyl, tetrahydrofuranyl, tetrahydropyranyl, and the like. The term also includes partially unsaturated monocyclic rings that are not aromatic, such as 2- or 4-pyridones attached through the nitrogen or N-substituted uracils.

The term "halogen" or variants such as "halide" or "halo" as used herein refers to fluorine, chlorine, bromine and iodine.

The term "heteroatom" or variants such as "hetero-" or "heterogroup" as used herein refers to O, N, NH and S.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_2$, NH(alkyl), N(alkyl)$_2$, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_2H$, $CO_2$alkyl, $C(O)NH_2$, —C(O)NH(alkyl), and —C(O)N(alkyl)$_2$. Preferred substituents include halogen, $C_1$-$C_6$alkyl, $C_2$-$C_6$alkenyl, $C_1$-$C_6$haloalkyl, $C_1$-$C_6$alkoxy, hydroxy($C_{1-6}$) alkyl, $C_3$-$C_6$cycloalkyl, C(O)H, C(O)OH, NHC(O)H, NHC(O)$C_1$-$C_4$alkyl, C(O)$C_1$-$C_4$alkyl, $NH_2$, NHC$_1$-$C_4$alkyl, N(C$_1$-$C_4$alkyl)$_2$, $NO_2$, OH and CN. Particularly preferred substituents include $C_{1-3}$alkyl, $C_{1-3}$alkoxy, halogen, OH, hydroxy($C_{1-3}$)alkyl (e.g. CH$_2$OH), C(O)C$_1$-C$_4$alkyl (e.g. C(O)CH$_3$), and $C_{1-3}$haloalkyl (e.g. CF$_3$, CH$_2$CF$_3$). Further preferred optional substituents include halogen, —OH, —SH, —C$_{1-3}$alkyl, —O—C$_{1-3}$alkyl, —CF$_3$, —CH$_2$CF$_3$, and —O—CF$_3$.

The term "bioisostere" refers to a compound resulting from the exchange of an atom or of a group of atoms with another, broadly similar, atom or group of atoms. The objective of a bioiosteric replacement is to create a new compound with similar biological properties to the parent compound. The bioisosteric replacement may be physiochemically or topologically based.

The present invention includes within its scope all stereoisomeric and isomeric forms of the compounds disclosed herein, including all diastereomeric isomers, racemates, enantiomers and mixtures thereof. It is also understood that the compounds described by Formula I may be present as E and Z isomers, also known as cis and trans isomers. Thus, the present disclosure should be understood to include, for example, E, Z, cis, trans, (R), (S), (L), (D), (+), and/or (−) forms of the compounds, as appropriate in each case. Where a structure has no specific stereoisomerism indicated, it should be understood that any and all possible isomers are encompassed. Compounds of the present invention embrace all conformational isomers. Compounds of the present invention may also exist in one or more tautomeric forms, including both single tautomers and mixtures of tautomers. Also included in the scope of the present invention are all polymorphs and crystal forms of the compounds disclosed herein.

The present invention includes within its scope isotopes of different atoms. Any atom not specifically designated as a particular isotope is meant to represent any stable isotope of that atom. Thus, the present disclosure should be understood to include deuterium and tritium isotopes of hydrogen.

All references cited in this application are specifically incorporated by cross-reference in their entirety. Reference to any such documents should not be construed as an admission that the document forms part of the common general knowledge or is prior art.

In the context of this specification the term "administering" and variations of that term including "administer" and "administration", includes contacting, applying, delivering or providing a compound or composition of the invention to an organism, or a surface by any appropriate means. In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION

Figure 1:
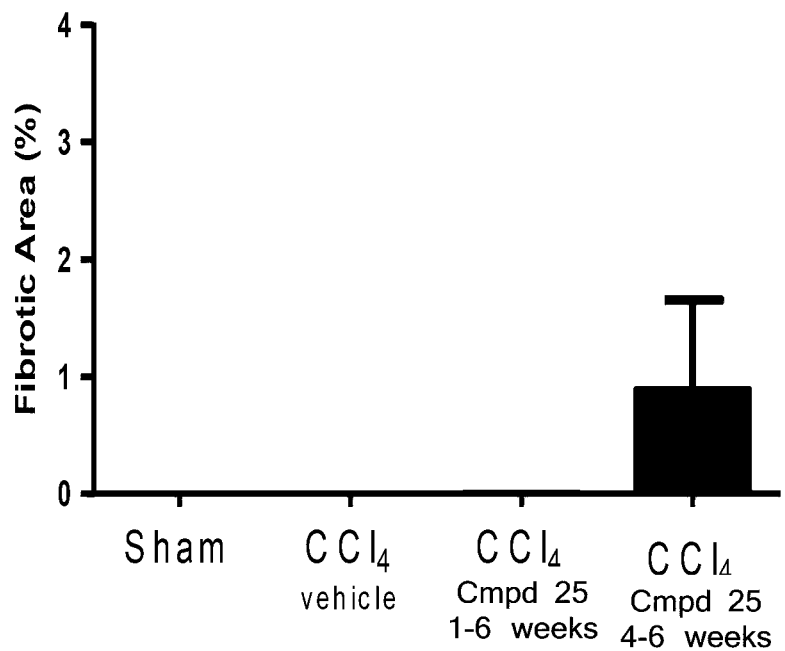
FIG. 1 shows the ability of Compound 25 to reduce fibrosis in a rat model of liver fibrosis.

The present invention relates to substituted fluoroallylamine derivatives which may inhibit lysyl oxidase (LOX), lysyl oxidase-like2 (LOXL2) and other lysyl oxidase isoenzymes. In particular the present invention relates to substituted fluoroallylamine derivatives with an indole or azaindole group.

In particular the present invention relates to compounds of Formula I:

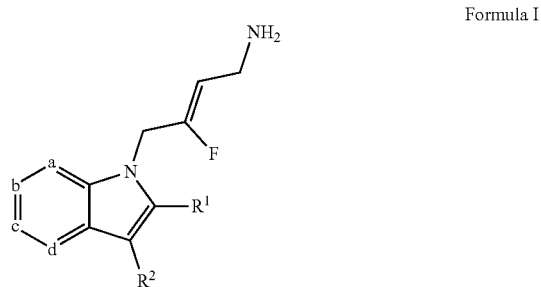

Formula I or a stereoisomer, pharmaceutically acceptable salt, polymorphic form, solvate, tautomeric form or prodrug thereof; wherein:

a is N or $CR^3$;
b is N or $CR^4$;
c is N or $CR^5$;
d is N or $CR^6$;
and from 0 to 2 of a, b, c and d are N;

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9C(O)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9C(O)R^{11}$, —$S(O_2)NR^9R^{10}$, —$NR^9S(O_2)R^{11}$, —$S(O)R^{11}$, —$S(O_2)R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9C(O)R^{11}$, —$S(O_2)NR^9R^{10}$, —$NR^9S(O_2)R^{11}$, —$S(O)R^{11}$ and —$S(O_2)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of the present invention none of a, b, c and d is N and a is $CR^3$, b is $CR^4$, c is $CR^5$ and d is $CR^6$ so that the compounds of Formula I are indole derivatives. In a further embodiment of compounds of the present invention one of a, b, c and d is N so that the compounds of Formula I are azaindole derivatives. In another embodiment of compounds of the present invention a is N, b is $CR^4$, c is $CR^5$ and d is $CR^6$. In a further embodiment of compounds of the present invention a is $CR^3$, b is N, c is $CR^5$ and d is $CR^6$. In another embodiment of compounds of the present invention a is $CR^3$, b is $CR^4$, c is N and d is $CR^6$. In a still further embodiment of compounds of the present invention a is $CR^3$, b is $CR^4$, c is $CR^5$ and d is N. In another embodiment of compounds of the present invention two of a, b, c and d are N. In a further embodiment of compounds of the present invention a is $CR^3$, b is $CR^4$, c is N and d is N. In another embodiment of compounds of the present invention a is $CR^3$, b is N, c is $CR^5$ and d is N. In another embodiment of compounds of the present invention a is N, b is $CR^4$, c is N and d is $CR^6$. In a further embodiment of compounds of the present invention a is CR³, b is N, c is N and d is CR⁶. In another embodiment of compounds of the present invention a is N, b is N, c is CR⁵ and d is CR⁶. In a further embodiment of compounds of the present invention a is N, b is CR⁴, c is CR⁵ and d is N.

In one embodiment of compounds of the present invention R¹ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR⁸, —C(O)NR⁹R¹⁰ and —NR⁹C(O)R¹¹; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF₃, —CH₂CF₃, and —O—CF₃. In another embodiment of compounds of the present invention each R¹ is independently selected from the group consisting of hydrogen, halogen, $C_{1-6}$alkyl, and —C(O)NR⁹R¹⁰; wherein each $C_{1-6}$alkyl is a straight or branched chain alkyl; and wherein each $C_{1-6}$alkyl is optionally substituted by one or more substituents selected from the group consisting of halogen, —OH, —O—$C_{1-3}$alkyl, —CF₃, —CH₂CF₃, and —O—CF₃. In a further embodiment of compounds of the present invention each R¹ is independently selected from the group consisting of hydrogen, halogen, $C_{1-3}$alkyl, and —C(O)N(CH₃)₂; wherein each $C_{1-3}$alkyl is a straight or branched chain alkyl; and wherein each $C_{1-3}$alkyl is optionally substituted by one or more substituents selected from the group consisting of halogen and —OH. In one embodiment of compounds of the present invention R¹ is selected from the group consisting of hydrogen, methyl, ethyl, isopropyl, 1-hydroxyethyl, 2-hydroxyisopropyl, chloro and —C(O)N(CH₃)₂. In another embodiment of compounds of the present invention R¹ is selected from the group consisting of hydrogen, methyl and isopropyl. In a further embodiment of compounds of the present invention R¹ is methyl. In another embodiment of compounds of the present invention R¹ is isopropyl.

In one embodiment of compounds of the present invention R² is aryl or heteroaryl where each R² is optionally substituted by one or more R¹². In another embodiment of compounds of the present invention R² is aryl optionally substituted by one or more R¹². In another embodiment of compounds of the present invention R² is phenyl substituted by one R¹². In a further embodiment of compounds of the present invention R² is heteroaryl substituted by one or more R¹². In another embodiment of compounds of the present invention R² is heteroaryl substituted by one or more R¹². In a further embodiment of compounds of the present invention R² is selected from the group consisting of phenyl

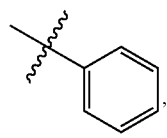

1,3-benzodioxolyl

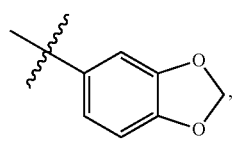 [SMILES: *c1ccc2c(c1)OCO2]

2-pyridinyl

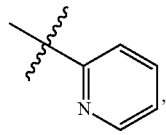 [SMILES: *c1ccccn1]

3-pyridinyl

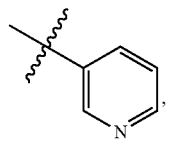 [SMILES: *c1cccnc1]

4-pyridinyl

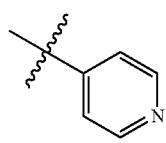

and 5-pyrimidinyl

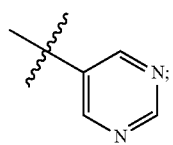

wherein each R² is optionally substituted by one or more R¹². In another embodiment of compounds of the present invention R² is phenyl

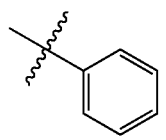 [SMILES: *c1ccccc1]

substituted by one R¹² or 1,3-benzodioxolyl

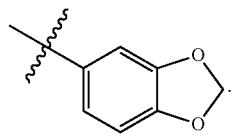 [SMILES: *c1ccc2c(c1)OCO2]

In a further embodiment of compounds of the present invention R² is a heteroaryl selected from the group consisting of 2-pyridinyl

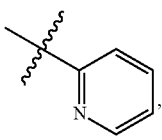

3-pyridinyl

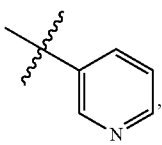

4-pyridinyl

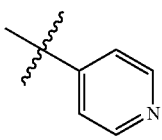 [SMILES: *c1ccncc1]

and 5-pyrimidinyl

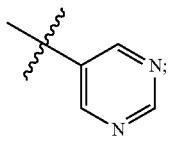

wherein each R² is optionally substituted by one or more R¹². In another embodiment of compounds of the present invention R² is a heteroaryl selected from the group consisting of 2-pyridinyl

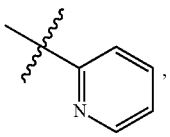

3-pyridinyl

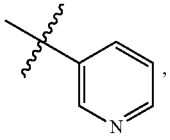 [SMILES: *c1cccnc1]

and 4-pyridinyl

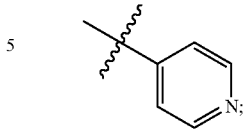

wherein each R² is substituted by one or two R¹². In a further embodiment of compounds of the present invention R² is 3-pyridinyl


substituted by one or two R¹². In another embodiment of compounds of the present invention R² is 3-pyridinyl

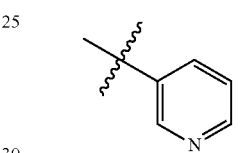

substituted by —S(O₂)NR⁹R¹⁰ or —S(O₂)R¹¹. In a further embodiment of compounds of the present invention R² is 3-pyridinyl

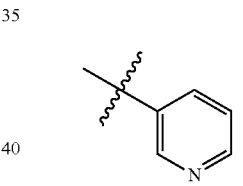

substituted by —S(O₂)N(CH₃)₂ or —S(O₂)CH₃.

In one embodiment of compounds of the present invention R² is substituted by one R¹². In another embodiment of compounds of the present invention R² is substituted by two R¹². In another embodiment of compounds of the present invention R² is substituted by one or two R¹². In a further embodiment of compounds of the present invention R² is substituted by three R². In another embodiment of compounds of the present invention R² is substituted by four or five R¹².

In one embodiment of compounds of the present invention R³, R⁴, R⁵ and R⁶ are each independently selected from the group consisting of hydrogen, halogen, hydroxyl, C₁₋₆alkyl, C₃₋₇cycloalkyl, —O—C₁₋₆alkyl, —O—C₃₋₇cycloalkyl, —CN, —NO₂, —NR⁹R¹⁰, —C(O)OR⁸, —C(O)NR⁹R¹⁰, —NR⁹C(O)R¹¹, —S(O₂)NR⁹R¹⁰, —NR⁹S(O₂)R¹¹, —S(O)R¹¹, —S(O₂)R¹¹, tetrazole and oxadiazole; wherein each C₁₋₆alkyl is a straight or branched chain alkyl; and wherein each C₁₋₆alkyl and C₃₋₇cycloalkyl is optionally substituted by one or more substituents selected from the group consisting of halogen, —OH, —SH, —C₁₋₃alkyl, —O—C₁₋₃alkyl, —CF₃, —CH₂CF₃, and —O—CF₃. In another embodiment of compounds of the present invention R³, R⁴, R⁵ and R⁶ are each independently selected from the group consisting of hydrogen, halogen, hydroxyl, C₁₋₆alkyl, C₃₋₇cycloalkyl, —O—C₁₋₆alkyl, —O—C₃₋₇cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$; wherein each C$_{1-6}$alkyl is a straight or branched chain alkyl; and wherein each C$_{1-6}$alkyl is optionally substituted by one or more substituents selected from the group consisting of halogen, —OH and —O—C$_{1-3}$alkyl. In a further embodiment of compounds of the present invention R$^3$, R$^4$, R$^5$ and R$^6$ are each independently selected from the group consisting of hydrogen, fluoro, chloro, hydroxyl, methyl, cyclopropyl, —CN, —NO$_2$, —NH$_2$, —C(O)OH, —C(O)OMe, —C(O)OEt, —C(O)NR$^9$R$^{10}$, —S(O$_2$)NR$^9$R$^{10}$, —NR$^9$S(O$_2$)R$^{11}$, —S(O)R$^{11}$, —S(O$_2$)R$^{11}$, tetrazole, oxadiazole, —CH$_2$F, —CHF$_2$, —OCF$_3$, —CH$_2$OCH$_3$, —CF$_3$, —CHF$_2$CH$_3$, —C(CH$_3$)$_2$OH.

In one embodiment of compounds of the present invention R$^8$ is selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$. In another embodiment of compounds of the present invention R$^8$ is hydrogen. In a further embodiment of compounds of the present invention R$^8$ is C$_{1-6}$alkyl or C$_{3-7}$cycloalkyl. In a still further embodiment of compounds of the present invention R$^8$ is hydrogen or C$_{1-6}$alkyl. In another embodiment of compounds of the present invention R$^8$ is C$_{1-6}$alkyl. In another embodiment of compounds of the present invention R$^8$ is C$_{1-3}$alkyl. In a further embodiment of compounds of the present invention R$^8$ is methyl or ethyl. In another embodiment of compounds of the present invention R$^8$ is selected from the group consisting of hydrogen, methyl and ethyl.

In one embodiment of compounds of the present invention R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$. In another embodiment of compounds of the present invention R$^9$ and R$^{10}$ are independently selected from the group consisting of hydrogen, C$_{1-6}$alkyl and C$_{3-7}$cycloalkyl. In another embodiment of compounds of the present invention R$^9$ and R$^{10}$ are independently selected from the group consisting of hydrogen and C$_{1-6}$alkyl. In another embodiment of compounds of the present invention R$^9$ and R$^{10}$ are hydrogen. In a further embodiment of compounds of the present invention R$^9$ and R$^{10}$ are C$_{1-6}$alkyl. In another embodiment of compounds of the present invention R$^9$ and R$^{10}$ are both methyl. In a further embodiment of compounds of the present invention R$^9$ and R$^{10}$ are independently selected from the group consisting of hydrogen and C$_{3-7}$cycloalkyl. In another embodiment of compounds of the present invention R$^9$ is hydrogen and R$^{10}$ is C$_{1-6}$alkyl. In one embodiment of compounds of the present invention R$^9$ is hydrogen and R$^{10}$ is methyl or isopropyl. In a further embodiment of compounds of the present invention R$^9$ is methyl and R$^{10}$ is isopropyl.

In one embodiment of compounds of the present invention R$^9$ and R$^{10}$ when attached to the same nitrogen atom are combined to form a 3- to 7-membered ring having from 0 to 2 additional heteroatoms as ring members. In another embodiment R$^9$ and R$^{10}$ when attached to the same nitrogen atom are combined to form a 3- to 7-membered ring having from 0 to 1 additional heteroatoms as ring members. In a further embodiment R$^9$ and R$^{10}$ when attached to the same nitrogen atom are combined to form a 3- to 7-membered ring having 1 additional heteroatom as ring members. In another embodiment R$^9$ and R$^{10}$ when attached to the same nitrogen atom are combined to form a 3- to 7-membered ring having 0 additional heteroatoms as ring members.

In one embodiment of compounds of the present invention R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$. In another embodiment of compounds of the present invention R$^{11}$ is selected from the group consisting of C$_{1-6}$alkyl and C$_{3-7}$cycloalkyl. In another embodiment of compounds of the present invention R$^{11}$ is C$_{1-6}$alkyl. In a further embodiment of compounds of the present invention R$^{11}$ is selected from the group consisting of methyl, ethyl and isopropyl. In another embodiment of compounds of the present invention R$^{11}$ is selected from the group consisting of methyl and isopropyl. In a further embodiment of compounds of the present invention R$^{11}$ is C$_{3-7}$cycloalkyl. In another embodiment of compounds of the present invention R$^{11}$ is cyclopropyl.

In one embodiment of compounds of the present invention R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$. In a further embodiment of compounds of the present invention R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$. In another embodiment of compounds of the present invention R$^{12}$ is selected from the group consisting of halogen, C$_{1-6}$alkyl, —O—C$_{1-6}$alkyl, —S—C$_{1-6}$alkyl, —C(O)OR$^8$, —C(O)NR$^9$R$^{10}$, —S(O$_2$)NR$^9$R$^{10}$—NR$^9$S(O$_2$)R$^{11}$ and —S(O$_2$)R$^{11}$. In a further embodiment of compounds of the present invention R$^{12}$ is selected from the group consisting of —S(O$_2$)NR$^9$R$^{10}$ and —S(O$_2$)R$^{11}$. In another embodiment of compounds of the present invention R$^{12}$ is —S(O$_2$)NR$^9$R$^{10}$. In a further embodiment of compounds of the present invention R$^{12}$ is —S(O$_2$)N(CH$_3$)$_2$. In another embodiment of compounds of the present invention R$^{12}$ is —S(O$_2$)R$^{11}$. In a further embodiment of compounds of the present invention R$^{12}$ is —S(O$_2$)CH$_3$. In another embodiment of compounds of the present invention R$^{12}$ is —S(O$_2$)$^i$Pr.

In one embodiment the present invention also relates to compounds of Formula Ia:

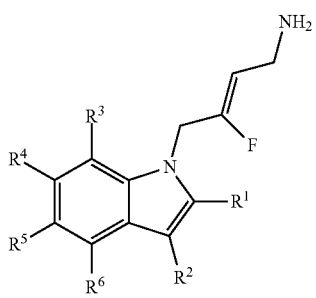

Formula Ia or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —CF$_3$, —CH$_2$CF$_3$, and —O—CF$_3$.

In another embodiment of compounds of Formula Ia of the invention $R^1$ is hydrogen, methyl or chlorine; $R^2$ is aryl or heteroaryl optionally substituted by one or more $R^{12}$; $R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen and —OH; and $R^{12}$ is selected from the group consisting selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen and —OH.

In another embodiment the present invention also relates to compounds of Formula Ib:

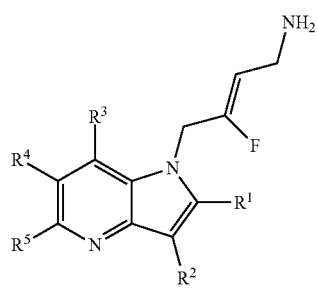

Formula Ib or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —CF$_3$, —CH$_2$CF$_3$, and —O—CF$_3$;

$R^2$ is aryl or heteroaryl; wherein each $R^2$ is optionally substituted by one or more $R^{12}$;

$R^3$, $R^4$ and $R^5$ are each independently selected from the group consisting of hydrogen, halogen, hydroxyl, $C_{1-6}$alkyl, $C_{3-7}$cycloalkyl, —O—$C_{1-6}$alkyl, —S—$C_{1-6}$alkyl, —O—$C_{3-7}$ cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

In one embodiment of compounds of Formula Ib of the invention R$^1$ is hydrogen, methyl, chlorine, isopropyl, 1-hydroxyethyl, 2-hydroxyisopropyl; R$^2$ is phenyl or 3-pyridyl optionally substituted by one or more R$^{12}$; R$^3$, R$^4$ and R$^5$ are each independently selected from the group consisting of hydrogen, halogen, hydroxyl, C$_{1-6}$alkyl, cyclopropyl, —O—C$_{1-6}$alkyl, —NR$^9$R$^{10}$, —C(O)OR$^8$ and —C(O)NR$^9$R$^{10}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen and —OH; and R$^{12}$ is selected from the group consisting selected from the group consisting of halogen, —S—C$_{1-6}$alkyl, —S(O$_2$)NR$^9$R$^{10}$, —S(O)R$^{11}$ and —S(O$_2$)R$^{11}$.

In a further embodiment of compounds of Formula Ib of the invention R$^1$ is hydrogen, methyl, chlorine, isopropyl, 1-hydroxyethyl, 2-hydroxyisopropyl; R$^2$ is phenyl or 3-pyridyl optionally substituted by one or more R$^{12}$; R$^3$, R$^4$ and R$^5$ are each independently selected from the group consisting of hydrogen, fluorine, chlorine, hydroxyl, methyl, cyclopropyl, —OCH$_3$, —CF$_3$, —CH$_2$F, —CHF$_2$CH$_3$, —CH$_2$OCH$_3$, —C(CH$_3$)$_2$OH, —N(CH$_3$)$_2$, —C(O)OH, —C(O)OEt, —C(O)NHCH$_3$, —C(O)N(CH$_3$)$_2$, —C(O)NH$^i$Pr; and R$^{12}$ is selected from the group consisting selected from the group consisting of chlorine, —S—CH$_3$, —S(O$_2$)N(CH$_3$)$_2$, —S(O$_2$)CH$_3$, —S(O$_2$)Et, —S(O$_2$)$^i$Pr and —S(O$_2$)cyclopropyl.

In another embodiment the present invention also relates to compounds of Formula Ic:

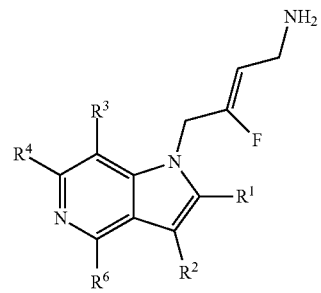

Formula Ic or a pharmaceutically acceptable salt, solvate or prodrug thereof; wherein:

R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^2$ is aryl or heteroaryl; wherein each R$^2$ is optionally substituted by one or more R$^2$;

R$^3$, R$^4$ and R$^6$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;

R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or R$^9$ and R$^{10}$ when attached to the same nitrogen atom are combined to form a 3- to 7-membered ring having from 0 to 2 additional heteroatoms as ring members;

R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)

$R^{11}$ and —$S(O_2)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Ic of the invention $R^1$ is methyl, $R^2$ is phenyl optionally substituted by $S(O_2)N(CH_3)_2$ or —$S(O_2)CH_3$; and $R^3$, $R^4$ and $R^6$ are independently selected from the group consisting of hydrogen and methyl.

In another embodiment the present invention also relates to compounds of Formula Id:

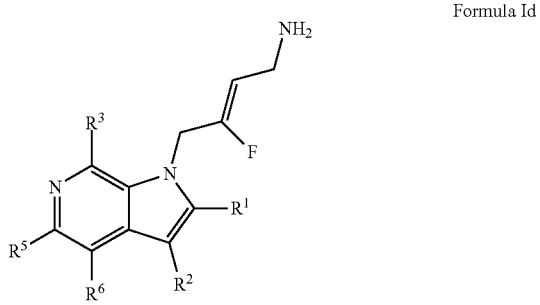

Formula Id or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —$C(O)OR^8$, —$C(O)NR^9R^{10}$ and —$NR^9C(O)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —$C(O)OR^8$, —$C(O)NR^9R^{10}$, —$NR^9C(O)R^{11}$, —$S(O_2)NR^9R^{10}$, —$NR^9S(O_2)R^{11}$, —$S(O)R^{11}$, —$S(O_2)R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —$C(O)OR^8$, —$C(O)NR^9R^{10}$, —$NR^9C(O)R^{11}$, —$S(O_2)NR^9R^{10}$, —$NR^9S(O_2)R^{11}$, —$S(O)R^{11}$ and —$S(O_2)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Id of the invention $R^1$ is methyl; $R^2$ is phenyl substituted by $S(O_2)N(CH_3)_2$; and $R^3$, $R^5$ and $R^6$ are hydrogen.

In another embodiment the present invention also relates to compounds of Formula Ie:

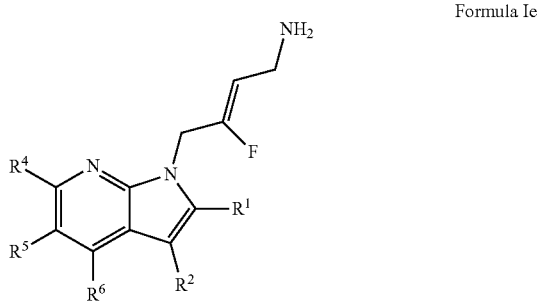

Formula Ie or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —$C(O)OR^8$, —$C(O)NR^9R^{10}$ and —$NR^9C(O)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —$C(O)OR^8$, —$C(O)NR^9R^{10}$, —$NR^9C(O)R^{11}$, —$S(O_2)NR^9R^{10}$, —$NR^9S(O_2)R^{11}$, —$S(O)R^{11}$, —$S(O_2)R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —$NR^9$C(O)$R^{11}$, —S($O_2$)N$R^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In one embodiment of compounds of Formula Ie of the invention $R^1$ is methyl, $R^2$ is phenyl or 3-pyridyl substituted by $S(O_2)N(CH_3)_2$; and $R^4$, $R^5$ and $R^6$ are independently selected from the group consisting of hydrogen and chlorine.

In another embodiment the present invention also relates to compounds of Formula If:

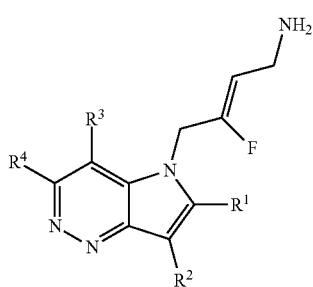

Formula If or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$ and $R^4$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)ORB, —C(O)N$R^9R^{10}$, —$NR^9$C(O)$R^{11}$, —S($O_2$)N$R^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)O$R^8$, —C(O)N$R^9R^{10}$, —$NR^9$C(O)$R^{11}$, —S($O_2$)N$R^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In another embodiment the present invention also relates to compounds of Formula Ig:

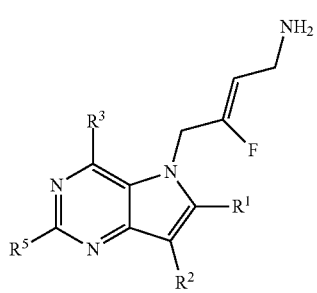

Formula Ig or a pharmaceutically acceptable salt, solvate or prodrug thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)O$R^8$, —C(O)N$R^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$ and $R^5$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9C(O)R^{11}$, —$S(O_2)NR^9R^{10}$, —$NR^9S(O_2)R^{11}$, —S(O)$R^{11}$, —$S(O_2)R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9C(O)R^{11}$, —$S(O_2)NR^9R^{10}$, —$NR^9S(O_2)R^{11}$, —S(O)$R^{11}$ and —$S(O_2)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

In the context of the present disclosure, any one or more aspect(s) or embodiment(s) may be combined with any other aspect(s) or embodiment(s).

Exemplary compounds according to the present invention include the compounds set forth in Table 1:

TABLE 1

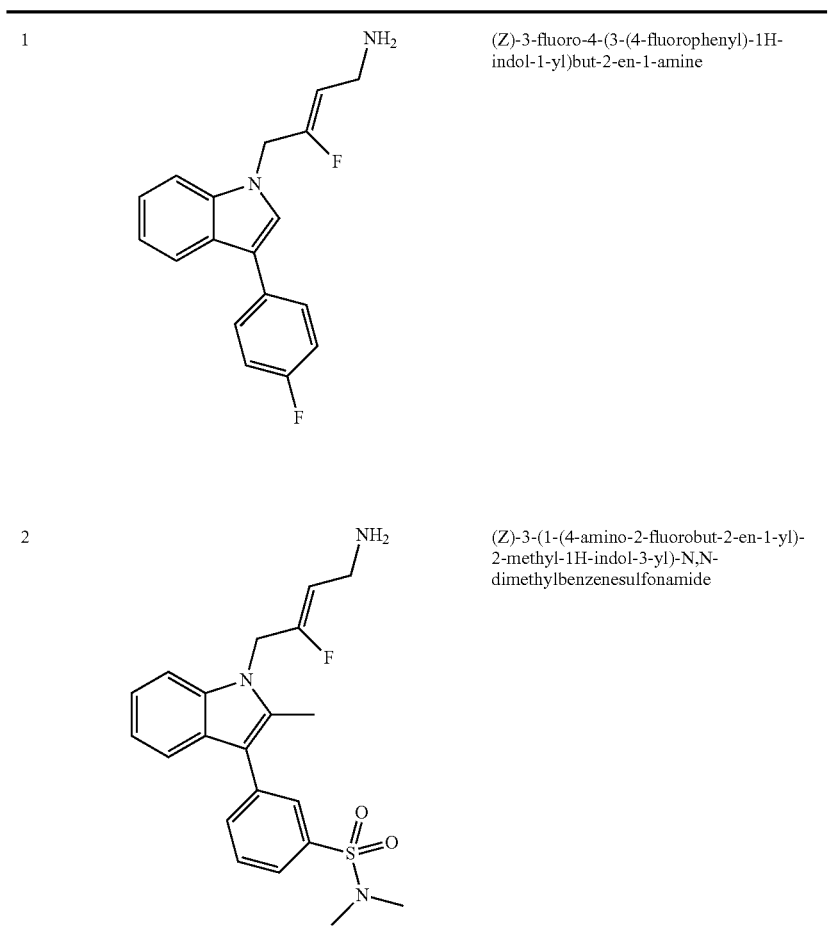

| 1 | | (Z)-3-fluoro-4-(3-(4-fluorophenyl)-1H-indol-1-yl)but-2-en-1-amine |
| 2 | | (Z)-3-(1-(4-amino-2-fluorobut-2-en-1-yl)-2-methyl-1H-indol-3-yl)-N,N-dimethylbenzenesulfonamide |

TABLE 1-continued
| | | |
|---|---|---|
| 3 | 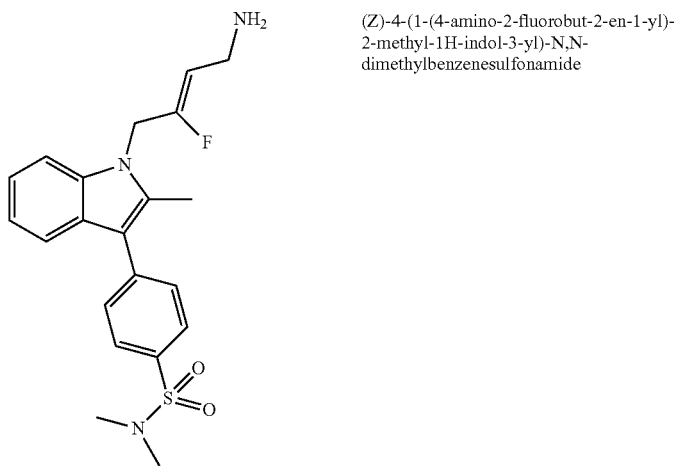 | (Z)-4-(1-(4-amino-2-fluorobut-2-en-1-yl)-2-methyl-1H-indol-3-yl)-N,N-dimethylbenzenesulfonamide |
| 4 | 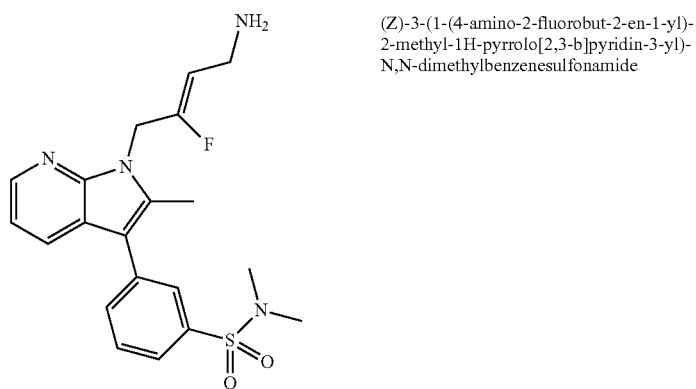 | (Z)-3-(1-(4-amino-2-fluorobut-2-en-1-yl)-2-methyl-1H-pyrrolo[2,3-b]pyridin-3-yl)-N,N-dimethylbenzenesulfonamide |
| 5 | 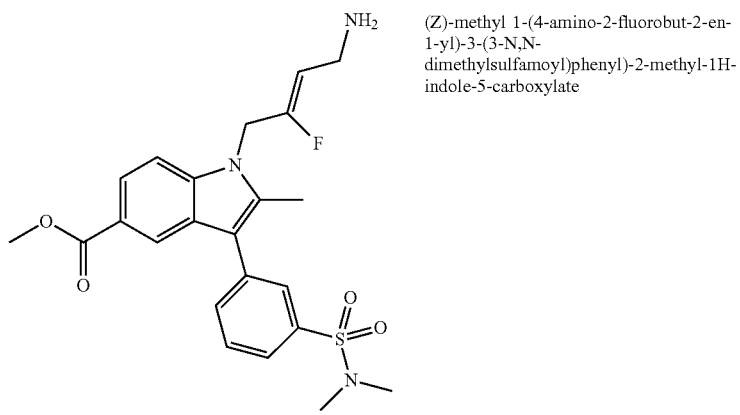 | (Z)-methyl 1-(4-amino-2-fluorobut-2-en-1-yl)-3-(3-N,N-dimethylsulfamoyl)phenyl)-2-methyl-1H-indole-5-carboxylate |

TABLE 1-continued

| | | |
|---|---|---|
| 6 | | (Z)-1-(4-amino-2-fluorobut-2-en-1-yl)-3-(3-(N,N-dimethylsulfamoyl)phenyl)-N,N,2-trimethyl-1H-indole-5-carboxamide |
| 7 | | (Z)-methyl 1-(4-amino-2-fluorobut-2-en-1-yl)-3-(3-(N,N-dimethylsulfamoyl)phenyl)-2-methyl-1H-indole-6-carboxylate |
| 8 | | (Z)-1-(4-amino-2-fluorobut-2-en-1-yl)-3-(3-(N,N-dimethylsulfamoyl)phenyl)-2-methyl-1H-indole-5-carboxylic acid |
| 9 | | (Z)-1-(4-amino-2-fluorobut-2-en-1-yl)-3-(3-(N,N-dimethylsulfamoyl)phenyl)-2-methyl-1H-indole-6-carboxylic acid |

TABLE 1-continued

| | | |
|---|---|---|
| 10 | | (Z)-1-(4-amino-2-fluorobut-2-en-1-yl)-3-(3-(N,N-dimethylsulfamoyl)phenyl)-N,N,2-trimethyl-1H-indole-6-carboxamide |
| 11 | | (Z)-1-(4-amino-2-fluorobut-2-en-1-yl)-3-(3-(N,N-dimethylsulfamoyl)phenyl)-2-methyl-1H-indole-6-carboxamide |
| 12 | | (Z)-ethyl 1-(4-amino-2-fluorobut-2-en-1-yl)-3-(3-(N,N-dimethylsulfamoyl)phenyl)-2-methyl-1H-indole-5-carboxylate |
| 13 | | (Z)-1-(4-amino-2-fluorobut-2-en-1-yl)-3-(3-(N,N-dimethylsulfamoyl)-2-methylphenyl)-2-methyl-1H-indole-5-carboxylic acid |

TABLE 1-continued
| | | |
|---|---|---|
| 14 | 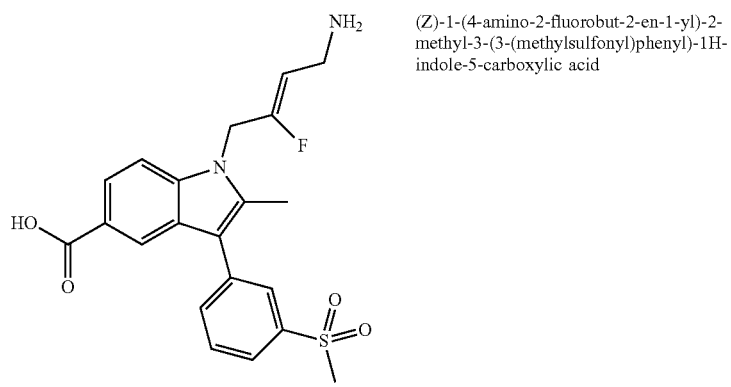 | (Z)-1-(4-amino-2-fluorobut-2-en-1-yl)-2-methyl-3-(3-(methylsulfonyl)phenyl)-1H-indole-5-carboxylic acid |
| 15 | 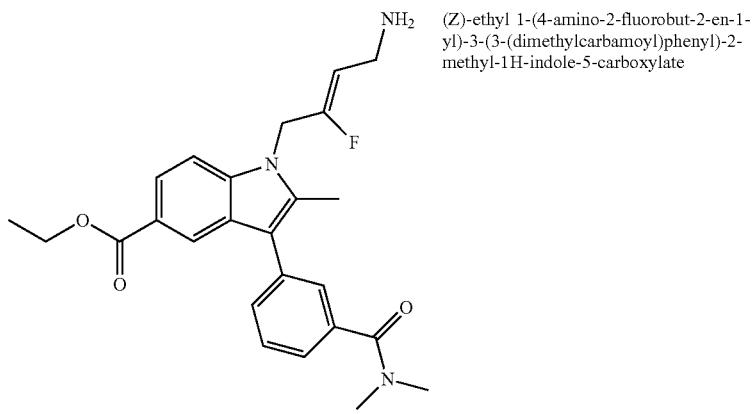 | (Z)-ethyl 1-(4-amino-2-fluorobut-2-en-1-yl)-3-(3-(dimethylcarbamoyl)phenyl)-2-methyl-1H-indole-5-carboxylate |
| 16 | 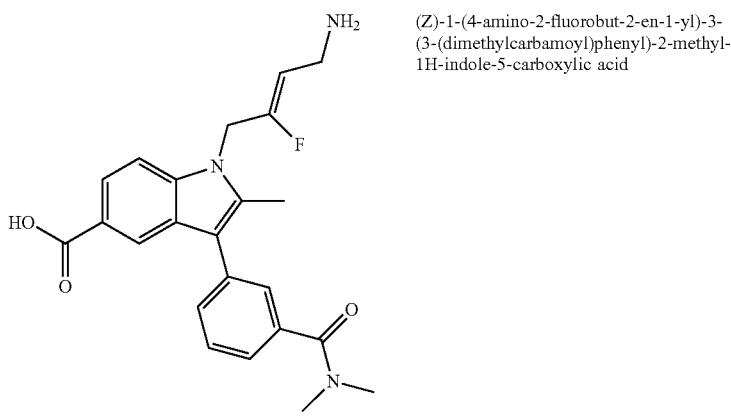 | (Z)-1-(4-amino-2-fluorobut-2-en-1-yl)-3-(3-(dimethylcarbamoyl)phenyl)-2-methyl-1H-indole-5-carboxylic acid |
| 17 | 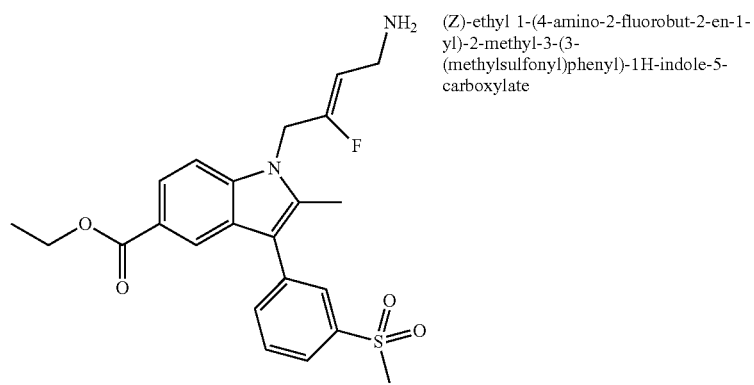 | (Z)-ethyl 1-(4-amino-2-fluorobut-2-en-1-yl)-2-methyl-3-(3-(methylsulfonyl)phenyl)-1H-indole-5-carboxylate |

TABLE 1-continued

| | | |
|---|---|---|
| 18 | | (Z)-1-(4-amino-2-fluorobut-2-en-1-yl)-2-methyl-3-(3-(N-methylsulfamoyl)phenyl)-1H-indole-5-carboxylic acid |
| 19 | | (Z)-ethyl 1-(4-amino-2-fluorobut-2-en-1-yl)-3-(5-(N,N-dimethylsulfamoyl)-2-methylphenyl)-2-methyl-1H-indole-5-carboxylate |
| 20 | | (Z)-1-(4-amino-2-fluorobut-2-en-1-yl)-3-(5-(N,N-dimethylsulfamoyl)-2-methylphenyl)-2-methyl-1H-indole-5-carboxylic acid |
| 21 | | (Z)-1-(4-amino-2-fluorobut-2-en-1-yl)-3-(3-(N,N-dimethylsulfamoyl)phenyl)-6-fluoro-2-methyl-1H-indole-5-carboxylic acid |

TABLE 1-continued
| | | |
|---|---|---|
| 22 | 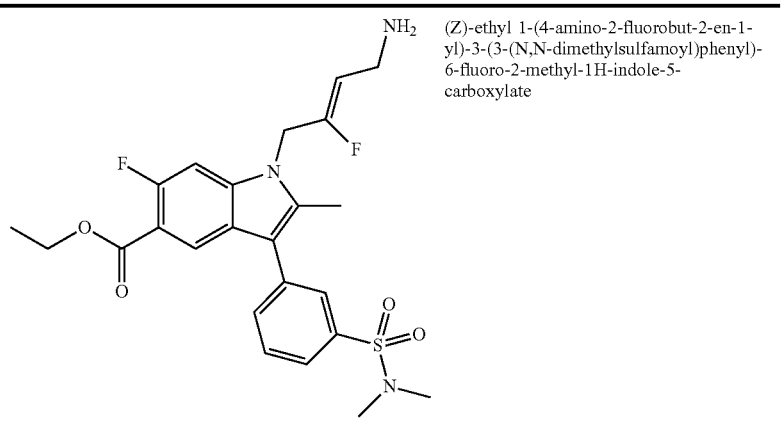 | (Z)-ethyl 1-(4-amino-2-fluorobut-2-en-1-yl)-3-(3-(N,N-dimethylsulfamoyl)phenyl)-6-fluoro-2-methyl-1H-indole-5-carboxylate |
| 23 | 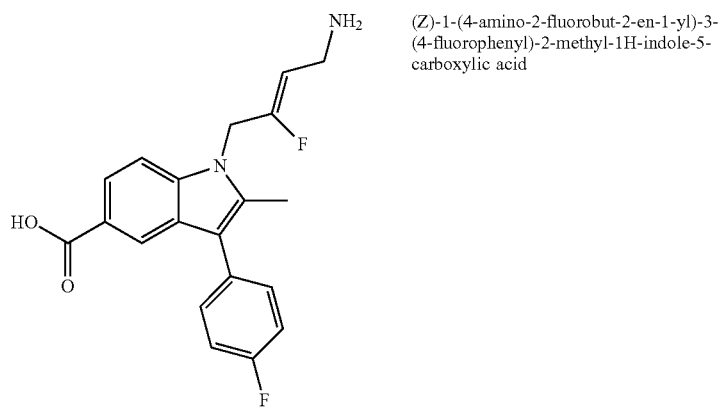 | (Z)-1-(4-amino-2-fluorobut-2-en-1-yl)-3-(4-fluorophenyl)-2-methyl-1H-indole-5-carboxylic acid |
| 24 | 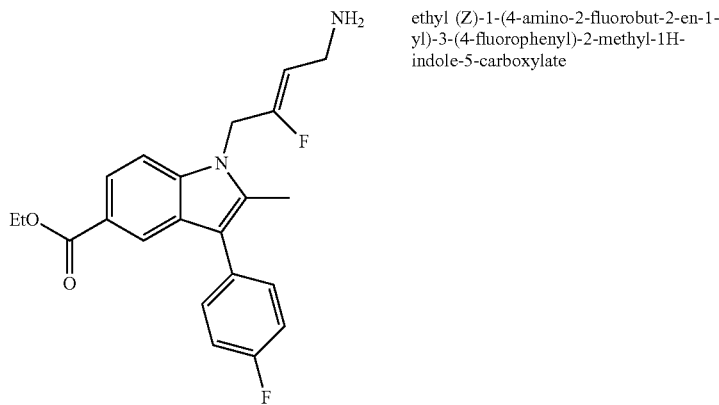 | ethyl (Z)-1-(4-amino-2-fluorobut-2-en-1-yl)-3-(4-fluorophenyl)-2-methyl-1H-indole-5-carboxylate |
| 25 | 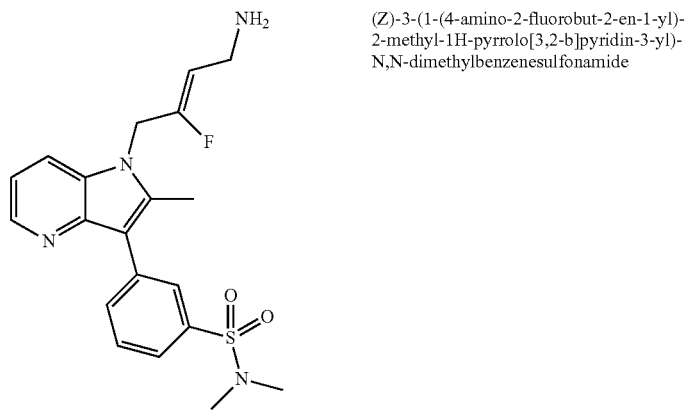 | (Z)-3-(1-(4-amino-2-fluorobut-2-en-1-yl)-2-methyl-1H-pyrrolo[3,2-b]pyridin-3-yl)-N,N-dimethylbenzenesulfonamide |

TABLE 1-continued
| | | |
|---|---|---|
| 26 | 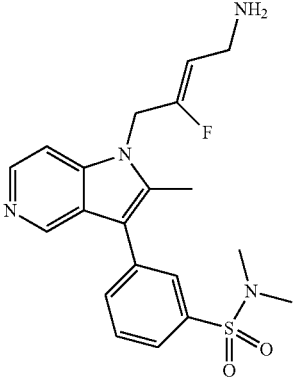 [SMILES: Cc1c(-c2cccc(S(=O)(=O)N(C)C)c2)c2cnccc2n1C/C(F)=C/CN] | (Z)-3-(1-(4-amino-2-fluorobut-2-en-1-yl)-2-methyl-1H-pyrrolo[3,2-c]pyridin-3-yl)-N,N-dimethylbenzenesulfonamide |
| 27 | 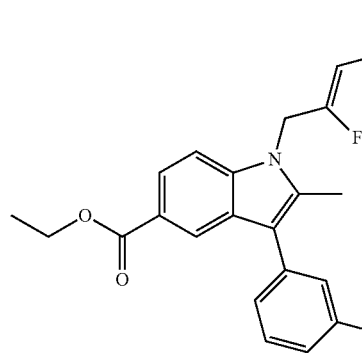 | ethyl (Z)-1-(4-amino-2-fluorobut-2-en-1-yl)-3-(3-chlorophenyl)-2-methyl-1H-indole-5-carboxylate |
| 28 | 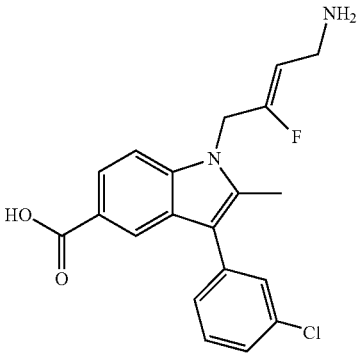 [SMILES: Cc1c(-c2cccc(Cl)c2)c2cc(C(=O)O)ccc2n1C/C(F)=C/CN] | (Z)-1-(4-amino-2-fluorobut-2-en-1-yl)-3-(3-chlorophenyl)-2-methyl-1H-indole-5-carboxylic acid |
| 29 | 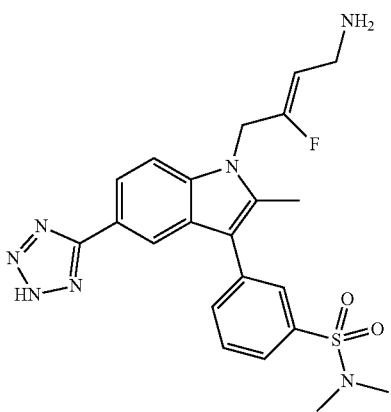 [SMILES: Cc1c(-c2cccc(S(=O)(=O)N(C)C)c2)c2cc(-c3nn[nH]n3)ccc2n1C/C(F)=C/CN] | (Z)-3-(1-(4-amino-2-fluorobut-2-en-1-yl)-2-methyl-5-(2H-tetrazol-5-yl)-1H-indol-3-yl)-N,N-dimethylbenzenesulfonamide |

TABLE 1-continued
| | | |
|---|---|---|
| 30 | 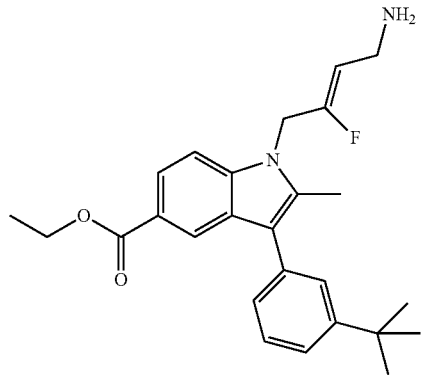 [SMILES: CCOC(=O)c1ccc2c(c1)c(-c1cccc(C(C)(C)C)c1)c(C)n2C/C(F)=C/CN] | ethyl (Z)-1-(4-amino-2-fluorobut-2-en-1-yl)-3-(3-(tert-butyl)phenyl)-2-methyl-1H-indole-5-carboxylate |
| 31 | 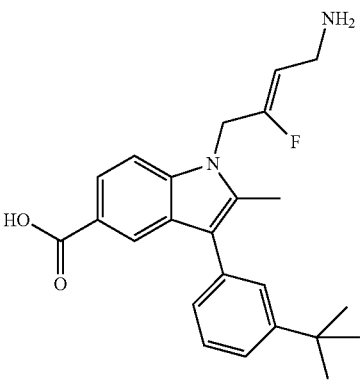 [SMILES: Cc1c(-c2cccc(C(C)(C)C)c2)c2cc(C(=O)O)ccc2n1C/C(F)=C/CN] | (Z)-1-(4-amino-2-fluorobut-2-en-l-yl)-3-(3-(tert-butyl)phenyl)-2-methyl-1H-indole-5-carboxylic acid |
| 32 | 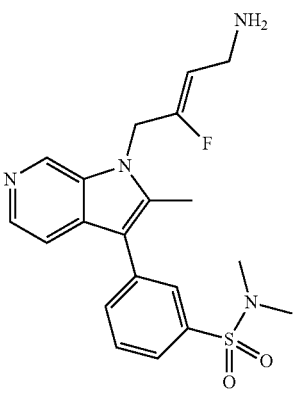 [SMILES: Cc1c(-c2cccc(S(=O)(=O)N(C)C)c2)c2ccncc2n1C/C(F)=C/CN] | (Z)-3-(1-(4-amino-2-fluorobut-2-en-1-yl)-2-methyl-1H-pyrrolo[2,3-c]pyridin-3-yl)-N,N-dimethylbenzenesulfonamide |
| 33 | 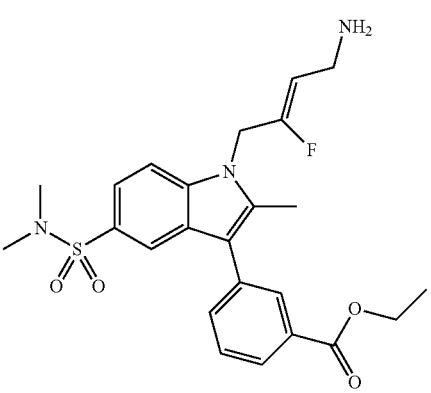 [SMILES: CCOC(=O)c1cccc(-c2c(C)n(C/C(F)=C/CN)c3ccc(S(=O)(=O)N(C)C)cc23)c1] | ethyl (Z)-3-(1-(4-amino-2-fluorobut-2-en-1-yl)-5-(N,N-dimethylsulfamoyl)-2-methyl-1H-indol-3-yl)benzoate |

TABLE 1-continued

| | | |
|---|---|---|
| 34 | 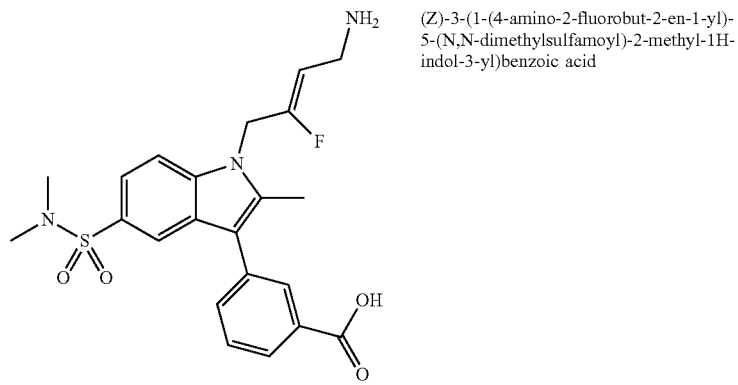 | (Z)-3-(1-(4-amino-2-fluorobut-2-en-1-yl)-5-(N,N-dimethylsulfamoyl)-2-methyl-1H-indol-3-yl)benzoic acid |
| 35 | 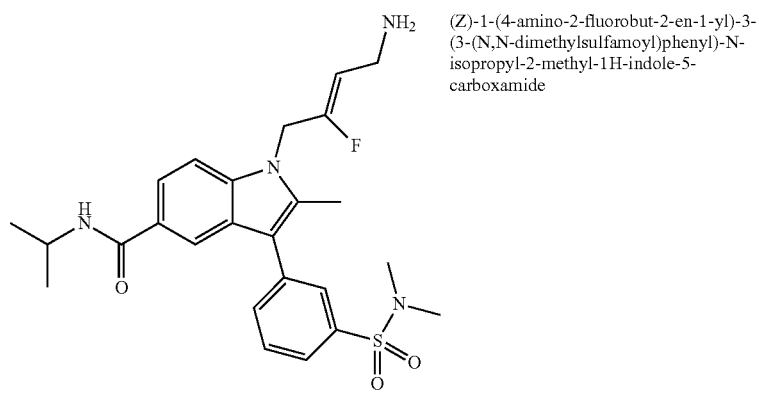 | (Z)-1-(4-amino-2-fluorobut-2-en-1-yl)-3-(3-(N,N-dimethylsulfamoyl)phenyl)-N-isopropyl-2-methyl-1H-indole-5-carboxamide |
| 36 | 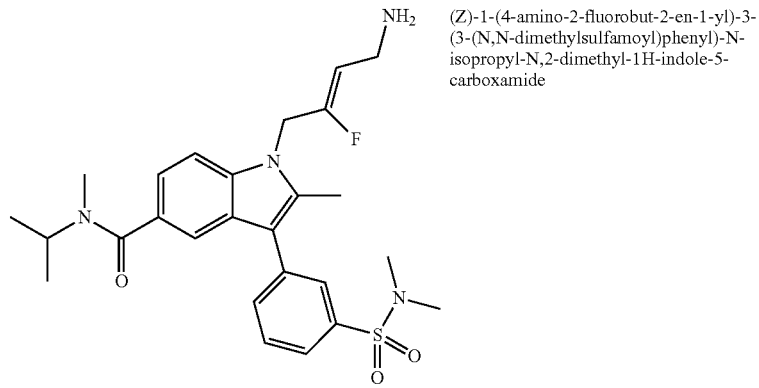 | (Z)-1-(4-amino-2-fluorobut-2-en-1-yl)-3-(3-(N,N-dimethylsulfamoyl)phenyl)-N-isopropyl-N,2-dimethyl-1H-indole-5-carboxamide |
| 37 | 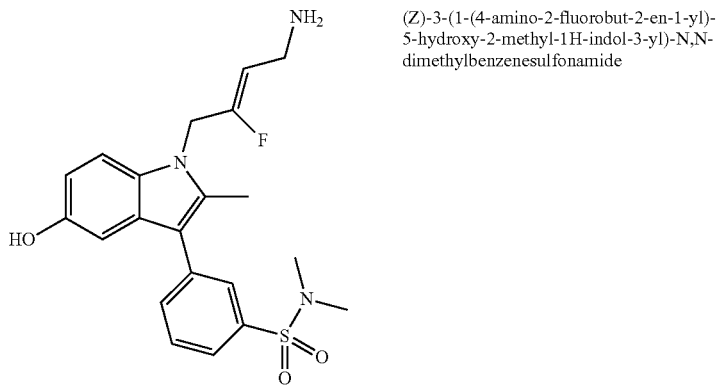 | (Z)-3-(1-(4-amino-2-fluorobut-2-en-1-yl)-5-hydroxy-2-methyl-1H-indol-3-yl)-N,N-dimethylbenzenesulfonamide |

TABLE 1-continued

| 38 | 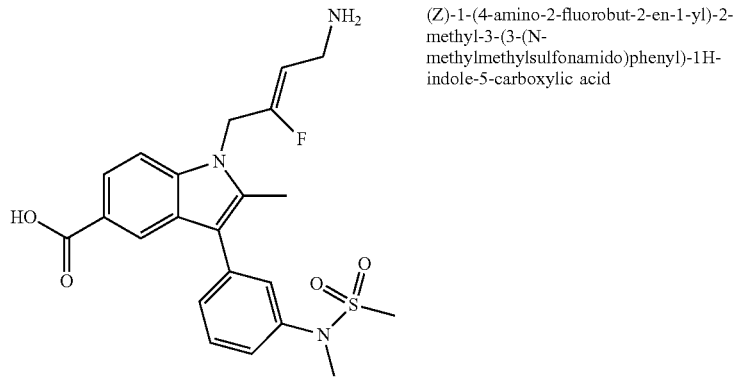 | (Z)-1-(4-amino-2-fluorobut-2-en-1-yl)-2-methyl-3-(3-(N-methylmethylsulfonamido)phenyl)-1H-indole-5-carboxylic acid |
| 39 | 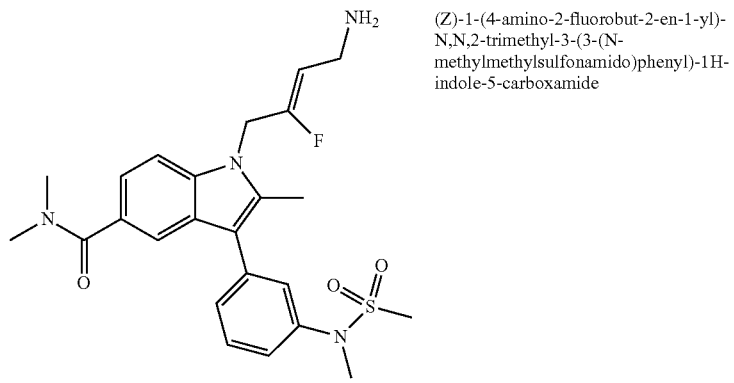 | (Z)-1-(4-amino-2-fluorobut-2-en-1-yl)-N,N,2-trimethyl-3-(3-(N-methylmethylsulfonamido)phenyl)-1H-indole-5-carboxamide |
| 40 | 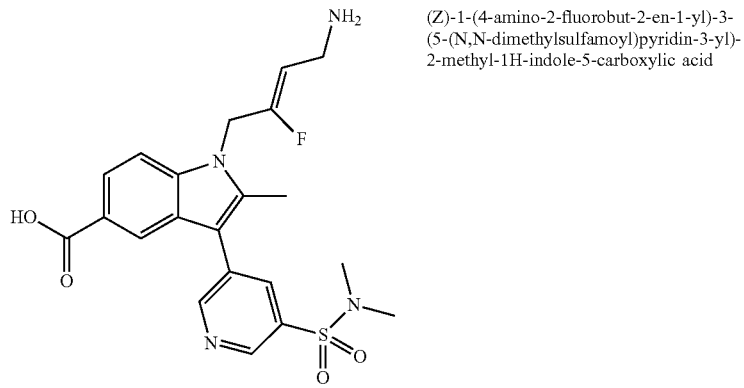 | (Z)-1-(4-amino-2-fluorobut-2-en-1-yl)-3-(5-(N,N-dimethylsulfamoyl)pyridin-3-yl)-2-methyl-1H-indole-5-carboxylic acid |
| 41 | 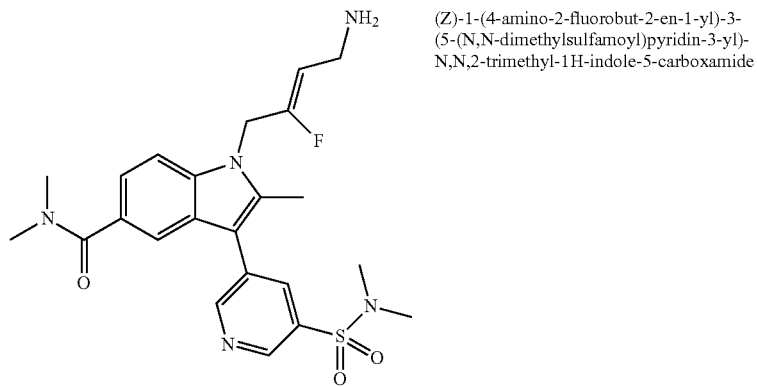 | (Z)-1-(4-amino-2-fluorobut-2-en-1-yl)-3-(5-(N,N-dimethylsulfamoyl)pyridin-3-yl)-N,N,2-trimethyl-1H-indole-5-carboxamide |

TABLE 1-continued

| | | |
|---|---|---|
| 42 | 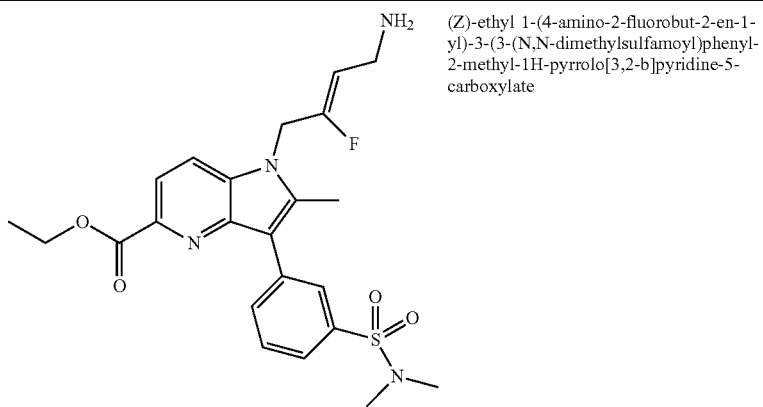 | (Z)-ethyl 1-(4-amino-2-fluorobut-2-en-1-yl)-3-(3-(N,N-dimethylsulfamoyl)phenyl-2-methyl-1H-pyrrolo[3,2-b]pyridine-5-carboxylate |
| 43 | 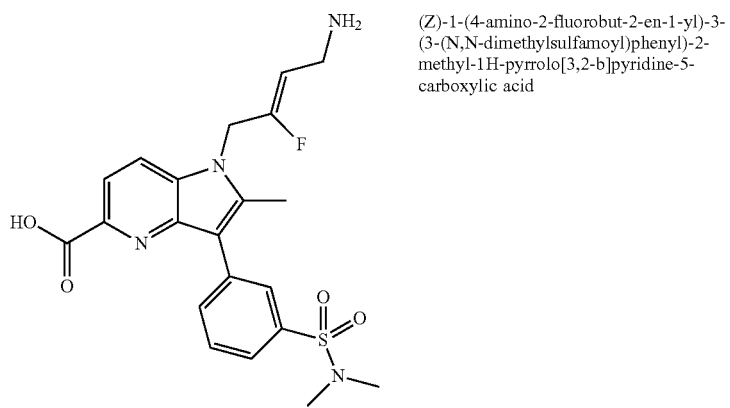 | (Z)-1-(4-amino-2-fluorobut-2-en-1-yl)-3-(3-(N,N-dimethylsulfamoyl)phenyl)-2-methyl-1H-pyrrolo[3,2-b]pyridine-5-carboxylic acid |
| 44 | 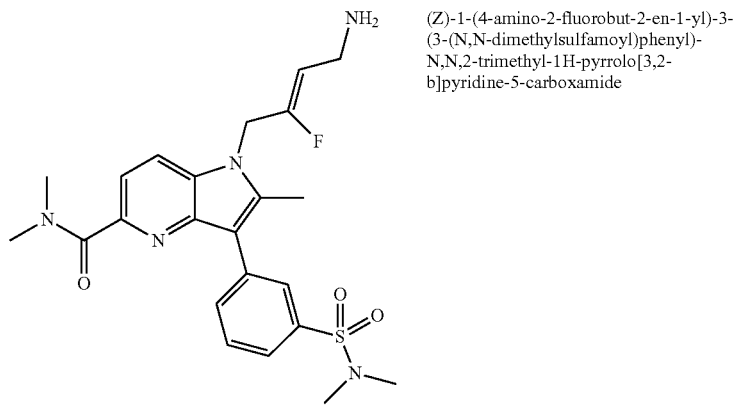 | (Z)-1-(4-amino-2-fluorobut-2-en-1-yl)-3-(3-(N,N-dimethylsulfamoyl)phenyl)-N,N,2-trimethyl-1H-pyrrolo[3,2-b]pyridine-5-carboxamide |
| 45 | 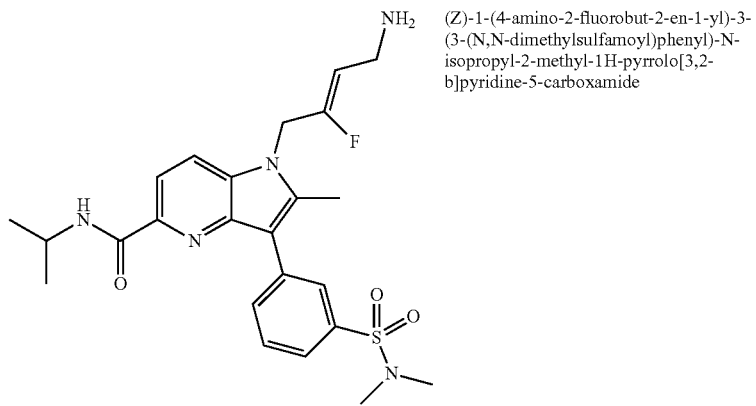 | (Z)-1-(4-amino-2-fluorobut-2-en-1-yl)-3-(3-(N,N-dimethylsulfamoyl)phenyl)-N-isopropyl-2-methyl-1H-pyrrolo[3,2-b]pyridine-5-carboxamide |

TABLE 1-continued

| | | |
|---|---|---|
| 46 | 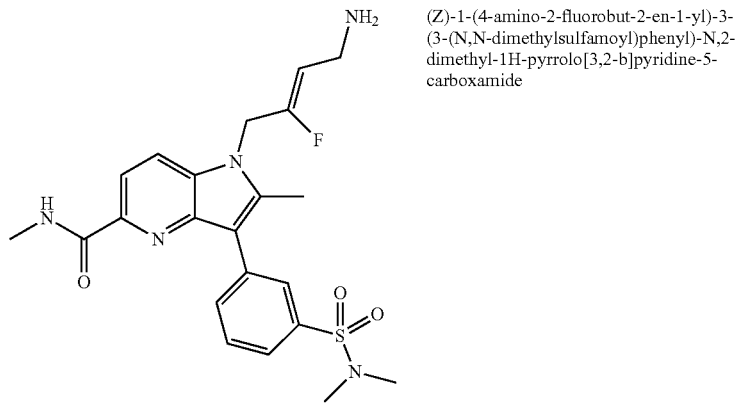 | (Z)-1-(4-amino-2-fluorobut-2-en-1-yl)-3-(3-(N,N-dimethylsulfamoyl)phenyl)-N,2-dimethyl-1H-pyrrolo[3,2-b]pyridine-5-carboxamide |
| 47 | 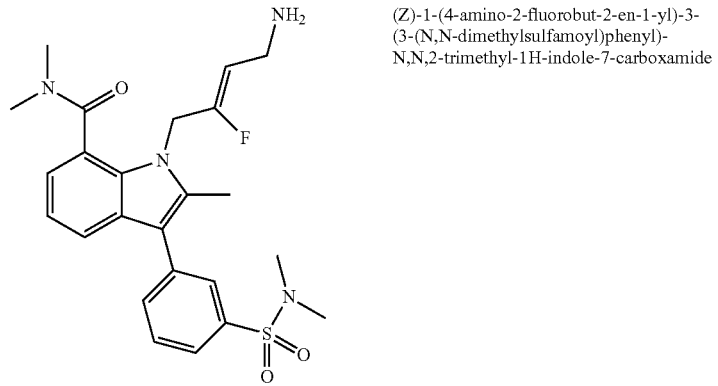 | (Z)-1-(4-amino-2-fluorobut-2-en-1-yl)-3-(3-(N,N-dimethylsulfamoyl)phenyl)-N,N,2-trimethyl-1H-indole-7-carboxamide |
| 48 | 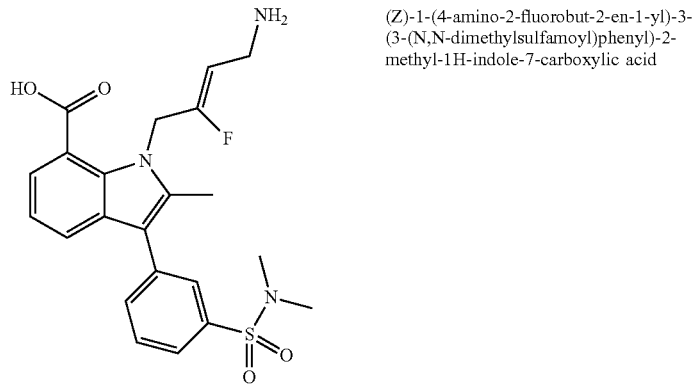 | (Z)-1-(4-amino-2-fluorobut-2-en-1-yl)-3-(3-(N,N-dimethylsulfamoyl)phenyl)-2-methyl-1H-indole-7-carboxylic acid |
| 49 | 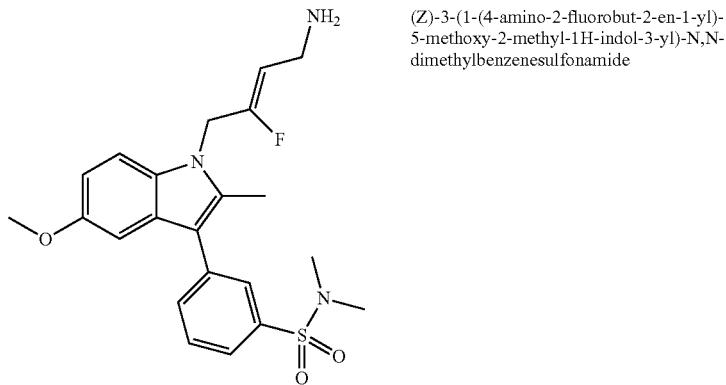 | (Z)-3-(1-(4-amino-2-fluorobut-2-en-1-yl)-5-methoxy-2-methyl-1H-indol-3-yl)-N,N-dimethylbenzenesulfonamide |

TABLE 1-continued

| 50 | 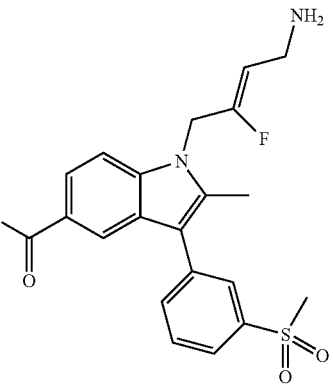 | (Z)-1-(4-amino-2-fluorobut-2-en-1-yl)-N,N,2-trimethyl-3-(3-(methylsulfonyl)phenyl)-1H-indole-5-carboxamide |
| 51 | 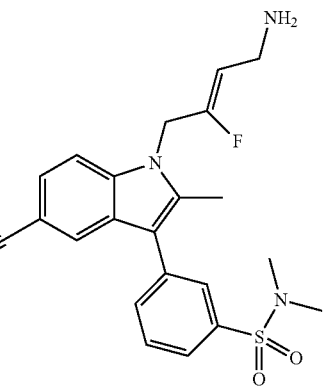 | (Z)-3-(1-(4-amino-2-fluorobut-2-en-1-yl)-5-cyano-2-methyl-1H-indol-3-yl)-N,N-dimethylbenzenesulfonamide |
| 52 | 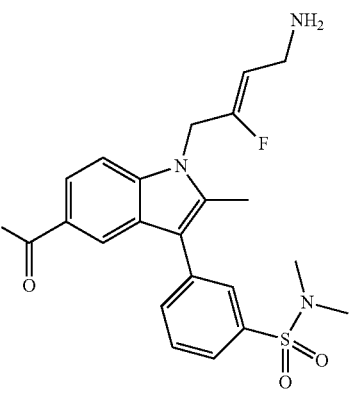 | (Z)-1-(4-amino-2-fluorobut-2-en-1-yl)-3-(3-(N,N-dimethylsulfamoyl)phenyl)-N,N,2-trimethyl-1H-indole-5-carboxamide |
| 53 | 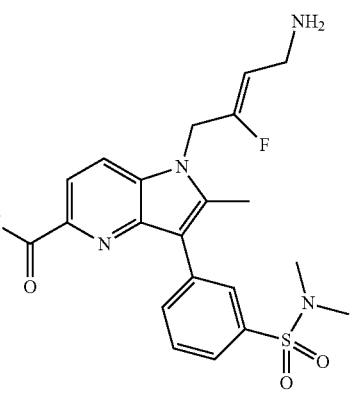 | (Z)-1-(4-amino-2-fluorobut-2-en-1-yl)-3-(3-(N,N-dimethylsulfamoyl)phenyl-N,N,2-trimethyl-1H-pyrrolo[3,2-b]pyridine-5-carboxamide |

TABLE 1-continued
| | | |
|---|---|---|
| 54 | 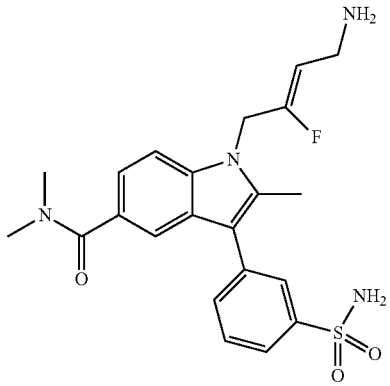 [SMILES: Cc1c(-c2cccc(S(N)(=O)=O)c2)c2cc(C(=O)N(C)C)ccc2n1C/C(F)=C/CN] | (Z)-1-(4-amino-2-fluorobut-2-en-1-yl)-N,N,2-trimethyl-3-(3-sulfamoylphenyl)-1H-indole-5-carboxamide |
| 55 | 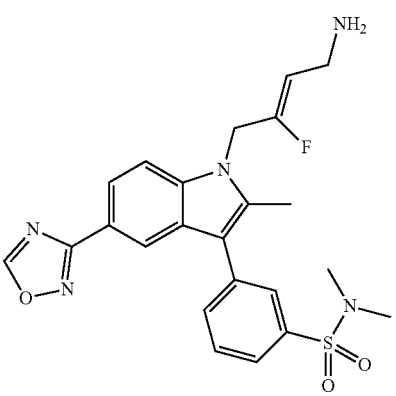 [SMILES: Cc1c(-c2cccc(S(=O)(=O)N(C)C)c2)c2cc(-c3ncon3)ccc2n1C/C(F)=C/CN] | (Z)-3-(1-(4-amino-2-fluorobut-2-en-1-yl)-2-methyl-5-(1,2,4-oxadiazol-3-yl)-1H-indol-3-yl)-N,N-dimethylbenzenesulfonamide |
| 56 | 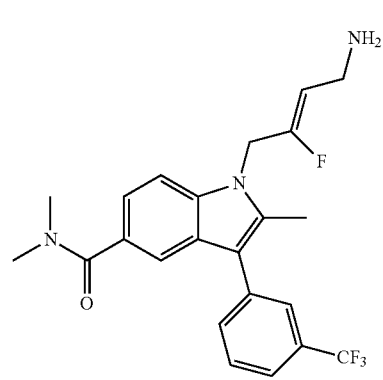 [SMILES: Cc1c(-c2cccc(C(F)(F)F)c2)c2cc(C(=O)N(C)C)ccc2n1C/C(F)=C/CN] | (Z)-1-(4-amino-2-fluorobut-2-en-1-yl)-N,N,2-trimethyl-3-(3-(trifluoromethyl)phenyl)-1H-indole-5-carboxamide |
| 57 | 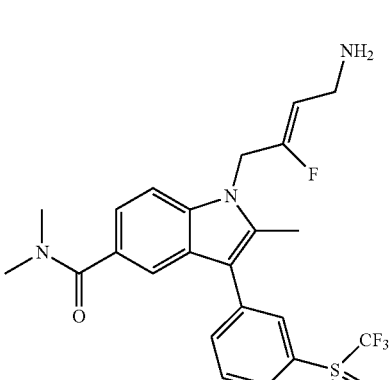 | (Z)-1-(4-amino-2-fluorobut-2-en-1-yl)-N,N,2-trimethyl-3-(3-((trifluoromethyl)sulfonyl)phenyl)-1H-indole-5-carboxamide |

TABLE 1-continued

| | | |
|---|---|---|
| 58 | *(structure)* | (Z)-1-(4-amino-2-fluorobut-2-en-1-yl)-3-(3-(N,N-dimethylsulfamoyl)phenyl)-N,N,2-trimethyl-1H-indole-5-sulfonamide |
| 59 | *(structure)* | (Z)-3-(1-(4-amino-2-fluorobut-2-en-1-yl)-5-(difluoromethyl)-2-methyl-1H-indol-3-yl)-N,N-dimethylbenzene-sulfonamide |
| 60 | *(structure)* | (Z)-3-(1-(4-amino-2-fluorobut-2-en-1-yl)-5-hydroxy-2-methyl-1H-pyrrolo[3,2-b]pyridin-3-yl)-N,N-dimethylbenzene-sulfonamide |
| 61 | *(structure)* | (Z)-3-(1-(4-amino-2-fluorobut-2-en-1-yl)-5-methoxy-2-methyl-1H-pyrrolo[3,2-b]pyridin-3-yl)-N,N-dimethylbenzene-sulfonamide |

| | | |
|---|---|---|
| 62 | 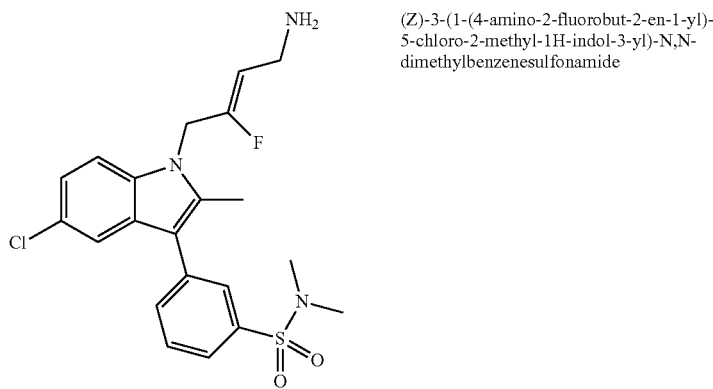 | (Z)-3-(1-(4-amino-2-fluorobut-2-en-1-yl)-5-chloro-2-methyl-1H-indol-3-yl)-N,N-dimethylbenzenesulfonamide |
| 63 | 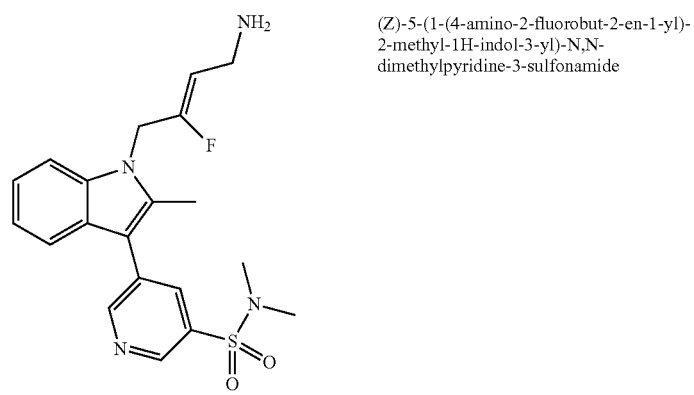 | (Z)-5-(1-(4-amino-2-fluorobut-2-en-1-yl)-2-methyl-1H-indol-3-yl)-N,N-dimethylpyridine-3-sulfonamide |
| 64 | 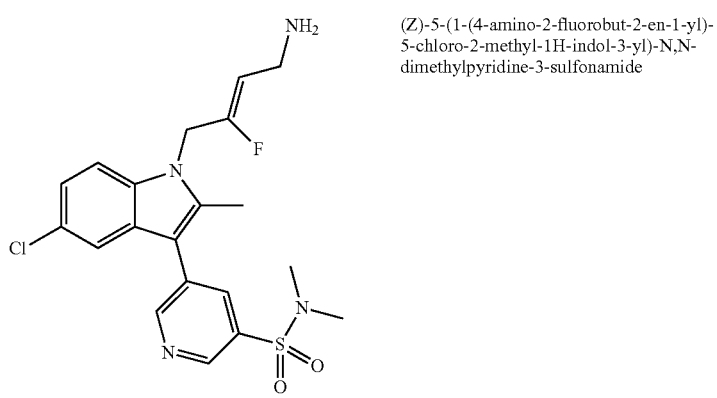 | (Z)-5-(1-(4-amino-2-fluorobut-2-en-1-yl)-5-chloro-2-methyl-1H-indol-3-yl)-N,N-dimethylpyridine-3-sulfonamide |
| 65 | 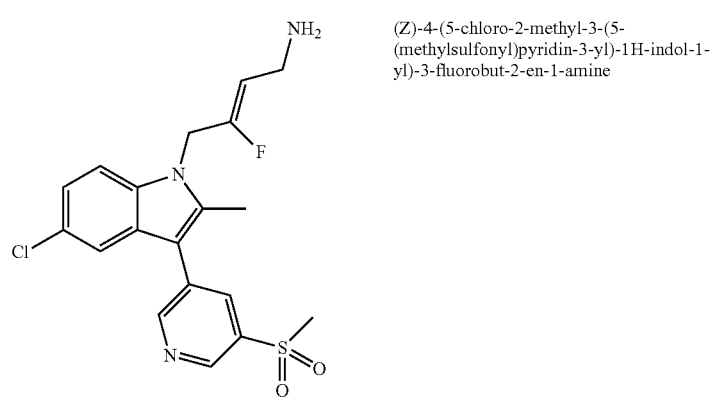 | (Z)-4-(5-chloro-2-methyl-3-(5-(methylsulfonyl)pyridin-3-yl)-1H-indol-1-yl)-3-fluorobut-2-en-1-amine |

TABLE 1-continued
| | | |
|---|---|---|
| 66 | 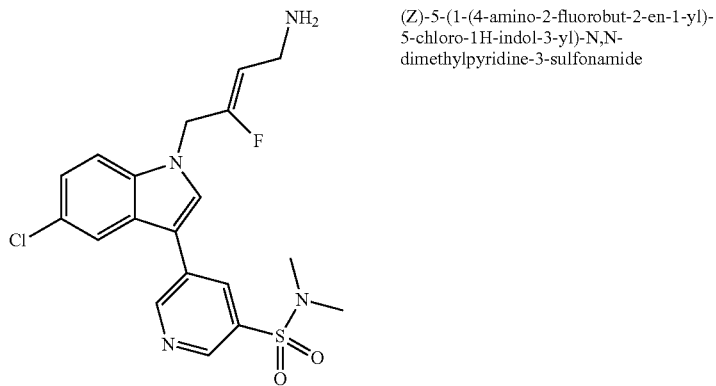 | (Z)-5-(1-(4-amino-2-fluorobut-2-en-1-yl)-5-chloro-1H-indol-3-yl)-N,N-dimethylpyridine-3-sulfonamide |
| 67 | 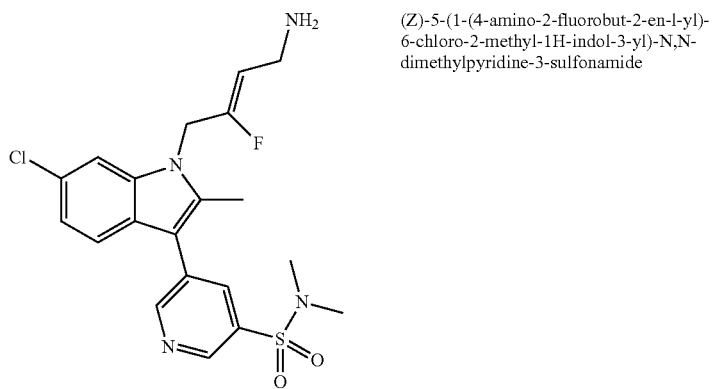 | (Z)-5-(1-(4-amino-2-fluorobut-2-en-1-yl)-6-chloro-2-methyl-1H-indol-3-yl)-N,N-dimethylpyridine-3-sulfonamide |
| 68 | 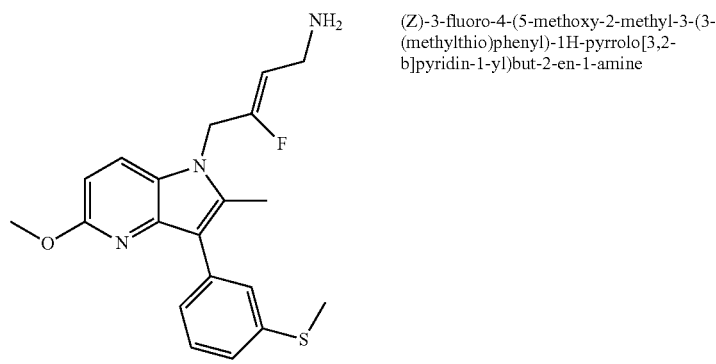 | (Z)-3-fluoro-4-(5-methoxy-2-methyl-3-(3-(methylthio)phenyl)-1H-pyrrolo[3,2-b]pyridin-1-yl)but-2-en-1-amine |
| 69 | 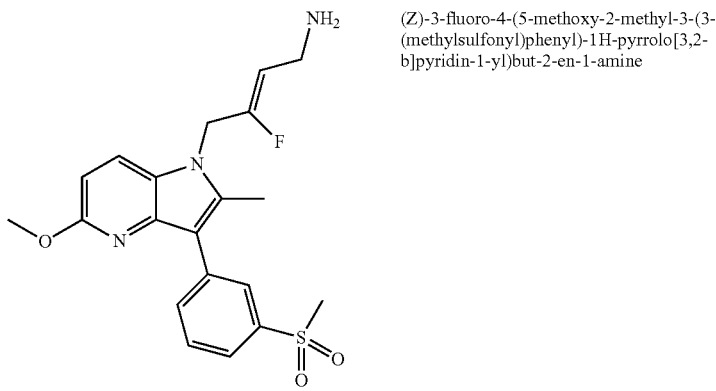 | (Z)-3-fluoro-4-(5-methoxy-2-methyl-3-(3-(methylsulfonyl)phenyl)-1H-pyrrolo[3,2-b]pyridin-1-yl)but-2-en-1-amine |

TABLE 1-continued

| | | |
|---|---|---|
| 70 | 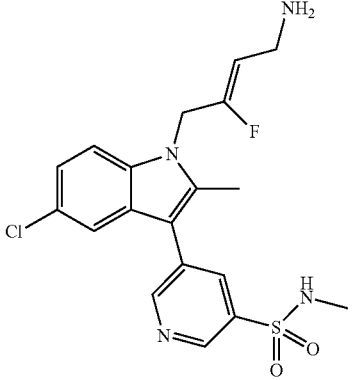 [SMILES: CNS(=O)(=O)c1cncc(-c2c(C)n(C/C(F)=C/CN)c3ccc(Cl)cc23)c1] | (Z)-5-(1-(4-amino-2-fluorobut-2-en-1-yl)-5-chloro-2-methyl-1H-indol-3-yl)-N-methylpyridine-3-sulfonamide |
| 71 | 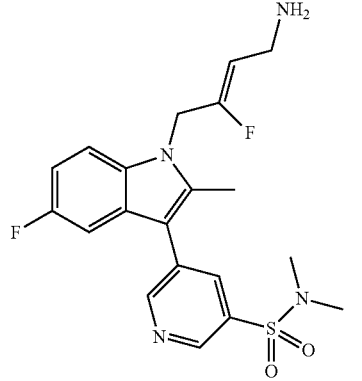 [SMILES: Cc1c(-c2cncc(S(=O)(=O)N(C)C)c2)c2cc(F)ccc2n1C/C(F)=C/CN] | (Z)-5-(1-(4-amino-2-fluorobut-2-en-1-yl)-5-fluoro-2-methyl-1H-indol-3-yl)-N,N-dimethylpyridine-3-sulfonamide |
| 72 | 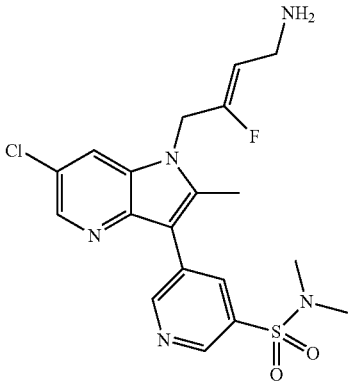 [SMILES: Cc1c(-c2cncc(S(=O)(=O)N(C)C)c2)c2ncc(Cl)cc2n1C/C(F)=C/CN] | (Z)-5-(1-(4-amino-2-fluorobut-2-en-1-yl)-6-chloro-2-methyl-1H-pyrrolo[3,2-b]pyridin-3-yl)-N,N-dimethylpyridine-3-sulfonamide |
| 73 | 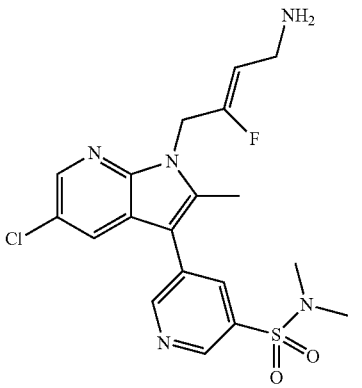 | (Z)-5-(1-(4-amino-2-fluorobut-2-en-1-yl)-5-chloro-2-methyl-1H-pyrrolo[2,3-b]pyridin-3-yl)-N,N-dimethylpyridine-3-sulfonamide |

TABLE 1-continued
| | | |
|---|---|---|
| 74 | 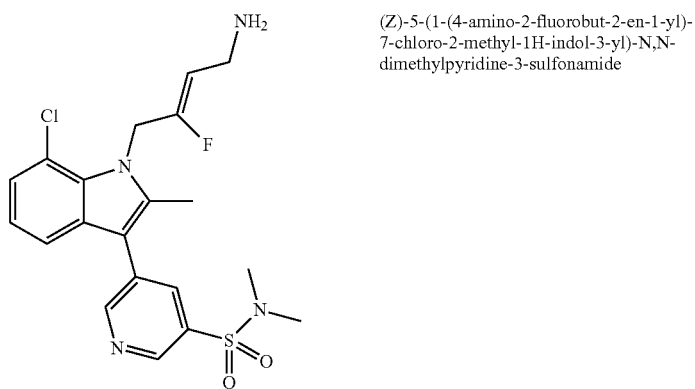 | (Z)-5-(1-(4-amino-2-fluorobut-2-en-1-yl)-7-chloro-2-methyl-1H-indol-3-yl)-N,N-dimethylpyridine-3-sulfonamide |
| 75 | 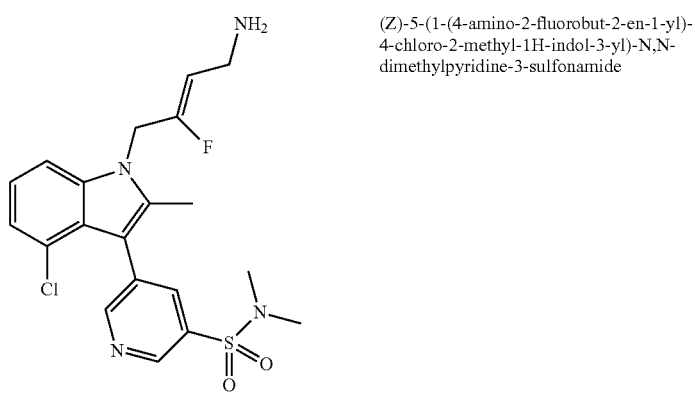 | (Z)-5-(1-(4-amino-2-fluorobut-2-en-1-yl)-4-chloro-2-methyl-1H-indol-3-yl)-N,N-dimethylpyridine-3-sulfonamide |
| 76 | 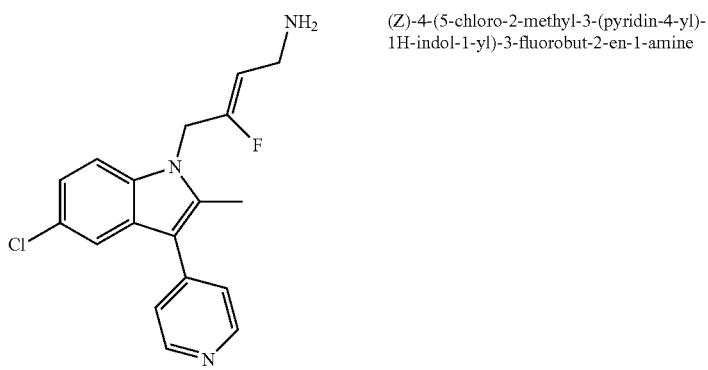 | (Z)-4-(5-chloro-2-methyl-3-(pyridin-4-yl)-1H-indol-1-yl)-3-fluorobut-2-en-1-amine |
| 77 | 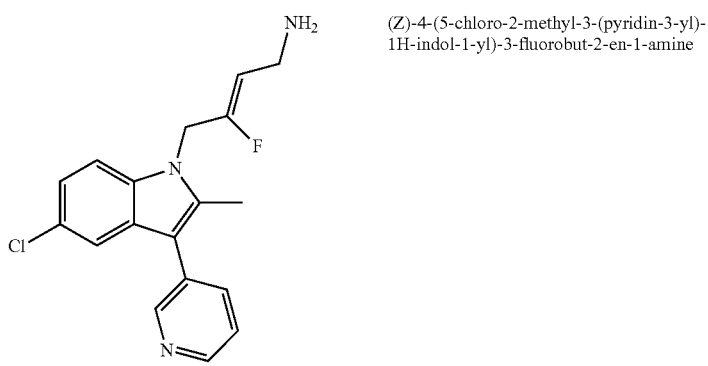 | (Z)-4-(5-chloro-2-methyl-3-(pyridin-3-yl)-1H-indol-1-yl)-3-fluorobut-2-en-1-amine |

TABLE 1-continued
| 78 | 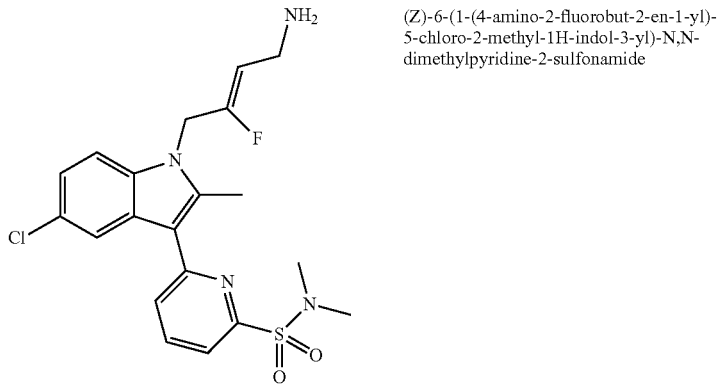 | (Z)-6-(1-(4-amino-2-fluorobut-2-en-1-yl)-5-chloro-2-methyl-1H-indol-3-yl)-N,N-dimethylpyridine-2-sulfonamide |
| --- | --- | --- |
| 79 | 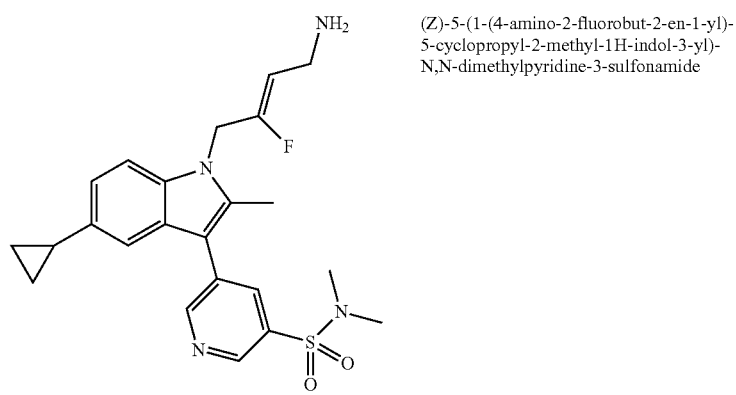 | (Z)-5-(1-(4-amino-2-fluorobut-2-en-1-yl)-5-cyclopropyl-2-methyl-1H-indol-3-yl)-N,N-dimethylpyridine-3-sulfonamide |
| 80 | 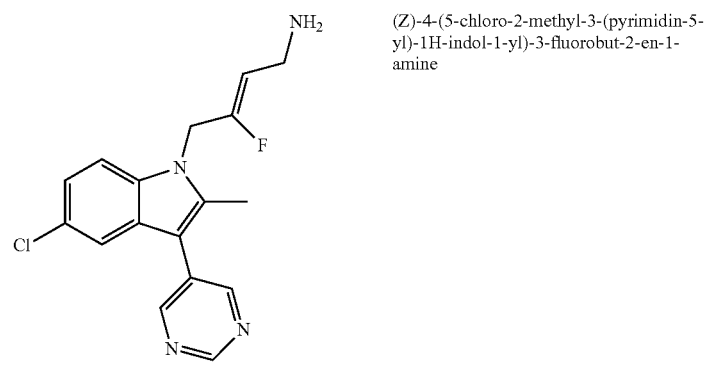 | (Z)-4-(5-chloro-2-methyl-3-(pyrimidin-5-yl)-1H-indol-1-yl)-3-fluorobut-2-en-1-amine |
| 81 | 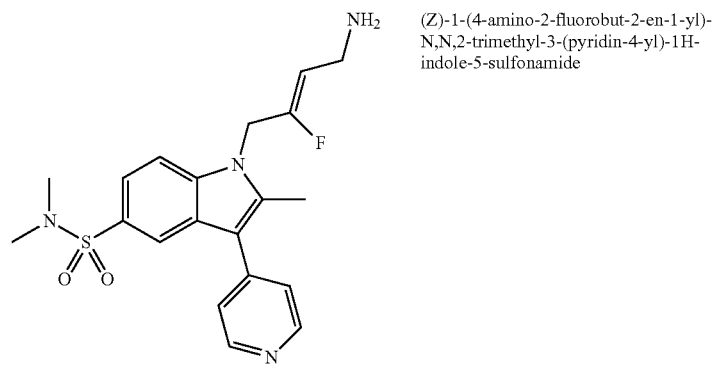 | (Z)-1-(4-amino-2-fluorobut-2-en-1-yl)-N,N,2-trimethyl-3-(pyridin-4-yl)-1H-indole-5-sulfonamide |

TABLE 1-continued

| | | |
|---|---|---|
| 82 | | (Z)-3-(1-(4-amino-2-fluorobut-2-en-1-yl)-5-chloro-7-fluoro-2-methyl-1H-indol-3-yl)-N,N,4-trimethylbenzenesulfonamide |
| 83 | | (Z)-5-(1-(4-amino-2-fluorobut-2-en-1-yl)-5-chloro-2-methyl-1H-indol-3-yl)pyridine-3-sulfonamide |
| 84 | | (Z)-1-(4-amino-2-fluorobut-2-en-1-yl)-2-methyl-3-(pyridin-4-yl)-1H-indole-5-sulfonamide |
| 85 | | (Z)-5-(1-(4-amino-2-fluorobut-2-en-1-yl)-2-methyl-5-(trifluoromethoxy)-1H-indol-3-yl)-N,N-dimethylpyridine-3-sulfonamide |

TABLE 1-continued
| | | |
|---|---|---|
| 86 | 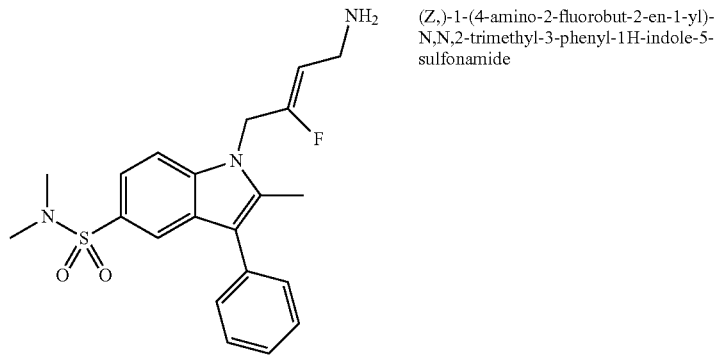 | (Z,)-1-(4-amino-2-fluorobut-2-en-1-yl)-N,N,2-trimethyl-3-phenyl-1H-indole-5-sulfonamide |
| 87 | 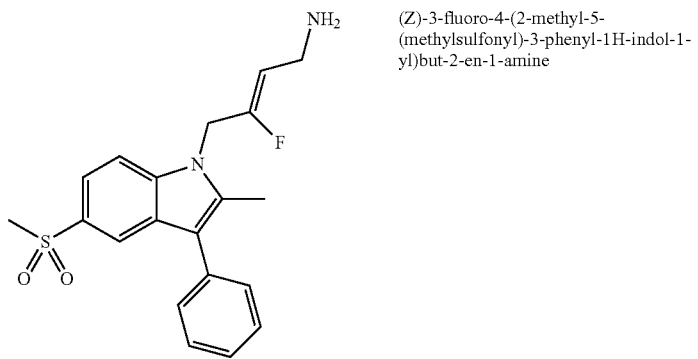 | (Z)-3-fluoro-4-(2-methyl-5-(methylsulfonyl)-3-phenyl-1H-indol-1-yl)but-2-en-1-amine |
| 88 | 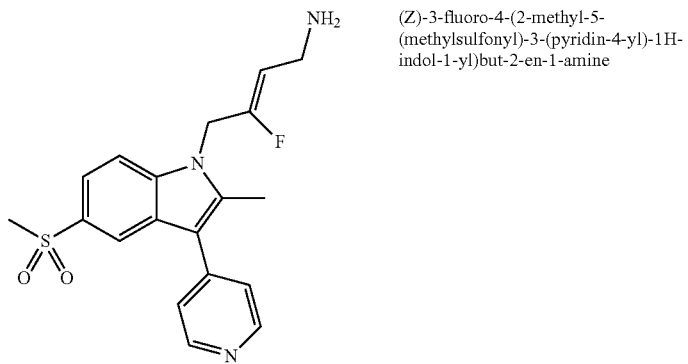 | (Z)-3-fluoro-4-(2-methyl-5-(methylsulfonyl)-3-(pyridin-4-yl)-1H-indol-1-yl)but-2-en-1-amine |
| 89 | 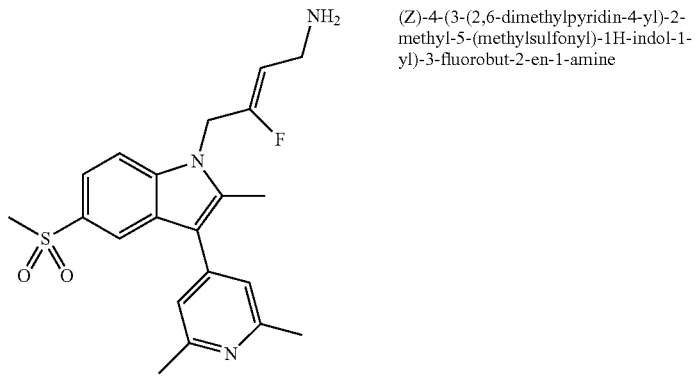 | (Z)-4-(3-(2,6-dimethylpyridin-4-yl)-2-methyl-5-(methylsulfonyl)-1H-indol-1-yl)-3-fluorobut-2-en-1-amine |

TABLE 1-continued
| 90 | 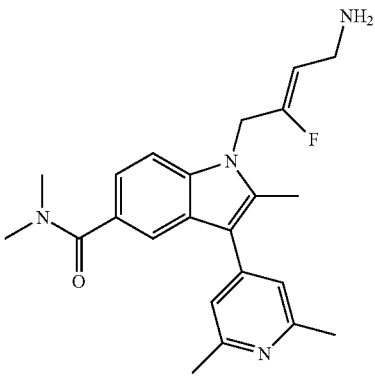 [SMILES: Cc1cc(-c2c(C)n(C/C(F)=C/CN)c3ccc(C(=O)N(C)C)cc23)cc(C)n1] | (Z)-1-(4-amino-2-fluorobut-2-en-1-yl)-3-(2,6-dimethylpyridin-4-yl)-N,N,2-trimethyl-1H-indole-5-carboxamide |
| 91 | 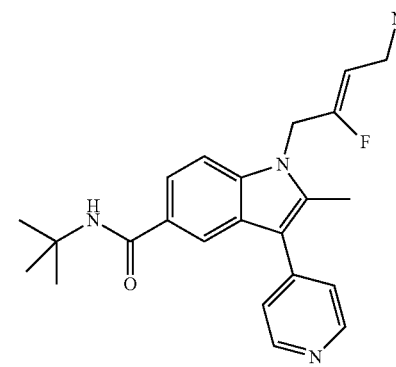 | (Z)-1-(4-amino-2-fluorobut-2-en-1-yl)-N-(tert-butyl)-2-methyl-3-(pyridin-4-yl)-1H-indole-5-carboxamide |
| 92 | 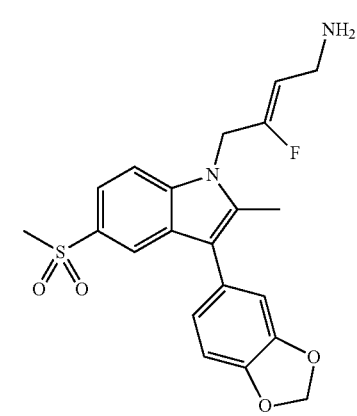 [SMILES: Cc1c(-c2ccc3c(c2)OCO3)c2cc(S(C)(=O)=O)ccc2n1C/C(F)=C/CN] | (Z)-4-(3-(benzo[d][1,3]dioxol-5-yl)-2-methyl-5-(methylsulfonyl)-1H-indol-1-yl)-3-fluorobut-2-en-1-amine |
| 93 | 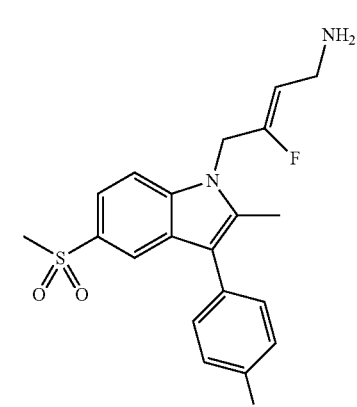 | (Z)-3-fluoro-4-(3-(4-fluorophenyl)-2-methyl-5-(methylsulfonyl)-1H-indol-1-yl)but-2-en-1-amine |

TABLE 1-continued
| | | |
|---|---|---|
| 94 | 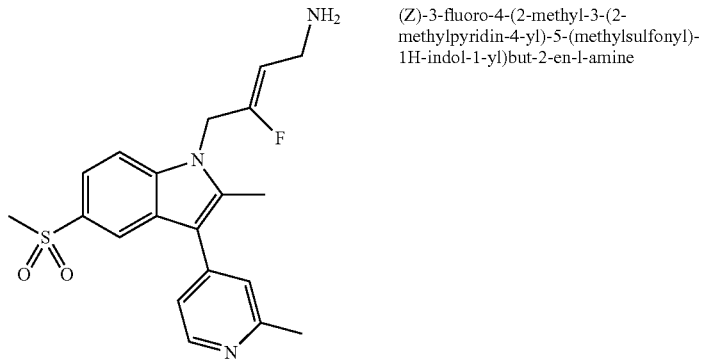 | (Z)-3-fluoro-4-(2-methyl-3-(2-methylpyridin-4-yl)-5-(methylsulfonyl)-1H-indol-1-yl)but-2-en-1-amine |
| 95 | 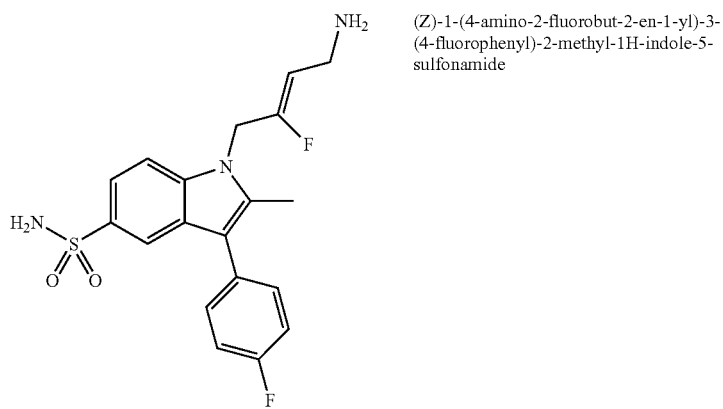 | (Z)-1-(4-amino-2-fluorobut-2-en-1-yl)-3-(4-fluorophenyl)-2-methyl-1H-indole-5-sulfonamide |
| 96 | 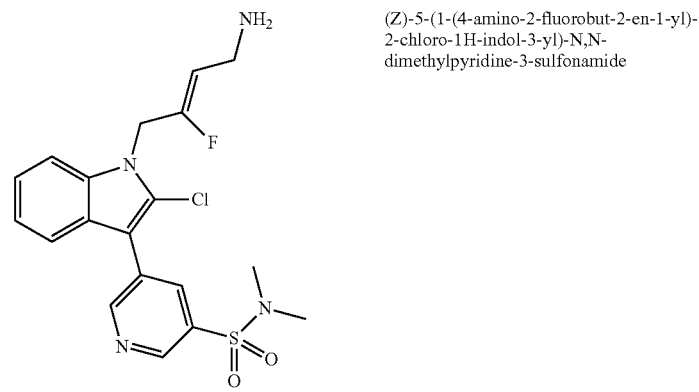 | (Z)-5-(1-(4-amino-2-fluorobut-2-en-1-yl)-2-chloro-1H-indol-3-yl)-N,N-dimethylpyridine-3-sulfonamide |
| 97 | 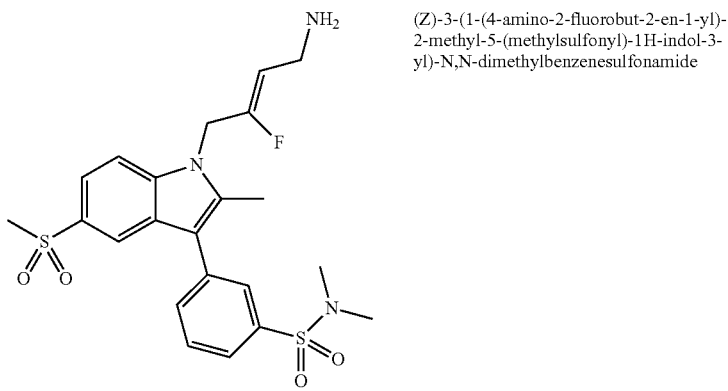 | (Z)-3-(1-(4-amino-2-fluorobut-2-en-1-yl)-2-methyl-5-(methylsulfonyl)-1H-indol-3-yl)-N,N-dimethylbenzenesulfonamide |

TABLE 1-continued
| | | |
|---|---|---|
| 98 | 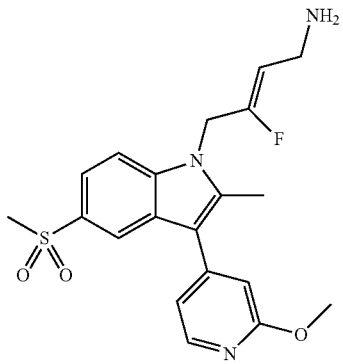 | (Z)-3-fluoro-4-(3-(2-methoxypyridin-4-yl)-2-methyl-5-(methylsulfonyl)-1H-indol-1-yl)but-2-en-1-amine |
| 99 | 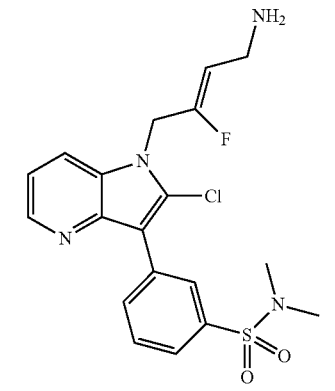 [SMILES: CN(C)S(=O)(=O)c1cccc(-c2c(Cl)n(C/C(F)=C/CN)c3cccnc23)c1] | (Z)-3-(1-(4-amino-2-fluorobut-2-en-1-yl)-2-chloro-1H-pyrrolo[3,2-b]pyridin-3-yl)-N,N-dimethylbenzenesulfonamide |
| 100 | 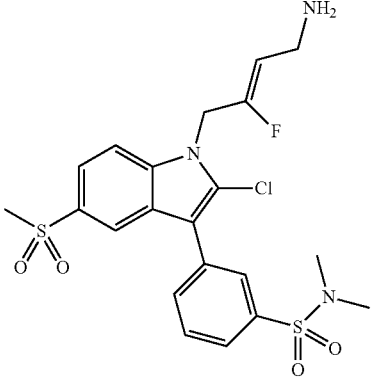 | (Z)-3-(1-(4-amino-2-fluorobut-2-en-1-yl)-2-chloro-5-(methylsulfonyl)-1H-indol-3-yl)-N,N-dimethylbenzenesulfonamide |
| 101 | 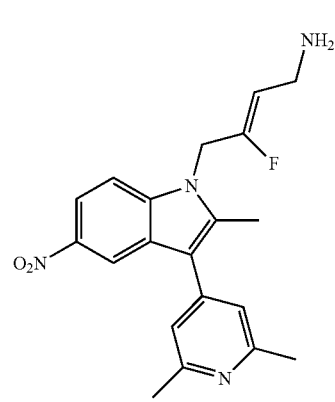 [SMILES: Cc1cc(-c2c(C)n(C/C(F)=C/CN)c3ccc([N+](=O)[O-])cc23)cc(C)n1] | (Z)-4-(3-(2,6-dimethylpyridin-4-yl)-2-methyl-5-nitro-1H-indol-1-yl)-3-fluorobut-2-en-1-amine |

TABLE 1-continued

| | | |
|---|---|---|
| 102 | 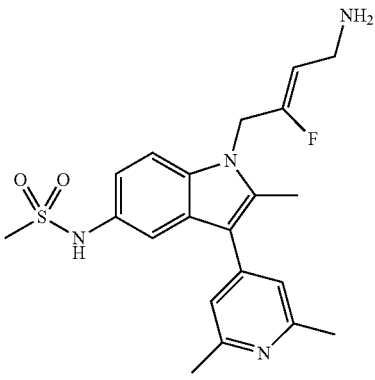 [SMILES: Cc1cc(-c2c(C)n(C/C(F)=C/CN)c3ccc(NS(C)(=O)=O)cc23)cc(C)n1] | (Z)-N-(1-(4-amino-2-fluorobut-2-en-1-yl)-3-(2,6-dimethylpyridin-4-yl)-2-methyl-1H-indol-5-yl)methanesulfonamide |
| 103 | 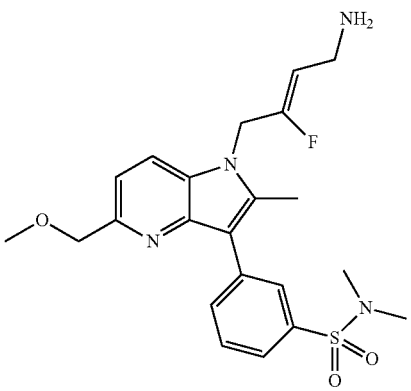 | (Z)-3-(1-(4-amino-2-fluorobut-2-en-1-yl)-5-(methoxymethyl)-2-methyl-1H-pyrrolo[3,2-b]pyridin-3-yl)-N,N-dimethylbenzenesulfonamide |
| 104 | 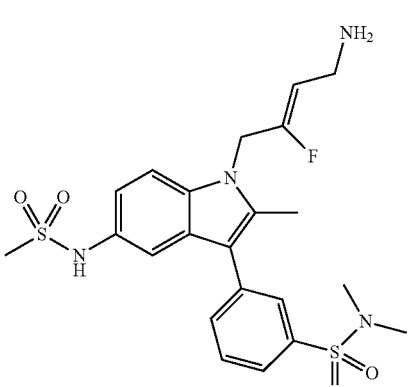 | (Z)-3-(1-(4-amino-2-fluorobut-2-en-1-yl)-2-methyl-5-(methylsulfonamido)-1H-indol-3-yl)-N,N-dimethylbenzenesulfonamide |
| 105 | 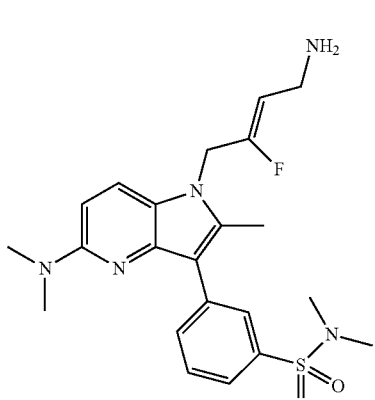 | (Z)-3-(1-(4-amino-2-fluorobut-2-en-1-yl)-5-(dimethylamino)-2-methyl-1H-pyrrolo[3,2-b]pyridin-3-yl)-N,N-dimethylbenzenesulfonamide |

TABLE 1-continued

| 106 | 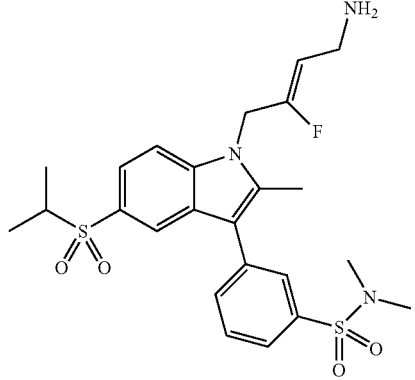 [SMILES: Cc1c(-c2cccc(S(=O)(=O)N(C)C)c2)c2cc(S(=O)(=O)C(C)C)ccc2n1C/C(F)=C/CN] | (Z)-3-(1-(4-amino-2-fluorobut-2-en-1-yl)-5-(isopropylsulfonyl)-2-methyl-1H-indol-3-yl)-N,N-dimethylbenzenesulfonamide |
| 107 | 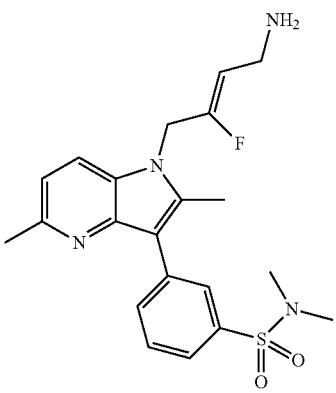 | (Z)-3-(1-(4-amino-2-fluorobut-2-en-1-yl)-2,5-dimethyl-1H-pyrrolo[3,2-b]pyridin-3-yl)-N,N-dimethylbenzenesulfonamide |
| 108 | 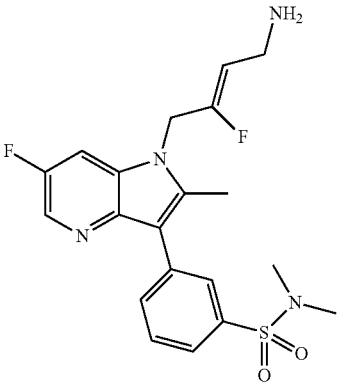 [SMILES: Cc1c(-c2cccc(S(=O)(=O)N(C)C)c2)c2ncc(F)cc2n1C/C(F)=C/CN] | (Z)-3-(1-(4-amino-2-fluorobut-2-en-1-yl)-6-fluoro-2-methyl-1H-pyrrolo[3,2-b]pyridin-3-yl)-N,N-dimethylbenzenesulfonamide |
| 109 | 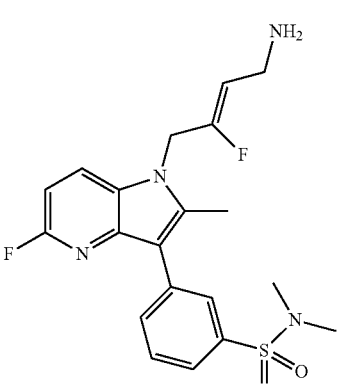 | (Z)-3-(1-(4-amino-2-fluorobut-2-en-1-yl)-5-fluoro-2-methyl-1H-pyrrolo[3,2-b]pyridin-3-yl)-N,N-dimethylbenzenesulfonamide |

TABLE 1-continued

| 110 | 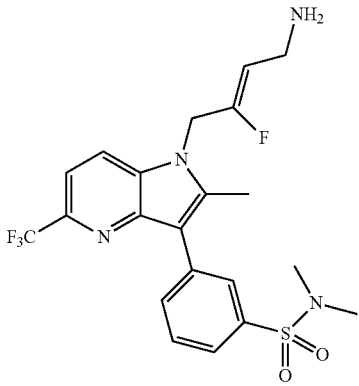 [SMILES: Cc1c(-c2cccc(S(=O)(=O)N(C)C)c2)c2nc(C(F)(F)F)ccc2n1C/C(F)=C/CN] | (Z)-3-(1-(4-amino-2-fluorobut-2-en-1-yl)-2-methyl-5-(trifluoromethyl)-1H-pyrrolo[3,2-b]pyridin-3-yl)-N,N-dimethylbenzenesulfonamide |
| 111 | 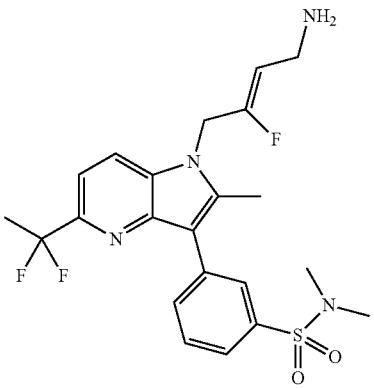 [SMILES: Cc1c(-c2cccc(S(=O)(=O)N(C)C)c2)c2nc(C(C)(F)F)ccc2n1C/C(F)=C/CN] | (Z)-3-(1-(4-amino-2-fluorobut-2-en-1-yl)-5-(1,1-difluoroethyl)-2-methyl-1H-pyrrolo[3,2-b]pyridin-3-yl)-N,N-dimethylbenzenesulfonamide |
| 112 | 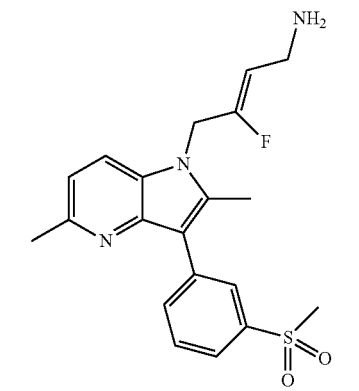 [SMILES: Cc1ccc2c(n1)c(-c1cccc(S(C)(=O)=O)c1)c(C)n2C/C(F)=C/CN] | (Z)-4-(2,5-dimethyl-3-(3-(methylsulfonyl)phenyl)-1H-pyrrolo[3,2-b]pyridin-1-yl)-3-fluorobut-2-en-1-amine |
| 113 | 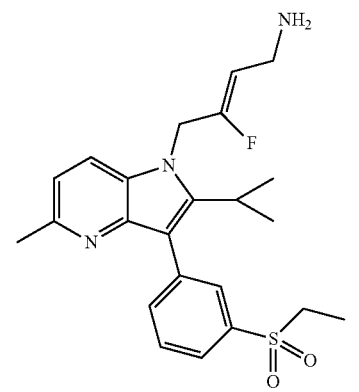 [SMILES: CCS(=O)(=O)c1cccc(-c2c(C(C)C)n(C/C(F)=C/CN)c3ccc(C)nc23)c1] | (Z)-4-(3-(3-(ethylsulfonyl)phenyl)-2-isopropyl-5-methyl-1H-pyrrolo[3,2-b]pyridin-1-yl)-3-fluorobut-2-en-1-amine |

TABLE 1-continued
| | | |
|---|---|---|
| 114 | 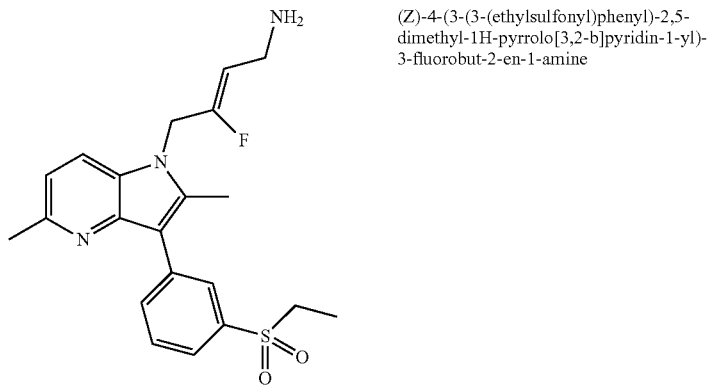 | (Z)-4-(3-(3-(ethylsulfonyl)phenyl)-2,5-dimethyl-1H-pyrrolo[3,2-b]pyridin-1-yl)-3-fluorobut-2-en-1-amine |
| 115 | 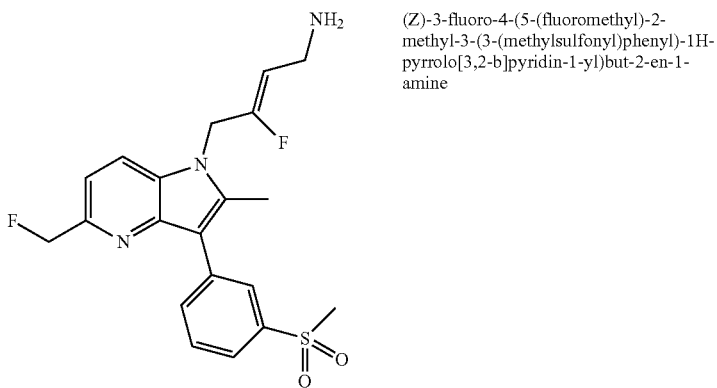 | (Z)-3-fluoro-4-(5-(fluoromethyl)-2-methyl-3-(3-(methylsulfonyl)phenyl)-1H-pyrrolo[3,2-b]pyridin-1-yl)but-2-en-1-amine |
| 116 | 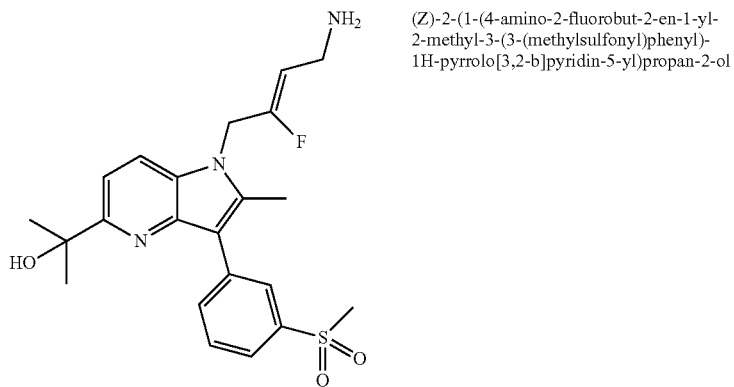 | (Z)-2-(1-(4-amino-2-fluorobut-2-en-1-yl-2-methyl-3-(3-(methylsulfonyl)phenyl)-1H-pyrrolo[3,2-b]pyridin-5-yl)propan-2-ol |
| 117 | 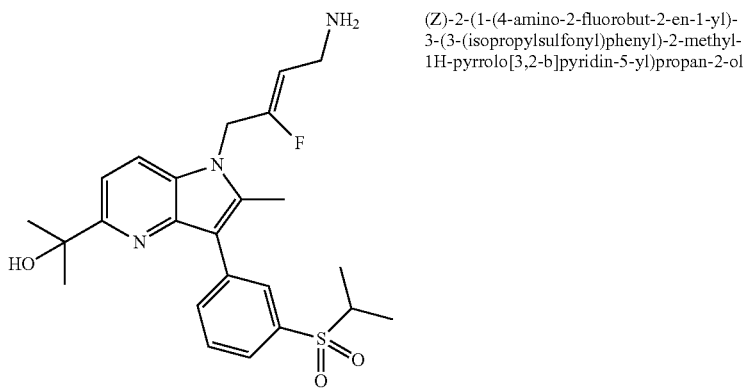 | (Z)-2-(1-(4-amino-2-fluorobut-2-en-1-yl)-3-(3-(isopropylsulfonyl)phenyl)-2-methyl-1H-pyrrolo[3,2-b]pyridin-5-yl)propan-2-ol |

Preparation of Compounds of Formula I

Compounds of Formula I can be readily prepared by those skilled in the art using methods and materials known in the art and with reference to standard textbooks, such as "Advanced Organic Chemistry" by Jerry March (third edition, 1985, John Wiley and Sons) or "Comprehensive Organic Transformations" by Richard C. Larock (1989, VCH Publishers).

Compounds of Formula I may be synthesised as described below. The following schemes provide an overview of representative non-limiting embodiments of the invention. Those skilled in the art will recognize that analogues of Formula I, including different isomeric forms, may also be prepared from the analogous starting materials.

Scheme 1:

The preparation of compounds described by Formula I is described in Scheme 1 below.

compound, as is described by Formula III. For example, a solution of compounds described by Formulae II and III in a solvent such as N,N-dimethylformamide (DMF) can be treated with a base, such as potassium carbonate, at ambient temperatures for up to 24 hours. The product described by Formula IV can be recovered by standard work-up procedures.

One convenient protocol for the conversion of compounds described by Formula IV to compounds described by Formula V is Method B which involves heating at 155° C. in DMSO/H$_2$O (10:1) for several hours. The product described by Formula V can be recovered by standard work-up procedures.

One convenient protocol for the conversion of compounds described by Formula V to compounds described by Formula VI is Method C which involves heating with palladium on carbon and ammonium formate at 70° C. in methanol for

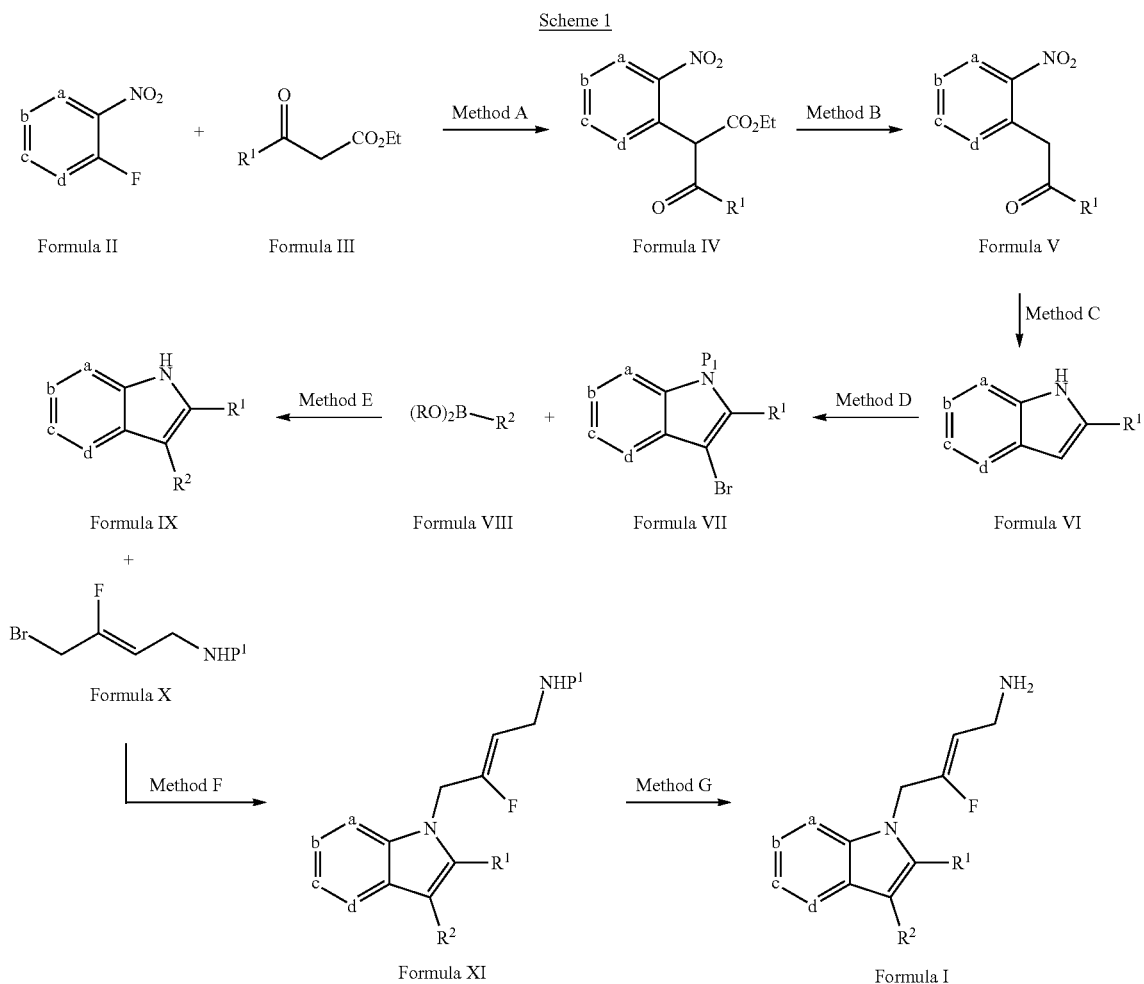

$P^1$ is a functional group used to protect a nitrogen functionality. Examples of $P^1$ are carbonates such as the tert-butyloxycarbonyl (BOC), the 9-fluorenylmethyloxycarbonyl (FMOC), and the benzyloxycarbonyl (CBZ) groups.

In general Scheme 1 the starting material described by Formula II can be obtained from commercial sources or can be prepared by many methods well known in the art. Method A involves reaction of this starting material with the anion derived from an appropriately substituted 1,3-dicarbonyl several hours. The product described by Formula VI can be recovered by standard work-up procedures.

One convenient protocol for the conversion of compounds described by Formula VI to compounds described by Formula VII is Method D which involves reaction with 1-bromopyrrolidine-2,5-dione in dichloromethane at ambient temperatures for 1 hour followed by the in situ incorporation of a suitable protecting group. For example if $P^1$ is a BOC protecting group, reaction with 4-(dimethylamino) pyridine and di-tert-butyl dicarbonate will afford the desired protected product. The protected product described by Formula VII can be recovered by standard work-up procedures.

In general Scheme 1 Method E involves the use of a Suzuki coupling reaction to combine compounds described by Formulae VII and VIII. There are numerous variants of the Suzuki reaction described in the literature. For example, a solution of the compounds described by Formulae VII and VIII, in the presence of $K_2CO_3$, can be dissolved in a solvent such as aqueous dioxane under an atmosphere of nitrogen, then treated with a catalytic amount of tetrakis(triphenylphosphine)palladium(0) and heated at reflux for several hours. Following standard extraction and purification methods, the protected coupled product can be obtained. Conversion of the protected compound to compounds described by Formula IX is readily achieved by the method best suited to removal of the particular protecting group.

Whilst there are many ways to achieve the reaction described by Method F, one convenient protocol involves reaction of compounds described by Formulae IX and X with a base such as cesium carbonate in a solvent such as N,N-dimethylfonnamide (DMF) at ambient temperature for approximately 16 hours. Following standard extraction and purification methods the product described by Formula XI can be obtained in good yield and purity.

There are many well established chemical procedures for the deprotection of the compounds described by Formula XI to the compounds described by Formula I (Method G). For example if $P^1$ is a BOC protecting group, compounds described by Formula XI can be treated with an acidic reagent such as dry hydrogen chloride in a solvent such as diethyl ether or dichloromethane to furnish the compounds described by Formula I as the hydrochloride salts. In general, the free amino compounds are converted to acid addition salts for ease of handling and for improved chemical stability. Examples of acid addition salts include but are not limited to hydrochloride, hydrobromide, 2,2,2-trifluoroacetate, methanesulfonate and toluenesulfonate salts.

Cis/trans (E/Z) isomers may be separated by conventional techniques well known to those skilled in the art, for example, chromatography and fractional crystallisation.

Therapeutic Uses and Formulations

Another aspect of the present invention relates to a pharmaceutical composition comprising a compound of Formula I, or a pharmaceutically acceptable salt or stereoisomer thereof, together with a pharmaceutically acceptable diluent, excipient or adjuvant.

The present invention also relates to use of the compounds of Formula I in therapy, in particular to inhibit members of the lysyl oxidase family members, LOX, LOXL1, LOXL2, LOXL3 and LOXL4. In one embodiment the invention provides for the selective inhibition of specific lysyl oxidase isoenzymes. In another embodiment the invention provides for the simultaneous inhibition of 2, 3 or 4 LOX isoenzymes. The relative inhibitory potencies of the compounds can be determined by the amount needed to inhibit the amine oxidase activity of LOX, LOXL1, LOXL2, LOXL3 and LOXL4 in a variety of ways, e.g., in an in vitro assay with recombinant or purified human protein or with recombinant or purified non-human enzyme, in cellular assays expressing normal rodent enzyme, in cellular assays which have been transfected with human protein, in in vivo tests in rodent and other mammalian species, and the like.

Accordingly, a further aspect of the invention is directed to a method of inhibiting the amine oxidase activity of LOX, LOXL1, LOXL2, LOXL3 and LOXL4 in a subject in need thereof, comprising administering to the subject an effective amount of a compound of Formula I, or a pharmaceutically acceptable salt or solvate thereof, or a pharmaceutical composition thereof.

In one embodiment the present invention is directed to a method of inhibiting the amine oxidase activity of LOXL2. In another embodiment the present invention is directed towards inhibiting the amine oxidase activity of LOX and LOXL2.

As discussed previously, LOX and LOXL1-4 enzymes are members of a large family of flavin-dependent and copper-dependent amine oxidases, which includes SSAO/VAP-1, monoamine oxidase-B (MAO-B) and diamine oxidase (DAO). In one embodiment compounds of the present invention selectively inhibit members of the lysyl oxidase isoenzyme family with respect to SSAO/VAP-1, MAO-B and other members of the amine oxidase family.

The present invention also discloses methods to use the compounds described by Formula I to inhibit one or more lysyl oxidase isoenzymes (LOX, LOXL1, LOXL2, LOXL3 and LOXL4) in patients suffering from a fibrotic disease, and methods to treat fibrotic diseases. Furthermore, the present invention discloses methods to use the compounds described by Formula I to inhibit one or more lysyl oxidase isoenzymes (LOX, LOXL1, LOXL2, LOXL3 and LOXL4) in patients suffering from cancer, including metastatic cancer, and methods to treat cancer and metastatic cancer.

In a further aspect of the invention there is provided a method of treating a condition associated with LOX, LOXL1, LOXL2, LOXL3 and LOXL4 protein, comprising administering to a subject in need thereof a therapeutically effective amount of compound of Formula I, or a pharmaceutically acceptable salt or solvate thereof, or a pharmaceutical composition thereof.

In another aspect there is a provided a method of treating a condition modulated by LOX, LOXL1, LOXL2, LOXL3 and LOXL4, comprising administering to a subject in need thereof a therapeutically effective amount of compound of Formula I, or a pharmaceutically acceptable salt or solvate thereof, or a pharmaceutical composition thereof.

In one embodiment of the methods of the present invention the condition is selected from the group consisting of fibrosis, cancer and angiogenesis.

In another aspect, the present invention provides a method for decreasing extracellular matrix formation by treating human subjects, pets and livestock with fluoroallylamine inhibitors of lysyl oxidase isoenzyme family of Formula I as described herein.

The above-described methods are applicable wherein the condition is a liver disorder. As described herein the term "liver disorder" includes any disorder affecting the liver, and in particular any acute or chronic liver disease that involves the pathological disruption, inflammation, degeneration, and/or proliferation of liver cells. In particular, the liver disorder is liver fibrosis, liver cirrhosis, or any other liver disease in which the level in the plasma of some markers of hepatocellular injury, alteration or necrosis, is elevated when compared to normal plasma levels. These biochemical markers associated to liver activity and status can be selected among those disclosed in the literature and in particular Alanine aminotransferase (ALAT), Aspartate aminotransfersase (ASAT), Alkaline Phosphatase (AP), Gamma Glutamyl transpeptidase (GGT), Cytokeratin-18 (CK-18) or Resistin. In a particular embodiment, the liver disorder is a fatty liver disease in which the elevation of one or more of these markers is associated to a more or less significant steatosis in the liver, as it can be confirmed by a liver biopsy. A non-exhaustive list of fatty liver diseases includes nonalcoholic fatty liver disease (NAFLD), nonalcoholic steatohepatitis (NASH), and fatty liver disease associated to disorders such as hepatitis or metabolic syndrome (obesity, insulin resistance, hypertriglyceridemia, and the like). In one embodiment the liver disorder is selected from the group consisting of biliary atresia, cholestatic liver disease, chronic liver disease, nonalcoholic steatohepatitis (NASH), nonalcoholic fatty liver disease (NAFLD), hepatitis C infection, alcoholic liver disease, primary biliary cirrhosis (PBC), primary schlerosing cholangitis (PSC), liver damage due to progressive fibrosis, liver fibrosis and liver cirrhosis.

The above-described methods are applicable wherein the condition is a kidney disorder. In one embodiment the kidney disorder is selected from the group consisting of kidney fibrosis, renal fibrosis, acute kidney injury, chronic kidney disease, diabetic nephropathy, glomerulosclerosis, vesicoureteral reflux, tubulointerstitial renal fibrosis and glomerulonephritis.

The above-described methods are applicable wherein the condition is a cardiovascular disease. In one embodiment the cardiovascular disease is selected from the group consisting of atherosclerosis, arteriosclerosis, hypercholesteremia, and hyperlipidemia.

The above-described methods are applicable wherein the condition is fibrosis. As employed here "fibrosis" includes such diseases as cystic fibrosis, idiopathic pulmonary fibrosis, liver fibrosis, kidney fibrosis, scleroderma, radiation-induced fibrosis, ocular fibrosis, Peyronie's disease, scarring and other diseases where excessive fibrosis contributes to disease pathology including Crohn's disease and inflammatory bowel disease.

In one embodiment the fibrosis is selected from the group consisting of liver fibrosis, lung fibrosis, kidney fibrosis, cardiac fibrosis, cystic fibrosis, idiopathic pulmonary fibrosis, radiation-induced fibrosis and scleroderma or is associated with respiratory disease, abnormal wound healing and repair, post-surgical operations, cardiac arrest and all conditions where excess or aberrant deposition of fibrous material is associated with disease. In another embodiment the fibrosis is selected from the group consisting of liver fibrosis, lung fibrosis, kidney fibrosis, cardiac fibrosis, and scleroderma.

In one embodiment, kidney fibrosis includes, but is not limited to, diabetic nephropathy, vesicoureteral reflux, tubulointerstitial renal fibrosis; glomerulonephritis or glomerular nephritis, including focal segmental glomerulosclerosis and membranous glomerulonephritis, and mesangiocapillary glomerular nephritis. In one embodiment, liver fibrosis results in cirrhosis, and includes associated conditions such as chronic viral hepatitis, non-alcoholic fatty liver disease (NAFLD), alcoholic steatohepantis (ASH), non-alcoholic steatohepatiris (NASH), primary biliary cirrhosis (PBC), biliary cirrhosis, and autoimmune hepatitis.

The above-described methods are also applicable wherein the condition is cancer. In one embodiment the cancer is selected from the group consisting of lung cancer; breast cancer; colorectal cancer; anal cancer; pancreatic cancer; prostate cancer; ovarian carcinoma; liver and bile duct carcinoma; esophageal carcinoma; non-Hodgkin's lymphoma; bladder carcinoma; carcinoma of the uterus; glioma, glioblastoma, medullablastoma, and other tumors of the brain; kidney cancer; myelofibrosis, cancer of the head and neck; cancer of the stomach; multiple myeloma; testicular cancer; germ cell tumor; neuroendocrine tumor; cervical cancer; oral cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma or a leiomysarcoma.

In one embodiment the cancer is selected from the group consisting of breast cancer, head and neck squamous cell carcinoma, brain cancer, prostate cancer, renal cell carcinoma, liver cancer, lung cancer, oral cancer, cervical cancer and tumour metastasis.

In one embodiment lung cancer includes lung adenocarcinoma, squamous cell carcinoma, large cell carcinoma, bronchoalveolar carcinoma, non-small-cell carcinoma, small cell carcinoma and mesothelioma. In one embodiment breast cancer includes ductal carcinoma, lobular carcinoma, inflammatory breast cancer, clear cell carcinoma, and mucinous carcinoma. In one embodiment colorectal cancer includes colon cancer and rectal cancer. In one embodiment pancreatic cancer includes pancreatic adenocarcinoma, islet cell carcinoma and neuroendocrine tumors.

In one embodiment ovarian carcinoma includes ovarian epithelial carcinoma or surface epithelial-stromal tumour including serous tumour, endometrioid tumor and mucinous cystadenocarcinoma, and sex-cord-stromal tumor. In one embodiment liver and bile duct carcinoma includes hepatocelluar carcinoma, cholangiocarcinoma and hemangioma. In one embodiment esophageal carcinoma includes esophageal adenocarcinoma and squamous cell carcinoma. In one embodiment carcinoma of the uterus includes endometrial adenocarcinoma, uterine papillary serous carcinoma, uterine clear-cell carcinoma, uterine sarcomas and leiomyosarcomas and mixed mullerian tumors. In one embodiment kidney cancer includes renal cell carcinoma, clear cell carcinoma and Wilm's tumor. In one embodiment cancer of the head and neck includes squamous cell carcinomas. In one embodiment cancer of the stomach includes stomach adenocarcinoma and gastrointestinal stromal tumor.

In one embodiment, the cancer is selected from the group consisting of colon cancer, ovarian cancer, lung cancer, esophageal carcinoma, breast cancer and prostate cancer.

The above-described methods are applicable wherein the condition is angiogenesis.

In one embodiment of the methods of the present invention the subject is selected from the group consisting of humans, pets and livestock. In another embodiment of the methods of the present invention the subject is a human.

A further aspect of the invention provides for use of a compound of Formula I, or a pharmaceutically acceptable salt or solvate thereof, for the manufacture of a medicament for treating a condition associated with LOX, LOXL1, LOXL2, LOXL3 and LOXL4 protein.

Another aspect of the invention provides for use of a compound of Formula I, or a pharmaceutically acceptable salt or solvate thereof, for the manufacture of a medicament for treating a condition modulated by LOX, LOXL1, LOXL2, LOXL3 and LOXL4.

Pharmaceutical and/or Therapeutic Formulations

In another embodiment of the present invention, there are provided compositions comprising a compound having Formula I and at least one pharmaceutically acceptable excipient, carrier or diluent thereof. The compound(s) of Formula I may also be present as suitable salts, including pharmaceutically acceptable salts.

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed. Pharmaceutically acceptable salts include amine salts of mineral acids (e.g., hydrochlorides, hydrobromides, sulfates, and the like); and amine salts of organic acids (e.g., formates, acetates, lactates, malates, tartrates, citrates, ascorbates, succinates, maleates, butyrates, valerates, fumarates, and the like).

For compounds of formula (I) having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention.

S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Pharmaceutically acceptable salts of compounds of formula I may be prepared by methods known to those skilled in the art, including for example:
(i) by reacting the compound of formula I with the desired acid or base;
(ii) by removing an acid- or base-labile protecting group from a suitable precursor of the compound of formula I or by ring-opening a suitable cyclic precursor, for example, a lactone or lactam, using the desired acid or base; or
(iii) by converting one salt of the compound of formula I to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

Thus, for instance, suitable pharmaceutically acceptable salts of compounds according to the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

In one embodiment the compounds of Formula I may be administered in the form of a "prodrug". The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, amides, esters, enol ethers, enol esters, acetates, formates, benzoate derivatives, and the like of alcohol and amine functional groups in the compounds of the present invention. The prodrug form can be selected from such functional groups as —C(O)alkyl, —C(O)cycloalkyl, —C(O)aryl, —C(O)-arylalkyl, C(O)heteroaryl, —C(O)-heteroarylalkyl, or the like. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach, Oxford University Press*, New York, pages 388-392).

Compositions herein comprise one or more compounds provided herein. The compounds are, in one embodiment, formulated into suitable pharmaceutical preparations such as solutions, suspensions, tablets, creams, gels, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated from there for dosages for humans.

The concentration of active compound in the pharmaceutical composition will depend on absorption, distribution, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of active ingredient of from about 0.1 ng/mL to about 50-100 µg/mL. The pharmaceutical compositions, in another embodiment, should provide a dosage of from about 0.001 mg to about 2000 mg of compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. Suitably, the dosage is in the range of 1 µg to 500 mg per kg of body weight per dosage, such as 1 µg to 200 mg per kg of body weight per dosage, or 1 µg to 100 mg per kg of body weight per dosage. Other suitable dosages may be in the range of 1 mg to 250 mg per kg of body weight, including 1 mg to 10, 20, 50 or 100 mg per kg of body weight per dosage or 10 µg to 100 mg per kg of body weight per dosage.

Suitable dosage amounts and dosing regimens can be determined by the attending physician and may depend on the particular condition being treated, the severity of the condition, as well as the general health, age and weight of the subject.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, dissolution in aqueous sodium bicarbonate, formulating the compounds of interest as nanoparticles, and the like. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. The active ingredient may be administered at once, or may be divided into a number of smaller doses to be administered at intervals of time. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoles and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001%-100% (wt %) active ingredient, in one embodiment 0.1-95% (wt %), in another embodiment 75-85% (wt %).

Modes of Administration

Convenient modes of administration include injection (subcutaneous, intravenous, etc.), oral administration, inhalation, transdermal application, topical creams or gels or powders, vaginal or rectal administration. Depending on the route of administration, the formulation and/or compound may be coated with a material to protect the compound from the action of enzymes, acids and other natural conditions which may inactivate the therapeutic activity of the compound. The compound may also be administered parenterally or intraperitoneally.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and ethanol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, olive oil, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% (vol %) isotonic solutions, pH about 5-7, with appropriate salts.

Compositions for Other Routes of Administration

Other routes of administration, such as transdermal patches, including iontophoretic and electrophoretic devices, vaginal and rectal administration, are also contemplated herein.

Transdermal patches, including iontophoretic and electrophoretic devices, are well known to those of skill in the art. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Co-Administration with Other Drugs

In accordance with another aspect of the present invention, it is contemplated that compounds of Formula I as described herein may be administered to a subject in need thereof in combination with medication considered by those of skill in the art to be current standard of care for the condition of interest. Such combinations provide one or more advantages to the subject, e.g., requiring reduced dosages to achieve similar benefit, obtaining the desired palliative effect in less time, and the like.

Compounds in accordance with the present invention may be administered as part of a therapeutic regimen with other drugs. It may desirable to administer a combination of active compounds, for example, for the purpose of treating a particular disease or condition. Accordingly, it is within the scope of the present invention that two or more pharmaceutical compositions, at least one of which contains a compound of Formula (I) according to the present invention, may be combined in the form of a kit suitable for co-administration of the compositions.

In one embodiment of the methods of the present inventions a compound of Formula I may be administered with a second therapeutic agent. In one embodiment the second therapeutic agent is selected from the group consisting of an anti-cancer agent, an anti-inflammatory agent, an anti-hypertensive agent, an anti-fibrotic agent, an anti-angiogenic agent and an immunosuppressive agent.

When two or more active ingredients are co-administered, the active ingredients may be administered simultaneously, sequentially or separately. In one embodiment the compound of Formula I is co-administered simultaneously with a second therapeutic agent. In another embodiment the compound of Formula I and the second therapeutic agent are administered sequentially. In a further embodiment the compound of Formula I and the second therapeutic agent are administered separately.

The invention will now be described in greater detail, by way of illustration only, with reference to the following non-limiting examples. The examples are intended to serve to illustrate the invention and should not be construed as limiting the generality of the disclosure of the description throughout this specification.

Example 1

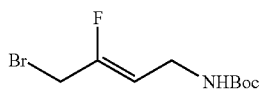

Preparation of (Z)-tert-butyl (4-bromo-3-fluorobut-2-en-1-yl)carbamate

Procedure A: Preparation of tert-butyl 2-oxoethylcarbamate

To a stirring solution of 3-amino-1,2-propanediol (20.0 g, 0.22 mol) in water (200 mL) at 0-5° C. was added di-tert-butyl dicarbonate (55.5 mL, 0.24 mol). After adjusting the alkalinity of the solution to pH~9 by addition of aq. NaOH (6 N), the mixture was left to stir at rt for 18 h. The reaction mixture was cooled to 0-5° C. and then acidified to pH~6 before the addition of sodium metaperiodate (56.3 g, 0.26 mol). The resulting suspension was stirred at rt for 2 h. The mixture was filtered to remove all solids and the filtrate was transferred to a separatory funnel and extracted with ethyl acetate (200 mL). Sodium chloride was added to the aqueous layer until a saturated solution was obtained. The aqueous layer was then extracted further with ethyl acetate (100 mL). The combined organics were dried over $Na_2SO_4$ and then concentrated in vacuo to give crude tert-butyl 2-oxoethylcarbamate (45.7 g) as a yellow gum. The crude material was used in the subsequent step without purification.

Procedure B: Preparation of (E)-ethyl 4-(tert-butoxycarbonylamino)-2-fluorobut-2-enoate and (Z)-ethyl 4-(tert-butoxycarbonylamino)-2-fluorobut-2-enoate

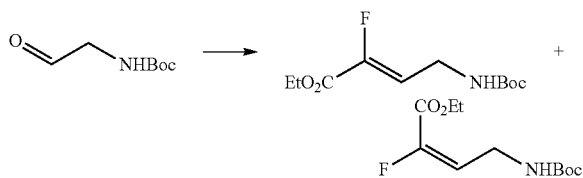

To a stirring suspension of crude tert-butyl 2-oxoethyl-carbamate (43.7 g, 0.22 mol) and magnesium sulfate (32.0 g) in acetonitrile (200 mL) at 0° C. under $N_2$ was added sequentially ethyl 2-fluorophosphonoacetate (55.7 mL, 0.27 mol) and 1,8-diazabicyclo[5.4.0]undec-7-ene (32.8 mL, 0.22 mol). The reaction mixture was allowed to warm to rt and stirring was continued for 3 h. After removing the solvent under reduced pressure the residue was taken up in ethyl acetate (200 mL) and then transferred to a separatory funnel. The organics were washed successively with aq. HCl (2 M; 100 mL×2), aq. NaOH (2 M; 100 mL×2) and brine (100 mL). After drying over $MgSO_4$, the organics were concentrated in vacuo to give the crude, desired product as a mixture of E/Z isomers (2:3; 57.0 g). This crude material was progressed to the next step without purification.

Procedure C: Preparation of (E)-tert-butyl 3-fluoro-4-hydroxybut-2-enylcarbamate and (Z)-tert-butyl 3-fluoro-4-hydroxybut-2-enylcarbamate

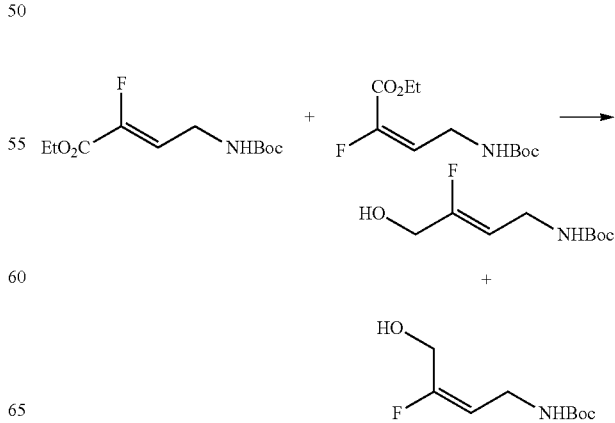

To a stirring solution of crude E/Z-ethyl 4-(tert-butoxy-carbonylamino)-2-fluorobut-2-enoate (18.0 g, 72.8 mmol) in THF (150 mL) at 0° C. under $N_2$ was added diisobutylaluminum hydride (1 M in toluene, 182 mL, 182 mmol) dropwise over 45 min. After complete addition, the mixture was left to stir at 0° C. for 3 h. The reaction mixture was transferred to a separatory funnel and added dropwise to a stirring mixture of ice (100 g) and aq. NaOH (2 M; 200 mL). Following addition the mixture was stirred for 2 h. The quenched reaction mixture was extracted with diethyl ether (100 mL×2) and the combined organics were washed with brine (100 mL). After drying over $MgSO_4$ the organics were concentrated in vacuo to give the crude alcohol as a mixture of E/Z isomers. This mixture was purified over silica gel (135 g), eluting with 25% ethyl acetate in n-hexane to give (Z)-tert-butyl 3-fluoro-4-hydroxybut-2-enylcarbamate (6.20 g, 30% over three steps) and (E)-tert-butyl 3-fluoro-4-hydroxybut-2-enylcarbamate (1.85 g, 8.9% over three steps). (E)-tert-butyl 3-fluoro-4-hydroxybut-2-enylcarbamate: $^1$H-NMR (200 MHz; $CDCl_3$) δ ppm: 1.43 (9H, s), 3.72 (2H, dd, J 7.5, 5.4 Hz), 4.25 (2H, d, J 21.5 Hz), 4.85 (1H, br. s), 5.18 (1H, dt, J 19.2, 8.5 Hz). (Z)-tert-butyl 3-fluoro-4-hydroxybut-2-enylcarbamate: $^1$H-NMR (300 MHz; $CDCl_3$) δ ppm: 1.46 (9H, s), 3.84 (2H, dd, J 6.2, 6.2 Hz), 4.13 (2H, d, J 13.9 Hz), 4.68 (1H, br. s), 5.03 (1H, dt, J 36.0, 7.1 Hz).

Procedure D: Preparation of (Z)-tert-butyl 4-bromo-3-fluorobut-2-enylcarbamate

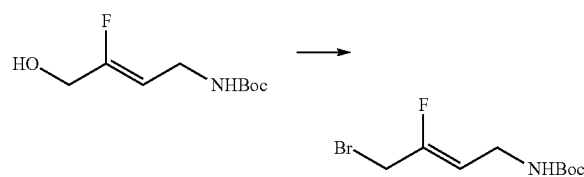

To a stirring solution of (Z)-tert-butyl 3-fluoro-4-hydroxybut-2-enylcarbamate (6.20 g, 30.2 mmol) and triethylamine (6.32 mL, 45.3 mmol) in acetone (100 mL) at 0° C. was added methanesulfonyl chloride (2.81 mL, 36.3 mmol) dropwise. After complete addition the mixture was left to stir at 0° C. for 30 min. After this time, lithium bromide (13.1 g, 0.15 mol) was added portionwise and the resulting suspension was stirred for a further 2 h. The reaction mixture was filtered to remove all solids and the filtrate was concentrated under reduced pressure. The residue was partitioned between water (50 mL) and $CH_2Cl_2$ (50 mL) and the aqueous layer was extracted with further $CH_2Cl_2$ (50 mL×2). The combined organics were dried over $Na_2SO_4$ and concentrated in vacuo. The crude residue was purified over silica gel (100 g) eluting with n-hexane followed by 25% ethyl acetate in n-hexane to afford (Z)-tert-butyl 4-bromo-3-fluorobut-2-enylcarbamate (7.00 g, 86%) as a colourless solid. $^1$H-NMR (300 MHz; $CDCl_3$) δ ppm: 1.46 (9H, s), 3.85 (2H, dd, J 6.2, 6.2 Hz), 3.93 (2H, d, J 19.5 Hz), 4.66 (1H, br. s), 5.16 (1H, dt, J 34.0, 6.5 Hz).

Example 2

Preparation of (Z)-1-(4-amino-2-fluorobut-2-en-1-yl)-3-(3-(N,N-dimethylsulfamoyl)phenyl)-N,N,2-trimethyl-1H-indole-5-carboxamide Hydrochloride (Compound 6)

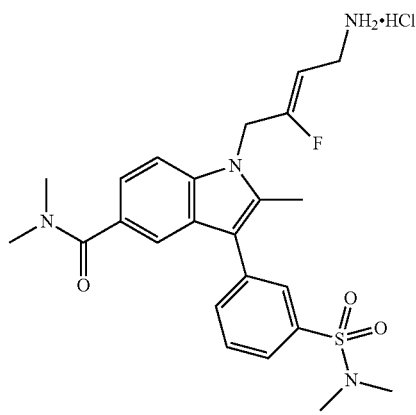

Procedure E: Preparation of 3-bromo-N,N,-dimethylbenzenesulfonamide

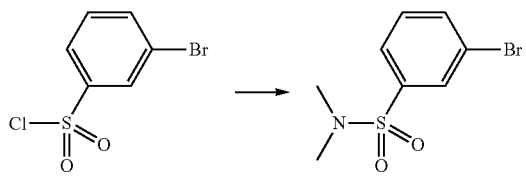

To a stirring solution of dimethylamine (6.00 mL, 40% w/w aqueous solution) in THF (20 mL) at 5° C. was added a solution of 3-bromobenzenesulfonyl chloride (5.11 g, 20 mmol) in THF (10 mL) over 5 min. Following addition, the mixture was left to stir at rt for 10 min. The reaction mixture was then concentrated in vacuo and the resultant residue partitioned between water (25 mL) and $CH_2Cl_2$ (20 mL) and the aqueous layer extracted with further $CH_2Cl_2$ (20 mL×2). The combined organics were dried over $Na_2SO_4$ and concentrated in vacuo to afford 3-bromo-N,N,-dimethylbenzenesulfonamide (5.30 g, Quant.) as white crystals. $^1$H-NMR (300 MHz; $CDCl_3$) δ ppm: 2.76 (6H, s), 7.44 (1H, dt, J 7.8, 0.3 Hz), 7.71-7.77 (2H, m), 7.94 (1H, dt, J 1.8, 0.3 Hz).

Procedure F: Preparation of N,N-dimethyl-3-(4,4,5,5-tetramethyl-1,3,2-dioxaborolan-2-yl)benzene Sulfonamide

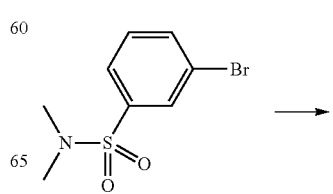

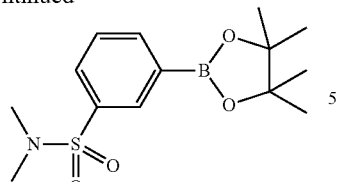

A stirring solution of 3-bromo-N,N-dimethyl-benzenesulfonamide (2.0 g, 7.57 mmol) 4,4,5,5-tetramethyl-2-(4,4,5,5-tetramethyl-1,3,2-dioxaborolan-2-yl)-1,3,2-dioxaborolane (2.31 g, 9.09 mmol) and potassium acetate (2.23 g, 22.7 mmol) in 1,4-dioxane (40 mL) was flushed with nitrogen for 15 min before the addition of 1,1'-bis(diphenylphosphino) ferrocene-palladium(II)dichloride dichloromethane complex (309 mg, 0.38 mmol). The resultant solution was heated at 80° C. under nitrogen for 16 h. The mixture was cooled to rt, filtered through Celite™, and then partitioned between ethyl acetate (20 mL) and water. The organic layer was separated and the aqueous layer was extracted with further ethyl acetate (20 mL×2). The combined organics were then washed with brine, dried over $Na_2SO_4$ and concentrated in vacuo. The crude residue thus obtained was purified over silica gel (40 g), eluting with 20% ethyl acetate in n-hexane, to afford N,N-dimethyl-3-(4,4,5,5-tetramethyl-1,3,2-dioxaborolan-2-yl)benzenesulfonamide (1.60 g, 68%) as a white solid. $^1$H-NMR (300 MHz; $CDCl_3$) δ ppm: 1.37 (12H, s), 2.74 (6H, s), 7.56 (1H, dd, J 7.4, 7.4 Hz), 7.88 (1H, ddd, J 7.9, 1.9, 1.3 Hz), 8.03 (1H, dd, J 7.4, 1.1 Hz), 8.22 (1H, br. s).

Procedure G: Preparation of Ethyl 3-(1-ethoxycarbonyl-2-oxo-propyl)-4-nitro-benzoate

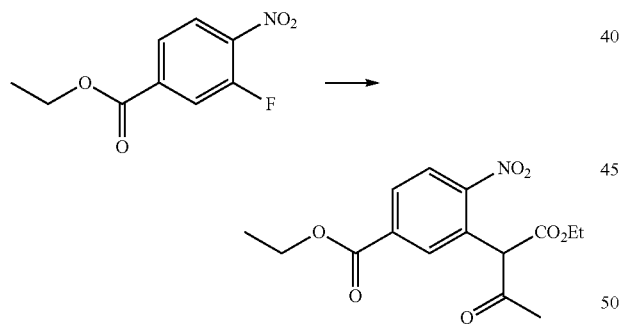

To a stirring mixture of ethyl 3-fluoro-4-nitro-benzoate (5.30 g, 24.9 mmol) and ethyl acetoacetate (3.80 mL, 29.9 mmol) in DMF (25 mL) at rt was added potassium carbonate (6.87 g, 49.8 mmol). The reaction mixture was stirred at rt overnight and then poured onto aq. HCl (1 M, 40 mL). The mixture was further diluted with water (200 mL) and extracted with EtOAc (100 mL×3). The combined organic layers were washed with saturated $NH_4Cl$ solution (50 mL) and brine (50 mL), dried over $Na_2SO_4$ and concentrated in vacuo to afford ethyl 3-(1-ethoxycarbonyl-2-oxo-propyl)-4-nitro-benzoate (8.70 g, 97%) as a yellow oil. $^1$H-NMR (300 MHz; $CDCl_3$) δ ppm: 1.13 (3H, t, J 6.9 Hz), 1.44 (3H, t, J 7.2 Hz), 1.90 (3H, s), 2.29 (1H, s), 4.17-4.31 (2H, m), 4.44 (2H, q, J 6.9 Hz), 7.99 (1H, d, J 1.8 Hz), 8.02 (1H, d, J 8.5 Hz), 8.12 (1H, d, J 8.5 Hz), 13.07 (1H, s).

Procedure H: Preparation of Ethyl 3-acetonyl-4-nitro-benzoate

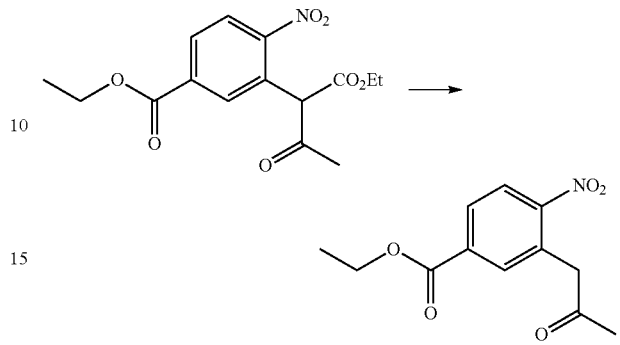

A stirring mixture of ethyl 3-(1-ethoxycarbonyl-2-oxo-propyl)-4-nitro-benzoate (8.70 g, 24.2 mmol) and water (7 mL) in DMSO (70 mL) was heated at 155° C. for 2 h. The mixture was then cooled to rt, diluted with water (250 mL) and extracted with EtOAc (200 mL×3). The combined organic layers were washed with brine (50 mL), dried over $Na_2SO_4$ and concentrated in vacuo. The crude residue thus obtained was purified over silica gel (100 g), eluting with 25%, then 40% ethyl acetate in n-hexane, to afford ethyl 3-acetonyl-4-nitro-benzoate (5.03 g, 83%) as a light yellow solid. $^1$H-NMR (300 MHz; $CDCl_3$) δ ppm: 1.43 (3H, t, J 7.2 Hz), 2.35 (3H, s), 4.22 (2H, s), 4.45 (2H, q, J 7.2 Hz), 7.96 (1H, d, J 1.2 Hz), 8.10-8.18 (2H, in).

Procedure I: Preparation of Ethyl 2-methyl-1H-indole-5-carboxylate

To a stirring solution of methyl 3-acetonyl-4-nitro-benzoate (600 mg, 2.53 mmol) and ammonium formate (7.92 g, 125 mmol) in methanol (120 mL) was added palladium on carbon (10% w/w; 3.20 g), suspended in water (4.5 mL), under a nitrogen blanket. The mixture was then immersed in a preheated oil bath and heated at reflux for 1 h. The reaction was allowed to cool to rt and filtered through Celite™, washing with methanol (10 mL×2). The filtrate was concentrated and then taken up in $CH_2Cl_2$ (200 mL), washed with water (50 mL×2), dried over $Na_2SO_4$ and concentrated in vacuo to afford ethyl 2-methyl-1H-indole-5-carboxylate (3.70 g, 91%) as an off-white solid. $^1$H-NMR (300 MHz; $CDCl_3$) δ ppm: 1.43 (3H, t, J 7.2 Hz), 2.47 (3H, s), 4.40 (2H, q, J 7.2 Hz), 6.33 (1H, s), 7.29 (1H, d, J 9.0 Hz), 7.86 (1H, dd, J 9.0, 1.8 Hz), 8.16 (1H, br.s), 8.30 (1H, d, J 1.8 Hz).

109

Procedure J: Preparation of 1-(tert-butyl) 5-ethyl 3-bromo-2-methyl-1H-indole-1,5-dicarboxylate

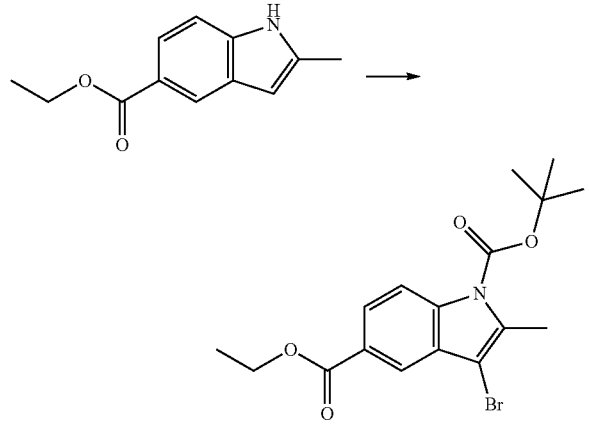

To a stirring solution of ethyl 2-methyl-1H-indole-5-carboxylate (500 mg, 2.46 mmol) in CH$_2$Cl$_2$ (15 mL) at rt under nitrogen was added 1-bromopyrrolidine-2,5-dione (460 mg, 2.58 mmol) in one lot. The resulting mixture was stirred at rt for 1 h then cooled to 0° C. before addition of 4-(dimethylamino) pyridine (300 mg, 2.46 mmol) followed by a solution of di-tert-butyl dicarbonate (1.07 g, 4.9 mmol) in of CH$_2$Cl$_2$ (5 mL). The mixture was allowed to slowly warm to rt over 1 h, concentrated in vacuo and purified over silica gel (40 g), eluting with 10% ethyl acetate in n-hexane, to afford 1-(tert-butyl) 5-ethyl 3-bromo-2-methyl-1H-indole-1,5-dicarboxylate (760 mg, 81%) as a white solid. $^1$H-NMR (300 MHz; CDCl$_3$) δ ppm: 1.45 (3H, t, J 7.2 Hz), 1.71 (9H, s), 2.68 (3H, s), 4.44 (2H, q, J 7.2 Hz), 8.02 (1H, dd, J 9.0, 1.8 Hz), 8.16 (1H, dd, J 9.0 Hz), 8.19 (1H, d, J 1.8 Hz).

Procedure K: Preparation of Ethyl 3-(3-(N,N-dimethylsulfamoyl)phenyl)-2-methyl-1H-indole-5-carboxylate

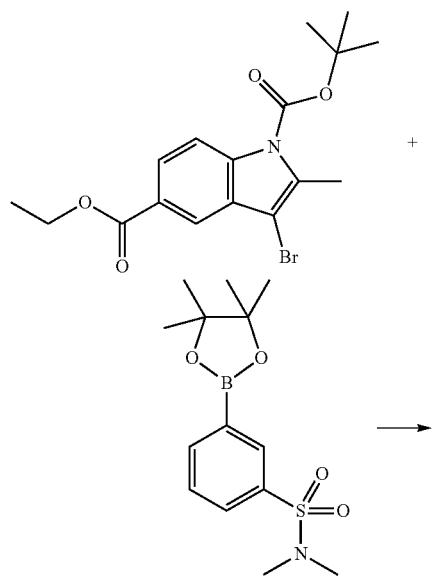

110

-continued

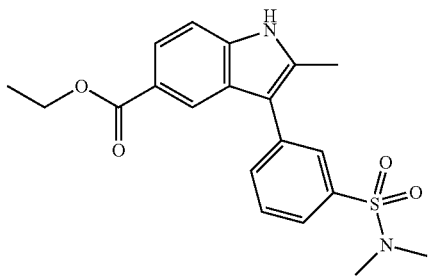

A stirred solution of 1-(tert-butyl) 5-ethyl 3-bromo-2-methyl-1H-indole-1,5-dicarboxylate (900 mg, 2.35 mmol), N,N-dimethyl-3-(4,4,5,5-tetramethyl-1,3,2-dioxaborolan-2-yl)benzenesulfonamide (186 mg, 0.60 mmol), aqueous potassium carbonate solution (21.2 mL, 42.4 mmol) and 1,4-dioxane (9 mL) was degassed by passing nitrogen through it for 5 mins. Tetrakis(triphenylphosphine)palladium(0) (272 mg, 0.24 mmol) was then added under nitrogen and the reaction mixture heated at 90° C. over 16 h. The reaction was allowed to cool to rt and filtered through Celite™, washing with ethyl acetate (20 mL). The organic layer was separated and the aqueous layer extracted with ethyl acetate (20 mL×2). The combined organic layers were dried over Na$_2$SO$_4$ and concentrated in vacuo. The residue thus obtained was then dissolved in CH$_2$Cl$_2$ (4 mL) with stirring and trifluoroacetic acid (4 mL) added. The mixture was stirred at rt for 1 hour, then concentrated in vacuo. Methanol (5 mL) was added to the residue and the resulting precipitate was filtered, washed with MeOH (1 mL×2), and dried under vacuum to afford ethyl 3-(3-(N,N-dimethylsulfamoyl)phenyl)-2-methyl-1H-indole-5-carboxylate (585 mg, 51%) as a yellow solid. $^1$H-NMR (300 MHz; CDCl$_3$) δ ppm: 1.41 (3H, t, J 7.1 Hz), 2.56 (3H, s), 2.84 (6H, s), 4.39 (2H, q, J 7.0 Hz), 7.39 (1H, d, J 8.5 Hz), 7.69 (1H, d, J 7.7 Hz), 7.75-7.80 (2H, m), 8.27 (1H, br. s), 8.36 (1H, br. s).

Procedure L: Preparation of Ethyl (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylate

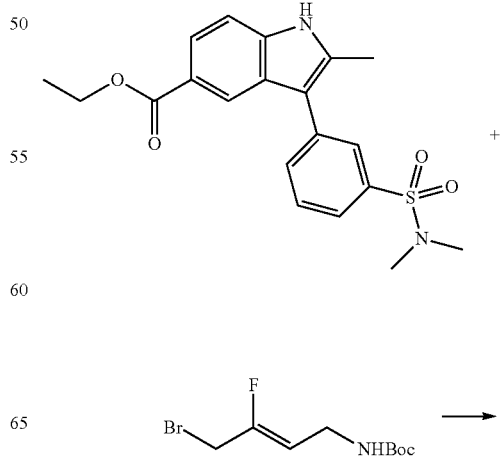

111
-continued

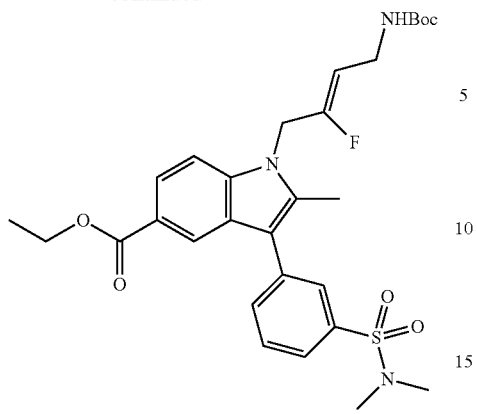

112
-continued

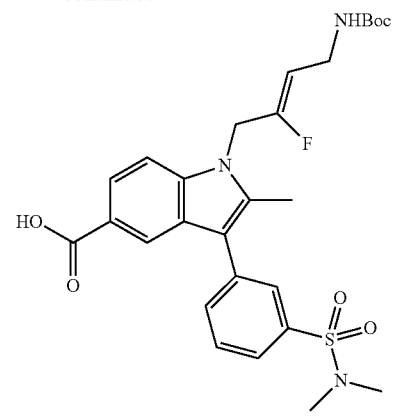

A mixture of ethyl 3-(3-(N,N-dimethylsulfamoyl)phenyl)-2-methyl-1H-indole-5-carboxylate (130 mg, 0.34 mmol), cesium carbonate (132 mg, 0.4 mmol) and tert-butyl (Z)-(4-bromo-3-fluorobut-2-en-1-yl)carbamate (99.0 mg, 0.37 mmol) in DMF (1.3 mL) was stirred at rt overnight. Water (13 mL) was then added, followed by brine (2.6 mL). The resulting suspension was stirred at rt for 5 mins and the precipitate was filtered and dried under vacuum. The crude solid thus obtained was purified over silica gel (25 g) eluting with a mixture of n-hexane, DCM and ethyl acetate in a ratio of 4:4:1, then 2:2:1 to afford ethyl (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylate (150 mg, 78%) as a light grey oil. $^1$H-NMR (300 MHz; CDCl$_3$) δ ppm: 1.40 (3H, t, J 7.1 Hz), 1.42 (9H, s), 2.51 (3H, s), 2.83 (6H, s), 3.82 (2H, apparent t, J 5.2 Hz), 4.38 (2H, q, J 7.1 Hz), 4.73-4.87 (1H, m), 4.86 (2H, d, J 9.8 Hz), 7.35 (1H, d, J 8.7 Hz), 7.65-7.79 (3H, m), 7.90 (1H, dd, J 1.6, 1.6 Hz), 7.97 (11H, dd, J 8.7, 1.6 Hz), 8.33 (1H, d, J 1.2 Hz).

To a stirring solution of ethyl (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylate (469 mg, 0.82 mmol) in MeOH (18 mL) was added aqueous KOH solution (10% w/w; 9 mL). The mixture was heated at 60° C. for 1 h, then cooled to rt and concentrated in vacuo. The residue thus obtained was taken up in water (20 mL) and made acidic by adding 2 M HCl (aq) until pH=4.5. The product was extracted with ethyl acetate (20 mL×3) and the combined organic layers dried over Na$_2$SO$_4$ and concentrated in vacuo to afford (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylic acid (390 mg, 87%) as an off white solid. $^1$H-NMR (300 MHz; DMSO-d$_6$) δ ppm: 1.36 (9H, s), 2.52 (3H, s), 2.70 (6H, s), 3.58 (2H, br. s), 4.98-5.17 (1H, m), 5.15 (2H, d, J 14.2 Hz), 7.00 (1H, br. s), 7.68 (1H, d, J 8.7 Hz), 7.71-7.83 (5H, m), 8.18 (1H, d, J 1.1 Hz), 12.49 (1H, br. s).

Procedure M: Preparation of (Z)-1-(4-((tert-butoxycarbonyl)amino)-2-fluorobut-2-en-1 yl)-3-(3-(N,N-dimethylsulfamoyl)phenyl)-2-methyl-1H-indole-5-carboxylic Acid Procedure N: Preparation of tert-butyl (Z)-(4-(5-(dimethylcarbamoyl)-3-(3-(N,N-dimethylsulfamoyl)phenyl)-2-methyl-1H-indol-1-yl)-3-fluorobut-2-en-1-yl)carbamate

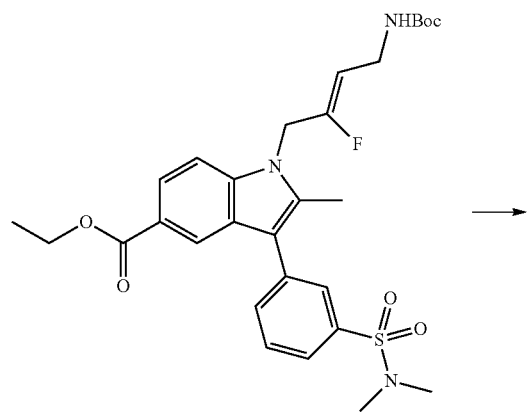

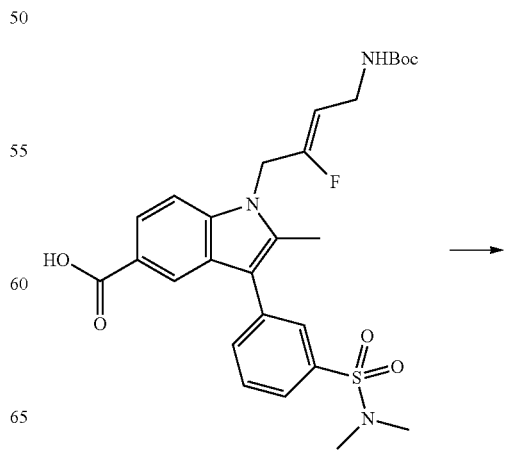

113

-continued

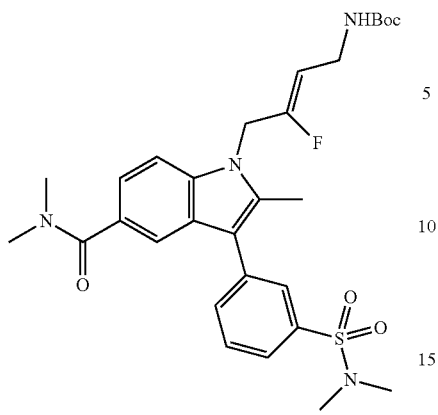

To a stirring mixture of dimethylamine hydrochloride (10 mg, 0.12 mmol) in DMF (0.5 mL), triethylamine (57 uL, 0.41 mmol) was added at rt. After 10 mins (Z)-1-(4-(((tert-butoxycarbonyl)amino)-2-fluorobut-2-en-1-yl)-3-(3-(N,N-dimethylsulfamoyl)phenyl)-2-methyl-1H-indole-5-carboxylic acid (45.0 mg, 0.08 mmol) was added, followed by HATU (38.0 mg, 0.10 mmol). The resulting mixture was stirred at rt for 2 h then diluted with water (10 mL). The pale yellow solid thus obtained was filtered and washed with aq. HCl (1 M; 5 mL) and water (5 mL), and then dried in oven at 60° C. to afford tert-butyl (Z)-(4-(5-(dimethylcarbamoyl)-3-(3-(N,N-dimethylsulfamoyl)phenyl)-2-methyl-1H-indol-1-yl)-3-fluorobut-2-en-1-yl)carbamate (45.0 mg, 95%) as a pale yellow solid. $^1$H-NMR (300 MHz; CDCl$_3$) δ ppm: 1.43 (9H, s), 2.52 (3H, s), 2.79 (6H, s), 3.10 (6H, br. s), 3.82-3.86 (2H, m), 4.71-4.86 (1H, m), 4.84 (2H, d, J 9.5 Hz), 7.34 (2H, apparent d, J 1.1 Hz), 7.65 (1H, dd, J 7.6, 7.6 Hz), 7.71-7.77 (3H, m), 7.87 (1H, dd, J 1.5, 1.5 Hz).

Procedure O: Preparation of Methyl (Z)-1-(4-amino-2-fluorobut-2-en-1-yl)-3-(3-(N,N-dimethylsulfamoyl)phenyl)-N,N,2-trimethyl-1H-indole-5-carboxamide Hydrochloride (Compound 6)

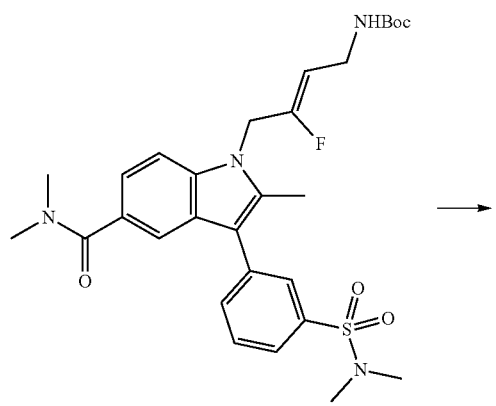

114

-continued

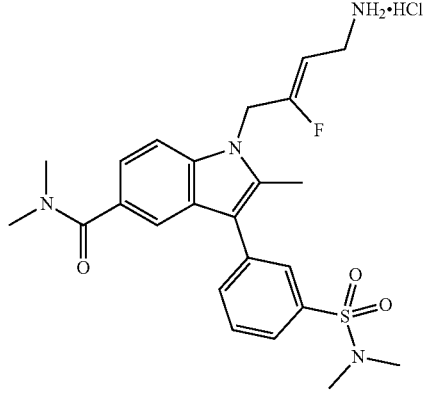

To a stirring solution of tert-butyl (Z)-(4-(5-(dimethylcarbamoyl)-3-(3-(N,N-dimethylsulfamoyl)phenyl)-2-methyl-1H-indol-1-yl)-3-fluorobut-2-en-1-yl)carbamate (45.0 mg, 0.08 mmol) in methanol (1 mL) was added HCl (2 M in diethyl ether, 4.0 mL, 8.0 mmol). The reaction was then stirred for 90 mins at rt, then concentrated in vacuo. Ethyl acetate (2 mL) was added and the resulting suspension stirred for 5 min during which time a fine white precipitate formed. The white solid was collected and dried to afford (Z)-1-(4-amino-2-fluorobut-2-en-1-yl)-3-(3-(N,N-dimethylsulfamoyl)phenyl)-N,N,2-trimethyl-1H-indole-5-carboxamide hydrochloride (37.0 mg, 98%) as a low melting point white solid; $^1$H-NMR (300 MHz, DMSO-d$_6$) δ ppm: 2.54 (3H, s), 2.69 (6H, s), 2.97 (6H, s), 3.43-3.54 (2H, m), 5.09 (1H, dt, J 36.0, 7.5 Hz), 5.23 (2H, d, J 12.5 Hz), 7.28 (1H, dd, J 8.4, 1.4 Hz), 7.56 (1H, d, J 1.3 Hz), 7.66 (1H, d, J 8.5 Hz), 7.69-7.86 (4H, m), 7.98 (2H, br. s).

Example 3

The following compounds were prepared according to the procedures set forth in Example 2.

(Z)-1-(4-amino-2-fluorobut-2-en-1-yl)-3-(3-(N,N-dimethylsulfamoyl)phenyl)-N,N,2-trimethyl-1H-indole-6-carboxamide Hydrochloride (Compound 10)

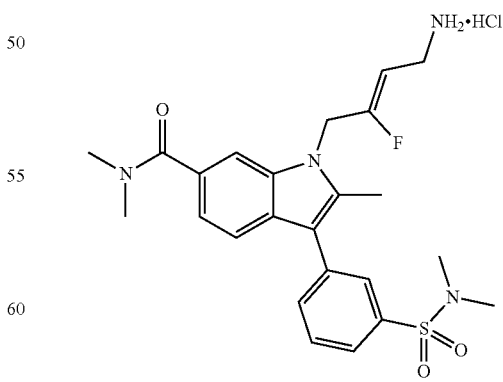

White solid; m.p 140-145° C.; H-NMR (300 MHz; Methanol-d$_4$) δ ppm: 2.58 (3H, s), 2.78 (6H, s), 3.12 (3H, br. s), 3.16 (3H, br. s), 3.63 (2H, br. d, J 7.3 Hz), 4.89 (1H, dt, J 34.2, 7.5 Hz), 5.18 (2H, d, J 9.1 Hz), 7.24 (1H, dd, J 8.3, 1.3 Hz), 7.59-7.65 (2H, m), 7.75-7.87 (4H m).

(Z)-1-(4-amino-2-fluorobut-2-en-1-yl)-3-(3-(N,N-dimethylsulfamoyl)phenyl)-2-methyl-1H-indole-6-carboxamide Hydrochloride (Compound 11)

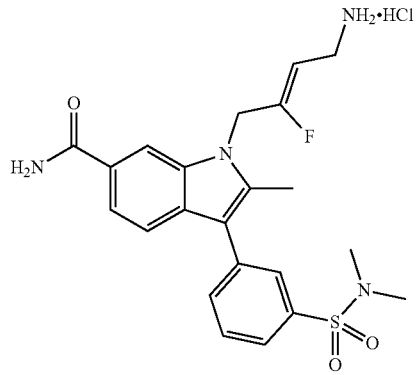

White solid; m.p 144-147° C.; $^1$H-NMR (300 MHz; Methanol-$d_4$) δ ppm: 2.59 (3H, s), 2.78 (6H, s), 3.64 (2H, br. d, J 7.4 Hz), 4.92 (1H, dt, J 33.6, 7.5 Hz), 5.21 (2H, d, J 8.8 Hz), 7.61 (1H, d, J 8.3 Hz), 7.69 (1H, dd, J 8.4, 1.5 Hz), 7.76-7.87 (4H, m), 8.11 (1H, d, J 0.9 Hz)

(Z)-1-(4-amino-2-fluorobut-2-en-1-yl)-3-(3-(N,N-dimethylsulfamoyl)phenyl)-N-isopropyl-2-methyl-1H-indole-5-carboxamide Hydrochloride (Compound 35)

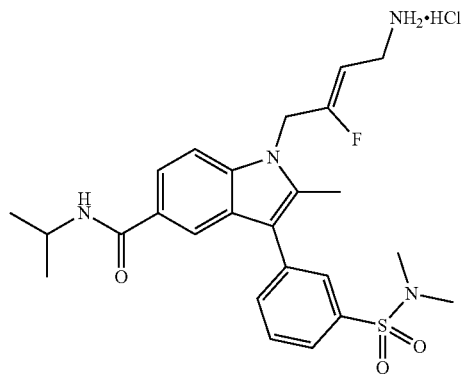

$^1$H NMR (300 MHz, DMSO-$d_6$) δ ppm: 8.11 (d, J=7.8 Hz, 1H), 8.06 (d, J=1.5 Hz, 1H), 7.97 (s, 3H), 7.86 (d, J=7.7 Hz, 1H), 7.83 (d, J=7.7 Hz, 1H), 7.79-7.70 (m, 3H), 7.65 (d, J=8.6 Hz, 1H), 5.23 (d, J=12.3 Hz, 2H), 5.05 (dt, J=36.0, 7.3 Hz, 1H), 4.17-4.04 (m, 1H), 3.55-3.39 (m, 3H), 2.73 (s, 6H), 2.53 (s, 3H), 1.15 (d, J=6.5 Hz, 6H).

(Z)-1-(4-amino-2-fluorobut-2-en-1-yl)-3-(3-(N,N-dimethylsulfamoyl)phenyl)-N-isopropyl-N,2-dimethyl-1H-indole-5-carboxamide Hydrochloride (Compound 36)

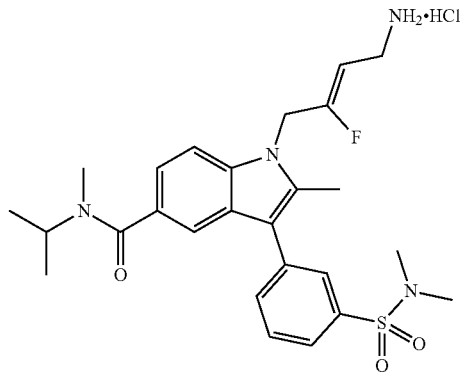

$^1$H NMR (300 MHz, DMSO-$d_6$) δ ppm: 7.95 (s, 3H), 7.85-7.69 (m, 4H), 7.66 (d, J=8.5 Hz, 1H), 7.50 (d, J=1.5 Hz, 1H), 7.22 (dd, J=8.3, 1.6 Hz, 1H), 5.23 (d, J=12.5 Hz, 2H), 5.08 (dt, J=35.9, 7.3 Hz, 1H), 3.70-3.57 (m, 1H), 3.54-3.43 (m, 2H), 2.79 (s, 3H), 2.69 (s, 6H), 2.54 (s, 3H), 1.11 (d, J=6.6 Hz, 6H).

(Z)-1-(4-amino-2-fluorobut-2-en-1-yl)-3-(3-(N,N-dimethylsulfamoyl)phenyl)-N,N,2-trimethyl-1H-indole-7-carboxamide Hydrochloride (Compound 47)

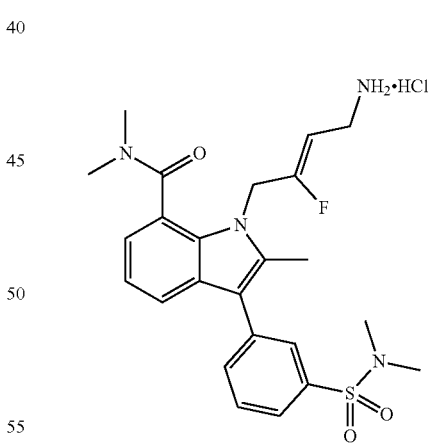

$^1$H NMR (300 MHz, Methanol-$d_4$) δ ppm: 7.86-7.77 (m, 5H), 7.64 (dd, J=7.9, 1.3 Hz, 1H), 7.23 (dd, J=7.9, 7.3 Hz, 1H), 7.15 (dd, J=7.3, 1.3 Hz, 1H), 5.20 (d, J=18.5 Hz, 2H), 4.36 (dt, J=34.3, 7.5 Hz, 1H), 3.24 (s, 3H), 2.94 (s, 3H), 2.78 (s, 6H), 2.53 (s, 3H).

(Z)-1-(4-amino-2-fluorobut-2-en-1-yl)-3-(3-(N,N-dimethylsulfamoyl)phenyl)-N,N,2-trimethyl-1H-indole-5-carboxamide Hydrochloride (Compound 52)

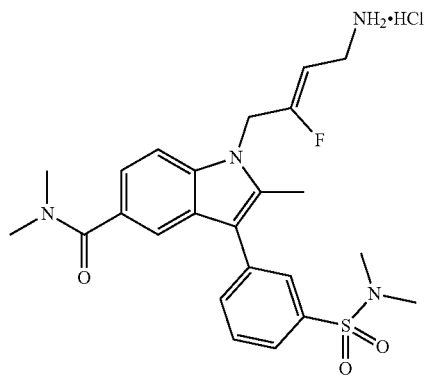

$^1$H NMR (300 MHz, Methanol-d$_4$) δ ppm: 7.87-7.84 (m, 1H), 7.84-7.73 (m, 3H), 7.67 (dd, J=1.6, 0.7 Hz, 1H), 7.49 (dd, J=8.5, 0.7 Hz, 1H), 7.31 (dd, J=8.5, 1.6 Hz, 1H), 5.39-5.26 (m, 1H), 5.04-4.95 (m, 2H), 3.53 (dd, J=6.8, 1.4 Hz, 2H), 3.10 (s, 6H), 2.77 (s, 6H), 2.54 (s, 3H).

Example 4

The following compound was prepared according to procedures F, G, H, I, J, K, L, M, N and O.

(Z)-1-(4-amino-2-fluorobut-2-en-1-yl)-N,N,2-trimethyl-3-(3-(methylsulfonyl)phenyl)-1H-indole-5-carboxamide Hydrochloride (Compound 50)

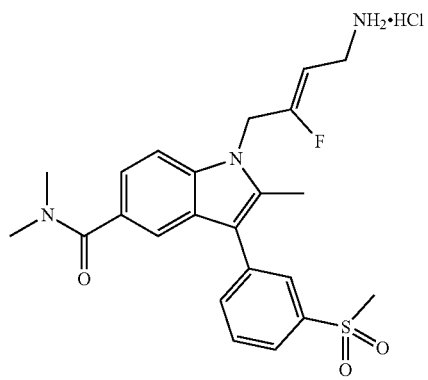

$^1$H NMR (300 MHz, Methanol-d$_4$) δ ppm: 8.03 (d, J=1.8 Hz, 1H), 7.95 (dt, J=7.5, 1.6 Hz, 1H), 7.85 (dt, J=7.7, 1.5 Hz, 1H), 7.79 (d, J=7.6 Hz, 1H), 7.69 (d, J=1.5 Hz, 1H), 7.62 (d, J=8.5 Hz, 1H), 7.36 (dd, J=8.5, 1.6 Hz, 1H), 5.19 (d, J=9.6 Hz, 2H), 4.97 (dt, J=34.2, 7.2 Hz, 1H), 3.64 (d, J=7.4 Hz, 2H), 3.21 (s, 3H), 3.13 (s, 6H), 2.58 (s, 3H).

Example 5

The following compounds were prepared according to procedures G, H, I, J, K, L, M, N and O.

(Z)-1-(4-amino-2-fluorobut-2-en-1-yl)-N,N,2-trimethyl-3-(3-(trifluoromethyl)phenyl)-1H-indole-5-carboxamide Hydrochloride (Compound 56)

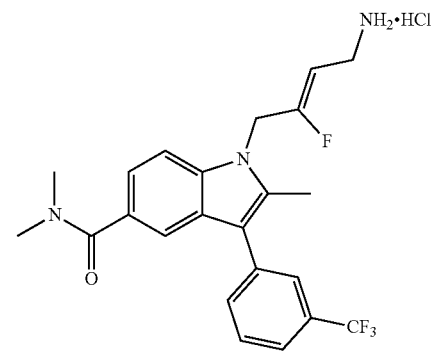

$^1$H NMR (300 MHz, Methanol-d$_4$) δ ppm: 7.78-7.64 (m, 4H), 7.62 (d, J=1.5 Hz, 1H), 7.57 (d, J=8.5 Hz, 1H), 7.33 (dd, J=8.5, 1.6 Hz, 1H), 5.17 (d, J=8.7 Hz, 2H), 4.85 (dt, J=33.9, 6.9 Hz, 1H), 3.67-3.60 (m, 2H), 3.09 (s, 6H), 2.56 (s, 3H).

(Z)-1-(4-amino-2-fluorobut-2-en-1-yl)-N,N,2-trimethyl-3-(3-((trifluoromethyl)sulfonyl)phenyl)-1H-indole-5-carboxamide Hydrochloride (Compound 57)

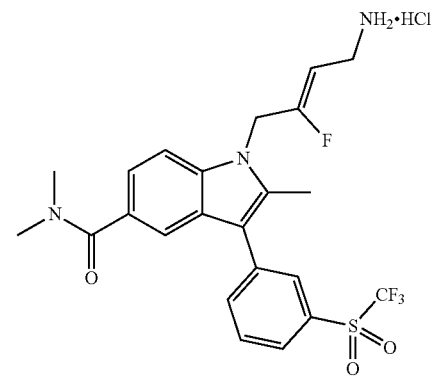

$^1$H NMR (300 MHz, Methanol-d$_4$) δ ppm: 8.15-8.04 (m, 3H), 7.94 (dd, J=8.0 Hz, 1H), 7.65 (s, 1H), 7.64 (d, J=11.1 Hz, 1H), 7.37 (dd, J=8.5, 1.6 Hz, 1H), 5.20 (d, J=9.6 Hz, 2H), 4.96 (dt, J=34.1, 7.2 Hz, 1H), 3.65 (d, J=7.4 Hz, 2H), 3.12 (s, 6H), 2.59 (s, 3H).

(Z)-1-(4-amino-2-fluorobut-2-en-1-yl)-3-(2,6-dimethylpyridin-4-yl)-N,N,2-trimethyl-1H-indole-5-carboxamide Dihydrochloride (Compound 90)

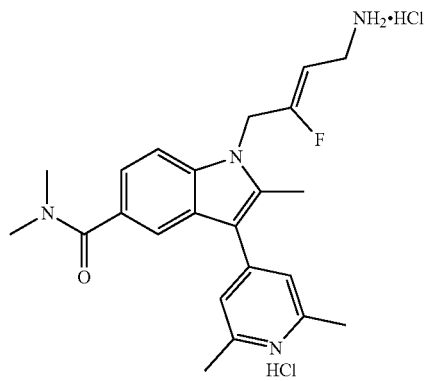

$^1$H NMR (300 MHz, DMSO-d$_6$) δ ppm: 8.31 (s, 3H), 7.80 (s, 3H), 7.74 (d, J=8.5 Hz, 1H), 7.32 (dd, J=8.5, 1.5 Hz, 1H), 5.32 (d, J=13.2 Hz, 2H), 5.22 (dt, J=34.9, 7.2 Hz, 1H), 3.52-3.39 (m, 2H), 2.98 (s, 6H), 2.78 (s, 6H), 2.68 (d, J=5.3 Hz, 3H).

(Z)-1-(4-amino-2-fluorobut-2-en-1-yl)-N-(tert-butyl)-2-methyl-3-(pyridin-4-yl)-1H-indole-5-carboxamide Dihydrochloride (Compound 91)

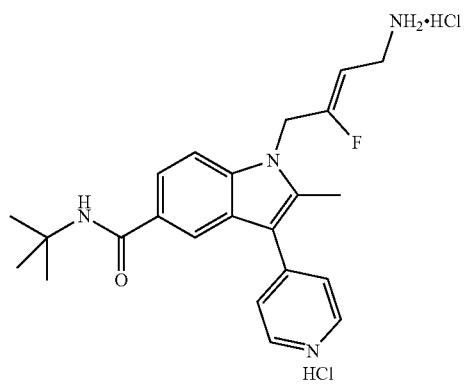

$^1$H NMR (300 MHz, Methanol-d$_4$) δ ppm: 8.84 (d, J=6.2 Hz, 2H), 8.30 (d, J=6.4 Hz, 2H), 8.26 (d, J=1.6 Hz, 1H), 7.78 (dd, J=8.7, 1.5 Hz, 1H), 7.70 (d, J=8.7 Hz, 1H), 5.28 (d, J=11.4 Hz, 2H), 5.12 (dt, J=35.4, 7.4 Hz, 1H), 3.66 (dd, J=6.9, 3.7 Hz, 2H), 2.78 (s, 3H), 1.51 (s, 9H).

Example 6

The following compounds were prepared according to the procedures G, H, I, J, K, L, M and O.

(Z)-1-(4-amino-2-fluorobut-2-en-1-yl)-3-(4-fluorophenyl)-2-methyl-1H-indole-5-carboxylic Acid Hydro-Chloride (Compound 23)

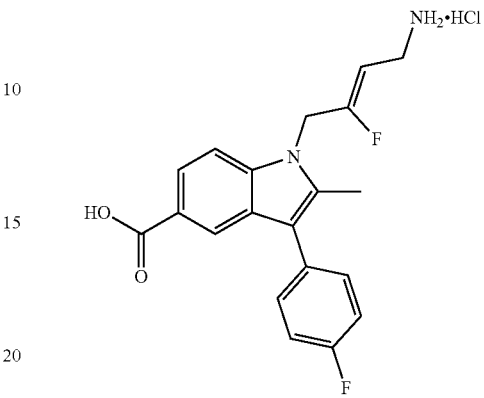

$^1$H NMR (300 MHz, DMSO-d$_6$) δ ppm: 8.13 (d, J=1.6 Hz, 1H), 7.79 (dd, J=8.6, 1.6 Hz, 1H), 7.65 (d, J=8.6 Hz, 1H), 7.49 (dd, J=8.6, 5.7 Hz, 2H), 7.37 (dd, J=8.9 Hz, 2H), 5.22 (d, J=12.4 Hz, 2H), 5.04 (dt, J=35.9, 7.3 Hz, 1H), 3.49 (d, J=7.2 Hz, 2H), 2.49 (s, 3H).

(Z)-1-(4-amino-2-fluorobut-2-en-1-yl)-3-(3-(tert-butyl)phenyl)-2-methyl-1H-indole-5-carboxylic Acid Hydrochloride (Compound 31)

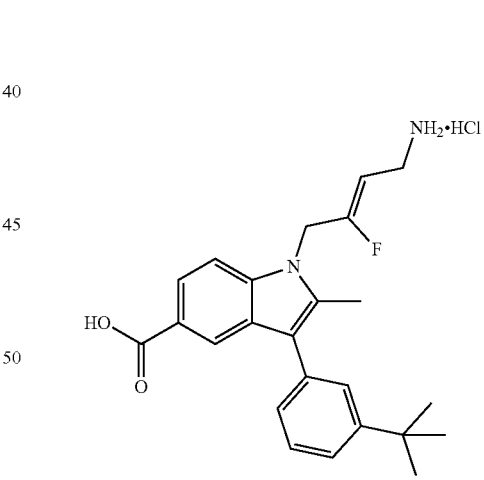

$^1$H NMR (300 MHz, DMSO-d$_6$) δ ppm: 12.47 (s, 1H), 8.19 (d, J=1.6 Hz, 1H), 7.90 (s, 3H), 7.79 (dd, J=8.6, 1.6 Hz, 1H), 7.65 (d, J=8.7 Hz, 1H), 7.50-7.43 (m, 2H), 7.40 (dt, J=8.1, 1.6 Hz, 1H), 7.28 (ddd, J=7.4, 1.5 Hz, 1H), 5.22 (d, J=12.6 Hz, 2H), 5.07 (dt, J=35.9, 7.3 Hz, 1H), 3.49 (s, 2H), 2.51 (s, 3H), 1.36 (s, 9H).

121
(Z)-1-(4-amino-2-fluorobut-2-en-1-yl)-3-(3-chlorophenyl)-2-methyl-1H-indole-5-carboxylic Acid Hydrochloride (Compound 28)

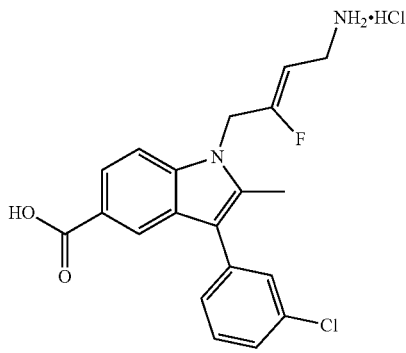

¹H NMR (300 MHz, Methanol-d₄) δ 8.27 (d, J=1.4 Hz, 1H), 7.93 (dd, J=8.7, 1.6 Hz, 1H), 7.54 (d, J=8.7 Hz, 1H), 7.52-7.49 (m, 1H), 7.47 (dd, J=1.8 Hz, 1H), 7.45-7.36 (m, 2H), 5.16 (d, J=8.7 Hz, 2H), 4.84 (dt, J=34.1, 7.4 Hz, 1H), 3.67-3.58 (m, 2H), 2.55 (s, 3H).

(Z)-3-fluoro-4-(3-(2-methoxypyridin-4-yl)-2-methyl-5-(methylsulfonyl)-1H-indol-1-yl)but-2-en-1-amine Dihydrochloride (Compound 98)

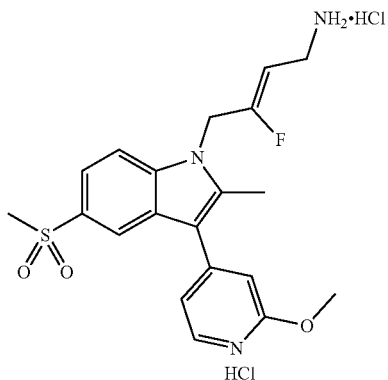

¹H NMR (300 MHz, DMSO-d₆) δ ppm: 8.31 (d, J=5.7 Hz, 1H), 8.10 (d, J=1.7 Hz, 1H), 8.06 (s, 4H), 7.89 (d, J=8.7 Hz, 1H), 7.74 (dd, J=8.7, 1.8 Hz, 1H), 7.18 (dd, J=5.3, 1.5 Hz, 1H), 6.95 (d, J=1.2 Hz, 1H), 5.32 (d, J=13.1 Hz, 2H), 5.15 (dt, J=35.9, 7.2 Hz, 1H), 3.94 (s, 3H), 3.52-3.41 (m, 3H), 3.20 (s, 3H), 2.59 (s, 3H).

Example 7

The following compounds were prepared according to the procedures E, F, G, H, I, J, K, L, M and O.

122
(Z)-1-(4-amino-2-fluorobut-2-en-1-yl)-3-(3-(N,N-dimethylsulfamoyl)phenyl)-6-fluoro-2-methyl-1H-indole-5-carboxylic Acid Hydrochloride (Compound 21)

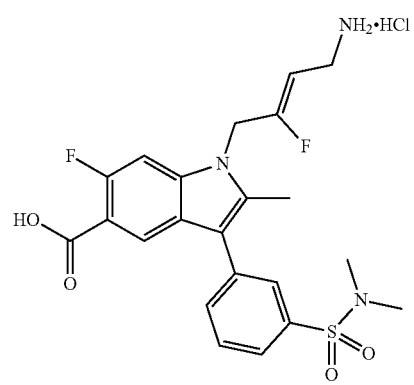

¹H NMR (300 MHz, Methanol-d₄) δ ppm: 8.18 (d, J=7.0 Hz, 1H), 7.86 (dt, J=1.0 Hz, 1H), 7.83-7.77 (m, 3H), 7.37 (d, J=11.9 Hz, 1H), 5.15 (d, J=9.3 Hz, 2H), 4.92 (dt, J=34-1, 7.5 Hz, 1H), 3.65 (d, J=7.4 Hz, 2H), 2.80 (s, 6H), 2.57 (s, 3H).

(Z)-1-(4-amino-2-fluorobut-2-en-1-yl)-3-(3-(N,N-dimethylsulfamoyl)phenyl)-2-methyl-1H-indole-7-carboxylic Acid Hydrochloride (Compound 48)

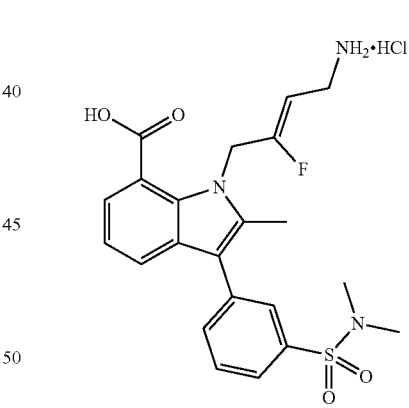

¹H NMR (300 MHz, Methanol-d₄) δ ppm: 7.83-7.78 (m, 4H), 7.77 (dd, J=7.6, 1.2 Hz, 1H), 7.72 (dd, J=7.9, 1.2 Hz, 1H), 5.51 (d, J=6.7 Hz, 2H), 4.55 (dt, J=34.3, 7.5 Hz, 1H), 3.56 (d, J=8.3 Hz, 2H), 2.78 (s, 6H), 2.55 (s, 3H).

Example 8

The following compounds were prepared according to the procedures G, H, I, J, K, L and O.

123

Ethyl (Z)-1-(4-amino-2-fluorobut-2-en-1-yl)-3-(4-fluorophenyl)-2-methyl-1H-indole-5-carboxylate Hydrochloride (Compound 24)

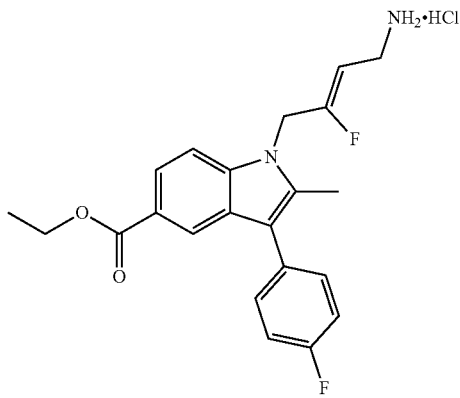

¹H NMR (300 MHz, Methanol-d₄) δ ppm: 8.22 (d, J=1.6 Hz, 1H), 7.90 (dd, J=8.7, 1.7 Hz, 1H), 7.53 (d, J=8.7 Hz, 1H), 7.48 (dd, J=8.8, 5.4 Hz, 2H), 7.26 (dd, J=8.8 Hz, 2H), 5.20-5.09 (m, 2H), 4.85 (dt, J=34.1, 7.5 Hz, 1H), 4.36 (q, J=7.1 Hz, 2H), 3.67-3.57 (m, 2H), 2.52 (s, 3H), 1.39 (t, J=7.1 Hz, 3H).

Ethyl (Z)-1-(4-amino-2-fluorobut-2-en-1-yl)-3-(3-(tert-butyl)phenyl)-2-methyl-1H-indole-5-carboxylate Hydrochloride (Compound 30)

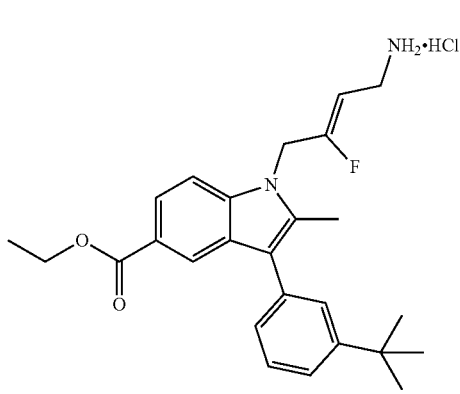

¹H NMR (300 MHz, DMSO-d₆) δ ppm: 8.22 (d, J=1.6 Hz, 1H), 7.97 (s, 3H), 7.80 (dd, J=8.7, 1.6 Hz, 1H), 7.68 (d, J=8.7 Hz, 1H), 7.50 (dd, J=1.8 Hz, 1H), 7.45 (d, J=7.5 Hz, 1H), 7.40 (dt, J=7.9, 1.5 Hz, 1H), 7.28 (dt, J=7.4, 1.5 Hz, 1H), 5.23 (d, J=13.0 Hz, 2H), 5.11 (dt, J=35.9, 7.6 Hz, 1H), 3.48 (d, J=7.2 Hz, 2H), 2.53 (s, 3H), 1.36 (s, 9H).

124

Ethyl (Z)-1-(4-amino-2-fluorobut-2-en-1-yl)-3-(3-chlorophenyl)-2-methyl-1H-indole-5-carboxylate Hydrochloride (Compound 27)

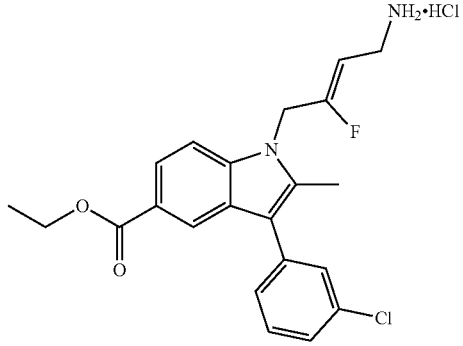

¹H NMR (300 MHz, Methanol-d₄) δ ppm: 8.24 (d, J=1.4 Hz, 1H), 7.92 (dd, J=8.7, 1.7 Hz, 1H), 7.55 (d, J=8.7 Hz, 1H), 7.51 (d, J=7.7 Hz, 1H), 7.46 (dd, J=1.8 Hz, 1H), 7.44-7.37 (m, 2H), 5.16 (d, J=8.9 Hz, 2H), 4.85 (dt, J=34.0, 7.5 Hz, 1H), 4.37 (q, J=7.1 Hz, 2H), 3.63 (d, J=7.5 Hz, 2H), 2.54 (s, 3H), 1.39 (t, J=7.1 Hz, 3H).

(Z)-3-fluoro-4-(2-methyl-5-(methylsulfonyl)-3-phenyl-1H-indol-1-yl)but-2-en-1-amine Hydrochloride (Compound 87)

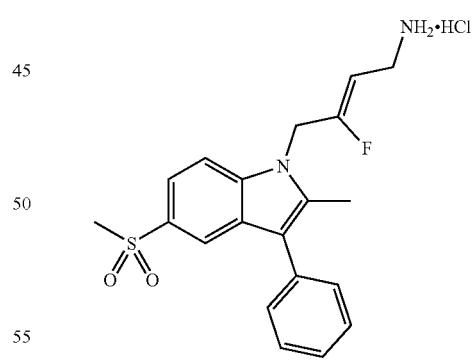

¹H NMR (300 MHz, Methanol-d₄) δ ppm: 8.12 (dd, J=1.8, 0.7 Hz, 1H), 7.77 (dd, J=8.7, 1.8 Hz, 1H), 7.71 (d, J=8.3 Hz, 1H), 7.58-7.46 (m, 4H), 7.43-7.37 (m, 1H), 5.22 (d, J=9.3 Hz, 2H), 4.88 (dt, J=33.9, 7.4 Hz, 1H), 3.67-3.60 (m, 2H), 3.11 (s, 3H), 2.57 (s, 3H).

125

(Z)-3-fluoro-4-(2-methyl-5-(methylsulfonyl)-3-(pyridin-4-yl)-1H-indol-1-yl)but-2-en-1-amine Hydro-Chloride (Compound 88)

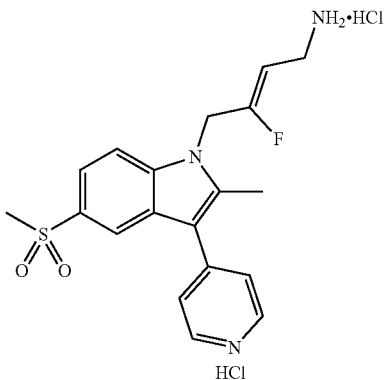

$^1$H NMR (300 MHz, Methanol-d$_4$) δ ppm: 8.88 (d, J=7.3 Hz, 2H), 8.41 (dd, J=1.7, 0.8 Hz, 1H), 8.29 (d, J=6.8 Hz, 2H), 7.93 (dd, J=8.7, 1.6 Hz, 1H), 7.89 (dd, J=8.5, 0.6 Hz, 1H), 5.35 (d, J=11.7 Hz, 2H), 5.20 (dt, J=34.1, 7.4 Hz, 1H), 4.90 (s, 7H), 3.66 (d, J=7.4 Hz, 2H), 3.19 (s, 3H), 2.80 (s, 3H).

(Z)-4-(3-(2,6-dimethylpyridin-4-yl)-2-methyl-5-(ethylsulfonyl)-1H-indol-1-yl)-3-fluorobut-2-en-1-amine Dihydrochloride (Compound 89)

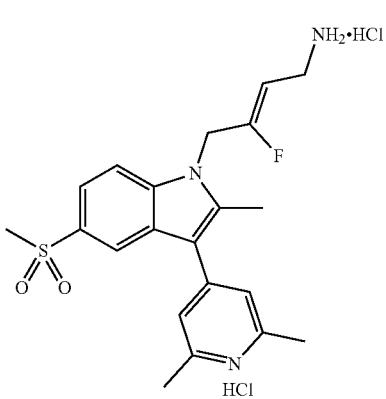

$^1$H NMR (300 MHz, Methanol-d$_4$) δ ppm: 8.34 (dd, J=1.7, 0.7 Hz, 1H), 7.90 (dd, J=8.8, 1.7 Hz, 1H), 7.88-7.83 (m, 3H), 5.32 (d, J=11.7 Hz, 2H), 5.18 (dt, J=34.1, 7.4 Hz, 1H), 3.66 (d, J=7.3 Hz, 2H), 3.19 (s, 3H), 2.84 (s, 6H), 2.76 (s, 3H).

126

(Z)-4-(3-(benzo[d][1,3]dioxol-5-yl)-2-methyl-5-(methylsulfonyl)-1H-indol-1-yl)-3-fluorobut-2-en-1-amine Hydrochloride (Compound 92)

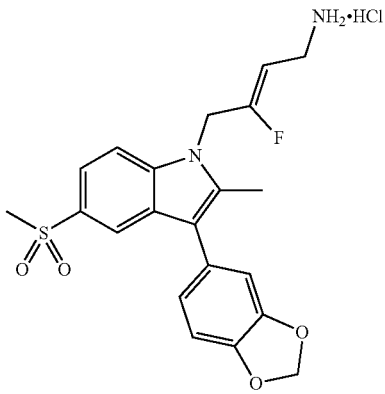

$^1$H NMR (300 MHz, Methanol-d$_4$) δ ppm: 8.10 (d, J=1.3 Hz, 1H), 7.75 (dd, J=8.7, 1.8 Hz, 1H), 7.69 (d, J=8.6 Hz, 1H), 7.00 (dd, J=7.7, 0.7 Hz, 1H), 6.96-6.91 (m, 2H), 6.04 (s, 2H), 5.19 (d, J=8.0 Hz, 1H), 4.80 (dt, J=35.2, 7.5 Hz, 1H), 3.63 (d, J=7.5 Hz, 2H), 3.12 (s, 3H), 2.55 (s, 3H).

(Z)-3-fluoro-4-(3-(4-fluorophenyl)-2-methyl-5-(methylsulfonyl)-1H-indol-1-yl)but-2-en-1-amine Hydro-Chloride (Compound 93)

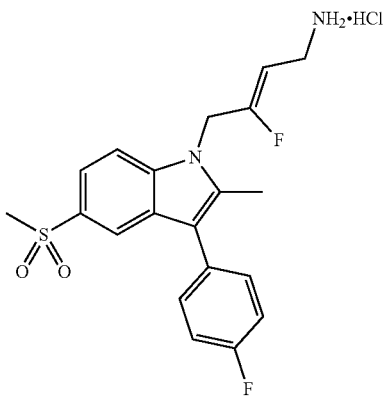

$^1$H NMR (300 MHz, Methanol-d$_4$) δ ppm: 8.11-8.07 (m, 1H), 7.77 (dd, J=8.7, 1.8 Hz, 1H), 7.71 (d, J=8.5 Hz, 1H), 7.54-7.46 (m, 2H), 7.33-7.23 (m, 2H), 5.21 (dd, J=9.5, 1.3 Hz, 2H), 4.89 (dt, J=35.3, 7.5 Hz, 1H), 3.64 (d, J=7.5 Hz, 2H), 3.12 (s, 3H), 2.55 (s, 3H).

(Z)-3-fluoro-4-(2-methyl-3-(2-methylpyridin-4-yl)-5-(methylsulfonyl)-1H-indol-1-yl)but-2-en-1-amine Dihydrochloride (Compound 94)

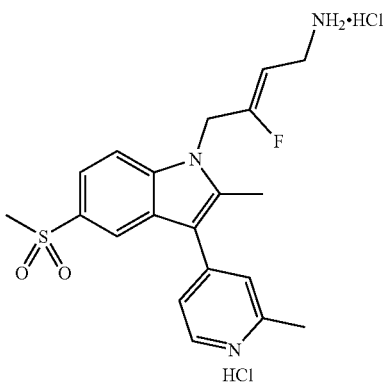

$^1$H NMR (300 MHz, Methanol-$d_4$) δ ppm: 8.71 (dd, J=6.3, 0.7 Hz, 1H), 8.37 (dd, J=1.6, 0.7 Hz, 1H), 8.10 (d, J=1.8 Hz, 1H), 8.07 (d, J=6.3 Hz, 1H), 7.92 (dd, J=8.7, 1.6 Hz, 1H), 7.87 (d, J=8.3 Hz, 1H), 5.34 (d, J=11.7 Hz, 2H), 5.19 (dt, J=34.1, 7.4 Hz, 1H), 3.66 (d, J=7.4 Hz, 2H), 3.19 (s, 3H), 2.89 (s, 3H), 2.78 (s, 3H).

Example 9

The following compound was prepared according to the procedures E, F, P, Q, R, J, K, L and O.

(Z)-ethyl 1-(4-amino-2-fluorobut-2-en-1-yl)-3-(3-(N,N-dimethylsulfamoyl)phenyl)-2-methyl-1H-pyrrolo[3,2-b]pyridine-5-carboxylate Dihydrochloride (Compound 42)

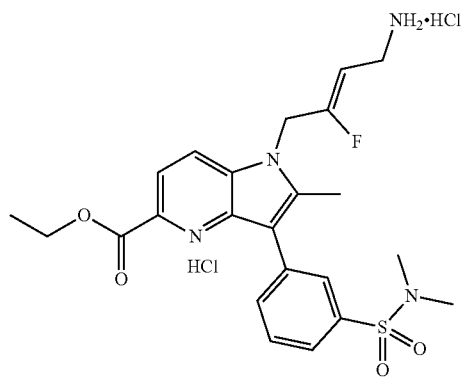

Procedure P: Preparation of 5-chloro-2-methyl-3-(methylthio)-1H-pyrrolo[3,2-b]pyridine

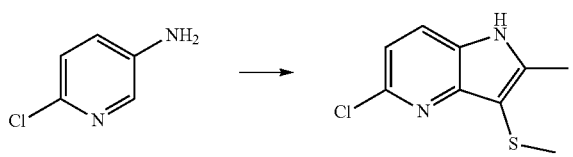

To a solution of 6-chloropyridin-3-amine (6.72 g, 62.0 mmol) in $CH_2Cl_2$ (150 mL) at −78° C. was added a solution of t-BuOCl (124 mmol, 14 mL) in $CH_2Cl_2$ (50 mL). The reaction stirred for 30 min prior to the addition of methylthioacetone (62.0 mmol, 6.47 g) in $CH_2Cl_2$ (50 mL). After 90 min, a solution of $NEt_3$ (62.0 mmol, 9.60 mL) in $CH_2C_2$ (50 mL) was added and the reaction warmed to ambient temperature. The reaction was quenched by the addition of water and the aqueous layer was extracted with $CH_2Cl_2$. The organic layer was dried over $Na_2SO_4$ and concentrated in vacuo. The residue was purified over silica gel, eluting with $CH_2Cl_2$/MeOH (20:1) to afford 5-chloro-2-methyl-3-(methylthio)-1H-pyrrolo[3,2-b]pyridine (9.50 g, 72%).

Procedure Q: Preparation of 5-chloro-2-methyl-1H-pyrrolo[3,2-b]pyridine

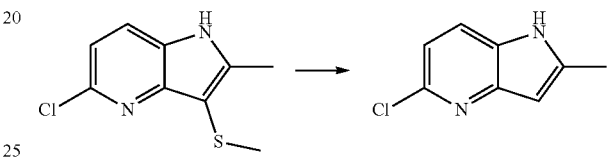

A mixture of 5-chloro-2-methyl-3-(methylthio)-1H-pyrrolo[3,2-b]pyridine (9.50 g, 45.0 mmol), AcOH (80 mL) and Raney Nickel (~150 g) in ethanol (85% w/w, 300 mL) was stirred for 6 h. Raney Nickel was removed by filtration through Celite™ and the reaction mixture was concentrated in vacuo. The residue was purified over silica gel, eluting with 50% ethyl acetate in hexane to afford 5-chloro-2-methyl-1H-pyrrolo[3,2-b]pyridine (2.70 g, 36%) as brown solid.

Procedure R: Preparation of Ethyl 2-methyl-1H-pyrrolo[3,2-b]pyridine-5-carboxylate

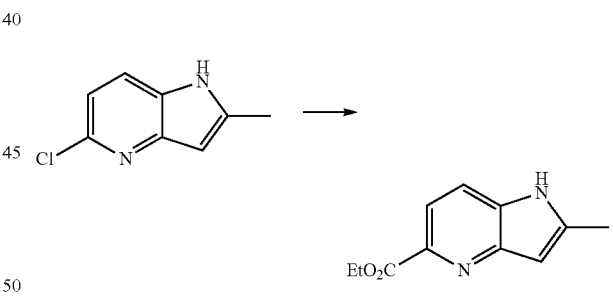

A mixture of 5-chloro-2-methyl-1H-pyrrolo[3,2-b]pyridine (2.70 g, 16.0 mmol) in ethanol (100 ml), $PdCl_2$dppf (587 mg, 0.80 mmol) and $Et_3N$ (4.80 g, 48.0 mmol) was transferred into a 300 mL autoclave and a carbon monoxide pressure of 15 bar was applied. The reaction mixture was heated at 120° C. overnight. After cooling to rt, the pressure was released, the reaction mixture was concentrated and then diluted with water (100 ml). The aqueous phase was extracted with dichloromethane (100 ml×3). The combined organic phases were dried over $Na_2SO_4$ and concentrated under reduced pressure. The residue was purified over silica gel, eluting with 50% ethyl acetate in hexane to afford ethyl 2-methyl-1H-pyrrolo[3,2-b]pyridine-5-carboxylate (1.21 g, 37%) as white solid. $^1$H-NMR (300 MHz, $CDCl_3$): δ ppm: 9.75 (s, 1H), 7.97-7.94 (m, 1H), 7.64-7.61 (m, 1H), 6.47 (s, 1H), 4.49-4.42 (m, 2H), 2.49 (s, 3H), 1.38-1.33 (m, 3H).

(Z)-ethyl 1-(4-amino-2-fluorobut-2-en-1-yl)-3-(3-(N,N-dimethylsulfamoyl)phenyl)-2-methyl-1H-pyrrolo[3,2-b]pyridine-5-carboxylate Dihydrochloride (Compound 42)

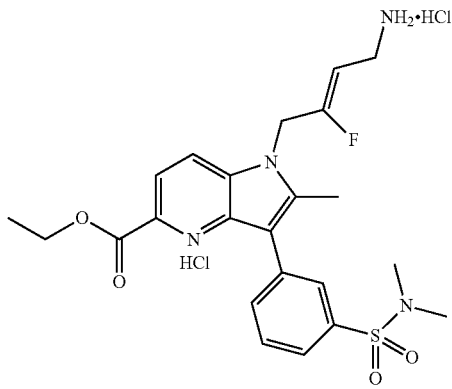

$^1$H NMR (300 MHz, DMSO-d$_6$) δ ppm: 8.17 (d, J=8.8 Hz, 2H), 8.01 (s, 3H), 7.97 (d, J=8.8 Hz, 2H), 7.79 (t, J=7.7 Hz, 1H), 7.71 (dt, J=7.8, 1.5 Hz, 1H), 5.33 (d, J=12.8 Hz, 2H), 5.11 (dt, J=36.1, 7.5 Hz, 1H), 4.33 (q, J=7.1 Hz, 2H), 3.55-3.40 (m, 2H), 2.75 (s, 6H), 2.67 (s, 3H), 1.32 (t, J=7.1 Hz, 3H).

Example 10

The following compounds were prepared according to the procedures E, F, P, Q, J, K, L, and O.

(Z)-3-(1-(4-amino-2-fluorobut-2-en-1-yl)-6-fluoro-2-methyl-1H-pyrrolo[3,2-b]pyridin-3-yl)-N,N-dimethylbenzenesulfonamide Dihydrochloride (Compound 108)

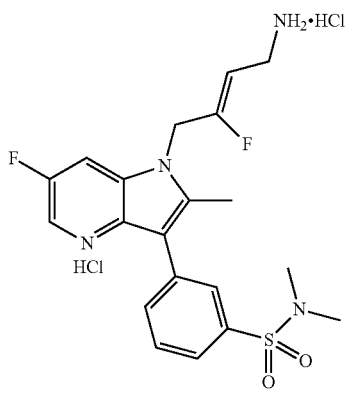

$^1$H NMR (300 MHz, Methanol-d$_4$) δ ppm: 8.74 (dd, J=8.6, 2.2 Hz, 1H), 8.65 (dd, J=3.4, 2.2 Hz, 1H), 7.97-7.82 (m, 4H), 5.40 (d, J=13.4 Hz, 2H), 5.37 (dt, J=35.2, 7.4 Hz, 1H), 3.69 (d, J=7.3 Hz, 21-), 2.78 (s, 6H), 2.66 (s, 3H).

(Z)-3-(1-(4-amino-2-fluorobut-2-en-1-yl)-5-fluoro-2-methyl-1H-pyrrolo[3,2-b]pyridin-3-yl)-N,N-dimethylbenzenesulfonamide Dihydrochloride (Compound 109)

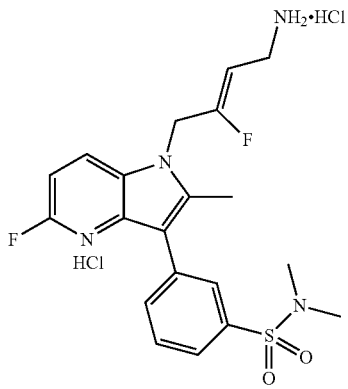

$^1$H-NMR (400 MHz, DMSO-d6): δ ppm: 8.25-8.21 (m, 1H), 8.15-8.12 (m, 3H), 7.98-7.95 (m, 2H), 7.78-7.74 (m, 1H), 7.70-7.68 (m, 1H), 6.99-6.96 (m, 1H), 5.30-5.27 (m, 2H), 5.21-5.10 (m, 1H), 3.48-3.44 (m, 2H), 2.67 (s, 6H), 2.63 (s, 3H).

(Z)-3-(1-(4-amino-2-fluorobut-2-en-1-yl)-2-methyl-5-(trifluoromethyl)-1H-pyrrolo[3,2-b]pyridin-3-yl)-N,N-dimethylbenzenesulfonamide Dihydrochloride (Compound 110)

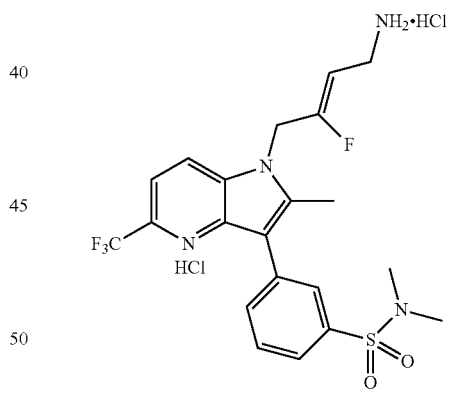

$^1$H NMR (300 MHz, DMSO-d$_6$) δ ppm: 8.30 (d, J=8.5 Hz, 1H), 8.14 (t, J=1.7 Hz, 1H), 8.05-7.87 (m, 5H), 7.80 (dd, J=7.7 Hz, 1H), 7.76-7.69 (m, 2H), 5.37 (d, J=12.5 Hz, 2H), 5.09 (dt, J=36.0, 7.2 Hz, 1H), 3.47 (d, J=7.0 Hz, 2H), 2.72 (s, 6H), 2.70 (s, 3H).

Example 11

The following compound was prepared according to the procedures E, F, P, Q, R, J, K, L, M, and O.

131

(Z)-1-(4-amino-2-fluorobut-2-en-1-yl)-3-(3-(N,N-dimethylsulfamoyl)phenyl)-2-methyl-1H-pyrrolo[3,2-b]pyridine-5-carboxylic Acid Dihydrochloride (Compound 43)

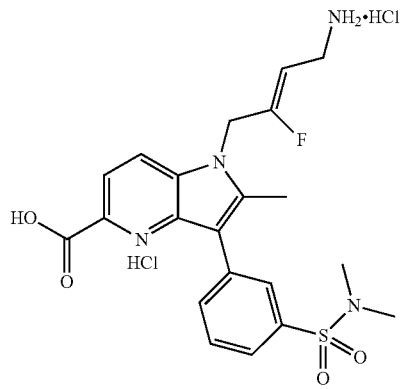

¹H NMR (300 MHz, DMSO-d$_6$) δ ppm: 8.15 (d, J=8.5 Hz, 2H), 8.15 (s, 1H) 8.02 (dt, J=7.7, 1.5 Hz, 1H), 7.96 (d, J=8.5 Hz, 1H), 7.96 (s, 3H), 7.78 (t, J=7.7 Hz, 1H), 7.70 (dt, J=7.9, 1.5 Hz, 1H), 5.32 (d, J=12.7 Hz, 1H), 5.10 (dt, J=35.9, 7.2 Hz, 1H), 3.48 (t, J=6.1 Hz, 2H), 2.73 (s, 6H), 2.67 (s, 3H).

Example 12

The following compounds were prepared according to the procedures E, F, P, Q, R, J, K, L, M, N and O.

(Z)-1-(4-amino-2-fluorobut-2-en-1-yl)-3-(3-(N,N-dimethylsulfamoyl)phenyl)-N,N,2-trimethyl-1H-pyrrolo[3,2-b]pyridine-5-carboxamide Dihydrochloride (Compound 44)

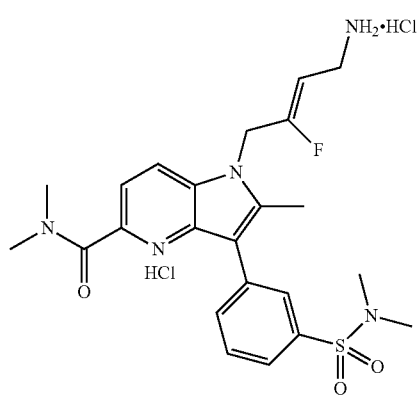

¹H NMR (300 MHz, DMSO-d$_6$) δ ppm: 8.18-8.10 (m, 2H), 8.03 (s, 3H), 7.97 (td, 1H), 7.77 (t, J=7.7 Hz, 1H), 7.68 (dt, J=7.8, 1.4 Hz, 1H), 7.45 (d, J=8.5 Hz, 1H), 5.30 (d, J=13.1 Hz, 2H), 5.14 (dt, J=35.8, 7.1 Hz, 1H), 3.47 (d, J=7.0 Hz, 2H), 3.05 (s, 3H), 3.01 (s, 3H), 2.68 (s, 6H), 2.67 (s, 3H).

132

(Z)-1-(4-amino-2-fluorobut-2-en-1-yl)-3-(3-(N,N-dimethylsulfamoyl)phenyl)-N-isopropyl-2-methyl-1H-pyrrolo[3,2-b]pyridine-5-carboxamide Dihydrochloride (Compound 45)

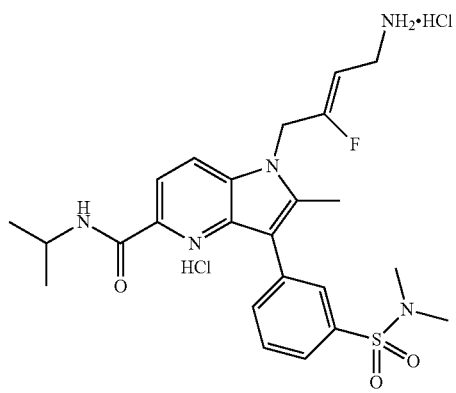

¹H NMR (300 MHz, DMSO-d$_6$) δ ppm: 8.42 (dd, J=1.8 Hz, 1H), 8.19 (d, J=8.5 Hz, 1H), 8.01 (dt, J=7.7, 1.5 Hz, 1H), 7.95 (dd, J=8.5 Hz, 1H), 7.79 (dd, J=7.7 Hz, 1H), 7.71 (dt, J=7.9, 1.5 Hz, 1H), 5.33 (d, J=13.0 Hz, 1H), 5.12 (dt, J=35.8, 7.2 Hz, 1H), 4.21-4.08 (m, 1H), 3.54-3.38 (m, 2H), 2.71 (s, 6H), 2.70 (s, 2H), 1.21 (d, J=6.6 Hz, 6H).

(Z)-1-(4-amino-2-fluorobut-2-en-1-yl)-3-(3-(N,N-dimethylsulfamoyl)phenyl)-N,2-dimethyl-1H-pyrrolo[3,2-b]pyridine-5-carboxamide Dihydrochloride (Compound 46)

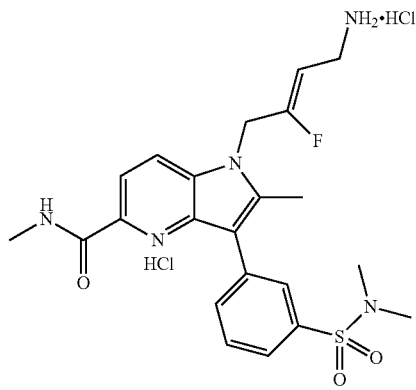

¹H NMR (300 MHz, DMSO-d$_6$) δ ppm: 8.24-7.97 (m, 6H), 7.93 (d, J=8.4 Hz, 1H), 7.79 (dd, J=7.8 Hz, 1H), 7.71 (d, J=7.6 Hz, 2H), 5.31 (d, J=13.0 Hz, 2H), 5.14 (dt, J=35.8, 7.0 Hz, 1H), 3.47 (s, 2H), 2.84 (d, J=4.6 Hz, 3H), 2.72 (s, 6H), 2.67 (s, 3H).

133

(Z)-1-(4-amino-2-fluorobut-2-en-1-yl)-3-(3-(N,N-dimethylsulfamoyl)phenyl)-N,N,2-trimethyl-1H-pyrrolo[3,2-b]pyridine-5-carboxamide Dihydrochloride (Compound 53)

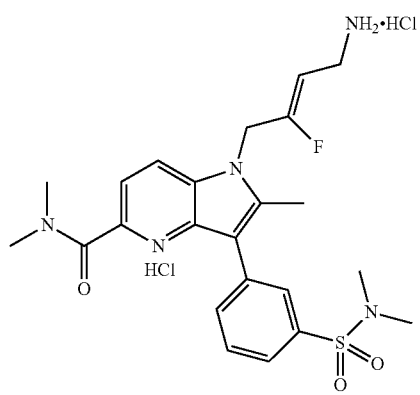

$^1$H NMR (300 MHz, DMSO-d$_6$) δ ppm: 8.17 (dd, J=1.7 Hz, 1H), 8.09 (s, 3H), 8.06 (d, J=8.5 Hz, 1H), 7.98 (dt, J=7.7, 1.5 Hz, 1H), 7.76 (dd, J=7.7 Hz, 1H), 7.67 (dt, J=8.0, 1.4 Hz, 1H), 7.43 (d, J=8.4 Hz, 1H), 5.42 (dt, J=14.4, 6.4 Hz, 1H), 5.03 (d, J=4.9 Hz, 2H), 3.46-3.36 (m, 2H), 3.05 (s, 3H), 3.01 (s, 3H), 2.69 (s, 6H).

Example 13

The following compounds were prepared according to procedures J, K, L and O.

(Z)-3-(1-(4-amino-2-fluorobut-2-en-1-yl)-2-methyl-1H-indol-3-yl)-N,N-dimethylbenzenesulfonamide Hydrochloride (Compound 2)

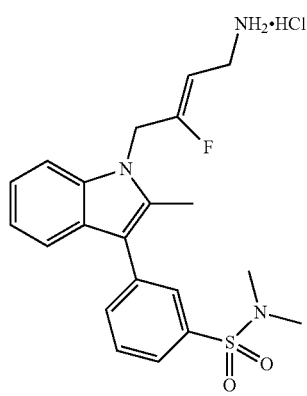

White solid; m.p 242-245° C.; $^1$H-NMR (300 MHz; d$_6$-DMSO) δ ppm: 2.52 (3H, s), 2.70 (6H, s), 3.47 (2H, br. d, J 7.1 Hz), 5.04 (1H, dt, J 36.0, 7.2 Hz), 51.9 (2H, d, J 12.3 Hz), 7.13 (1H, dt, J 7.0, 7.0, 1.0 Hz), 7.21 (1H, dt, J 6.9, 6.9, 1.1 Hz), 7.53 (1H, d, J 7.6 Hz), 7.61 (1H, d, J 8.0 Hz), 7.70 (1H, dd, J 7.2, 1.8 Hz), 7.73-7.76 (1H, m), 7.79 (1H, d, J 7.9 Hz), 7.83 (1H, dd, J 7.6, 1.7 Hz), 7.97 (2H, br. s).

134

(Z)-4-(1-(4-amino-2-fluorobut-2-en-1-yl)-2-methyl-1H-indol-3-yl)-N,N-dimethylbenzenesulfonamide Hydrochloride (Compound 3)

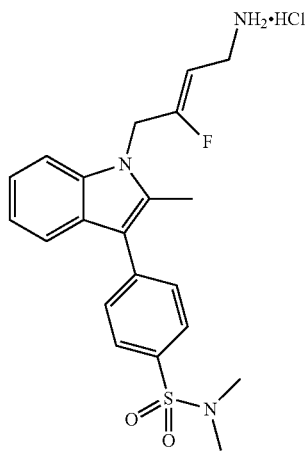

Glassy solid; m.p 145-150° C.; $^1$H-NMR (300 MHz; d$_6$-DMSO) δ ppm: 2.55 (3H, s), 2.68 (6H, s), 3.41-3.53 (2H, in), 5.06 (1H, dt, J 36.0, 7.3 Hz), 5.20 (2H, d, J 12.2 Hz), 7.13 (1H, dd, J 7.4, 7.4 Hz), 7.21 (1H, dd, J 7.4, 7.4 Hz), 7.61 (2H, apparent d, J 7.9 Hz), 7.74 (2H, d, J 8.4 Hz), 7.85 (2H, d, J 8.4 Hz), 8.04 (2H, br. s).

(Z)-3-(1-(4-amino-2-fluorobut-2-en-1-yl)-2-methyl-1H-pyrrolo[2,3-b]pyridin-3-yl)-N,N dimethylbenzene-sulfonamide Dihydrochloride (Compound 4)

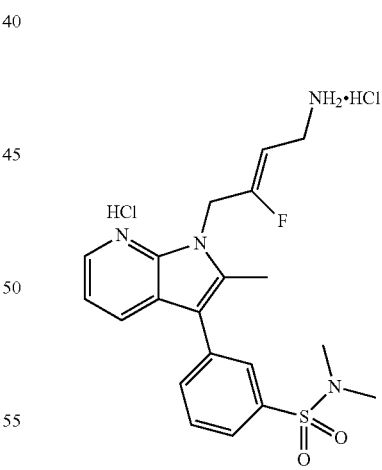

$^1$H NMR (300 MHz, DMSO-d$_6$) δ ppm: 8.31 (dd, J=4.7, 1.5 Hz, 1H), 8.11 (s, 3H), 7.87 (ddd, J=7.6, 1.6 Hz, 1H), 7.84-7.69 (m, 4H), 7.23 (dd, J=7.9, 4.7 Hz, 1H), 5.27 (d, J=11.2 Hz, 2H), 5.02 (dt, J=35.9, 7.3 Hz, 1H), 3.55-3.40 (m, 2H), 2.70 (s, 6H), 2.59 (s, 3H).

135

(Z)-4-(5-chloro-2-methyl-3-(5-(methylsulfonyl)pyridin-3-yl)-1H-indol-1-yl)-3-fluorobut-2-en-1-amine Dihydrochloride (Compound 65)

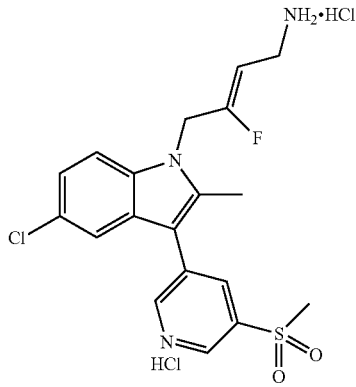

¹H NMR (300 MHz, Methanol-d₄) δ ppm: 9.25 (s, 1H), 9.20 (s, 1H), 8.86 (t, J=2.0 Hz, 1H), 7.69-7.65 (m, 1H), 7.58 (d, J=8.8 Hz, 1H), 7.28 (dd, J=8.7, 2.0 Hz, 1H), 5.20 (d, J=10.2 Hz, 2H), 5.03 (dt, J=34.2, 7.5 Hz, 1H), 3.65 (d, J=7.6 Hz, 3H), 3.42 (s, 3H), 2.63 (s, 3H).

(Z)-4-(5-chloro-2-methyl-3-(pyridin-4-yl)-1H-indol-1-yl)-3-fluorobut-2-en-1-amine Dihydrochloride (Compound 76)

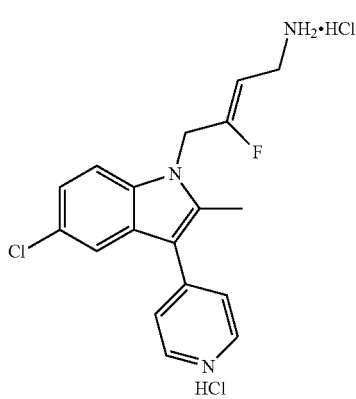

¹H NMR (300 MHz, Methanol-d₄) δ ppm: 8.80 (d, J=7.0 Hz, 2H), 8.20 (d, J=7.0 Hz, 2H), 7.86 (dd, J=2.0, 0.5 Hz, 1H), 7.65-7.60 (m, 1H), 7.34 (dd, J=8.8, 2.0 Hz, 1H), 5.24 (dd, J=11.0, 1.1 Hz, 3H), 5.11 (dt, J=34.1, 7.4 Hz, 1H), 3.65 (d, J=7.4 Hz, 2H), 2.75 (s, 3H).

136

(Z)-4-(5-chloro-2-methyl-3-(pyridin-3-yl)-1H-indol-1-yl)-3-fluorobut-2-en-1-amine Dihydrochloride (Compound 77)

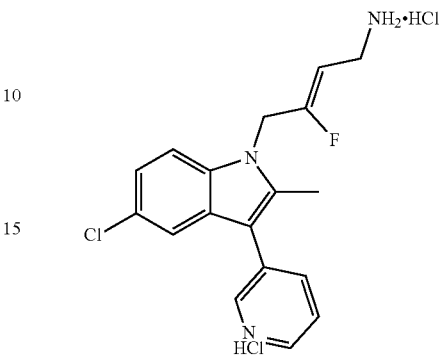

¹H NMR (300 MHz, Methanol-d₄) δ ppm: 8.99 (s, 1H), 8.81 (d, J=5.7 Hz, 1H), 8.74 (ddd, J=8.2, 2.1, 1.4 Hz, 1H), 8.20 (dd, J=8.2, 5.7 Hz, 1H), 7.67 (d, J=2.0 Hz, 1H), 7.56 (d, J=8.8 Hz, 1H), 7.29 (dd, J=8.7, 2.0 Hz, 1H), 5.19 (d, J=10.9 Hz, 1H), 5.05 (dt, J=34.1, 7.5 Hz, 1H), 3.65 (d, J=7.4 Hz, 2H), 2.62 (s, 3H).

(Z)-4-(5-chloro-2-methyl-3-(pyrimidin-5-yl)-1H-indol-1-yl)-3-fluorobut-2-en-1-amine Dihydrochloride (Compound 80)

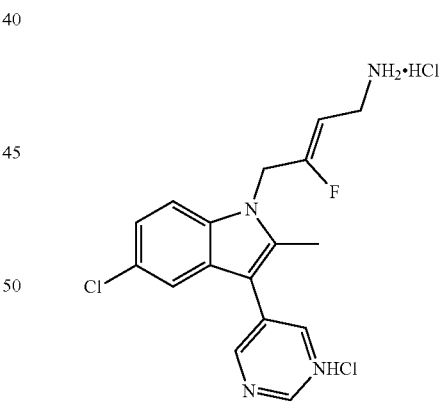

¹H NMR (300 MHz, Methanol-d₄) δ ppm: 9.32 (s, 1H), 9.16 (s, 2H), 7.63 (dd, J=2.0, 0.5 Hz, 1H), 7.55 (d, J=8.7 Hz, 1H), 7.27 (dd, J=8.7, 2.0 Hz, 1H), 5.18 (d, J=10.0 Hz, 2H), 4.98 (dt, J=34.1, 7.5 Hz, 1H), 3.64 (d, J=7.4 Hz, 3H), 2.60 (s, 3H).

(Z)-4-(3-(2,6-dimethylpyridin-4-yl)-2-methyl-5-nitro-1H-indol-1-yl)-3-fluorobut-2-en-1-amine Dihydro-Chloride (Compound 101)

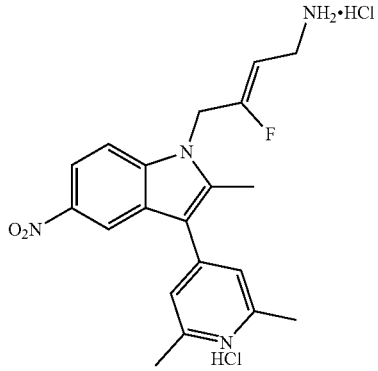

$^1$H NMR (300 MHz, DMSO-d$_6$) δ ppm: 8.58 (d, J=2.2 Hz, 1H), 8.18 (dd, J=9.1, 2.2 Hz, 1H), 8.10 (s, 3H), 7.94 (d, J=9.1 Hz, 1H), 7.86 (s, 2H), 5.41 (d, J=14.1 Hz, 2H), 5.28 (dt, J=36.0, 7.2 Hz, 1H), 3.47 (d, J=6.3 Hz, 1H), 2.77 (s, 6H), 2.68 (s, 3H).

Example 14

The following compounds were prepared according to procedures E, F, G, H, I, J, K, L and O

Methyl (Z)-1-(4-amino-2-fluorobut-2-en-1-yl)-3-(3-(N,N-dimethylsulfamoyl)phenyl)-2-methyl-1H-indole-5-carboxylate Hydrochloride (Compound 5)

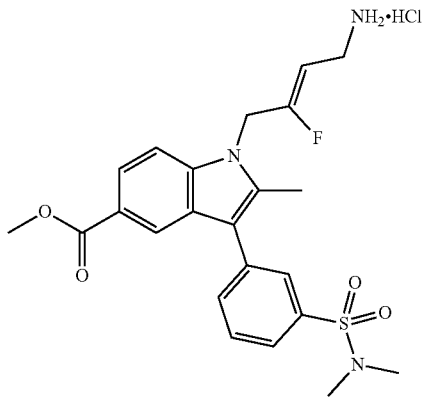

Off-white solid; m.p 242-244° C.; $^1$H-NMR (300 MHz; d$_6$-DMSO) δ ppm: 2.55 (3H, s), 2.73 (6H, s), 3.48 (2H, br. d, J 6.5 Hz), 3.83 (3H, s), 5.09 (1H, dt, J 36.0, 7.1 Hz), 5.27 (2H, d, J 12.7 Hz), 7.71-7.87 (6H, m), 7.91 (2H, br. s), 8.20 (1H, d, J 1.3 Hz).

Methyl (Z)-1-(4-amino-2-fluorobut-2-en-1-yl)-3-(3-(N,N-dimethylsulfamoyl)phenyl)-2-methyl-1H-indole-6-carboxylate Hydrochloride (Compound 7)

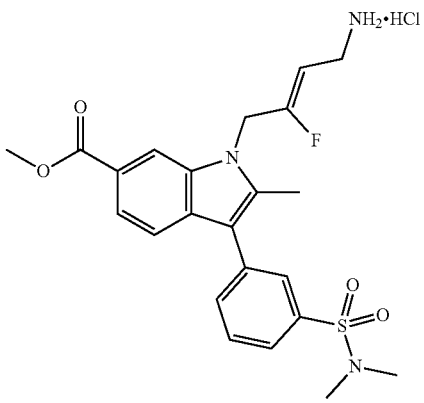

White solid; m.p 265-266° C.; $^1$H-NMR (300 MHz; Methanol-d$_4$) δ ppm: 2.59 (3H, s), 2.78 (6H, s), 3.64 (2H, br. d, J 7.6 Hz), 3.95 (3H, s), 4.87 (1H, dt, J 34.0, 7.5 Hz), 5.23 (2H, d, J 8.7 Hz), 7.61 (1H, d, J 8.3 Hz), 7.76-7.86 (5H, m), 8.22 (1H, d, J 0.9 Hz).

(Z)-3-(1-(4-amino-2-fluorobut-2-en-1-yl)-2-methyl-5-(methylsulfonyl)-1H-indol-3-yl)-N,N-dimethylbenzenesulfonamide Hydrochloride (Compound 97)

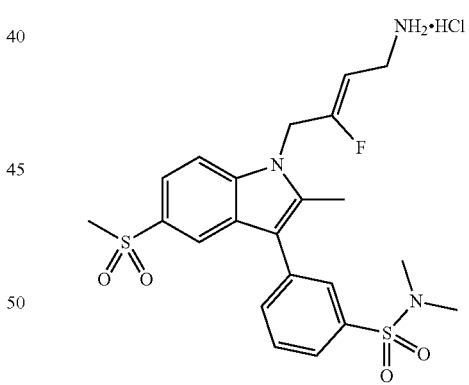

$^1$H NMR (300 MHz, DMSO-d$_6$) δ ppm: 8.07 (s, 3H), 8.06 (d, J=1.9 Hz, 1H), 7.93-7.80 (m, 3H), 7.80-7.71 (m, 3H), 5.33 (d, J=12.8 Hz, 2H), 5.14 (dt, J=36.0, 7.2 Hz, 1H), 3.48 (s, 2H), 3.18 (s, 3H), 2.72 (s, 6H), 2.57 (s, 3H).

Example 15

The following compound was prepared according to procedures F, G, H, I, J, K, L and O.

(Z)-ethyl 1-(4-amino-2-fluorobut-2-en-1-yl)-2-methyl-3-(3-(methylsulfonyl)phenyl)-1H-indole-5-carboxylate Hydrochloride (Compound 17)

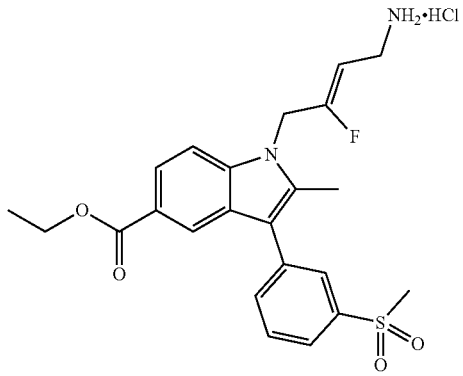

$^1$H NMR (300 MHz, DMSO-d$_6$) δ 8.17 (d, J=1.6 Hz, 1H), 7.99-7.91 (m, 2H), 7.88-7.79 (m, 3H), 7.72 (d, J=8.7 Hz, 1H), 5.27 (d, J=12.7 Hz, 2H), 5.10 (dt, J=35.9, 7.3 Hz, 1H), 4.30 (q, J=7.1 Hz, 2H), 3.54-3.45 (m, 2H), 3.30 (s, 3H), 2.54 (s, 3H), 1.31 (t, J=7.1 Hz, 3H).

Example 16

The following compound was prepared according to procedures K, L and O

(Z)-3-fluoro-4-(3-(4-fluorophenyl)-1H-indol-1-yl)but-2-en-1-amine Hydrochloride (Compound 1)

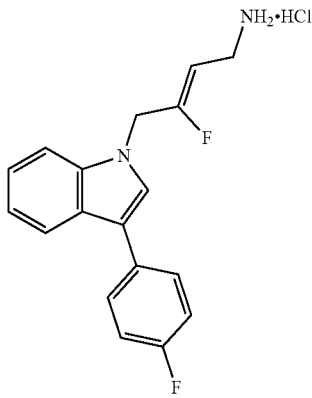

Pale brown; m.p 184-187° C.; $^1$H-NMR (300 MHz; Methanol-d$_4$) δ ppm: 3.62 (2H, br. d, J 7.5 Hz), 4.96 (1H, dt, J 33.8, 7.5 Hz), 5.10 (2H, dd, J 10.7, 0.8 Hz), 7.14-7.22 (3H, m), 7.28 (1H, ddd, J 8.3, 7.1, 1.1 Hz), 7.48 (1H, s), 7.51 (1H, d, J 8.2 Hz), 7.63-7.70 (2H, m), 7.85 (1H, ddd, J 8.0, 1.1, 0.9 Hz).

Example 17

The following compound was prepared according to procedures E, F, G, H, I, J, K, S, L, M and T.

(Z)-1-(4-amino-2-fluorobut-2-en-1-yl)-2-methyl-3-(3-(N-methylsulfamoyl)phenyl)-1H-indole-5-carboxylic Acid Hydrochloride (Compound 18)

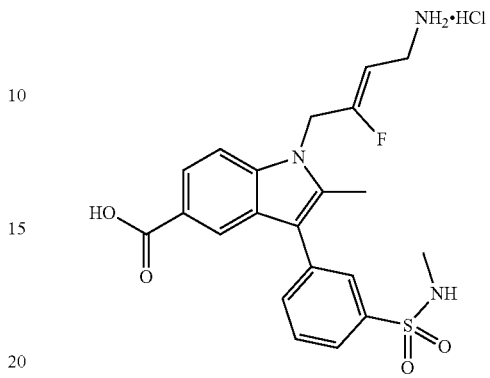

Procedure S: Preparation of Ethyl 3-(3-(N-(4-methoxybenzyl)-N-methylsulfamoyl)phenyl)-2-methyl-1H-indole-5-carboxylate

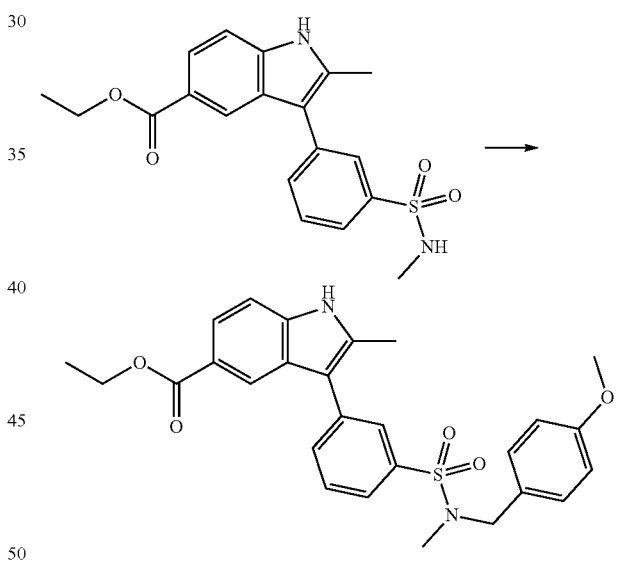

To a stirring suspension of ethyl 2-methyl-3-(3-(N-methylsulfamoyl)phenyl)-1H-indole-5-carboxylate (195 mg, 0.52 mmol) and potassium carbonate (73.0 mg, 0.53 mmol) in DMF (1 mL) at rt was added 4-methoxybenzyl chloride (81 uL, 0.58 mmol) and stirring continued for 3 h. Water (10 mL) was then added and the product was extracted with ethyl acetate (10 mL×3). The combined organic layers were dried over Na$_2$SO$_4$ and concentrated in vacuo. The crude residue thus obtained was purified over silica gel (12 g), eluting with 35% ethyl acetate in n-hexane, to afford ethyl 3-(3-(N-(4-methoxybenzyl)-N-methylsulfamoyl)phenyl)-2-methyl-1H-indole-5-carboxylate (105 mg, 41%) as a white solid. H-NMR (300 MHz; CDCl$_3$) δ ppm: 1.37 (3H, t, J 7.1 Hz), 2.57 (3H, s), 2.70 (3H, s), 3.81 (3H, s), 4.20 (2H, s), 4.37 (2H, q, J 7.1 Hz), 6.88 (2H, d, J 8.7 Hz), 7.28 (2H, d, J 8.6 Hz), 7.39 (1H, d, J 8.5 Hz), 7.69 (1H, dd, J 7.7, 7.7 Hz), 7.78-7.84 (2H, m), 7.93-7.97 (2H, m), 8.26 (1H, br. s), 8.38 (1H, br. s).

Procedure T: Preparation of (Z)-1-(4-amino-2-fluorobut-2-en-1-yl)-2-methyl-3-(3-(N-methylsulfamoyl)phenyl)-1H-indole-5-carboxylic Acid Hydrochloride (Compound 18)

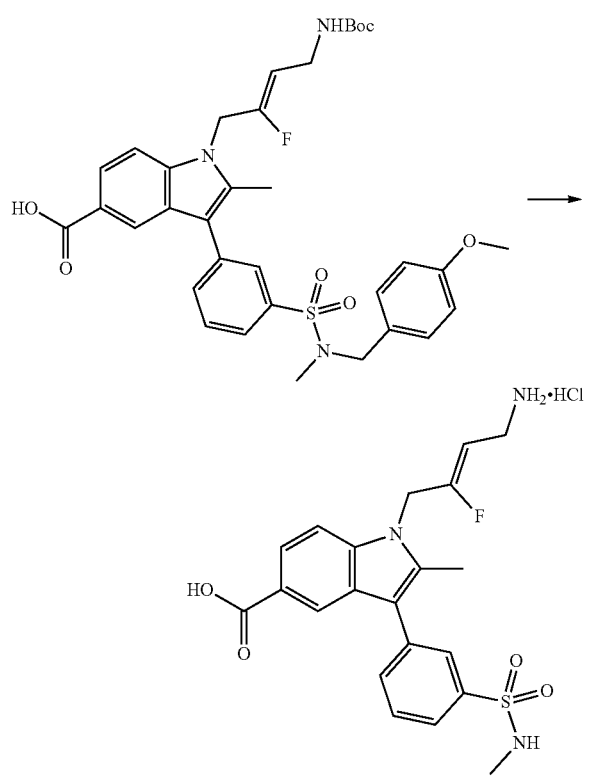

To a stirring solution of (Z)-1-(4-((tert-butoxycarbonyl)amino)-2-fluorobut-2-en-1-yl)-3-(3-(N-(4-methoxybenzyl)-N-methylsulfamoyl)phenyl)-2-methyl-1H-indole-5-carboxylic acid (95 mg, 0.15 mmol) in CH$_2$Cl$_2$ (1 mL), was added triflouroacetic acid (1 mL). The reaction was stirred for 3 hours at rt, then concentrated in vacuo. Ethyl acetate (2 mL) was added followed by ethereal HCl (2 M, 1.00 mL) and the resulting suspension stirred for 5 min forming a fine white precipitate. The solid was collected and dried to afford (Z)-1-(4-amino-2-fluorobut-2-en-1-yl)-2-methyl-3-(3-(N-methylsulfamoyl)phenyl)-1H-indole-5-carboxylic acid hydrochloride (55 mg, 81%) as an off white solid; m.p. 275-278° C.; $^1$H-NMR (300 MHz; DMSO-d$_6$) δ ppm: 2.54 (3H, s), 3.34 (3H, br. s), 3.43-3.54 (2H, m), 5.09 (1H, dt, J 36.0, 7.4 Hz), 5.26 (2H, d, J 12.4 Hz), 7.60 (1H, q, J 5.0 Hz), 7.70 (1H, d, J 8.7 Hz), 7.74-7.87 (5H, m), 7.95 (2H, br. s), 8.17 (1H, d, J 1.1 Hz).

Example 18

The following compound was prepared according to procedures E, F, G, H, I, J, K, L, M and U.

(Z)-1-(4-amino-2-fluorobut-2-en-1-yl)-3-(3-(N,N-dimethylsulfamoyl)phenyl)-2-methyl-1H-indole-5-carboxylic Acid Hydrochloride (Compound 8)

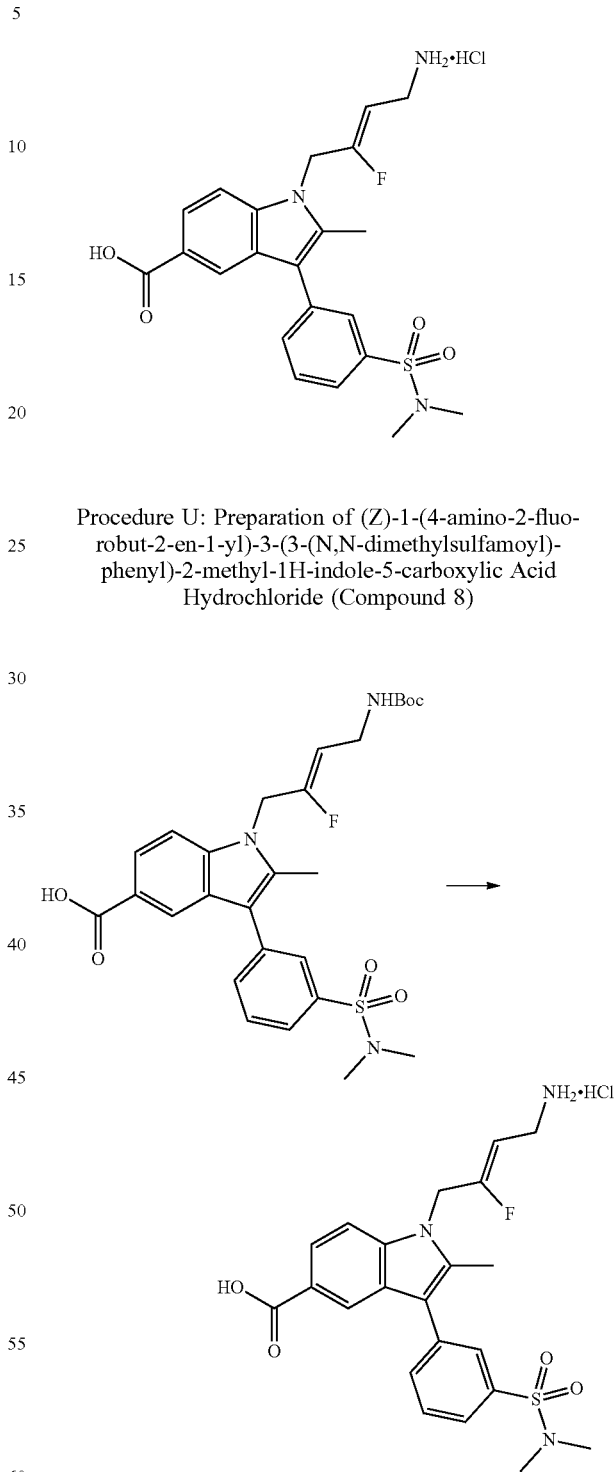

Procedure U: Preparation of (Z)-1-(4-amino-2-fluorobut-2-en-1-yl)-3-(3-(N,N-dimethylsulfamoyl)phenyl)-2-methyl-1H-indole-5-carboxylic Acid Hydrochloride (Compound 8)

To a stirring solution of (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylic acid (200 mg, 0.37 mmol) in CH$_2$Cl$_2$ (4 mL), was added trifluoroacetic acid (1 mL). The resulting mixture was stirred at rt for 1 h then concentrated in vacuo. The solid thus obtained was purified over C-18-reversed phase silica gel (40 g), eluting over a gradient of 20-50% acetonitrile in water (+0.1% HCl) to afford (Z)-1-(4-amino-2-fluorobut-2-en-1-yl)-3-(3-(N,N-dimethylsulfamoyl)phenyl)-2-methyl-1H-indole-5-carboxylic acid hydrochloride (102 mg, 58%) as an off-white solid; m.p. 240-242° C.; $^1$H-NMR (300 MHz; $d_6$-DMSO) δ ppm: 2.55 (3H, s), 2.71 (6H, s), 3.49 (2H, br. d, J 7.0 Hz), 5.07 (1H, dt, J 35.9, 7.3 Hz), 5.26 (2H, d, J 12.8 Hz), 7.70 (1H, d, J 8.7 Hz), 7.73-7.87 (7H, m), 8.20 (1H, d, J 1.2 Hz).

Example 19

The following examples were prepared according to the procedures set forth in Example 18.

(Z)-1-(4-amino-2-fluorobut-2-en-1-yl)-3-(3-(N,N-dimethylsulfamoyl)phenyl)-2-methyl-1H-indole-6-carboxylic Acid Hydrochloride (Compound 9)

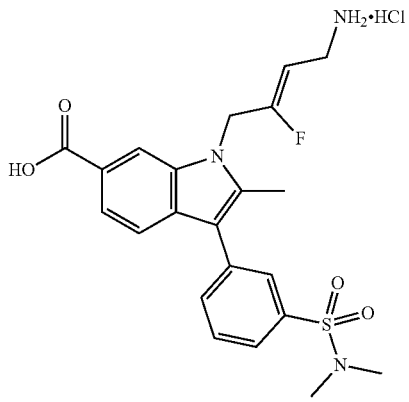

White solid; m.p 255-257° C.; $^1$H-NMR (300 MHz; DMSO-$d_6$) δ ppm: 2.56 (3H, s), 2.70 (6H, s), 3.49 (2H, br. s), 5.02 (1H, dt, J 35.9, 7.3 Hz), 5.32 (2H, d, J 12.0 Hz), 7.58 (1H, d, J 8.3 Hz), 7.70-7.88 (5H, m), 7.94 (2H, br. s), 8.25 (1H, s), 12.67 (1H, s).

(Z)-1-(4-amino-2-fluorobut-2-en-1-yl)-3-(3-(N,N-dimethylsulfamoyl)-2-methylphenyl)-2-methyl-1H-indole-5-carboxylic Acid Hydrochloride (Compound 13)

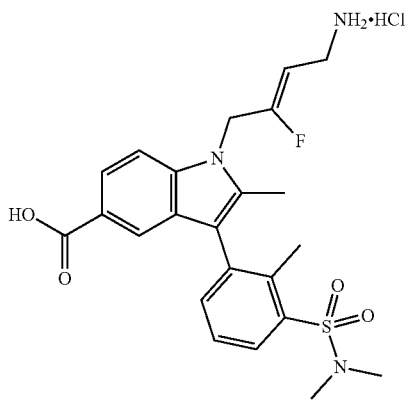

Beige solid; m.p 180-185° C.; $^1$H-NMR (300 MHz; DMSO-$d_6$) δ ppm: 2.28 (3H, s), 2.33 (3H, s), 2.84 (6H, s), 3.44-3.55 (2H, m), 5.03 (1H, dt, J 35.9, 7.2 Hz), 5.23 (2H, d, J 11.7 Hz), 7.51-7.56 (2H, m), 7.67 (1H, d, J 8.7 Hz), 7.70 (1H, d, J 1.2 Hz), 7.79 (1H, dd, J 8.6, 1.5 Hz), 7.82-7.94 (4H, in), 12.50 (1H, br. s).

Example 20

The following compounds were prepared according to procedures E, F, G, H, I, J, K, L and V.

Ethyl (Z)-1-(4-amino-2-fluorobut-2-en-1-yl)-3-(3-(N,N-dimethylsulfamoyl)phenyl)-2-methyl-1H-indole-5-carboxylate Hydrochloride (Compound 12)

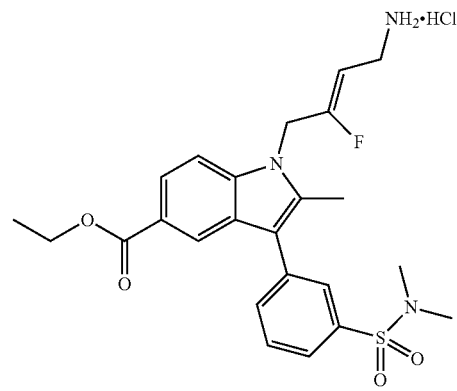

Procedure V: Preparation of ethyl (Z)-1-(4-amino-2-fluorobut-2-en-1-yl)-3-(3-(N,N-dimethylsulfamoyl)phenyl)-2-methyl-1H-indole-5-carboxylate Hydrochloride (Compound 12)

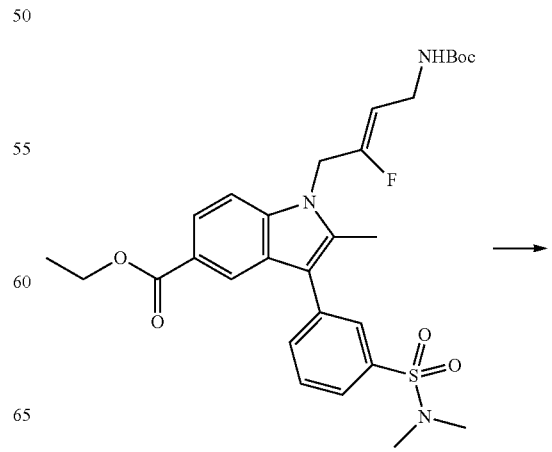

-continued

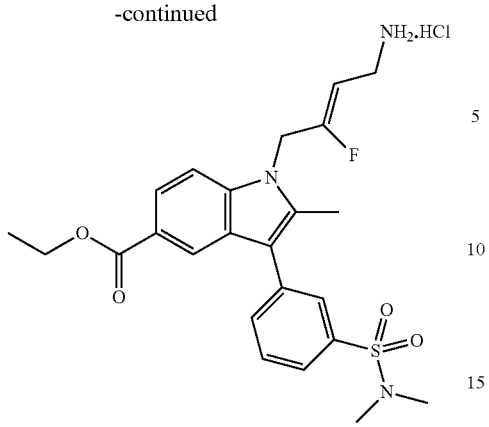

To a stirring solution of ethyl (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylate (510 mg, 0.89 mmol) in ethanol (5 mL) was added HCl (2 M in diethyl ether, 20 mL, 40 mmol). The reaction was stirred for 5 hours at rt, then concentrated in vacuo. Diethyl ether (25 mL) was added and the resulting suspension stirred for 5 min forming a fine, off-white, precipitate. The solid was collected and dried to afford ethyl (Z)-1-(4-amino-2-fluorobut-2-en-1-yl)-3-(3-(N,N-dimethylsulfamoyl)phenyl)-2-methyl-1H-indole-5-carboxylate hydrochloride (403 mg, 89%) as an off-white solid; m.p. 145-147° C.; $^1$H-NMR (300 MHz; Methanol-d$_4$) δ ppm: 1.38 (3H, t, J 7.1 Hz), 2.59 (3H, s), 2.81 (6H, s), 3.64 (2H, br. d, J 7.3 Hz), 4.36 (2H, q, J 7.1 Hz), 4.88 (1H, dt, J 33.8, 7.5 Hz), 5.19 (2H, d, J 8.8 Hz), 7.58 (1H, d, J 8.7 Hz), 7.78-7.83 (3H, m), 7.87 (1H, br. s), 7.94 (1H, dd, J 8.7, 1.6 Hz), 8.29 (1H, d, J 1.2 Hz).

(Z)-ethyl 1-(4-amino-2-fluorobut-2-en-1-yl)-3-(3-(N,N-dimethylsulfamoyl)phenyl)-6-fluoro-2-methyl-1H-indole-5-carboxylate Hydrochloride (Compound 22)

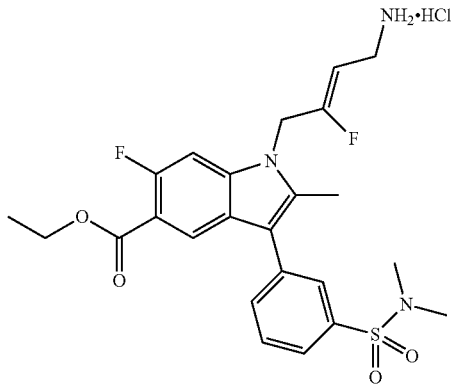

$^1$H NMR (300 MHz, DMSO-d$_6$) δ ppm: 8.05 (d, J=6.9 Hz, 1H), 8.02 (s, 1H), 7.86-7.72 (m, 4H), 7.67 (d, J=12.2 Hz, 1H), 5.24 (d, J=13.0 Hz, 2H), 5.13 (dt, J=36.1, 7.4 Hz, 1H), 3.56-3.42 (m, 4H), 2.72 (s, 6H), 2.52 (s, 3H), 1.06 (t, J=7.0 Hz, 3H).

Example 21

The following compound was prepared according to procedures W, F, G, H, I, J, K, L and V.

Ethyl (Z)-1-(4-amino-2-fluorobut-2-en-1-yl)-3-(5-(N,N-dimethylsulfamoyl)-2-methylphenyl)-2-methyl-1H-indole-5-carboxylate Hydrochloride (Compound 19)

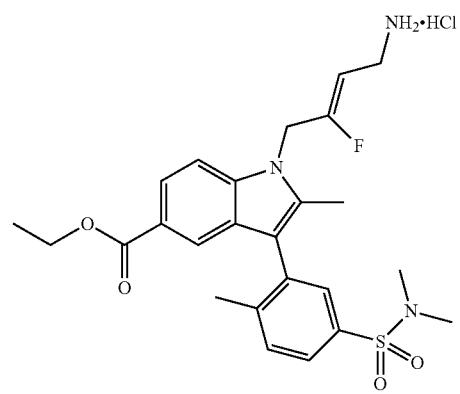

Procedure W: Preparation of 3-bromo-N,N,-dimethylbenzenecarboxamide

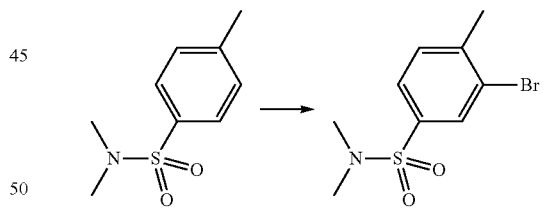

To a stirring mixture of N,N,4-trimethylbenzenesulfonamide (1.00 g, 5.0 mmol) in concentrated sulfuric acid (4.5 mL, 84 mmol) at rt was added 1-bromopyrrolidine-2,5-dione (983 mg, 5.5 mmol) and the resulting solution allowed to stir at rt for 3 h. The reaction mixture was then poured into cold water and the resulting off-white precipitate filtered and dried to afford 3-bromo-N,N,4-trimethyl-benzenesulfonamide (1.36 g, 97%) as a white solid. $^1$H-NMR (300 MHz; Methanol-d$_4$) δ ppm: 2.50 (3H, s), 2.70 (6H, s), 7.56 (1H, d, J 8.0 Hz), 7.67 (1H, dd, J 8.0, 1.8 Hz), 7.93 (1H, d, J 1.8 Hz).

Ethyl (Z)-1-(4-amino-2-fluorobut-2-en-1-yl)-3-(5-(N,N-dimethylsulfamoyl)-2-methylphenyl)-2-methyl-1H-indole-5-carboxylate Hydrochloride (Compound 19)

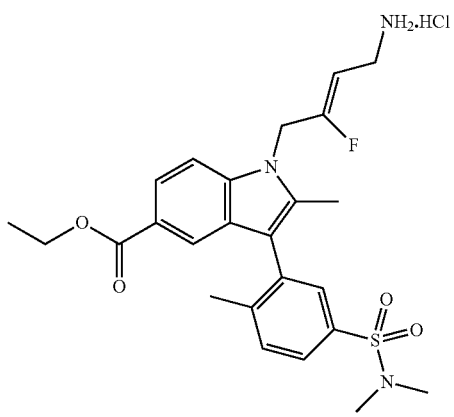

Off-white solid; m.p 147-150° C.; $^1$H-NMR (300 MHz; DMSO-d) δ ppm: 1.28 (3H, t, J 7.1 Hz), 2.22 (3H, s), 2.32 (3H, s), 2.68 (6H, s), 3.49 (2H, d, J 7.1 Hz), 4.26 (2H, q, J 7.1 Hz), 5.05 (1H, dt, J 35.5, 7.2 Hz), 5.25 (2H, d, J 12.0 Hz), 7.53 (1H, s), 7.70-7.83 (5H, m), 7.91 (2H, br. s).

Example 22

The following compound was prepared according to procedures F, G, H, I, J, K, L M and U.

(Z)-1-(4-amino-2-fluorobut-2-en-1-yl)-2-methyl-3-(3-(methylsulfonyl)phenyl)-1H-indole-5-carboxylic Acid Hydrochloride (Compound 14)

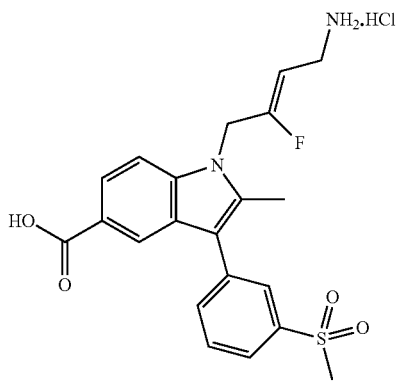

Off-white solid; m.p 268-269° C.; $^1$H-NMR (300 MHz; Methanol-d$_4$) δ ppm: 2.58 (3H, s), 3.22 (3H, s), 3.64 (2H, br. d, J 7.3 Hz), 4.88 (1H, dt, J 34.0, 7.5 Hz), 5.19 (2H, d, J 8.8 Hz), 7.57 (1H, d, J 8.7 Hz), 7.82 (1H, dd, J 7.5, 7.5 Hz), 7.87 (1H, ddd, J 7.7, 1.5, 1.5 Hz), 7.95 (1H, dd, J 8.9, 1.6 Hz), 7.98 (1H, ddd, J 7.7, 1.5, 1.5 Hz), 8.03 (1H, s), 8.28 (1H, d, J 1.2 Hz).

Example 23

The following compound was prepared according to procedures W, F, G, H, I, J, K, L, M and U.

(Z)-1-(4-amino-2-fluorobut-2-en-1-yl)-3-(5-(N,N-dimethylsulfamoyl)-2-methylphenyl)-2-methyl-1H-indole-5-carboxylic Acid Hydrochloride (Compound 20)

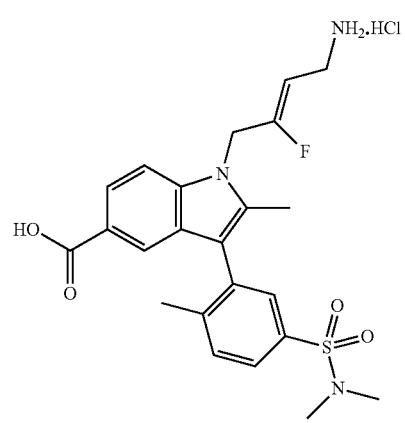

Off-white solid; m.p 248-251° C.; $^1$H-NMR (300 MHz; DMSO-d$_6$) δ ppm: 2.21 (3H, s), 2.33 (3H, s), 2.66 (3H, s), 3.45-3.55 (2H, m), 5.06 (1H, dt, J 35.9, 7.1 Hz), 5.24 (2H, d, J 12.2 Hz), 7.52 (1H, s), 7.67-7.82 (5H, m), 7.98 (2H, br. s), 12.47 (1H, br. s).

Example 24

The following compound was prepared according to procedures G, H, I, J, K, L, X and O.

(Z)-3-(1-(4-amino-2-fluorobut-2-en-1-yl)-2-methyl-5-(2H-tetrazol-5-yl)-1H-indol-3-yl)-N,N-dimethyl-benzenesulfonamide Hydrochloride (Compound 29)

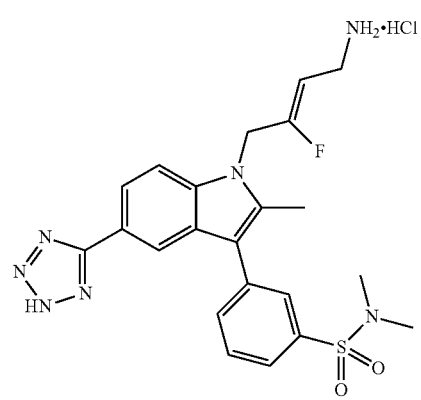

149

Procedure X: Preparation of (Z)-3-(1-(4-amino-2-fluorobut-2-en-1-yl)-2-methyl-5-(2H-tetrazol-5-yl)-1H-indol-3-yl)-N,N-dimethylbenzenesulfonamide Hydrochloride (Compound 29)

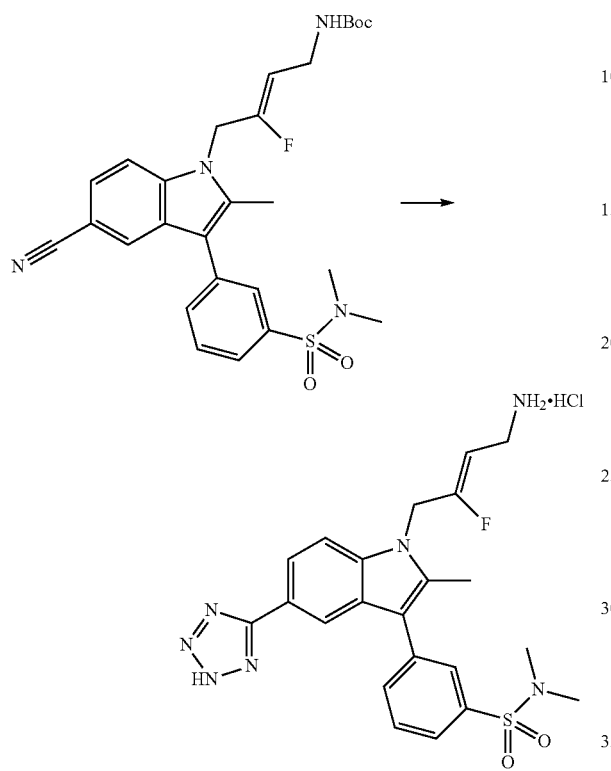

A stirring solution of tert-butyl (Z)-(4-(5-cyano-3-(3-(N,N-dimethylsulfamoyl)phenyl)-2-methyl-1H-indol-1-yl)-3-fluorobut-2-en-1-yl)carbamate (120 mg, 0.23 mmol), triethylamine hydrochloride (94.1 mg, 0.68 mmol) and sodium azide (44.4 mg, 0.68 mmol) in DMF (2 mL) under $N_2$ was heated at 100° C. for 5 h. The reaction mixture was partitioned between aq. HCl (2 M, 20 mL) and ethyl acetate (20 mL). The organic layer was washed with sat aq. NaCl (20 mL), dried over $Na_2SO_4$. $^1$H-NMR analysis of the crude material indicated only 10% conversion. The crude residue was taken up in toluene (2 mL) and to this was added triethylamine hydrochloride (94.1 mg, 0.68 mmol) followed by sodium azide (44.4 mg, 0.68 mmol). The resulting mixture was heated under reflux for 12 h. The reaction mixture was partitioned between aq. HCl (2 M, 20 mL) and ethyl acetate (20 mL). The organic layer was washed with sat aq. NaCl (20 mL), dried over $Na_2SO_4$. The crude material was purified over silica gel (adsorbed onto 1 g; 10 g silica in total) eluting with 50% ethyl acetate in hexane followed by ethyl acetate to give (Z)-3-(1-(4-amino-2-fluorobut-2-en-1-yl)-2-methyl-5-(2H-tetrazol-5-yl)-1H-indol-3-yl)-N,N-dimethylbenzenesulfonamide hydrochloride (14.0 mg, 11%). $^1$H NMR (300 MHz, Methanol-$d_4$) δ ppm: 8.27 (dd, J=1.7, 0.6 Hz, 1H), 7.92 (dd, J=8.6, 1.7 Hz, 1H), 7.89-7.79 (m, 4H), 7.73 (d, J=8.6 Hz, 1H), 5.22 (d, J=9.4 Hz, 2H), 4.96 (dt, J=34.1, 7.3 Hz, 1H), 3.65 (d, J=7.4 Hz, 2H), 2.80 (s, 6H), 2.60 (s, 3H).

150

Example 25

The following compound was prepared according to procedures G, H, I, J, Y, K, L, M, N and O.

(Z)-1-(4-amino-2-fluorobut-2-en-1-yl)-N,N,2-trimethyl-3-(3-(N-methylmethylsulfonamido)phenyl)-1H-indole-5-carboxamide Hydrochloride (Compound 39)

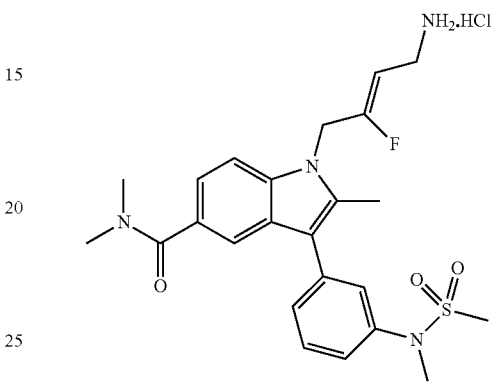

Procedure Y: Preparation of 1-(tert-butyl) 5-ethyl 2-methyl-3-(3-(N-methylmethylsulfonamido)phenyl)-1H-indole-1,5-dicarboxylate

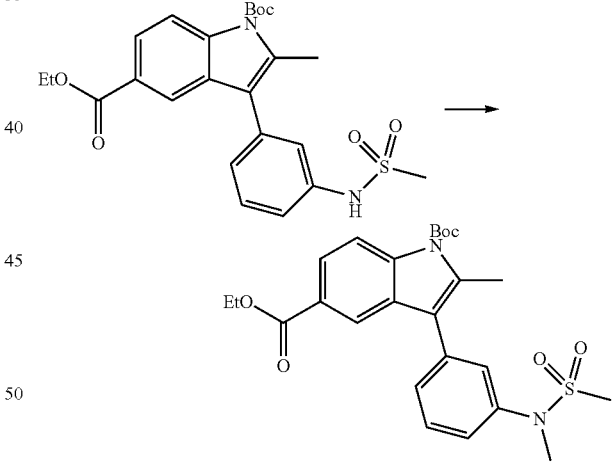

To a stirring solution of 1-(tert-butyl) 5-ethyl 2-methyl-3-(3-(methylsulfonamido)phenyl)-1H-indole-1,5-dicarboxylate (150 mg, 0.32 mmol) in DMF (3 mL) was added potassium carbonate (65.8 mg, 0.48 mmol) followed by iodomethane (30 uL, 0.48 mmol). The resulting reaction mixture was stirred at rt overnight. Water (20 mL) was added to the reaction mixture, and the resulting precipitated solid was isolated by filtration. The solid was dissolved in dichloromethane, and then dried over $MgSO_4$. After removal of the solvent in vacuo, 1-(tert-butyl) 5-ethyl 2-methyl-3-(3-(N-methylmethylsulfonamido)phenyl)-1H-indole-1,5-dicarboxylate (153 mg, 99%) was afforded as a white solid. $^1$H NMR (300 MHz, $CDCl_3$) δ ppm: 8.23 (dd, J=8.8, 0.7 Hz, 1H), 8.17 (dd, J=1.8, 0.7 Hz, 1H), 8.01 (dd, J=8.8, 1.8 Hz, 1H), 7.55 (t, J=7.7 Hz, 1H), 7.39-7.48 (m, 3H), 4.39 (q, J=7.1 Hz, 2H), 3.41 (s, 3H), 2.94 (s, 3H), 2.65 (s, 3H), 1.74 (s, 9H), 1.40 (t, J=7.1 Hz, 3H).

(Z)-1-(4-amino-2-fluorobut-2-en-1-yl)-N,N,2-trimethyl-3-(3-(N-methylmethylsulfonamido)phenyl)-1H-indole-5-carboxamide Hydrochloride (Compound 39)

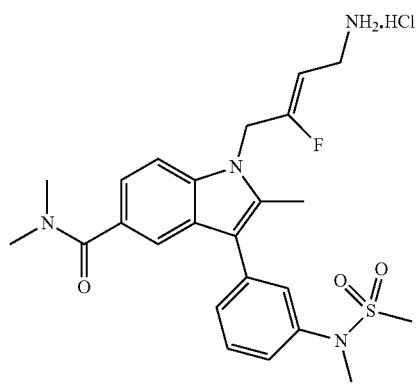

$^1$H NMR (300 MHz, DMSO-d$_6$) δ ppm: 8.20 (d, J=1.5 Hz, 1H), 7.80 (dd, J=8.6, 1.6 Hz, 1H), 7.67 (d, J=8.7 Hz, 1H), 7.59 (d, J=7.7 Hz, 1H), 7.49-7.40 (m, 3H), 5.23 (d, J=12.6 Hz, 2H), 5.06 (dt, J=36.2, 7.2 Hz, 1H), 3.49 (d, J=7.2 Hz, 2H), 3.32 (d, J=2.5 Hz, 6H), 3.00 (s, 3H), 2.53 (s, 3H).

Example 26

The following compound was prepared according to procedures G, H, I, J, Y, K, L, and O.

(Z)-1-(4-amino-2-fluorobut-2-en-1-yl)-2-methyl-3-(3-(N-methylmethylsulfonamido)phenyl)-1H-indole-5-carboxylic Acid Hydrochloride (Compound 38)

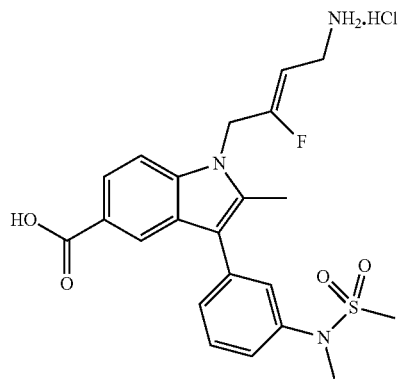

$^1$H NMR (300 MHz, DMSO-d$_6$) δ ppm: 8.20 (d, J=1.5 Hz, 1H), 7.80 (dd, J=8.6, 1.6 Hz, 1H), 7.67 (d, J=8.7 Hz, 1H), 7.59 (dd, J=7.7 Hz, 1H), 7.50-7.40 (m, 3H), 5.23 (d, J=12.6 Hz, 2H), 5.06 (dt, J=36.0, 7.2 Hz, 1H), 3.49 (d, J=7.1 Hz, 2H), 3.32 (s, 5H), 3.00 (s, 3H), 2.53 (s, 1H).

Example 27

The following compounds were prepared according to procedures Z, G, H, I, J, K, L and O.

Ethyl (Z)-3-(1-(4-amino-2-fluorobut-2-en-1-yl)-5-(N,N-dimethylsulfamoyl)-2-methyl-1H-indol-3-yl)benzoate Hydrochloride (Compound 33)

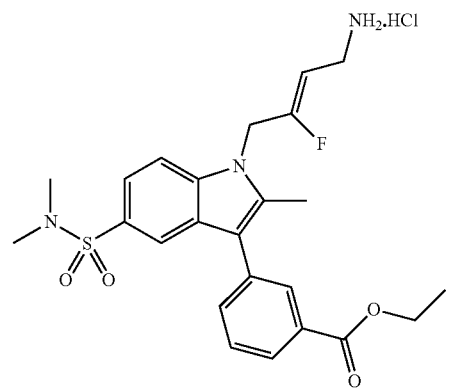

Procedure Z: Preparation of 3-fluoro-N,N-dimethyl-4-nitrobenzenesulfonamide

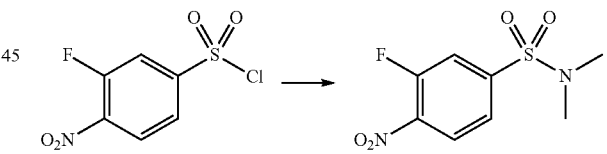

To a stirring solution of dimethylamine hydrochloride (340 mg, 4.17 mmol) in dichloromethane at 0° C. was added triethylamine (1.28 mL, 9.18 mmol). After stirring for 2 mins, 3-fluoro-4-nitrobenzenesulfonyl chloride (1.00 g, 4.17 mmol) was added in one portion. The resulting mixture was stirred at 0° C. for a further 20 mins. The reaction mixture was partitioned between dichloromethane (30 mL) and water (10 mL) and the organic layer was washed with sat. aq. NaCl, dried over MgSO$_4$ and concentrated in vacuo to afford 3-fluoro-N,N-dimethyl-4-nitrobenzenesulfonamide (1.02 g, 98%) as a yellow solid. $^1$H NMR (300 MHz, CDCl$_3$) δ ppm: 8.23 (dd, J=8.7, 6.8 Hz, 1H), 7.77-7.69 (m, 2H), 2.83 (s, 6H), 1.57 (s, 3H).

153

Ethyl (Z)-3-(1-(4-amino-2-fluorobut-2-en-1-yl)-5-(N,N-dimethylsulfamoyl)-2-methyl-1H-indol-3-yl)benzoate Hydrochloride (Compound 33)

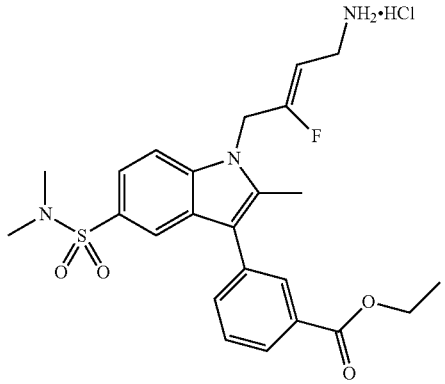

$^1$H NMR (300 MHz, DMSO-d$_6$) δ ppm: 8.04 (d, J=1.8 Hz, 1H), 7.98 (dt, J=7.4, 1.6 Hz, 1H), 7.95 (s, 3H), 7.87 (d, J=8.7 Hz, 1H), 7.84 (d, J=1.7 Hz, 1H), 7.77 (dt, J=7.7, 1.7 Hz, 1H), 7.72 (d, J=7.5 Hz, 1H), 7.57 (dd, J=8.6, 1.8 Hz, 1H), 5.30 (d, J=13.0 Hz, 2H), 5.13 (dt, J=36.0, 7.3 Hz, 1H), 4.35 (q, J=7.1 Hz, 2H), 3.50 (d, J=8.6 Hz, 2H), 2.59 (s, 6H), 2.55 (s, 3H), 1.33 (t, J=7.1 Hz, 3H).

(Z)-1-(4-amino-2-fluorobut-2-en-1-yl)-N,N,2-trimethyl-3-(pyridin-4-yl)-1H-indole-5-sulfonamide Dihydrochloride (Compound 81)

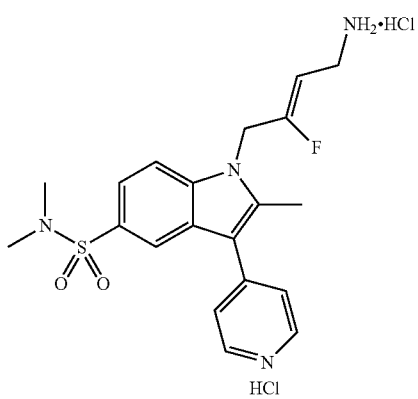

$^1$H NMR (300 MHz, DMSO-d$_6$) δ ppm: 8.93 (d, J=6.8 Hz, 2H), 8.18 (s, 3H), 8.11 (d, J=6.8 Hz, 1H), 8.05 (d, J=1.7 Hz, 1H), 7.98 (d, J=8.7 Hz, 1H), 7.65 (dd, J=8.7, 1.7 Hz, 1H), 5.37 (d, J=1.9 Hz, 2H), 5.31 (dt, J=35.2, 7.6 Hz, 1H), 3.53-3.42 (m, 2H), 2.71 (s, 3H), 2.62 (s, 6H).

154

(Z)-1-(4-amino-2-fluorobut-2-en-1-yl)-N,N,2-trimethyl-3-phenyl-1H-indole-5-sulfonamide (Compound 86)

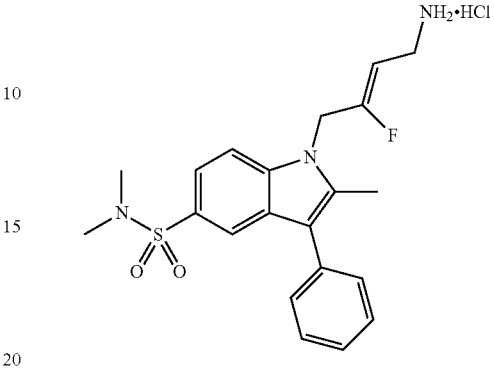

$^1$H NMR (300 MHz, Methanol-d$_4$) δ ppm: 7.95 (d, J=1.5 Hz, 1H), 7.70 (d, J=8.7 Hz, 1H), 7.61 (dd, J=8.6, 1.8 Hz, 1H), 7.57-7.50 (m, 2H), 7.50-7.44 (m, 2H), 7.43-7.36 (m, 1H), 5.21 (d, J=9.9 Hz, 1H), 4.91 (dt, J=35.3, 7.5 Hz, 1H), 3.64 (d, J=7.4 Hz, 2H), 2.65 (s, 6H), 2.57 (s, 3H).

Example 28

The following compound was prepared according to procedures E, F, Z, G, H, I, J, K, L and O.

(Z)-1-(4-amino-2-fluorobut-2-en-1-yl)-3-(3-(N,N-dimethylsulfamoyl)phenyl)-N,N,2-trimethyl-1-indole-5-sulfonamide Hydrochloride (Compound 58)

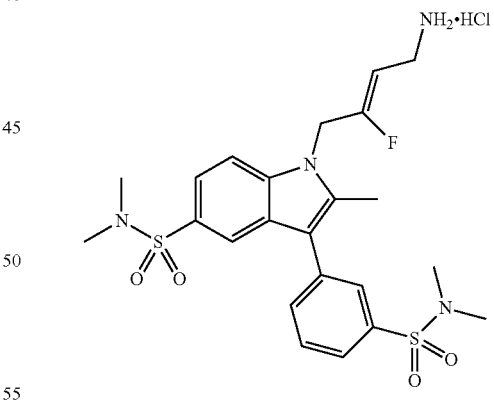

$^1$H NMR (300 MHz, Methanol-d$_4$) δ ppm: 7.99 (d, J=1.7 Hz, 1H), 7.89 (s, 1H), 7.83-7.79 (m, 3H), 7.74 (d, J=8.7 Hz, 1H), 7.65 (dd, J=8.7, 1.7 Hz, 1H), 5.24 (d, J=9.7 Hz, 2H), 4.94 (dt, J=34.4, 7.3 Hz, 1H), 3.65 (d, J=7.4 Hz, 2H), 2.80 (s, 6H), 2.67 (s, 6H), 2.62 (s, 3H).

Example 29

The following compound was prepared according to procedures Z, G, H, I, J, K, L, AA and U.

(Z)-3-(1-(4-amino-2-fluorobut-2-en-1-yl)-5-(N,N-dimethylsulfamoyl)-2-methyl-1H-indol-3-yl)benzoic Acid Hydrochloride (Compound 34)

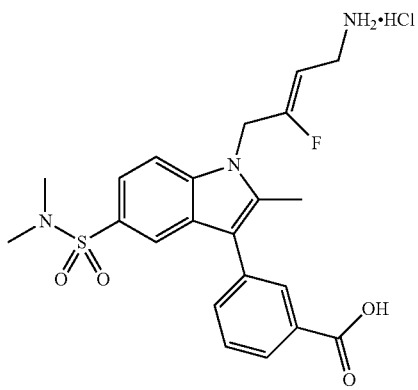

Procedure AA: Preparation of (Z)-3-(1-(4-((tert-butoxycarbonyl)amino)-2-fluorobut-2-en-1-yl)-5-(N,N-dimethylsulfamoyl)-2-methyl-1H-indol-3-yl)benzoic Acid

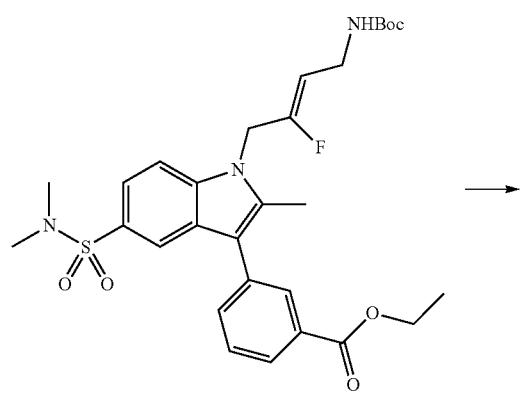

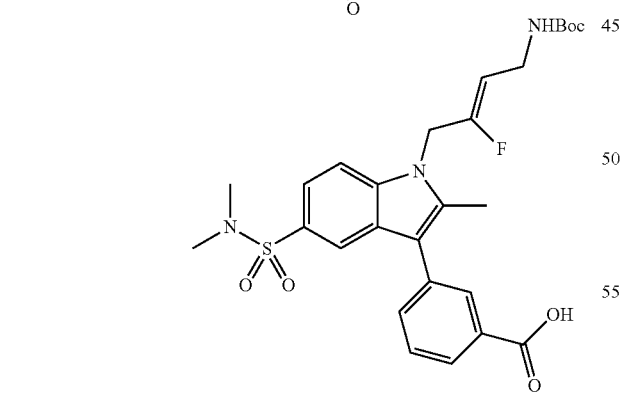

In a 25 mL round bottom, ethyl (Z)-3-(1-(4-((tert-butoxycarbonyl)amino)-2-fluorobut-2-en-1-yl)-5-(N,N-dimethylsulfamoyl)-2-methyl-1H-indol-3-yl)benzoate (120 mg, 0.21 mmol) was added, followed by MeOH (2 mL), THF (2 mL) and aqueous KOH (10 w %, 2 mL). The resulting mixture was stirred at 60° C. for 2 h. The reaction mixture was then concentrated in vacuo. To the residue was added water (10 mL), and the aqueous mixture was acidified to pH=4.5 by addition of 2M aq. HCl. The resulting white solid was collected by filtration, and the solid "cake" was washed with water (2 mL×3). The solid was re-dissolved in ethyl acetate, and organics were dried over $Na_2SO_4$, and concentrated in vacuo to give (Z)-3-(1-(4-((tert-butoxycarbonyl)amino)-2-fluorobut-2-en-1-yl)-5-(N,N-dimethylsulfamoyl)-2-methyl-1H-indol-3-yl)benzoic acid (110 mg, 96%) as a pale yellow foam. $^1$H NMR (300 MHz, CDCl$_3$) δ ppm: 8.19 (t, J=1.8 Hz, 1H), 8.12 (dt, J=7.8, 1.5 Hz, 1H), 8.04 (d, J=1.7 Hz, 1H), 7.73 (dt, J=7.7, 1.5 Hz, 1H), 7.67-7.58 (m, 2H), 7.44 (d, J=8.7 Hz, 1H), 4.88 (d, J=10.5 Hz, 2H), 3.83 (s, 2H), 2.71 (s, 6H), 2.54 (s, 3H), 1.43 (s, 9H).

(Z)-3-(1-(4-amino-2-fluorobut-2-en-1-yl)-5-(N,N-dimethylsulfamoyl)-2-methyl-1H-indol-3-yl)benzoic Acid Hydrochloride (Compound 34)

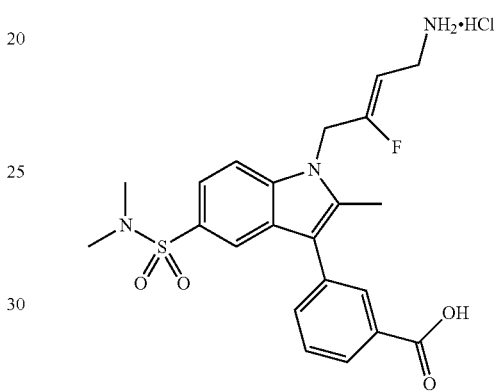

$^1$H NMR (300 MHz, DMSO-d$_6$) δ ppm: 13.08 (s, 1H), 8.02 (d, J=1.8 Hz, 1H), 7.96 (dt, J=7.3, 1.7 Hz, 1H), 7.93 (s, 3H), 7.87 (d, J=8.9 Hz, 1H), 7.84 (d, J=1.8 Hz, 1H), 7.74 (dt, J=7.7, 1.7 Hz, 1H), 7.70 (d, J=7.5 Hz, 1H), 7.56 (dd, J=8.6, 1.8 Hz, 1H), 5.30 (d, J=12.8 Hz, 2H), 5.12 (dt, J=35.9, 7.3 Hz, 1H), 3.49 (s, 2H), 2.58 (s, 6H), 2.55 (s, 3H).

Example 30

The following compound was prepared according to procedures Z, G, H, I, J, K, L, AB and AC.

(Z)-3-(1-(4-amino-2-fluorobut-2-en-1-yl)-5-hydroxy-2-methyl-1H-indol-3-yl)-N,N-dimethylbenzene-sulfonamide Hydrochloride (Compound 37)

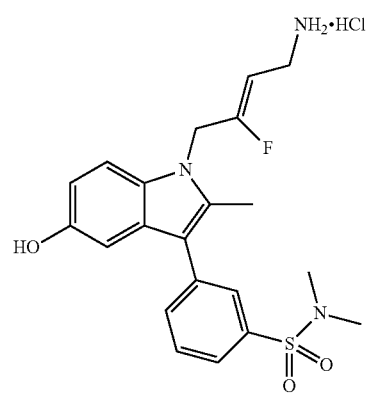

Procedure AB: Preparation of 2-methyl-1H-indol-5-yl 4-nitrobenzoate

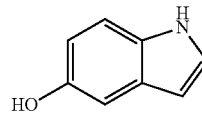

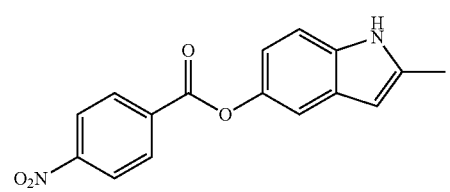

HATU (1.36 g, 3.60 mmol) was added to a solution of 4-nitrobenzoic acid (552 mg, 3.30 mmol), 2-methyl-1H-indol-5-ol (442 mg, 3.00 mmol), triethylamine (1.46 mL, 10.5 mmol) in DMF (6 mL). The mixture was stirred at rt for 2 hours and then left overnight at ambient temperature. Water (60 mL) was added to the reaction mixture, and the suspension was stirred at rt for 10 min. The yellow solid was filtered and washed with water (25 mL). The solid was dried in oven at 60° C. for 1 h to afford 2-methyl-1H-indol-5-yl 4-nitrobenzoate (900 mg, 100%) as a yellow solid. $^1$H NMR (300 MHz, CDCl$_3$) δ ppm: 8.43 (d, J=9.1 Hz, 2H), 8.37 (d, J=9.1 Hz, 2H), 7.98 (s, 1H), 7.36 (d, J=2.4 Hz, 1H), 7.33 (dt, J=8.7, 0.7 Hz, 1H), 6.97 (dd, J=8.6, 2.3 Hz, 1H), 6.26 (dt, J=2.2, 1.0 Hz, 1H), 2.49 (d, J=1.0 Hz, 2H).

Procedure AC: Preparation of (Z)-3-(1-(4-amino-2-fluorobut-2-en-1-yl)-5-hydroxy-2-methyl-1H-indol-3-yl)-N,N-dimethylbenzenesulfonamide Hydrochloride

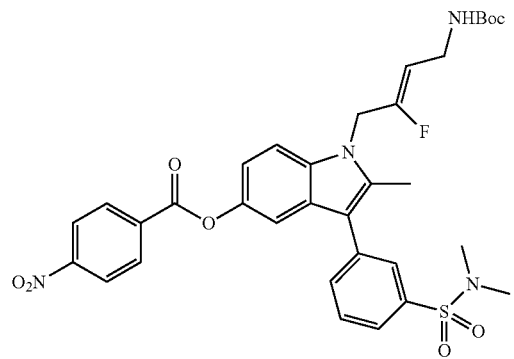

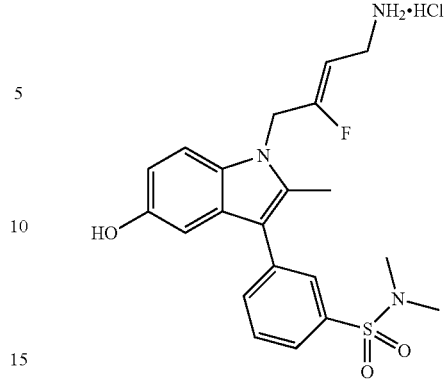

To a stirring solution of (Z)-1-(4-((tert-butoxycarbonyl)amino)-2-fluorobut-2-en-1-yl)-3-(3-(N,N-dimethylsulfamoyl)phenyl)-2-methyl-1H-indol-5-yl 4-nitrobenzoate (50.0 mg, 0.08 mmol) in methanol (1 mL) at rt was added aqueous sodium hydroxide (2 M, 75 uL, 0.15 mmol). The resulting mixture was stirred at rt for 1 h. Ethereal HCl (2.0 M, 4.00 mL, 8.00 mmol) was added and stirring was continued for 2 h. The reaction mixture was concentrated under vacuum. Methanol (2 mL) was then added and the precipitated inorganics were filtered off. The filtrate was concentrated again under vacuum and to the residue was added ethyl acetate (3 mL). The residue was triturated and the supernatant was decanted off. This was repeated two more times to ensure complete removal of the 4-nitrobenzoic acid. The solid was isolated and then dried in an oven at 60° C. for 2 h to give (Z)-3-(1-(4-amino-2-fluorobut-2-en-1-yl)-5-hydroxy-2-methyl-1H-indol-3-yl)-N,N-dimethylbenzenesulfonamide hydrochloride (21.0 mg, 62%) as an off-white solid. $^1$H NMR (300 MHz, DMSO-d$_6$) δ ppm: 8.90 (s, 1H), 8.00 (s, 3H), 7.79-7.64 (m, 3H), 7.38 (d, J=8.7 Hz, 1H), 6.89 (d, J=2.3 Hz, 1H), 6.70 (dd, J=8.7, 2.3 Hz, 1H), 5.09 (d, J=11.7 Hz, 2H), 5.01 (dt, J=37.1, 7.2 Hz, 1H), 3.47 (s, 2H), 3.32 (s, 6H), 2.70 (s, 3H).

(Z)-3-(1-(4-amino-2-fluorobut-2-en-1-yl)-5-hydroxy-2-methyl-1H-indol-3-yl)-N,N-dimethylbenzene-sulfonamide Hydrochloride (Compound 37)

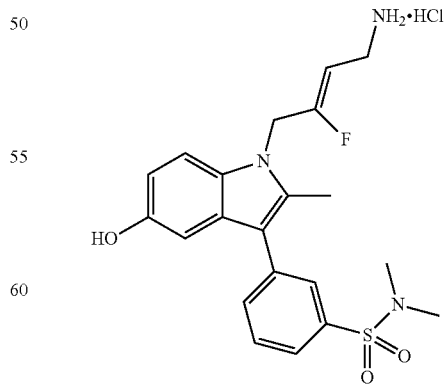

$^1$H NMR (300 MHz, DMSO-d$_6$) δ ppm: 8.90 (s, 1H), 8.00 (s, 3H), 7.80-7.63 (m, 4H), 7.38 (d, J=8.7 Hz, 1H), 6.89 (d, J=2.3 Hz, 1H), 6.70 (dd, J=8.7, 2.3 Hz, 1H), 5.09 (d, J=11.7 Hz, 2H), 5.01 (dt, J=34.5, 7.1 Hz, 1H), 3.47 (s, 2H), 2.70 (s, 6H), 2.47 (s, 3H).

Example 31

The following compound was prepared according to procedures AD, AE, G, H, I, J, K, L, M and AF (Z)-1-(4-amino-2-fluorobut-2-en-1-yl)-3-(5-(N,N-dimethylsulfamoyl)pyridin-3-yl)-2-methyl-1H-indole-5-carboxylic Acid Dihydrochloride (Compound 40)

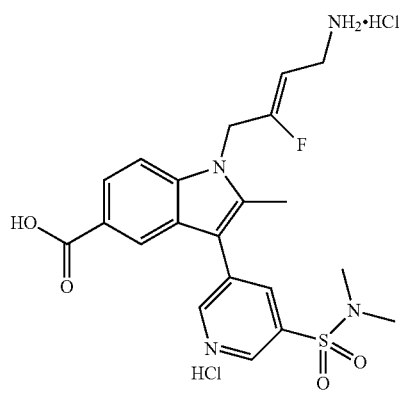

Procedure AD: Preparation of N,N-dimethylpyridine-3-sulfonamide

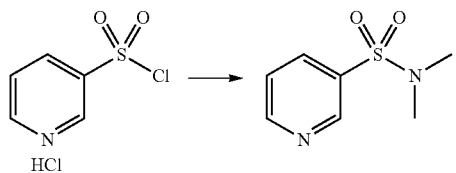

To a stirring suspension of pyridine-3-sulfonyl chloride hydrochloride (8.00 g, 37.4 mmol) in THF (80 mL) at 0° C. was added dimethylamine solution (40 w % in water; 25.0 mL, 187 mmol) drop-wise over 5 min. The resulting homogeneous mixture was left to stir at 0° C. for 30 min and then rt for a further 1 h. The reaction mixture was partitioned between water (100 mL) and ethyl acetate (70 mL) and the aqueous layer was extracted with further ethyl acetate (50 mL). The combined organics were washed with sat. aq. NaCl (50 mL); dried over $Na_2SO_4$, and concentrated in vacuo to give N,N-dimethylpyridine-3-sulfonamide (6.01 g, 86%) as a white solid. $^1$H NMR (300 MHz, $CDCl_3$) δ ppm: 9.02 (dd, J=2.3, 0.9 Hz, 1H), 8.85 (dd, J=4.9, 1.7 Hz, 1H), 8.09 (ddd, J=8.0, 2.3, 1.7 Hz, 1H), 7.52 (ddd, J=8.0, 4.9, 0.9 Hz, 1H), 2.78 (s, 6H).

Procedure AE: Preparation of 4-bromo-N,N-dimethylpyridine-2-sulfonamide

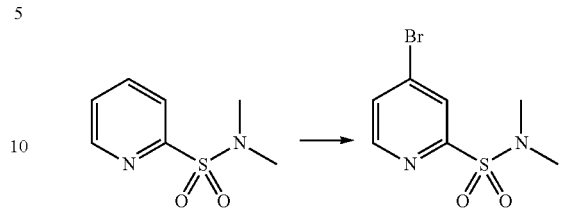

To a stirring suspension of N,N-dimethylpyridine-2-sulfonamide (920 mg, 4.94 mmol) and sodium acetate (1.22 g, 14.8 mmol) in AcOH (10 mL) at rt was added molecular bromine (506 uL, 9.88 mmol). The resulting mixture was heated to 60° C., and stirring was continued overnight. The reaction mixture was poured into water (100 mL) and then solid $Na_2CO_3$ was added until a neutral pH was attained. The aqueous mixture was extracted with ethyl acetate (20 mL×3) and the combined organics were dried over $Na_2SO_4$, and then concentrated in vacuo. The crude material was purified over silica gel eluting with 50% ethyl acetate in hexane, followed by ethyl acetate to give 4-bromo-N,N-dimethylpyridine-2-sulfonamide (520 mg, 37%) as a light yellow solid. $^1$H NMR (300 MHz, $CDCl_3$) δ 8.91 (dd, J=5.5, 2.1 Hz, 1H), 8.22 (dd, J=2.1 Hz, 1H), 7.28 (s, 1H), 2.82 (s, 6H).

Procedure AF: Preparation of (Z)-1-(4-amino-2-fluorobut-2-en-1-yl)-3-(5-(N,N-dimethylsulfamoyl)pyridin-3-yl)-2-methyl-1H-indole-5-carboxylic Acid Dihydrochloride

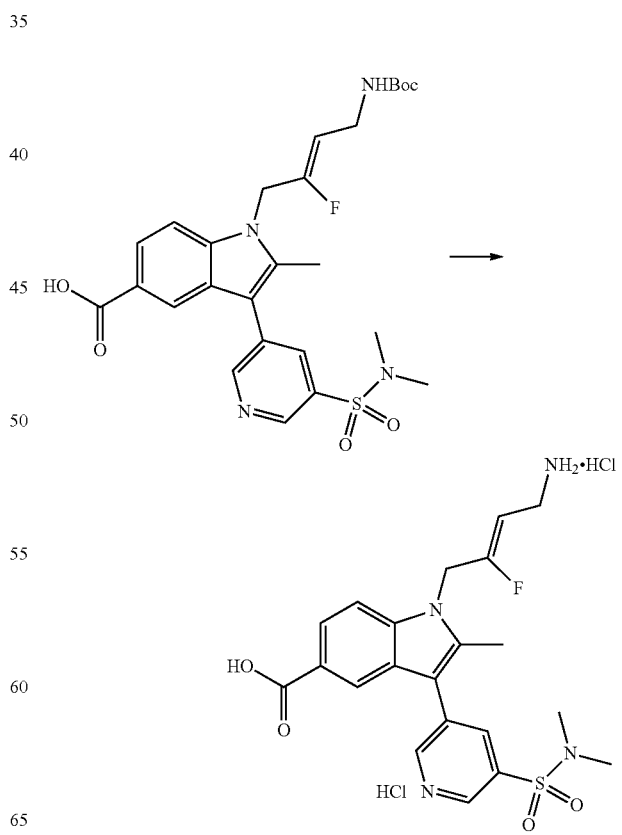

To a stirring solution of (Z)-1-(4-((tert-butoxycarbonyl) amino)-2-fluorobut-2-en-1-yl)-3-(5-(N,N-dimethylsulfamoyl)pyridin-3-yl)-2-methyl-1H-indole-5-carboxylic acid (30 mg, 0.05 mmol) in dichloromethane (2 mL) was added trifluoroacetic acid (500 uL, 0.05 mmol). The resulting mixture was stirred at rt for 1 h. The reaction mixture was concentrated in vacuo, and co-evaporated with dichloromethane (5 mL×2) to remove traces of trifluoroacetic acid. To the residue was added THF (10 mL), and to this was added ethereal HCl (2.00 mL). The resulting mixture was left to stir at rt for 15 mins. The reaction mixture was again concentrated in vacuo. To the residue was added ethyl acetate (5 mL) at which time an off-white solid precipitated. The solid was isolated and dried under high vacuum to afford (Z)-1-(4-amino-2-fluorobut-2-en-1-yl)-3-(5-(N,N-dimethylsulfamoyl)pyridin-3-yl)-2-methyl-1H-indole-5-carboxylic acid dihydrochloride (24.0 mg, 90%) as an off-white solid. $^1$H NMR (300 MHz, Methanol-$d_4$) δ ppm: 9.11 (s, 1H), 9.06 (s, 1H), 8.51 (s, 1H), 8.35 (d, J=1.5 Hz, 1H), 7.99 (dd, J=8.7, 1.6 Hz, 1H), 7.64 (d, J=8.7 Hz, 1H), 5.24 (d, J=10.0 Hz, 2H), 5.01 (dt, J=34.0, 7.4 Hz, 1H), 3.65 (d, J=7.3 Hz, 2H), 2.92 (s, 6H), 2.65 (s, 3H).

(Z)-1-(4-amino-2-fluorobut-2-en-1-yl)-3-(5-(N,N-dimethylsulfamoyl)pyridin-3-yl)-2-methyl-1H-indole-5-carboxylic Acid Dihydrochloride (Compound 40)

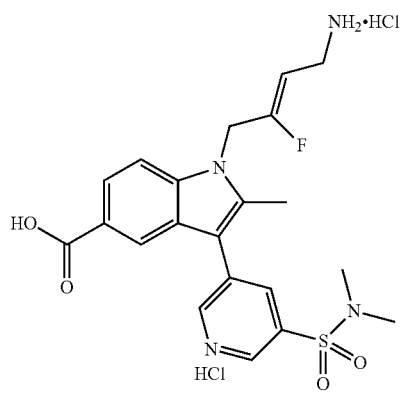

$^1$H NMR (300 MHz, Methanol-$d_4$) δ ppm: 9.11 (s, 1H), 9.06 (s, 1H), 8.51 (s, 1H), 8.35 (d, J=1.5 Hz, 1H), 7.99 (dd, J=8.7, 1.6 Hz, 1H), 7.64 (d, J=8.7 Hz, 1H), 5.24 (d, J=10.0 Hz, 2H), 5.01 (dt, J=34.0, 7.4 Hz, 1H), 3.65 (d, J=7.3 Hz, 2H), 2.92 (s, 6H), 2.65 (s, 3H).

Example 32

The following compound was prepared according to procedures AD, AE, G, H, I, J, K, L, M, N and O.

(Z)-1-(4-amino-2-fluorobut-2-en-1-yl)-3-(5-(N,N-dimethylsulfamoyl)pyridin-3-yl)-N,N,2-trimethyl-1H-indole-5-carboxamide Dihydrochloride (Compound 41)

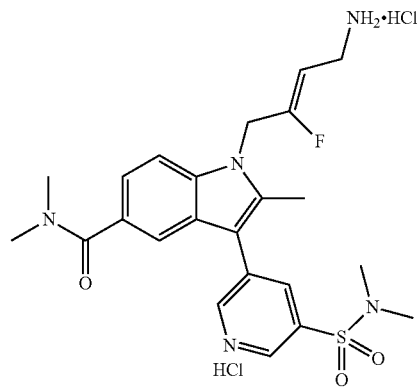

$^1$H NMR (300 MHz, Methanol-$d_4$) δ ppm: 9.22 (s, 2H), 8.60 (s, 1H), 7.73 (s, 1H), 7.65 (d, J=8.4 Hz, 1H), 7.39 (d, J=8.3 Hz, 1H), 5.22 (d, J=10.4 Hz, 2H), 5.06 (dt, J=34.3, 7.4 Hz, 1H), 3.64 (d, J=6.6 Hz, 2H), 3.10 (s, 6H), 2.90 (s, 6H), 2.64 (s, 3H).

Example 33

The following compounds were prepared according to procedures AD, AE, J, K, L, and O.

(Z)-3-(1-(4-amino-2-fluorobut-2-en-1-yl)-5-chloro-2-methyl-1H-indol-3-yl)-N,N-dimethylbenzenesulfonamide Hydrochloride (Compound 62)

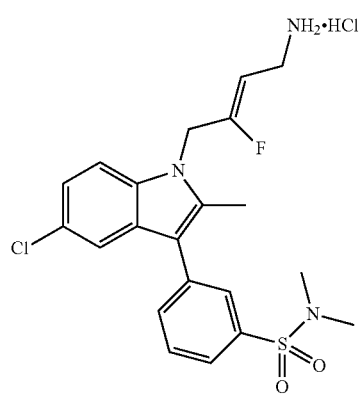

$^1$H NMR (300 MHz, DMSO-$d_6$) δ ppm: 8.06 (s, 3H), 7.86-7.76 (m, 2H), 7.75-7.70 (m, 2H), 7.67 (d, J=8.7 Hz, 1H), 7.48 (d, J=2.0 Hz, 1H), 7.23 (dd, J=8.7, 2.0 Hz, 1H), 5.22 (d, J=12.7 Hz, 2H), 5.09 (dt, J=36.0, 7.3 Hz, 1H), 3.47 (d, J=7.2 Hz, 2H), 2.70 (s, 6H), 2.52 (s, 3H).

163

(Z)-5-(1-(4-amino-2-fluorobut-2-en-1-yl)-2-methyl-1H-indol-3-yl)-N,N-dimethylpyridine-3-sulfonamide Dihydrochloride (Compound 63)

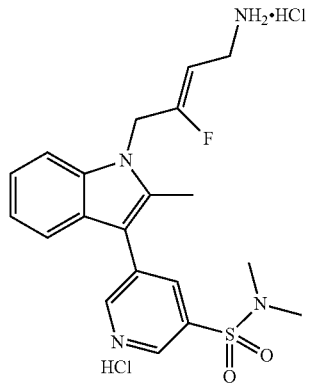

$^1$H NMR (300 MHz, Methanol-d$_4$) δ ppm: 9.08 (s, 1H), 9.02 (s, 1H), 8.48 (dd, J=2.0 Hz, 1H), 7.62 (dd, J=7.8, 1.2 Hz, 1H), 7.56 (d, J=8.1 Hz, 1H), 7.31 (ddd, J=8.3, 7.1, 1.2 Hz, 1H), 7.22 (ddd, J=8.1, 7.1, 1.1 Hz, 1H), 5.18 (d, J=9.2 Hz, 2H), 4.92 (dt, J=35.2, 7.4 Hz, 1H), 3.63 (d, J=7.5 Hz, 2H), 2.89 (s, 6H), 2.62 (s, 3H).

(Z)-5-(1-(4-amino-2-fluorobut-2-en-1-yl)-5-chloro-2-methyl-1H-indol-3-yl)-N,N-dimethylpyridine-3-sulfonamide Dihydrochloride (Compound 64)

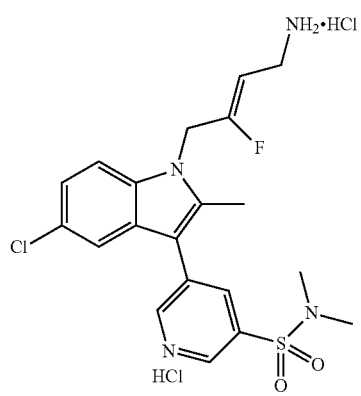

$^1$H NMR (300 MHz, DMSO-d$_6$) δ ppm: 9.02 (d, J=2.1 Hz, 1H), 8.89 (d, J=2.2 Hz, 1H), 8.19 (s, 3H), 8.10 (dd, J=2.1 Hz, 1H), 7.69 (d, J=8.7 Hz, 1H), 7.51 (d, J=2.0 Hz, 1H), 7.25 (dd, J=8.7, 2.0 Hz, 1H), 5.24 (d, J=12.9 Hz, 2H), 5.14 (dt, J=35.4, 7.6 Hz, 1H), 3.46 (t, J=6.4 Hz, 2H), 2.76 (s, 6H), 2.53 (s, 3H).

164

(Z)-5-(1-(4-amino-2-fluorobut-2-en-1-yl)-5-chloro-1H-indol-3-yl)-N,N-dimethylpyridine-3-sulfonamide Dihydrochloride (Compound 66)

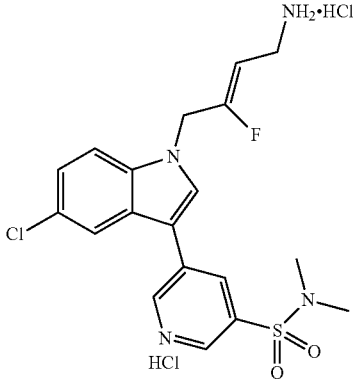

$^1$H NMR (300 MHz, Methanol-d$_4$) δ ppm: 9.27 (s, 1H), 8.99 (s, 1H), 8.66 (dd, J=2.0 Hz, 1H), 8.09 (s, 1H), 7.93 (dd, J=2.0, 0.6 Hz, 1H), 7.65 (d, J=8.8 Hz, 1H), 7.37 (dd, J=8.8, 2.0 Hz, 1H), 5.22 (dt, J=35.2, 7.5 Hz, 1H), 5.21 (d, J=13.2 Hz, 2H), 3.66 (d, J=7.4 Hz, 2H), 2.90 (s, 6H).

(Z)-5-(1-(4-amino-2-fluorobut-2-en-1-yl)-6-chloro-2-methyl-1H-indol-3-yl)-N,N-dimethylpyridine-3-sulfonamide Dihydrochloride (Compound 67)

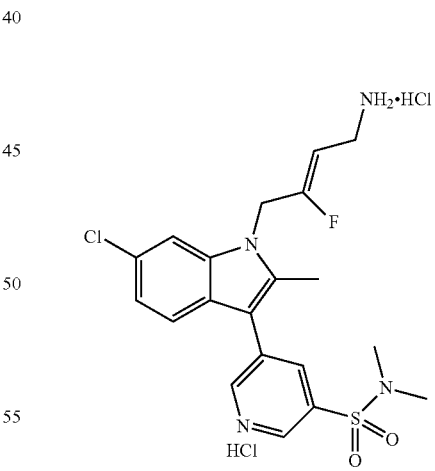

$^1$H NMR (300 MHz, Methanol-d$_4$) δ ppm: 9.18 (s, 1H), 9.14 (s, 1H), 8.68 (d, J=1.8 Hz, 1H), 7.66 (d, J=1.8 Hz, 1H), 7.61 (d, J=8.5 Hz, 1H), 7.22 (dd, J=8.5, 1.8 Hz, 1H), 5.19 (d, J=10.0 Hz, 2H), 5.04 (dt, J=34.1, 7.4 Hz, 1H), 3.65 (dd, J=7.1, 2.6 Hz, 2H), 2.92 (s, 6H), 2.63 (s, 3H).

165

(Z)-5-(1-(4-amino-2-fluorobut-2-en-1-yl)-5-fluoro-2-methyl-1H-indol-3-yl)-N,N-dimethylpyridine-3-sulfonamide Dihydrochloride (Compound 71)

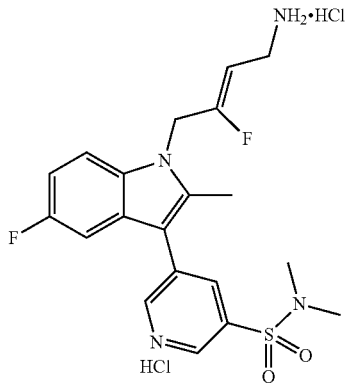

$^1$H NMR (300 MHz, Methanol-$d_4$) δ ppm: 9.16 (s, 1H), 9.12 (s, 1H), 8.65 (dd, J=1.9 Hz, 1H), 7.58 (dd, J=9.0, 4.3 Hz, 1H), 7.35 (dd, J=9.5, 2.4 Hz, 1H), 7.09 (dt, J=9.1, 2.5 Hz, 1H), 5.20 (d, J=10.7 Hz, 2H), 5.04 (dt, J=34.2, 7.4 Hz, 1H), 3.64 (d, J=7.5 Hz, 2H), 2.93 (s, 6H), 2.63 (s, 3H).

(Z)-5-(1-(4-amino-2-fluorobut-2-en-1-yl)-6-chloro-2-methyl-1H-pyrrolo[3,2-b]pyridin-3-yl)-N,N-dimethylpyridine-3-sulfonamide Trihydrochloride (Compound 72)

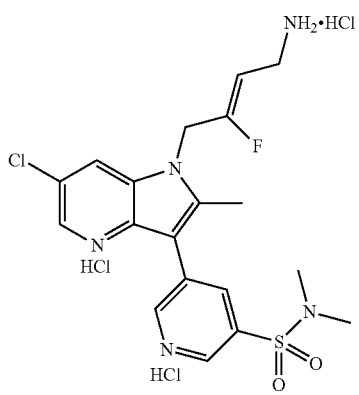

$^1$H NMR (300 MHz, Methanol-$d_4$) δ ppm: 9.36 (s, 1H), 9.29 (s, 1H), 8.93 (s, 1H), 8.91 (s, 1H), 8.73 (s, 1H), 5.45 (d, J=11.2 Hz, 2H), 5.41 (dt, J=33.9, 7.2 Hz, 1H), 3.69 (d, J=6.6 Hz, 2H), 2.93 (s, 6H), 2.74 (s, 3H).

166

(Z)-5-(1-(4-amino-2-fluorobut-2-en-1-yl)-5-chloro-2-methyl-1H-pyrrolo[2,3-b]pyridin-3-yl)-N,N-dimethylpyridine-3-sulfonamide Trihydrochloride (Compound 73)

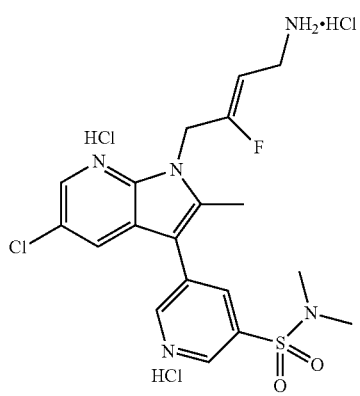

$^1$H NMR (300 MHz, Methanol-$d_4$) δ ppm: 9.14 (d, J=2.0 Hz, 1H), 9.10 (d, J=2.0 Hz, 1H), 8.55 (dd, J=1.8 Hz, 1H), 8.32 (d, J=2.2 Hz, 1H), 8.07 (d, J=2.2 Hz, 1H), 5.29 (d, J=10.7 Hz, 2H), 5.06 (dt, J=34.0, 7.4 Hz, 1H), 3.64 (d, J=7.4 Hz, 2H), 2.90 (s, 6H), 2.67 (s, 3H).

(Z)-5-(1-(4-amino-2-fluorobut-2-en-1-yl)-7-chloro-2-methyl-1H-indol-3-yl)-N,N-dimethylpyridine-3-sulfonamide Dihydrochloride (Compound 74)

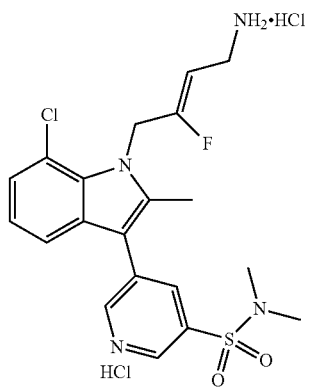

$^1$H NMR (300 MHz, DMSO-$d_6$) δ ppm: 8.96 (dd, J=21.2, 2.1 Hz, 1H), 8.10 (dd, J=2.1 Hz, 1H), 8.08 (s, 1H), 7.48 (dd, J=7.9, 1.1 Hz, 1H), 7.27 (dd, J=7.7, 1.1 Hz, 1H), 7.14 (dd, J=7.8 Hz, 1H), 5.51 (d, J=7.5 Hz, 1H), 4.83 (dt, J=36.2, 7.3 Hz, 1H), 3.48 (t, J=6.3 Hz, 2H), 2.76 (s, 6H), 2.51 (s, 3H).

(Z)-5-(1-(4-amino-2-fluorobut-2-en-1-yl)-4-chloro-2-methyl-1H-indol-3-yl)-N,N-dimethylpyridine-3-sulfonamide Dihydrochloride (Compound 75)

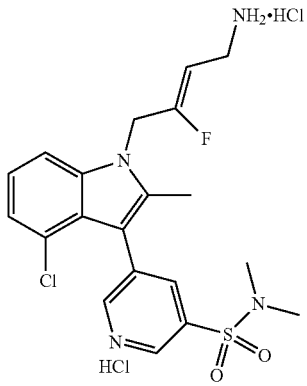

$^1$H NMR (300 MHz, DMSO-$d_6$) δ ppm: 8.91 (s, 1H), 8.89 (d, J=2.0 Hz, 1H), 8.06 (dd, J=2.1 Hz, 1H), 7.66 (dd, J=8.1, 1.0 Hz, 1H), 7.20 (dd, J=7.9 Hz, 1H), 7.13 (dd, J=7.7, 1.0 Hz, 1H), 5.25 (d, J=12.2 Hz, 2H), 5.07 (dt, J=36.0, 7.2 Hz, 1H), 3.47 (t, J=6.3 Hz, 2H), 2.73 (s, 6H), 2.36 (s, 3H).

Example 34

The following compound was prepared according to procedures AG, J, K, L, M and O

(Z)-3-(1-(4-amino-2-fluorobut-2-en-1-yl)-5-methoxy-2-methyl-1H-indol-3-yl)-N,N-dimethyl-benzene-sulfonamide Hydrochloride (Compound 49)

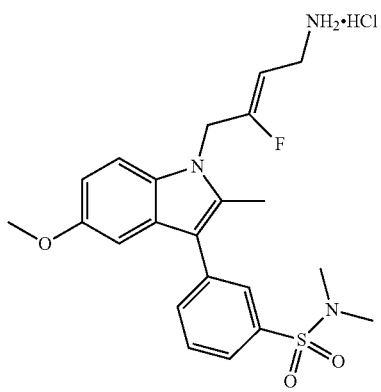

Procedure AG: Preparation of 5-methoxy-2-methyl-1H-indole

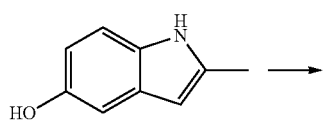 →

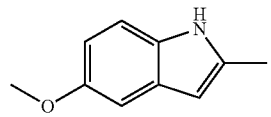

To a suspension of 5-hydroxy-2-methylindole (442 mg, 3.00 mmol), and potassium carbonate (517 mg, 3.74 mmol) in DMF (2.5 mL) at rt was added iodomethane (0.70 mL, 11.2 mmol). The resulting mixture was stirred at rt overnight. Water (25 mL) and aqueous NaOH (2 M, 5 mL) was added, and the mixture was stirred for a further 5 min. The product was extracted with ethyl acetate (25 mL×3) and the combined organics were washed with water (20 mL×2) and brine (25 mL), dried over Na$_2$SO$_4$ and concentrated in vacuo to afford 5-methoxy-2-methyl-1H-indole (517 mg, 100%) as a brown oil. $^1$H NMR (300 MHz, CDCl$_3$) δ ppm: 7.77 (s, 1H), 7.19 (dt, J=8.7, 0.7 Hz, 1H), 7.02 (d, J=2.5 Hz, 1H), 6.78 (dd, J=8.7, 2.5 Hz, 1H), 6.17 (dt, J=2.2, 1.0 Hz, 1H), 3.86 (s, 3H), 2.44 (d, J=0.9 Hz, 3H).

(Z)-3-(1-(4-amino-2-fluorobut-2-en-1-yl)-5-methoxy-2-methyl-1H-indol-3-yl)-N,N-dimethyl-benzene-sulfonamide Hydrochloride (Compound 49)

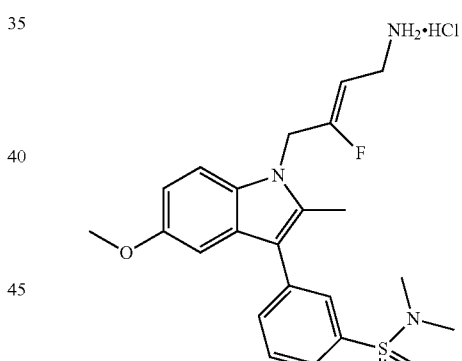

$^1$H NMR (300 MHz, DMSO-$d_6$) δ ppm: 7.96 (s, 3H), 7.82 (ddd, J=7.6, 1.7, 1.7, 1H), 7.79 (d, J=7.6 Hz, 1H), 7.75 (d, J=2.2 Hz, 1H), 7.69 (dt, J=7.2, 1.8 Hz, 1H), 7.51 (d, J=8.9 Hz, 1H), 7.00 (d, J=2.4 Hz, 1H), 6.85 (dd, J=8.9, 2.4 Hz, 1H), 5.14 (d, J=11.9 Hz, 2H), 5.00 (dt, J=35.9, 7.3 Hz, 1H), 3.73 (s, 3H), 3.47 (d, J=7.2 Hz, 2H), 3.32 (s, 3H), 2.71 (s, 6H).

Example 35

The following compound was prepared according to procedures AD, AE, J, K, AH, L and O (Z)-5-(1-(4-amino-2-fluorobut-2-en-1-yl)-2-chloro-1H-indol-3-yl)-N,N-dimethylpyridine-3-sulfonamide Dihydrochloride (Compound 96)

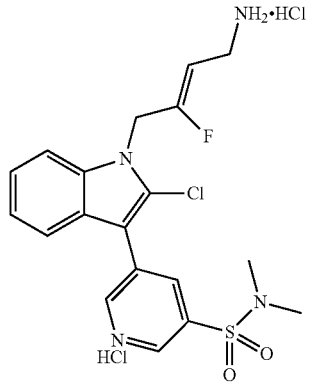

Procedure AH: Preparation of 5-(2-chloro-1H-indol-3-yl)-N,N-dimethylpyridine-3-sulfonamide

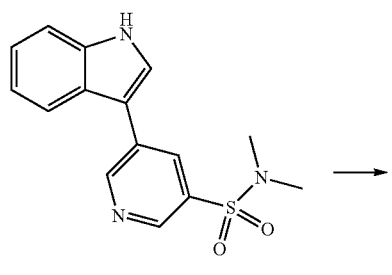

To a stirring solution of 5-(1H-indol-3-yl)-N,N-dimethylpyridine-3-sulfonamide (141 mg, 0.47 mmol) in DMF (5 mL) at 0° C. was added N-chlorosuccinimide (68.7 mg, 0.51 mmol). Stirring at 0° C. for 30 mins and then rt for 2 h. The reaction mixture was partitioned between ethyl acetate and water. The organic layer was washed with further water and brine, then dried over Na$_2$SO$_4$, and concentrated in vacuo. Purification was performed using a 12 g RediSep cartridge, eluting over a gradient of 30-80% ethyl acetate in hexane to afford the title compound 5-(2-chloro-1H-indol-3-yl)-N,N-dimethylpyridine-3-sulfonamide (62.0 mg, 39%) as a white solid. $^1$H NMR (300 MHz, CDCl$_3$) δ ppm: 9.16 (d, J=2.1 Hz, 1H), 8.97 (d, J=2.2 Hz, 1H), 8.86 (s, 1H), 8.37 (dd, J=2.1 Hz, 1H), 7.67 (ddd, J=7.8, 1.5, 0.7 Hz, 1H), 7.43 (ddd, J=8.1, 1.3, 0.8 Hz, 1H), 7.32 (dd, J=8.3, 1.2 Hz, 1H), 7.25 (ddd, J=7.8, 7.1, 1.3 Hz, 1H), 2.86 (s, 6H).

(Z)-5-(1-(4-amino-2-fluorobut-2-en-1-yl)-2-chloro-1H-indol-3-yl)-N,N-dimethylpyridine-3-sulfonamide Dihydrochloride (Compound 96)

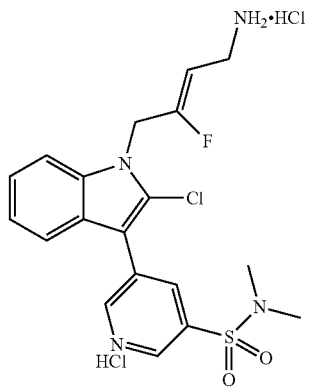

$^1$H NMR (300 MHz, Methanol-d$_4$) δ ppm: 9.26 (s, 1H), 9.09 (s, 1H), 8.70 (dd, J=1.8 Hz, 1H), 7.75 (d, J=8.1 Hz, 1H), 7.66 (d, J=8.2 Hz, 1H), 7.42 (ddd, J=8.3, 7.2, 1.1 Hz, 1H), 7.33 (ddd, J=8.1, 7.2, 1.0 Hz, 1H), 5.29 (d, J=11.1 Hz, 2H), 5.13 (dt, J=33.9, 7.4 Hz, 1H), 3.71-3.61 (m, 2H), 2.90 (s, 6H).

Example 36

The following compound was prepared according to procedures E, F, J, K, AH, L and O (Z)-3-(1-(4-amino-2-fluorobut-2-en-1-yl)-2-chloro-1H-pyrrolo[3,2-b]pyridin-3-yl)-N,N-dimethylbenzene-sulfonamide Dihydrochloride (Compound 99)

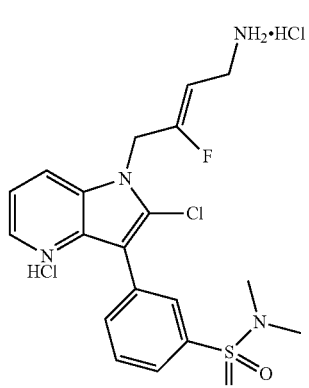

$^1$H NMR (300 MHz, Methanol-d$_4$) δ ppm: 8.88 (d, J=8.5 Hz, 1H), 8.64 (dd, J=5.8, 1.0 Hz, 1H), 8.09-8.05 (m, 1H), 8.03-7.95 (m, 2H), 7.93-7.84 (m, 2H), 5.53 (d, J=14.2 Hz, 2H), 5.49 (dt, J=35.2, 7.4 Hz, 1H), 3.69 (d, J=7.3 Hz, 2H), 2.78 (s, 6H).

Example 37

The following compound was prepared according to procedures J, K, AI, L and O.

171

(Z)-5-(1-(4-amino-2-fluorobut-2-en-1-yl)-5-chloro-2-methyl-1H-indol-3-yl)-N-methylpyridine-3-sulfonamide Dihydrochloride (Compound 70)

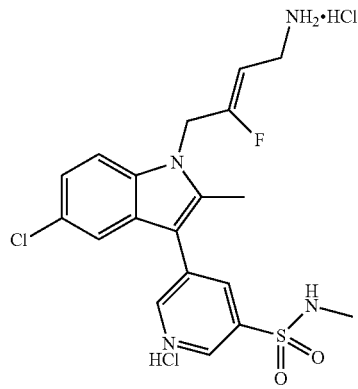

Procedure AI: Preparation of tert-butyl ((5-(5-chloro-2-methyl-1H-indol-3-yl)pyridin-3-yl)sulfonyl)(methyl)carbamate

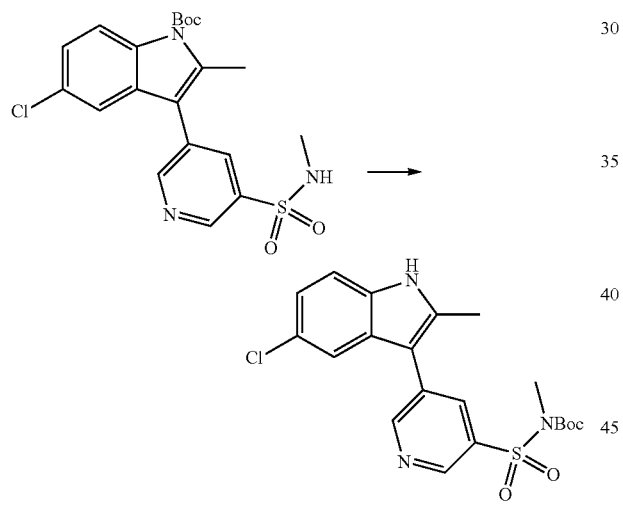

Trifluoroacetic acid (3.00 mL, 0.39 mmol) was added to a stirring solution of tert-butyl 5-chloro-2-methyl-3-(5-(N-methylsulfamoyl)pyridin-3-yl)-1H-indole-1-carboxylate (172 mg, 0.39 mmol) in dichloromethane (3 mL) at rt. The mixture was stirred at rt for 45 min. All volatiles were then removed in vacuo. To the residue was added sat. aq. NaHCO$_3$ (5 mL) and the product was extracted with ethyl acetate (15 mL×3). The combined organics were dried over Na$_2$SO$_4$ and concentrated in vacuo. The crude material was taken up in DMF (1.5 mL), and to this was added di-tert-butyl dicarbonate (172 mg, 0.79 mmol) and potassium carbonate (109 mg, 0.79 mmol). The resulting suspension was stirred at rt for 30 min. Tlc after this time showed approximately 20-30% conversion. Triethylamine (0.11 mL, 0.79 mmol) was added and stirring was continued overnight at rt. Water (10 mL) was added and the product was extracted with ethyl acetate (10 mL×3). The combined organics were dried over Na$_2$SO$_4$ and concentrated in vacuo.

172

The crude material was purified over silica gel eluting with 20-50% ethyl acetate in hexane gave impure tert-butyl ((5-(5-chloro-2-methyl-1H-indol-3-yl)pyridin-3-yl)sulfonyl)(methyl)carbamate (80.0 mg, 47%). This material was progressed to the next step without further purification.

(Z)-5-(1-(4-amino-2-fluorobut-2-en-1-yl)-5-chloro-2-methyl-1H-indol-3-yl)-N-methylpyridine-3-sulfonamide Dihydrochloride (Compound 70)

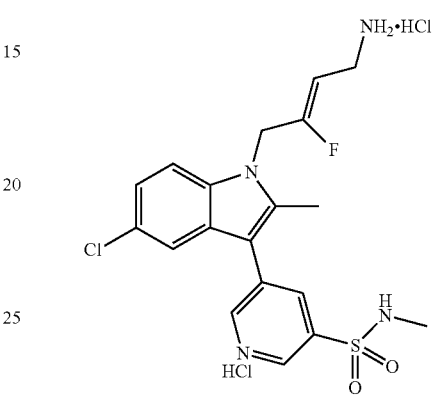

$^1$H NMR (300 MHz, Methanol-d$_4$) δ ppm: 9.04 (s, 2H), 8.54 (s, 1H), 7.61 (d, J=2.0 Hz, 1H), 7.55 (d, J=8.7 Hz, 1H), 7.27 (dd, J=8.8, 2.0 Hz, 1H), 5.18 (d, J=9.8 Hz, 2H), 4.96 (dt, J=34.4, 7.6 Hz, 1H), 3.64 (d, J=7.4 Hz, 2H), 2.72 (s, 3H), 2.61 (s, 3H).

Example 38

The following compound was prepared according to procedures AJ, F, G, H, I, J, K, L, M, N and AK.

(Z)-1-(4-amino-2-fluorobut-2-en-1-yl)-N,N,2-trimethyl-3-(3-sulfamoylphenyl)-1H-indole-5-carboxamide Hydrochloride (Compound 54)

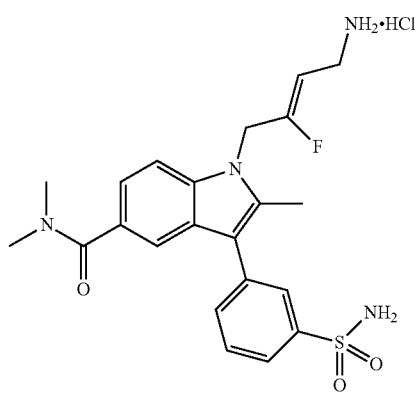

Procedure AJ: Preparation of 3-bromo-N,N-bis(4-methoxybenzyl)benzenesulfonamide

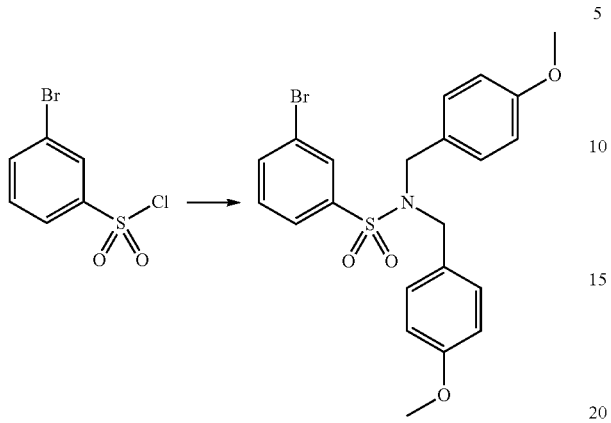

To a stirring solution of bis(4-methoxybenzyl)amine (771 mg, 3.00 mmol) and triethylamine (0.72 mL, 3.00 mmol) in THF (10 mL) at 0° C. was added 3-bromobenzenesulfonyl chloride (766 mg, 3.00 mmol) was added portion-wise. The mixture was stirred at rt for 30 min. The reaction mixture was diluted with water (30 mL) and then acidified to pH 2 using aqueous 2 M HCl. The product was extracted in ethyl acetate (20 mL×3). The combined organics were dried over $Na_2SO_4$ and concentrated in vacuo to afford 3-bromo-N,N-bis(4-methoxybenzyl)benzenesulfonamide (1.24 g, 87%) as a white solid. $^1$H NMR (300 MHz, $CDCl_3$) δ ppm: 7.86 (dd, J=1.8 Hz, 1H), 7.74 (ddd, J=7.9, 1.8, 1.0 Hz, 1H), 7.69 (ddd, J=8.0, 1.9, 1.0 Hz, 1H), 7.36 (dd, J=7.9 Hz, 1H), 7.03 (d, J=8.6 Hz, 4H), 6.80 (d, J=8.6 Hz, 4H), 3.81 (s, 6H).

Procedure AK: Preparation of (Z)-1-(4-amino-2-fluorobut-2-en-1-yl)-N,N,2-trimethyl-3-(3-sulfamoylphenyl)-1H-indole-5-carboxamide Hydrochloride (Compound 54)

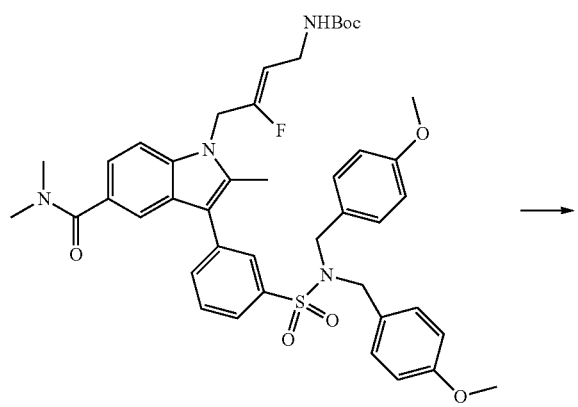

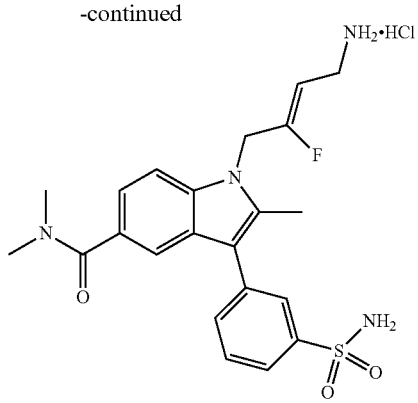

To a stirring solution of tert-butyl (Z)-(4-(3-(3-(N,N-bis(4-methoxybenzyl)sulfamoyl)phenyl)-5-(dimethylcarbamoyl)-2-methyl-1H-indol-1-yl)-3-fluorobut-2-en-1-yl)carbamate (309 mg, 0.39 mmol) in dichloromethane (5 mL) at rt was added TFA (5 mL). The resulting mixture was stirred for 3 h. The reaction mixture was concentrated under vacuum, and then ethyl acetate (5 mL) was added to dissolve the residue. Ethereal HCl (2 M, 5 mL) was added and the mixture was stirred at rt for 5 min. The reaction mixture was again concentrated under vacuum, and then ethyl acetate (10 mL) was added. The solid was triturated, and then isolated by, firstly, spinning it down in a centrifuge, thus forming a solid "cake" and then decanting off the solvent. The solid was dried in oven at 60° C. for 3 h. The solid was purified by reverse-phase chromatography (gradient elution: 10% Acetonitrile then 10-30% acetonitrile over 20 min). The combined fractions containing the desired product were concentrated to a volume of approximately 5 mL. The aqueous solution of the product was transferred to a 7 mL vial and lyophilized to afford (Z)-1-(4-amino-2-fluorobut-2-en-1-yl)-N,N,2-trimethyl-3-(3-sulfamoylphenyl)-1H-indole-5-carboxamide hydrochloride (115 mg, 60%) as an off-white powder. $^1$H NMR (300 MHz, DMSO-$d_6$) δ ppm: 8.03 (s, 3H), 7.91 (d, J=2.0 Hz, 1H), 7.80 (dt, J=6.9, 2.0 Hz, 1H), 7.72 (d, J=7.7 Hz, 1H), 7.68 (s, 1H), 7.65 (d, J=8.5 Hz, 1H), 7.56 (d, J=1.4 Hz, 1H), 7.46 (s, 2H), 7.26 (dd, J=8.4, 1.5 Hz, 1H), 5.23 (d, J=12.3 Hz, 2H), 5.08 (dt, J=35.9, 7.2 Hz, 1H), 3.48 (dt, J=6.3 Hz, 3H), 2.97 (s, 6H), 2.53 (s, 3H).

Example 39

The following compound was prepared according to procedures AJ, F, J, K, and AK.

(Z)-5-(1-(4-amino-2-fluorobut-2-en-1-yl)-5-chloro-2-methyl-1H-indol-3-yl)pyridine-3-sulfonamide Dihydrochloride (Compound 83)

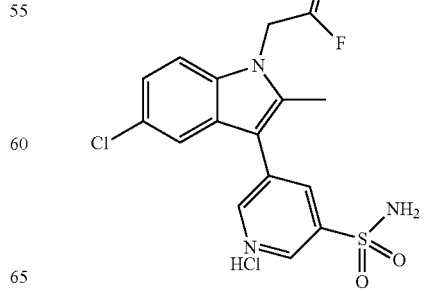

¹H NMR (300 MHz, DMSO-d₆) δ ppm: 8.94 (s, 2H), 8.24 (s, 1H), 8.04 (s, 3H), 7.74 (s, 2H), 7.69 (d, J=8.7 Hz, 1H), 7.55 (d, J=2.0 Hz, 1H), 7.25 (dd, J=8.7, 2.0 Hz, 1H), 5.24 (d, J=12.5 Hz, 2H), 5.08 (dt, J=36.0, 7.3 Hz, 11H), 3.47 (s, 2H), 2.53 (s, 3H).

Example 40

The following compound was prepared according to procedures AL, F, J, K, L and O.

(Z)-3-(1-(4-amino-2-fluorobut-2-en-1-yl)-5-chloro-7-fluoro-2-methyl-1H-indol-3-yl)-N,N,4-trimethyl-benzenesulfonamide Dihydrochloride (Compound 84)

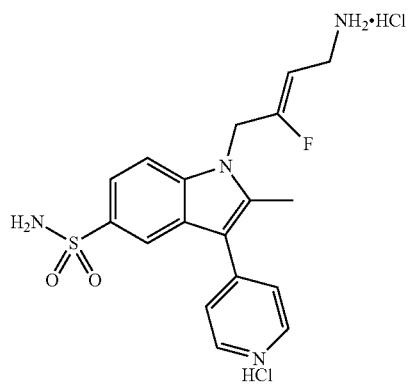

(Z)-3-(1-(4-amino-2-fluorobut-2-en-1-yl)-5-chloro-7-fluoro-2-methyl-1H-indol-3-yl)-N,N,4-trimethyl-benzenesulfonamide Hydrochloride (Compound 84)

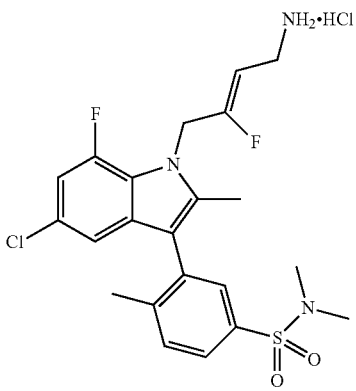

¹H NMR (300 MHz, Methanol-d₄) δ 7.76 (dd, J=8.0, 2.0 Hz, 1H), 7.66 (ddd, J=8.1, 0.6 Hz, 1H), 7.57 (d, J=2.0 Hz, 1H), 7.00 (dd, J=12.3, 1.8 Hz, 1H), 6.89 (d, J=1.8 Hz, 1H), 5.21 (dd, J=9.8, 2.7 Hz, 2H), 4.92 (dt, J=35.4, 7.5 Hz, 1H) 3.65 (dd, J=7.4, 1.6 Hz, 2H), 2.73 (s, 6H), 2.33 (s, 3H), 2.23 (s, 3H).

Example 41

The following compound was prepared according to procedures E, F, AM, AN, J, K, L and O.

(Z)-3-(1-(4-amino-2-fluorobut-2-en-1-yl)-5-cyano-2-methyl-1H-indol-3-yl)-N,N-dimethylbenzene-sulfonamide Hydrochloride (Compound 51)

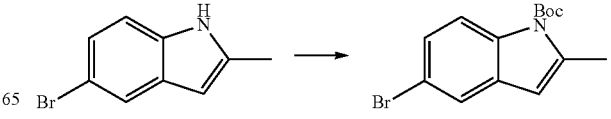

Procedure AL: Preparation of 3-bromo-N,N,4-trimethylbenzenesulfonamide

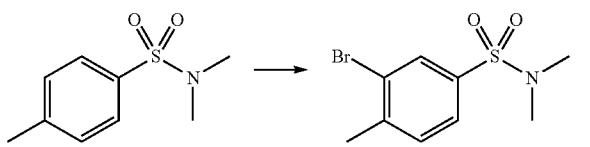

A stirring mixture of N,N,4-trimethylbenzenesulfonamide (1.00 g, 5.02 mmol) in concentrated sulfuric acid (4.50 mL, 84.4 mmol) at rt was added 1-bromopyrrolidine-2,5-dione (983 mg, 5.52 mmol). The resulting solution was left to stir at rt for 3 h. The reaction mixture was poured into cold water and the resulting off-white precipitate was filtered and washed with further water. The solid was left to air dry, affording 3-bromo-N,N,4-trimethylbenzenesulfonamide (1.36 g, 97%). ¹H NMR (300 MHz, Methanol-d₄) δ ppm: 7.93 (d, J=1.9 Hz, 1H), 7.67 (dd, J=8.0, 1.9 Hz, 1H), 7.56 (d, J=8.1 Hz, 1H), 2.70 (s, 6H), 2.50 (s, 3H).

Procedure AM: Preparation of tert-butyl 5-bromo-2-methyl-1H-indole-1-carboxylate To a stirring solution of 5-bromo-2-methyl-1H-indole (1.00 g, 4.76 mmol) and di-tert-butyl dicarbonate (2.08 g, 9.52 mmol) in DMF (5 mL) at rt was added 4-(dimethylamino)pyridine (0.58 g, 4.76 mmol) in three portions over 10 mins. Then the resulting mixture was stirred at rt for 30 mins. Water (50 mL) was added slowly to the mixture and the product was extracted with ethyl acetate (20 mL×3). The combined organic layers were washed with sat. aq. NH$_4$Cl (20 mL) and brine (20 mL), dried over Na$_2$SO$_4$ and concentrated in vacuo to give tert-butyl 5-bromo-2-methyl-1H-indole-1-carboxylate (1.46 g, 99%) as a yellow solid. $^1$H NMR (300 MHz, CDCl$_3$) δ ppm: 7.99 (dt, J=8.9, 0.7 Hz, 1H), 7.57 (d, J=2.0 Hz, 1H), 7.32 (dd, J=8.9, 2.0 Hz, 1H), 6.27 (s, 1H), 2.60 (d, J=1.2 Hz, 3H), 1.70 (s, 9H).

Procedure AN: Preparation of tert-butyl 5-cyano-2-methyl-1H-indole-1-carboxylate

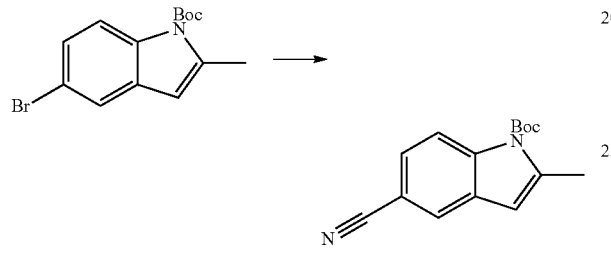

A stirring mixture of tert-butyl 5-bromo-2-methyl-1H-indole-1-carboxylate (250 mg, 0.81 mmol) and copper cyanide (361 mg, 4.03 mmol) in DMF (2.0 mL) under N$_2$ was heated at 150° C. for 4 h. The reaction mixture was poured into ethyl acetate (30 mL) slowly and then water (20 mL) was added. The mixture was sonicated for 2 mins and then filtered through Celite™. The filtrate was transferred to a separatory funnel and the aqueous layer was extracted with ethyl acetate (20 mL×2). The combined organic layers were washed with sat. aq. NH$_4$Cl (20 mL×2), and brine (20 mL), dried over Na$_2$SO$_4$ and concentrated in vacuo to afford tert-butyl 5-cyano-2-methyl-1H-indole-1-carboxylate (146 mg, 0.93 mmol, 100%) as a brown solid. $^1$H NMR (300 MHz, CDCl$_3$) δ ppm: 8.44 (s, 1H), 7.85 (s, 1H), 7.35 (s, 2H), 6.31 (s, 1H), 2.49 (d, J=1.0 Hz, 3H).

(Z)-3-(1-(4-amino-2-fluorobut-2-en-1-yl)-5-cyano-2-methyl-1H-indol-3-yl)-N,N-dimethylbenzene-sulfonamide Hydrochloride (Compound 51)

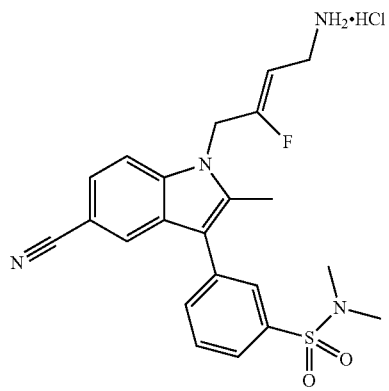

$^1$H NMR (300 MHz, Methanol-d$_4$) δ ppm: 7.87 (d, J=1.5 Hz, 1H), 7.80 (dq, J=3.2, 2.0, 1.4 Hz, 4H), 7.70 (d, J=8.5 Hz, 1H), 7.52 (dd, J=8.5, 1.5 Hz, 1H), 5.21 (d, J=10.3 Hz, 2H), 5.01 (dt, J=34.1, 7.4 Hz, 1H), 3.70-3.60 (m, 2H), 2.78 (s, 6H), 2.59 (s, 3H).

Example 42

The following compound was prepared according to procedures E, F, AM, AN, J, K, AO, AP, L and O.

(Z)-3-(1-(4-amino-2-fluorobut-2-en-1-yl)-2-methyl-5-(1,2,4-oxadiazol-3-yl)-1H-indol-3-yl)-N,N-dimethylbenzenesulfonamide Hydrochloride (Compound 55)

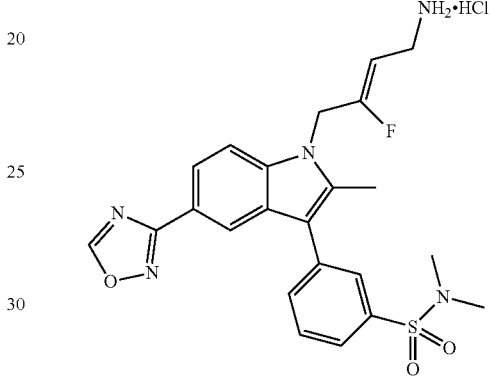

Procedure AO: Preparation of 3-(3-(N,N-dimethylsulfamoyl)phenyl)-N-hydroxy-2-methyl-1H-indole-5-carboximidamide

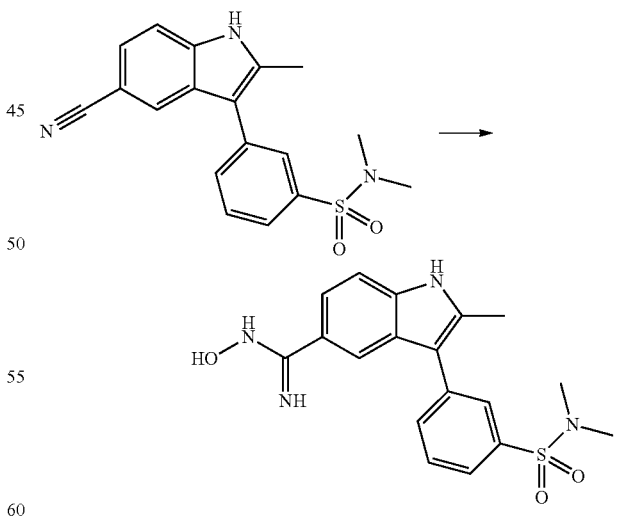

To a stirring mixture of 3-(5-cyano-2-methyl-1H-indol-3-yl)-N,N-dimethylbenzenesulfonamide (55.0 mg, 0.16 mmol) in ethanol (2 mL) and THF (2 mL) at rt was added hydroxylamine (45 uL, 0.81 mmol). The resulting mixture was stirred at this temperature over the weekend. Tlc analysis showed approximately 50% conversion. Additional hydroxylamine (45 uL, 0.81 mmol) was added and the mixture was heated to 45° C. for 2 days. The reaction mixture was concentrated in vacuo to afford 3-(3-(N,N-dimethylsulfamoyl)phenyl)-N-hydroxy-2-methyl-1H-indole-5-carboximidamide (55.0 mg, 91%) as a yellow solid. This material was progressed to the next step without further purification.

Procedure AP: Preparation of N,N-dimethyl-3-(2-methyl-5-(1,2,4-oxadiazol-3-yl)-1H-indol-3-yl)benzenesulfonamide

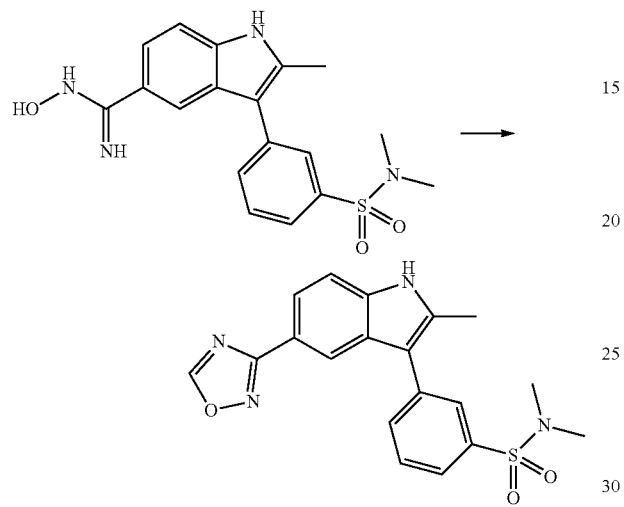

To a stirring mixture of 3-(3-(N,N-dimethylsulfamoyl)phenyl)-N-hydroxy-2-methyl-1H-indole-5-carboximidamide (55.0 mg, 0.15 mmol) and diethoxymethoxyethane (37 uL, 0.22 mmol) in THF (1 mL) and acetonitrile (1 mL) at 45° C. was added trifluoroacetic acid (0.6 uL, 7.4 h mol). The resulting mixture was stirred at 110° C. overnight. The mixture was concentrated in vacuo and dried under high vacuum to give N,N-dimethyl-3-(2-methyl-5-(1,2,4-oxadiazol-3-yl)-1H-indol-3-yl)benzenesulfonamide (39.0 mg, 69%) as a yellow solid. This material was progressed to the next step without further purification.

(Z)-3-(1-(4-amino-2-fluorobut-2-en-1-yl)-2-methyl-5-(1,2,4-oxadiazol-3-yl)-1H-indol-3-yl)-N,N-dimethylbenzenesulfonamide Hydrochloride (Compound 55)

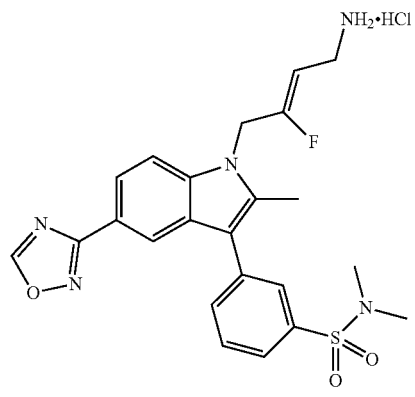

$^1$H NMR (300 MHz, Methanol-d$_4$) δ ppm: 9.21 (s, 1H), 8.36 (d, J=1.6 Hz, 1H), 8.00 (dd, J=8.6, 1.6 Hz, 1H), 7.93-7.88 (m, 1H), 7.87-7.76 (m, 3H), 7.66 (d, J=8.6 Hz, 1H), 5.20 (d, J=8.7 Hz, 2H), 4.80 (m, 1H), 3.64 (dd, J=7.5, 1.6 Hz, 2H), 2.83 (s, 6H), 2.60 (s, 3H).

Example 43

The following compound was prepared according to procedures E, F, G, H, I, J, K, L, AQ, AR, AS and O.

(Z)-3-(1-(4-amino-2-fluorobut-2-en-1-yl)-5-(difluoromethyl)-2-methyl-1H-indol-3-yl)-N,N-dimethylbenzenesulfonamide Hydrochloride (Compound 59)

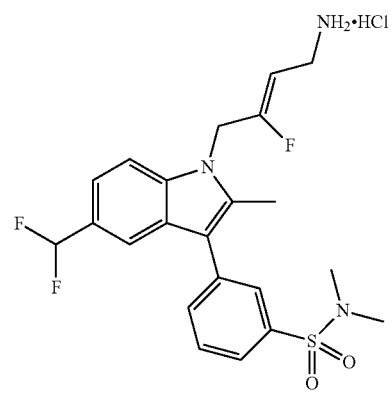

Procedure AQ: Preparation of tert-butyl (Z)-(4-(3-(3-(N,N-dimethylsulfamoyl)phenyl)-5-(hydroxymethyl)-2-methyl-1H-indol-1-yl)-3-fluorobut-2-en-1-yl)carbamate

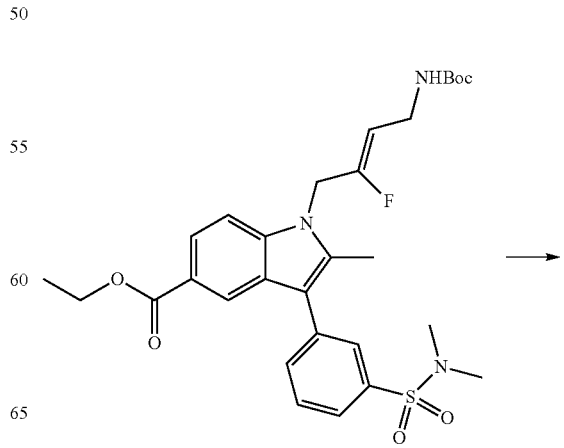

181

-continued

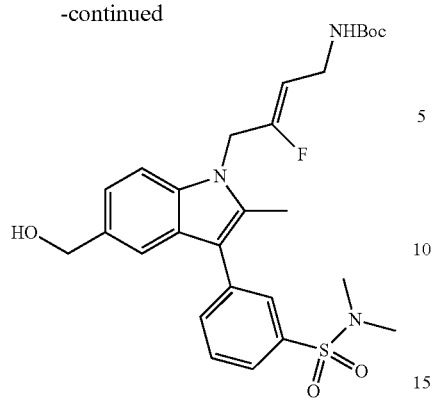

To a stirring solution of ethyl (Z)-1-(4-((tert-butoxycarbonyl)amino)-2-fluorobut-2-en-1-yl)-3-(3-(N,N-dimethylsulfamoyl)phenyl)-2-methyl-1H-indole-5-carboxylate (500 mg, 0.88 mmol) in dry THF (3 mL) at 0° C. was added diisobutylaluminum hydride (1.10 mL, 1.10 mmol). The mixture was stirred at 0° C. for 5 min and then at ambient temperature for 1 h. The reaction was quenched by addition of ethyl acetate (1 mL) followed by stirring for 10 min. Aqueous NaOH (2 M, 20 mL) was added and stirring was continued for a further 2 min. The product was then extracted with ethyl acetate (20 mL×4). The combined organics were washed with brine (10 mL), dried over Na$_2$SO$_4$ and concentrated in vacuo to afford crude tert-butyl (Z)-(4-(3-(3-(N,N-dimethylsulfamoyl)phenyl)-5-(hydroxymethyl)-2-methyl-1H-indol-1-yl)-3-fluorobut-2-en-1-yl)carbamate (300 mg) as a viscous oil. This material was progressed to the next step without purification. $^1$H NMR (300 MHz, CDCl$_3$) δ ppm: 7.87 (dt, J=1.8, 0.6 Hz, 1H), 7.76-7.70 (m, 2H), 7.65 (d, J=7.3 Hz, 1H), 7.60 (dd, J=1.6, 0.8 Hz, 1H), 7.32 (d, J=8.2 Hz, 1H), 7.25 (dd, J=8.4, 1.6 Hz, 1H), 4.82 (d, J=9.5 Hz, 2H), 4.75 (s, 2H), 4.68-4.86 (m, 1H), 4.64 (s, 1H), 3.78 (s, 2H), 2.78 (s, 6H), 2.49 (s, 3H), 1.41 (s, 9H).

Procedure AR: Preparation of tert-butyl (Z)-(4-(3-(3-(N,N-dimethylsulfamoyl)phenyl)-5-formyl-2-methyl-1H-indol-1-yl)-3-fluorobut-2-en-1-yl)carbamate

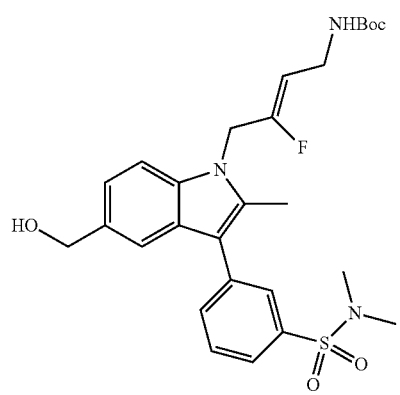

182

-continued

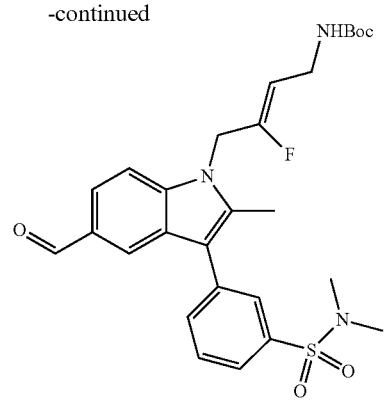

To a stirring solution crude of crude tert-butyl (Z)-(4-(3-(3-(N,N-dimethylsulfamoyl)phenyl)-5-(hydroxymethyl)-2-methyl-1H-indol-1-yl)-3-fluorobut-2-en-1-yl)carbamate (300 mg) in dichloromethane (3 mL) was added Dess-Martin periodinane (230 mg, 0.54 mmol) in one lot. The mixture was stirred at ambient temperature for 45 min. The reaction was quenched by addition of IPA (0.3 mL) followed by stirring for 5 min. The reaction mixture was adsorbed directly onto silica gel. Purification was performed over silica gel, eluting with 50% ethyl acetate in hexane to afford tert-butyl (Z)-(4-(3-(3-(N,N-dimethylsulfamoyl)phenyl)-5-formyl-2-methyl-1H-indol-1-yl)-3-fluorobut-2-en-1-yl)carbamate (188 mg, 81%) as a glassy foam. $^1$H NMR (300 MHz, CDCl$_3$) δ 10.03 (s, 1H), 8.13 (d, J=1.3 Hz, 1H), 7.89 (dd, J=1.9 Hz, 1H), 7.74-7.84 (m, 3H), 7.71 (d, J=7.3 Hz, 1H), 7.45 (d, J=8.5 Hz, 1H), 4.88 (d, J=10.4 Hz, 2H), 4.79-4.95 (m, 1H), 4.60 (s, 1H), 3.83 (s, 2H), 2.82 (s, 6H), 2.54 (s, 3H), 1.43 (s, 9H).

Procedure AS: Preparation of tert-butyl (Z)-(4-(5-(difluoromethyl)-3-(3-(N,N-dimethylsulfamoyl)phenyl)-2-methyl-1H-indol-1-yl)-3-fluorobut-2-en-1-yl)carbamate

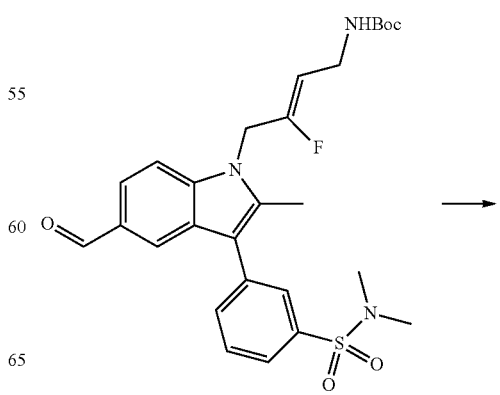

-continued

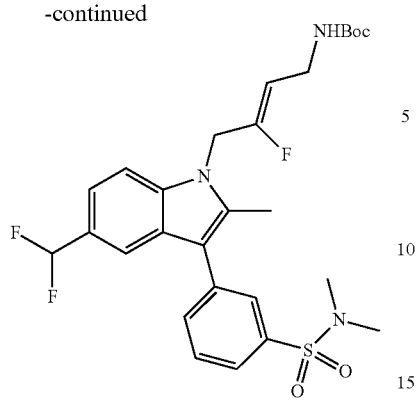

To a stirring solution of tert-butyl (Z)-(4-(3-(3-(N,N-dimethylsulfamoyl)phenyl)-5-formyl-2-methyl-1H-indol-1-yl)-3-fluorobut-2-en-1-yl)carbamate (90 mg, 0.17 mmol) in CDCl₃ (the reaction progress was monitored by ¹H-NMR) at rt was added diethylaminosulfur trifluoride (0.20 mL, 1.51 mmol). The reaction was stirred at rt for 30 h. ¹H-NMR analysis after this time showed about 60% conversion. The reaction was quenched by the addition of water (5 mL) and the product was extracted with ethyl acetate (10 mL×3). The combined organic layer was dried over Na₂SO₄ and concentrated under vacuum. Purification was performed using reverse-phase chromatography eluting with 20% acetonitrile/water followed by 50-70% acetonitrile/water over 25 min to afford tert-butyl (Z)-(4-(5-(difluoromethyl)-3-(3-(N,N-dimethylsulfamoyl)phenyl)-2-methyl-1H-indol-1-yl)-3-fluorobut-2-en-1-yl)carbamate (36.0 mg, 38%). ¹H NMR (300 MHz, CDCl₃) δ ppm: 7.87 (d, J=1.8 Hz, 1H), 7.73-7.80 (m, 3H), 7.69 (d, J=7.8 Hz, 1H), 7.41 (s, 2H), 6.74 (t, J=56.9 Hz, 1H), 4.86 (d, J=10.2 Hz, 2H), 4.73-4.90 (m, 1H), 4.59 (s, 1H), 3.81 (s, 2H), 2.81 (s, 6H), 2.52 (s, 3H), 1.42 (s, 9H).

(Z)-3-(1-(4-amino-2-fluorobut-2-en-1-yl)-5-(difluoromethyl)-2-methyl-1H-indol-3-yl)-N,N-dimethyl-benzene-sulfonamide Hydrochloride (Compound 59)

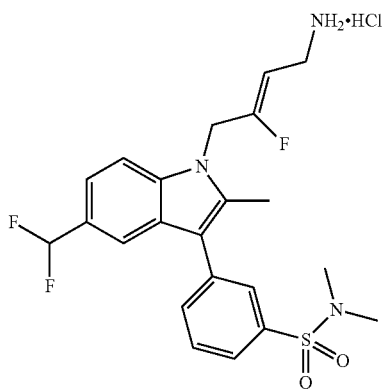

¹H NMR (300 MHz, DMSO-d₆) δ ppm: 7.99 (s, 3H), 7.88-7.70 (m, 6H), 7.41 (d, J=9.1 Hz, 1H), 7.08 (t, J=56.3 Hz, 1H), 5.26 (d, J=12.3 Hz, 2H), 5.07 (dt, J=35.9, 7.2 Hz, 1H), 3.47 (d, J=7.1 Hz, 2H), 2.70 (s, 6H), 2.54 (s, 3H).

Example 44

The following compound was prepared according to procedures AT, F, J, K, L and O.

(Z)-6-(1-(4-amino-2-fluorobut-2-en-1-yl)-5-chloro-2-methyl-1H-indol-3-yl)-N,N-dimethylpyridine-2-sulfonamide Dihydrochloride (Compound 78)

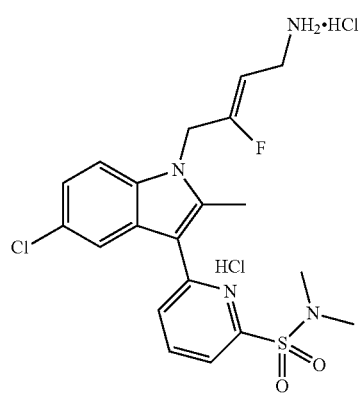

Procedure AT: Preparation of 6-bromo-N,N-dimethylpyridine-2-sulfonamide

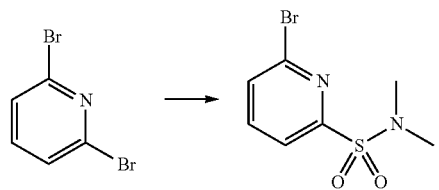

To a stirring mixture of 2,6-dibromopyridine (2.00 g, 8.44 mmol) in THF (5 mL) at 0° C. under N₂ was added isopropylmagnesium chloride (5.07 mL, 10.1 mol). The resulting mixture was stirred at rt for 1 h and then cooled to 0° C. To this was added a solution of sulfuryl chloride (1.30 mL, 16.0 mmol) in hexane (60 mL). The resulting mixture was warmed to rt and stirring was continued for a further 1 h. The reaction mixture was then concentrated in vacuo. After co-evaporated with hexane (50 mL), the reaction mixture was dried under high vacuum. The material thus obtained was redissolved in THF (5 mL), and then added dropwise to a mixture of dimethylamine (5.34 mL, 105 mmol) in THF (25 mL) at 0° C. The resulting mixture was stirred at this temperature for 30 mins. The reaction mixture was concentrated in vacuo, and the yellow residue was partitioned between ethyl acetate (100 mL) and water (30 mL). Then the organic layer was dried over Na₂SO₄ and then concentrated in vacuo. The crude material was purified over silica gel, eluting with 20% ethyl acetate in hexane to afford 6-bromo-N,N-dimethyl-pyridine-2-sulfonamide (1.10 g, 46%) as a yellow solid. ¹H NMR (300 MHz, CDCl₃) δ ppm: 7.91 (dd, J=7.5, 1.0 Hz, 1H), 7.77 (dd, J=8.0, 7.5 Hz, 1H), 7.67 (dd, J=7.9, 1.0 Hz, 1H), 3.00 (s, 6H).

(Z)-6-(1-(4-amino-2-fluorobut-2-en-1-yl)-5-chloro-2-methyl-1H-indol-3-yl)-N,N-dimethylpyridine-2-sulfonamide Dihydrochloride (Compound 78)

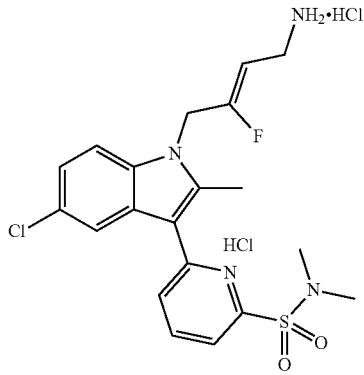

$^1$H NMR (300 MHz, Methanol-$d_4$) δ ppm: 8.12 (dd, J=7.9 Hz, 1H), 8.06 (d, J=2.0 Hz, 1H), 7.86 (dd, J=7.9, 0.9 Hz, 1H), 7.82 (dd, J=7.6, 0.9 Hz, 1H), 7.49 (d, J=8.7 Hz, 1H), 7.23 (dd, J=8.7, 2.1 Hz, 1H), 5.16 (d, J=8.7 Hz, 2H), 4.85 (dt, J=35.3, 7.5 Hz, 1H), 3.62 (d, J=7.3 Hz, 2H), 2.97 (s, 6H), 2.76 (s, 3H).

Example 45

The following compound was prepared according to procedures AD, AE, AU, AV, AW, J, K, L and O.

(Z)-5-(1-(4-amino-2-fluorobut-2-en-1-yl)-5-cyclopropyl-2-methyl-1H-indol-3-yl)-N,N-dimethylpyridine-3-sulfonamide Dihydrochloride (Compound 79)

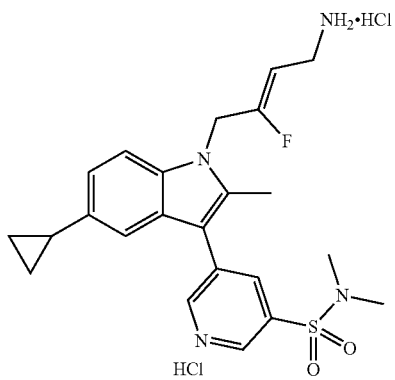

Procedure AU: Preparation of tert-butyl 5-bromo-2-methyl-1H-indole-1-carboxylate

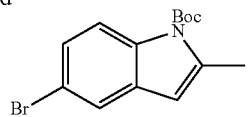

To a stirring solution of 5-bromo-2-methyl-1H-indole (1.00 g, 4.76 mmol) and 4-(dimethylamino)pyridine (0.58 g, 4.76 mmol) in $CH_2Cl_2$ (20 mL) at rt under Ar was added di-tert-butyl dicarbonate (1.56 g, 7.14 mmol) as a solution in $CH_2Cl_2$ (5 mL). The resulting mixture was left to stir at rt for 2 h. The reaction mixture was partitioned between aqueous HCl (2 M, 50 mL) and $CH_2Cl_2$ (30 mL), and the organic layer was washed with sat. aq. NaCl (30 mL). After drying over $Na_2SO_4$, the organics were concentrated in vacuo to give tert-butyl 5-bromo-2-methyl-1H-indole-1-carboxylate (1.59 g, 100%) as a straw colored solid. This material was progressed to the next step without further purification. $^1$H NMR (300 MHz, $CDCl_3$) δ ppm: 7.99 (dt, J=8.9, 0.6 Hz, 1H), 7.56 (d, J=2.0 Hz, 1H), 7.32 (dd, J=8.9, 2.0 Hz, 1H), 6.27 (s, 1H), 2.60 (d, J=1.1 Hz, 3H), 1.70 (s, 9H).

Procedure AV: Preparation of tert-butyl 5-cyclopropyl-2-methyl-1H-indole-1-carboxylate

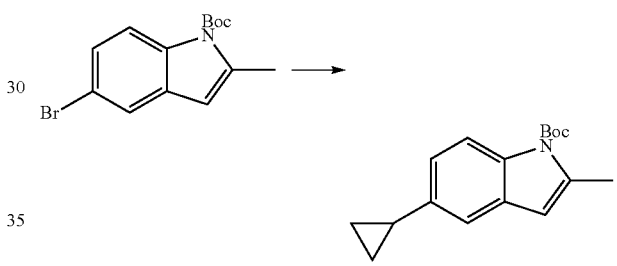

To a stirring suspension of tert-butyl 5-bromo-2-methyl-1H-indole-1-carboxylate (620 mg, 2.00 mmol), cyclopropylboronic acid (214 mg, 2.50 mmol), tricyclohexylphosphine (56.1 mg, 0.20 mmol) and potassium phosphate tribasic (1.61 g, 7.00 mmol) in toluene (8 mL) and water (0.4 mL) was added palladium (II) acetate (44.9 mg, 0.20 mmol). The resulting mixture was heated at 100° C. for 3 h. After cooling to rt, the reaction mixture was filtered through Celite™, rinsing with ethyl acetate. The filtrate was then dried over $Na_2SO_4$ and concentrated in vacuo to give tert-butyl 5-cyclopropyl-2-methyl-1H-indole-1-carboxylate (563 mg, 100%) as a yellow/orange oil. This material was progressed to the next step without purification. $^1$H NMR (300 MHz, $CDCl_3$) δ ppm: 7.98 (dt, J=8.6, 0.8 Hz, 1H), 7.16 (d, J=1.9 Hz, 1H), 6.99 (dd, J=8.6, 1.9 Hz, 1H), 6.26 (s, 1H), 2.60 (d, J=1.2 Hz, 3H), 2.05-1.94 (m, 1H), 1.70 (s, 9H), 1.01-0.90 (m, 2H), 0.77-0.67 (m, 2H).

Procedure AW: Preparation of 5-cyclopropyl-2-methyl-1H-indole

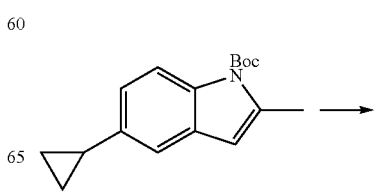

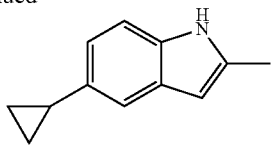

To a stirring solution of tert-butyl 5-cyclopropyl-2-methyl-1H-indole-1-carboxylate (543 mg, 2.00 mmol) in CH$_2$Cl$_2$ (5 mL) at rt was added trifluoroacetic acid (5.0 mL, 67.3 mmol). The resulting brown coloured mixture was left to stir at rt for 1 h. All volatiles were removed in vacuo, and the residue was partitioned between ethyl acetate (40 mL) and sat. aq. NaHCO$_3$ (40 mL). The organic layer was dried over Na$_2$SO$_4$ and concentrated in vacuo to give 5-cyclopropyl-2-methyl-1H-indole (343 mg, 100%) as a brown oil. This material was progressed to the next step, and purification was performed subsequently. $^1$H NMR (300 MHz, CDCl$_3$) δ ppm: 7.78 (s, 1H), 7.29 (dd, J=1.7, 0.8 Hz, 1H), 7.18 (dt, J=8.3, 0.9 Hz, 1H), 6.94 (dd, J=8.3, 1.7 Hz, 1H), 6.18 (dq, J=2.0, 1.0 Hz, 1H), 2.43 (d, J=1.0 Hz, 3H), 2.09-1.98 (m, 1H), 1.01-0.92 (m, 2H), 0.79-0.69 (m, 2H).

(Z)-5-(1-(4-amino-2-fluorobut-2-en-1-yl)-5-cyclopropyl-2-methyl-1H-indol-3-yl)-N,N-dimethylpyridine-3-sulfonamide Dihydrochloride (Compound 79)

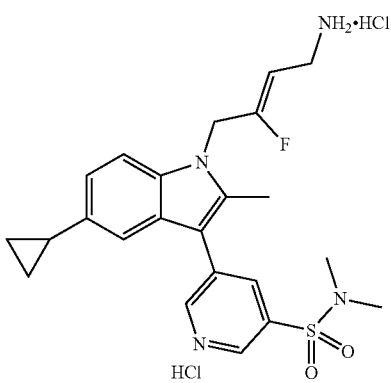

$^1$H NMR (300 MHz, Methanol-d$_4$) δ ppm: 9.05 (s, 1H), 9.01 (s, 1H), 8.45 (dd, J=1.9 Hz, 1H), 7.43 (d, J=8.5 Hz, 1H), 7.33 (d, J=1.6 Hz, 1H), 7.06 (dd, J=8.5, 1.6 Hz, 1H), 5.13 (d, J=8.8 Hz, 2H), 4.86 (dt, J=36.0, 7.6, Hz, 1H), 3.62 (d, J=7.4 Hz, 2H), 2.90 (s, 6H), 2.59 (s, 3H), 2.07-1.96 (m, 1H), 1.00-0.91 (m, 2H), 0.70-0.61 (m, 2H).

Example 46

The following compounds were prepared according to procedures AX, G, H, I, J, K, L and T.

Procedure AX: Preparation of 3-fluoro-N,N-bis(4-methoxybenzyl)-4-nitrobenzenesulfonamide

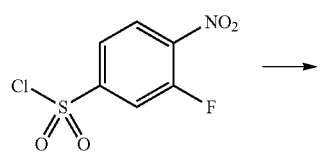

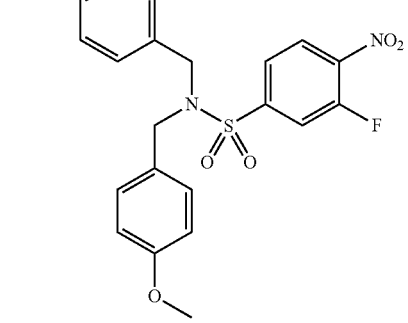

To a stirring solution of bis(4-methoxybenzyl)amine (1.07 g, 4.17 mmol) and triethylamine (1.28 mL, 9.18 mmol) in THF at 0° C. was added 3-fluoro-4-nitrobenzenesulfonyl chloride (1.00 g, 4.17 mmol) in one lot. The thick, bright yellow suspension was stirred at 0° C. for a further 30 min. The reaction mixture was concentrated in vacuo. To the residue was added aq. HCl (2 M, 10 mL) followed by water (100 mL). The resulting suspension was stirred at rt for 10 min, and the solid, thus formed, was filtered and washed with water. The solid was then dried in an oven at 60° C. for 2 h to afford 3-fluoro-N,N-bis(4-methoxybenzyl)-4-nitrobenzenesulfonamide (1.50 g, 78%) as a pale yellow solid. $^1$H NMR (300 MHz, CDCl$_3$) 3 ppm: 8.09 (dd, J=8.6, 6.9 Hz, 1H), 7.63 (dt, J=8.5, 1.4 Hz, 1H), 7.56 (dd, J=9.9, 1.9 Hz, 1H), 7.06 (d, J=8.6 Hz, 4H), 6.82 (d, J=8.6 Hz, 4H), 4.34 (s, 4H), 3.81 (s, 6H).

(Z)-1-(4-amino-2-fluorobut-2-en-1-yl)-2-methyl-3-(pyridin-4-yl)-1H-indole-5-sulfonamide Dihydrochloride (Compound 84)

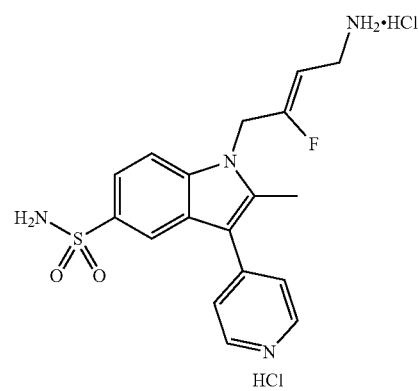

$^1$H NMR (300 MHz, Methanol-d$_4$) δ ppm: 8.86 (d, J=7.0 Hz, 2H), 8.41-8.36 (m, 1H), 8.25 (d, J=7.0 Hz, 2H), 7.90 (dd, J=8.7, 1.7 Hz, 1H), 7.80 (d, J=8.7 Hz, 1H), 5.32 (d, J=11.4 Hz, 2H), 5.17 (dt, J=34.1, 7.4 Hz, 1H), 3.66 (d, J=7.6 Hz, 2H), 2.79 (s, 3H).

(Z)-1-(4-amino-2-fluorobut-2-en-1-yl)-3-(4-fluorophenyl)-2-methyl-1H-indole-5-sulfonamide Hydrochloride (Compound 95)

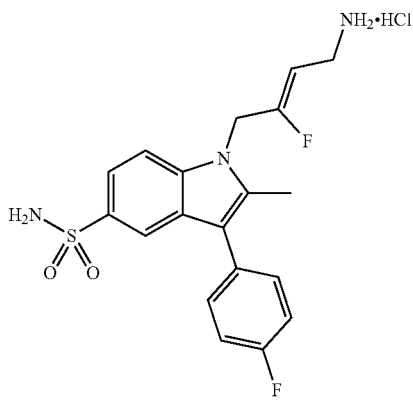

¹H NMR (300 MHz, DMSO-d₆) δ ppm: 8.01 (s, 3H), 7.97 (d, J=1.8 Hz, 1H), 7.75 (d, J=8.7 Hz, 1H), 7.63 (dd, J=8.7, 1.8 Hz, 1H), 7.49 (dd, J=8.6, 5.7 Hz, 2H), 7.38 (dd, J=8.9 Hz, 2H), 7.16 (s, 2H), 5.25 (d, J=12.2 Hz, 2H), 5.05 (dt, J=35.9, 7.2 Hz, 1H), 3.47 (s, 2H), 3.34 (s, 3H).

Example 47

The following compound was prepared according to procedures AY, E, F, G, H, I, J, K, AH, L and O.

(Z)-3-(1-(4-amino-2-fluorobut-2-en-1-yl)-2-chloro-5-(methylsulfonyl)-1H-indol-3-yl)-N,N-dimethyl-benzenesulfonamide Hydrochloride (Compound 100)

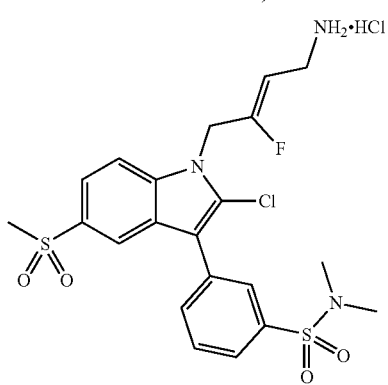

Procedure AY: Preparation of 2-methyl-5-(methylsulfonyl)-1H-indole

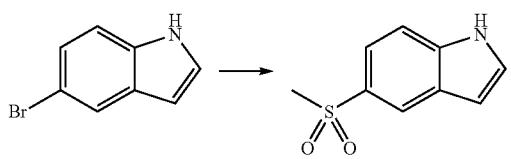

To a stirring solution of 5-bromo-1H-indole (1.00 g, 5.10 mmol), sodium pyrrolidine-2-carboxylate (140 mg, 1.02 mmol) in DMSO (5 mL) under Ar was added cuprous iodide (97.2 mg, 0.51 mmol). The resulting mixture was heated at 100° C. for 22 h. The reaction mixture was cooled to rt and diluted with ethyl acetate (50 mL) and brine/water (1:1, 40 mL). After filtering the biphasic mixture through Celite™, the organic layer was separated, washed with water and brine; dried over MgSO₄ and then concentrated in vacuo. The crude material was purified using a 40 g RediSep cartridge, eluting over a gradient of 10-80% ethyl acetate in hexane to afford the title compound 5-(methylsulfonyl)-1H-indole (483 mg, 49%) as a white solid. ¹H NMR (300 MHz, CDCl₃) δ ppm: 8.62 (s, 1H), 8.32 (dt, J=1.7, 0.7 Hz, 1H), 7.76 (dd, J=8.7, 1.8 Hz, 1H), 7.55 (dt, J=8.6, 0.8 Hz, 1H), 7.40 (dd, J=3.3, 2.4 Hz, 1H), 6.73 (ddd, J=3.1, 2.0, 1.0 Hz, 1H), 3.11 (s, 3H).

(Z)-3-(1-(4-amino-2-fluorobut-2-en-1-yl)-2-chloro-5-(methylsulfonyl)-1H-indol-3-yl)-N,N-dimethyl-benzenesulfonamide Hydrochloride (Compound 100)

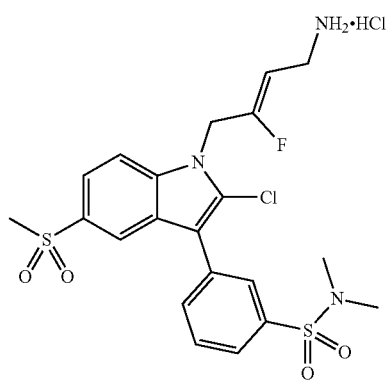

¹H NMR (300 MHz, DMSO-d₆) δ ppm: 8.16 (d, J=1.7 Hz, 1H), 8.06-7.80 (m, 9H), 5.40 (d, J=13.7 Hz, 2H), 5.27 (dt, J=35.9, 7.3 Hz, 1H), 3.49 (s, 2H), 3.23 (s, 3H), 2.71 (s, 6H).

Example 48

The following compound was prepared according to procedures E, F, J, K, L, AZ, AAA and O.

(Z)-3-(1-(4-amino-2-fluorobut-2-en-1-yl)-5-(methoxymethyl)-2-methyl-1H-pyrrolo[3,2-b]pyridin-3-yl)-N,N-dimethylbenzenesulfonamide Dihydrochloride (Compound 103)

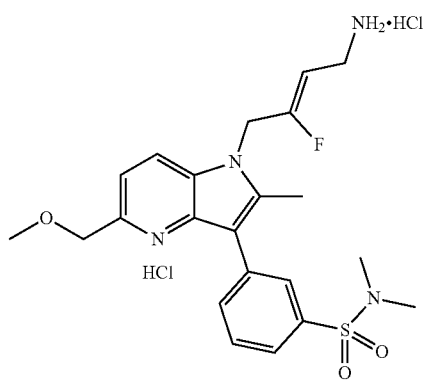

Procedure AZ: Preparation of tert-butyl (Z)-(4-(3-(3-(N,N-dimethylsulfamoyl)phenyl)-5-(hydroxymethyl)-2-methyl-1H-pyrrolo[3,2-b]pyridin-1-yl)-3-fluorobut-2-en-1-yl)carbamate

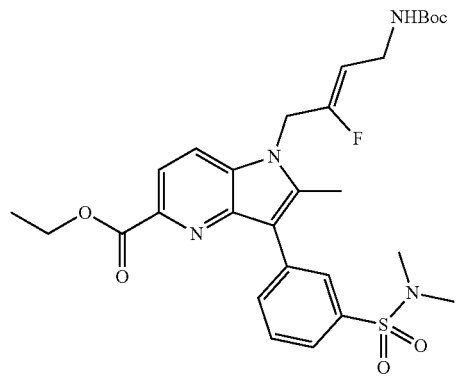

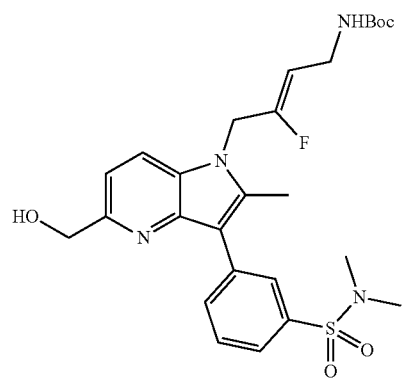

Diisobutylaluminium hydride (1 M in CH$_2$Cl$_2$, 2.00 mL) was added to a solution of ethyl (Z)-1-(4-((tert-butoxycarbonyl)amino)-2-fluorobut-2-en-1-yl)-3-(3-(N,N-dimethylsulfamoyl)phenyl)-2-methyl-1H-pyrrolo[3,2-b]pyridine-5-carboxylate (400 mg, 0.70 mmol) in dichloromethane (5 mL) at 0° C. The ice bath was then removed and the mixture was allowed to stir at ambient temperature for 30 min. TLC analysis after this time showed approximately 40-50% conversion. Additional diisobutylaluminium hydride (1 M in CH$_2$Cl$_2$, 2.00 mL) was added at rt, and the reaction stirred for a further 30 min. TLC analysis after this time showed approximately 80-90% conversion. An additional, final amount, of diisobutylaluminium hydride (1 M in CH$_2$Cl$_2$, 1.00 mL) was added, and stirring was continued at rt for a further for 1 h. Methanol (2 mL) was added and then the reaction mixture was poured on a mixture of aq. NaOH solution (2 M, 20 mL) and dichloromethane (20 mL). The aqueous layer was extracted with dichloromethane (20 mL×2). The combined organics were washed with aq. NaOH (1 M, 25 mL), brine, dried over Na$_2$SO$_4$ and concentrated in vacuo to afford tert-butyl (Z)-(4-(3-(3-(N,N-dimethylsulfamoyl)phenyl)-5-(hydroxymethyl)-2-methyl-1H-pyrrolo[3,2-b]pyridin-1-yl)-3-fluorobut-2-en-1-yl)carbamate (300 mg, 81%). This material was progressed to the next step without purification.

Procedure AAA: Preparation of tert-butyl (Z)-(4-(3-(3-(N,N-dimethylsulfamoyl)phenyl)-5-(methoxymethyl)-2-methyl-1H-pyrrolo[3,2-b]pyridin-1-yl)-3-fluorobut-2-en-1-yl)carbamate

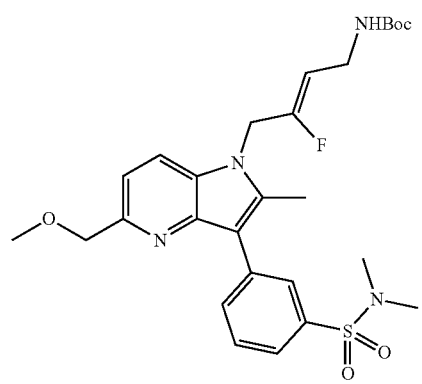

Sodium hydride (15.0 mg, 0.31 mmol) was added in one lot to a solution of tert-butyl (Z)-(4-(3-(3-(N,N-dimethylsulfamoyl)phenyl)-5-(hydroxymethyl)-2-methyl-1H-pyrrolo[3,2-b]pyridin-1-yl)-3-fluorobut-2-en-1-yl)carbamate (133 mg, 0.25 mmol) in DMF (1.5 mL) under nitrogen at 0° C. The mixture was stirred for 10 min, and then iodomethane (19 uL, 0.31 mmol) was added in one lot. The mixture was stirred at ambient temperature for 1 h. The reaction mixture was diluted with water (20 mL) and the product was extracted with ethyl acetate (15 mL×3). The combined organics were washed with water, dried over Na$_2$SO$_4$ and concentrated under vacuum. The crude material was purified using combiflash to afford tert-butyl (Z)-(4-(3-(3-(N,N-dimethylsulfamoyl)phenyl)-5-(methoxymethyl)-2-methyl-1H-pyrrolo[3,2-b]pyridin-1-yl)-3-fluorobut-2-en-1-yl)carbamate (41.0 mg, 28%). $^1$H NMR (300 MHz, CDCl$_3$) δ ppm: 8.16 (dt, J=1.8, 0.9 Hz, 1H), 7.99 (dt, J=7.6, 1.5 Hz, 1H), 7.72 (ddd, J=7.8, 1.9, 1.3 Hz, 1H), 7.65 (d, J=7.7 Hz, 1H), 7.63 (d, J=7.7 Hz, 1H), 7.32 (d, J=8.4 Hz, 1H), 4.83 (d, J=9.9 Hz, 2H), 4.77-4.52 (m, 4H), 3.80 (s, 2H), 3.48 (s, 3H), 2.83 (s, 6H), 2.61 (s, 3H), 1.42 (s, 9H).

193

(Z)-3-(1-(4-amino-2-fluorobut-2-en-1-yl)-5-(methoxymethyl)-2-methyl-1H-pyrrolo[3,2-b]pyridin-3-yl)-N,N-dimethylbenzenesulfonamide Dihydrochloride (Compound 103)

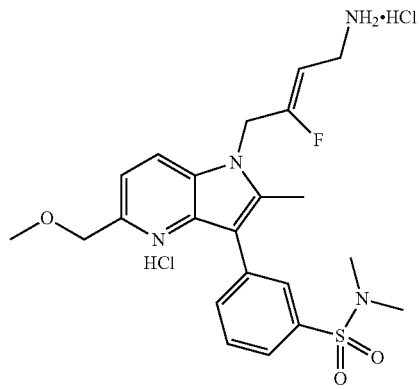

$^1$H NMR (300 MHz, Methanol-d$_4$) δ 8.74 (d, J=8.4 Hz, 1H), 8.00-7.82 (m, 4H), 7.76 (d, J=8.5 Hz, 1H), 5.43 (d, J=13.2 Hz, 3H), 5.39 (dt, J=35.2, 7.3 Hz, 1H), 4.81 (s, 2H), 3.68 (d, J=7.3 Hz, 2H), 3.51 (s, 3H), 2.78 (s, 6H), 2.64 (s, 3H).

Example 49

The following compound was prepared according to procedures E, F, AAB, AAC, J, K, L and O.

(Z)-3-(1-(4-amino-2-fluorobut-2-en-1-yl)-5-(isopropylsulfonyl)-2-methyl-1H-indol-3-yl)-N,N-dimethylbenzenesulfonamide Hydrochloride (Compound 106)

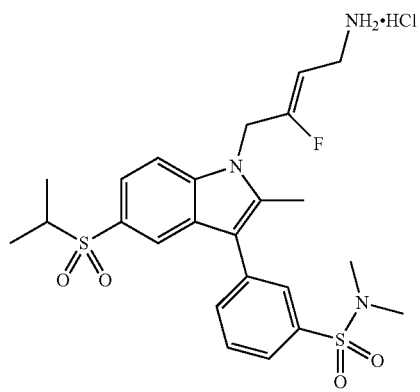

Procedure AAB: Preparation of 5-(isopropylthio)-2-methyl-1H-indole

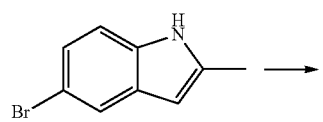

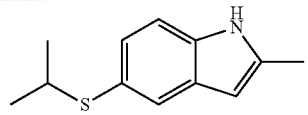

A stirring solution of 5-bromo-2-methyl-1H-indole (1.05 g, 5.00 mmol), sodium 2-propanethiolate (589 mg, 6.00 mmol), sodium t-butoxide (961 mg, 10.0 mmol) and cyclopentyl(diphenyl)phosphane; iron (339 mg, 0.60 mmol) in 1,4-dioxane was degassed by passing through it a stream of N$_2$ gas for 15 min. Diacetoxypalladium (112 mg, 0.50 mmol) was then added and the reaction mixture was heated at 90° C. overnight. After cooling to rt, the reaction mixture was diluted with ethyl acetate, and then filtered through Celite™. The filtrate washed with water and brine, dried over Na$_2$SO$_4$ and concentrated in vacuo. The crude material was adsorbed onto silica gel, and purification was performed using a 40 g Redisep cartridge eluting with a gradient of 0-20% ethyl acetate in hexane to afford crude 5-(isopropylthio)-2-methyl-1H-indole (1.09 g, 71%). This material was progressed to the next step without further purification.

Procedure AAC: Preparation of tert-butyl 3-bromo-5-(isopropylsulfonyl)-2-methyl-1H-indole-1-carboxylate

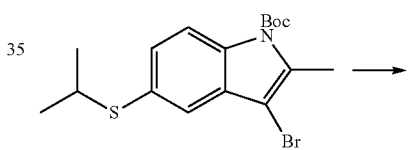

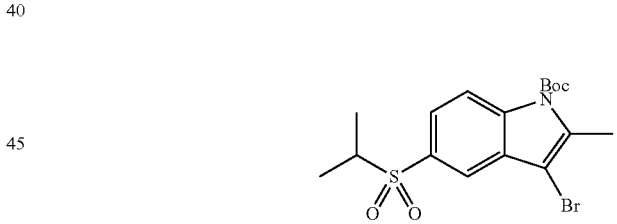

To a stirred solution of 5-(isopropylthio)-2-methyl-1H-indole (300 mg, 0.39 mmol) in THF:MeOH (3 mL: 3 mL) at 0° C. was added a solution of Oxone™ (0.96 g, 1.56 mmol) in water (5 mL). The resulting mixture stirred at 0° C. for 1 h, then at rt for 2 h. The reaction mixture was poured into a mixture of water (20 mL) and ethyl acetate (30 mL). The organic layer was washed with brine, dried over MgSO$_4$, and concentrated in vacuo. Purification was performed using a 12 g RediSep cartridge, eluting over a gradient of 0-30% ethyl acetate in hexane to afford the title compound, tert-butyl 3-bromo-5-(isopropylsulfonyl)-2-methyl-1H-indole-1-carboxylate (68.0 mg, 42%) as a white solid. $^1$H NMR (300 MHz, CDCl$_3$) δ ppm: 8.31 (dd, J=8.8, 0.6 Hz, 1H), 8.03 (dd, J=1.9, 0.6 Hz, 1H), 7.80 (dd, J=8.8, 1.9 Hz, 1H), 3.25 (p, J=6.9 Hz, 1H), 2.69 (s, 3H), 1.72 (s, 9H), 1.32 (d, J=6.9 Hz, 6H).

195

(Z)-3-(1-(4-amino-2-fluorobut-2-en-1-yl)-5-(isopropylsulfonyl)-2-methyl-1H-indol-3-yl)-N,N-dimethyl-benzenesulfonamide Hydrochloride (Compound 106)

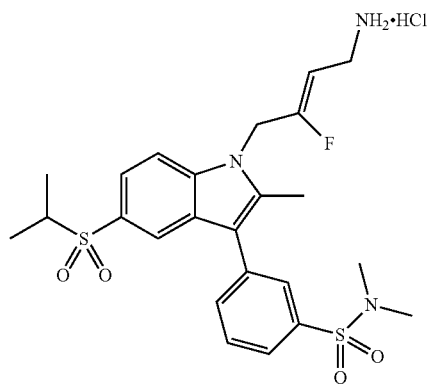

$^1$H NMR (300 MHz, Methanol-d$_4$) δ ppm: 8.07 (dd, J=1.7, 0.6 Hz, 1H), 7.89-7.85 (m, 1H), 7.81 (t, J=1.3 Hz, 3H), 7.77 (d, J=8.7 Hz, 1H), 7.71 (dd, J=8.7, 1.7 Hz, 1H), 5.25 (d, J=9.9 Hz, 2H), 4.98 (dt, J=34.1, 7.5 Hz, 1H), 3.65 (dd, J=7.3, 1.5 Hz, 2H), 3.33-3.26 (m, 1H), 2.80 (s, 6H), 2.62 (s, 3H), 1.25 (d, J=6.8 Hz, 6H).

Example 50

The following compound was prepared according to procedures E, F, J, K, L, AAD, AAE and O.

(Z)-3-(1-(4-amino-2-fluorobut-2-en-1-yl)-2-methyl-5-(methylsulfonamido)-1H-indol-3-yl)-N,N-dimethylbenzenesulfonamide Hydrochloride (Compound 104)

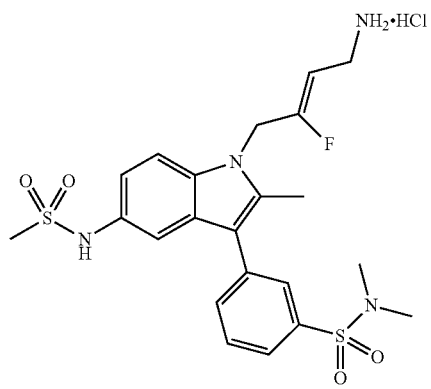

196

Procedure AAD: Preparation of tert-butyl (Z)-(4-(5-amino-3-(3-(N,N-dimethylsulfamoyl)phenyl)-2-methyl-1H-indol-1-yl)-3-fluorobut-2-en-1-yl)carbamate

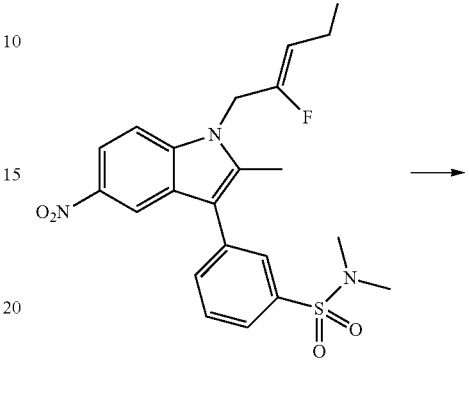

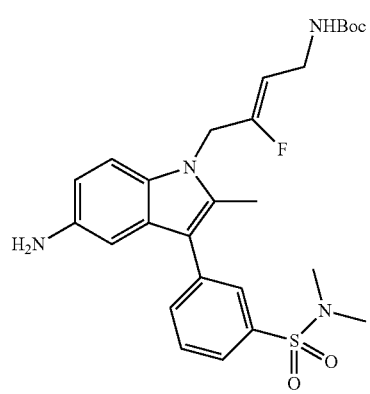

To a vigorously stirring suspension of tert-butyl (Z)-(4-(3-(3-(N,N-dimethylsulfamoyl)phenyl)-2-methyl-5-nitro-1H-indol-1-yl)-3-fluorobut-2-en-1-yl)carbamate (270 mg, 0.49 mmol) and zinc (powder) (484 mg, 7.41 mmol) in THF (3 mL) at rt was added methanol (3 mL) followed by ammonium chloride (396 mg, 7.41 mmol). The resulting mixture was left to stir at rt for 2 h. The reaction mixture was diluted with ethyl acetate (20 mL) and then filtered through a pad of Celite™ to remove inorganics. The filtrate was concentrated in vacuo to give tert-butyl (Z)-(4-(5-amino-3-(3-(N,N-dimethylsulfamoyl)phenyl)-2-methyl-1H-indol-1-yl)-3-fluorobut-2-en-1-yl)carbamate (255 mg, 100%) as a red colored oil. This material was progressed to the next step and purification was performed subsequently.

Procedure AAE: Preparation of tert-butyl (Z)-(4-(3-(3-(N,N-dimethylsulfamoyl)phenyl)-2-methyl-5-(methylsulfonamido)-1H-indol-1-yl)-3-fluorobut-2-en-1-yl)carbamate

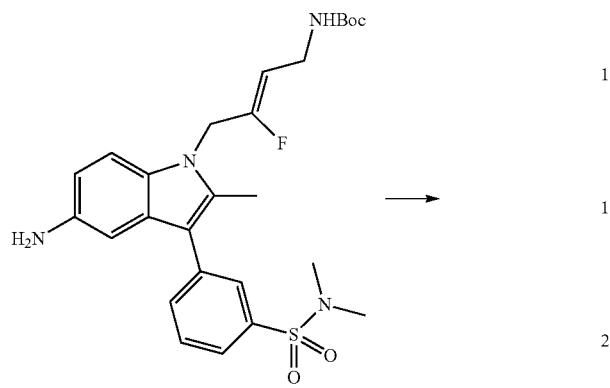

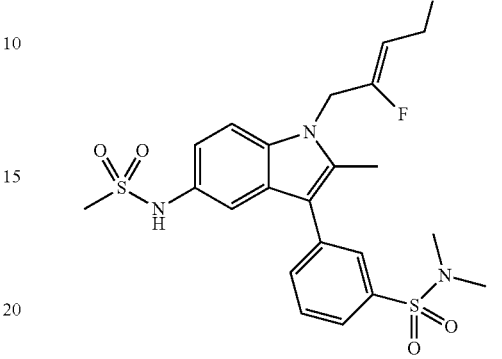

To a stirring solution of tert-butyl (Z)-(4-(5-amino-3-(3-(N,N-dimethylsulfamoyl)phenyl)-2-methyl-1H-indol-1-yl)-3-fluorobut-2-en-1-yl)carbamate (255 mg, 0.49 mmol) in CH$_2$Cl$_2$ (4 mL) at 0° C. was added pyridine (0.06 mL, 0.74 mmol) followed by methanesulfonyl chloride (0.04 mL, 0.54 mmol). The resulting solution was warmed to rt, and stirring was continued for 2 h. The reaction mixture was partitioned between aq. HCl (1 M; 30 mL) and CH$_2$Cl$_2$ (30 mL). The organic layer was washed with sat. aq. NaCl (20 mL), dried over Na$_2$SO$_4$, and then concentrated in vacuo to give a red/brown oil. The crude material was purified over silica gel eluting with 60% ethyl acetate in hexane to afford tert-butyl (Z)-(4-(3-(3-(N,N-dimethylsulfamoyl)phenyl)-2-methyl-5-(methylsulfonamido)-1H-indol-1-yl)-3-fluorobut-2-en-1-yl)carbamate (150 mg, 51%) as an orange solid. $^1$H NMR (300 MHz, CDCl$_3$) δ ppm: 7.87 (ddd, J=1.8, 0.9 Hz, 1H), 7.74 (ddd, J=7.3, 1.8, 1.8 Hz, 1H), 7.69 (ddd, J=7.4, 1.7, 1.7 Hz, 1H), 7.66 (d, J=7.7 Hz, 1H), 7.53 (d, J=2.1 Hz, 1H), 7.31 (d, J=8.7 Hz, 1H), 7.14 (dd, J=8.6, 2.1 Hz, 1H), 6.76 (s, 1H), 4.82 (d, J=10.2 Hz, 2H), 4.64 (s, 1H), 3.81 (s, 2H), 2.95 (s, 3H), 2.80 (s, 6H), 2.50 (s, 31-), 1.42 (s, 9H).

(Z)-3-(1-(4-amino-2-fluorobut-2-en-1-yl)-2-methyl-5-(methylsulfonamido)-1H-indol-3-yl)-N,N-dimethylbenzenesulfonamide Hydrochloride (Compound 104)

$^1$H NMR (300 MHz, Methanol-d$_4$) δ ppm: 7.85 (s, 1H), 7.81-7.73 (m, 3H), 7.52 (d, J=2.1 Hz, 1H), 7.50 (d, J=8.8 Hz, 1H), 7.16 (dd, J=8.7, 2.1 Hz, 1H), 5.13 (d, J=8.7 Hz, 2H), 4.91 (dt, J=35.4, 7.6 Hz, 1H), 3.63 (d, J=7.5 Hz, 2H), 2.89 (s, 3H), 2.79 (s, 6H), 2.55 (s, 3H).

Example 51

The following compound was prepared according to procedures J, K, L, AAB, AAC and O.

(Z)—N-(1-(4-amino-2-fluorobut-2-en-1-yl)-3-(2,6-dimethylpyridin-4-yl)-2-methyl-1H-indol-5-yl)methanesulfonamide Dihydrochloride (Compound 102)

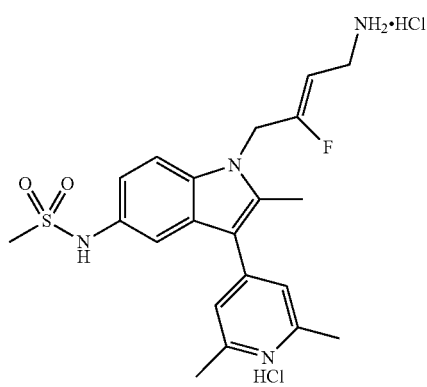

$^1$H NMR (300 MHz, DMSO-d$_6$) δ ppm: 9.53 (s, 1H), 8.16 (s, 3H), 7.75 (s, 2H), 7.72-7.63 (m, 2H), 7.19 (dd, J=8.7, 2.0 Hz, 1H), 5.33-5.11 (m, 3H), 2.92 (s, 3H), 2.76 (s, 6H), 2.65 (s, 3H).

Example 52

The following compound was prepared according to procedures AD, AE, AAF, Q, J, K, L, and O.

199

(Z)-5-(1-(4-amino-2-fluorobut-2-en-1-yl)-2-methyl-5-(trifluoromethoxy)-1H-indol-3-yl)-N,N-dimethyl-pyridine-3-sulfonamide Dihydrochloride (Compound 85)

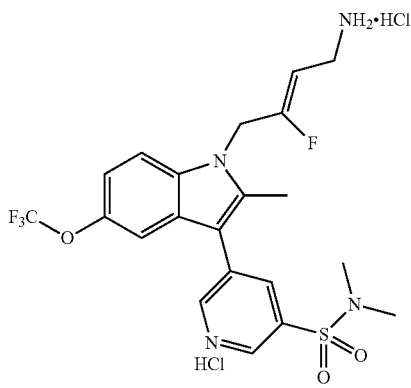

Procedure AAF: Preparation of 2-methyl-5-(trifluoromethoxy)-1H-indole

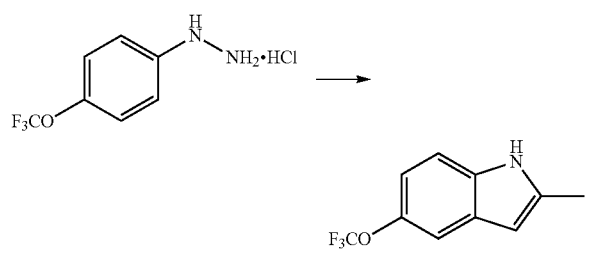

To a stirring suspension of 4-(trifluoromethoxy)phenylhydrazine hydrochloride (1.00 g, 4.37 mmol) in tert-butanol (20 mL) at rt was added (phenylthio)propanone (727 mg, 4.37 mmol). The resulting mixture was heated at reflux for 1 h. After cooling to rt, the reaction mixture was diluted with water (70 mL) and then transferred to a separatory funnel. The aqueous layer was extracted with ethyl acetate (50 mL×2), and the combined organics were washed with sat. aq. NaCl (50 mL); dried over Na$_2$SO$_4$ and concentrated in vacuo to give a dark red residue. To this residue was taken up in trifluoroacetic acid (20 mL), and to this was added 2-sulfanylbenzoic acid (1.35 g, 8.75 mmol) followed by (phenylthio)propanone (727 mg, 4.37 mmol). The resulting mixture was left to stir at rt for 30 h. The reaction mixture was then poured into water (100 mL) and then transferred en masse to a seperatory funnel. The aqueous mixture was extracted with ethyl acetate (50 mL×2), and the combined organics were washed with aqueous NaOH (1 M, 70 mL) and sat. aq. NaCl (50 mL); dried over Na$_2$SO$_4$ and concentrated in vacuo to give a dark red residue. The crude material was purified over silica gel eluting with 10% ethyl acetate in hexane to give only crude 2-methyl-5-(trifluoromethoxy)-1H-indole. This material was progressed to the next step, and purification was performed subsequently.

200

(Z)-5-(1-(4-amino-2-fluorobut-2-en-1-yl)-2-methyl-5-(trifluoromethoxy)-1H-indo-3-yl)-N,N-dimethyl-pyridine-3-sulfonamide Dihydrochloride (Compound 85)

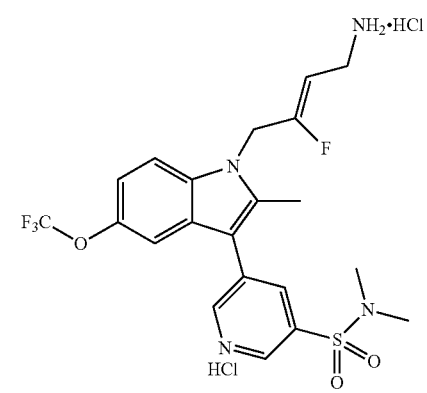

$^1$H NMR (300 MHz, Methanol-d$_4$) δ ppm: 9.08 (d, J=6.3 Hz, 2H), 8.51 (dd, J=2.0 Hz, 1H), 7.66 (d, J=8.9 Hz, 1H), 7.50 (d, J=2.2 Hz, 1H), 7.22 (d, J=8.8 Hz, 1H), 5.22 (d, J=9.9 Hz, 2H), 5.01 (dt, J=34.1, 7.4 Hz, 1H), 3.65 (d, J=7.4 Hz, 2H), 2.90 (s, 6H), 2.63 (s, 3H).

Example 53

The following compound was prepared according to procedures P, AAG, AAH, Q, J, AAI, K, L, and O.

(Z)-3-(1-(4-amino-2-fluorobut-2-en-1-yl)-5-(1,1-difluoroethyl)-2-methyl-1H-pyrrolo[3,2-b]pyridin-3-yl)-N,N-dimethylbenzenesulfonamide Dihydrochloride (Compound 111)

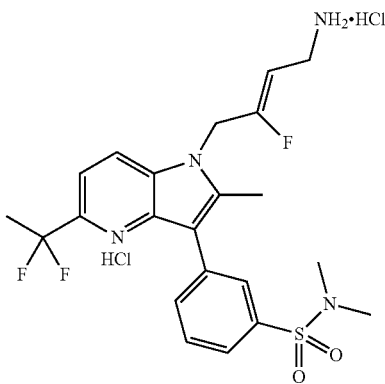

Procedure AAG: Preparation of 2-methyl-3-(methylthio)-1H-indole-5-carbonitrile

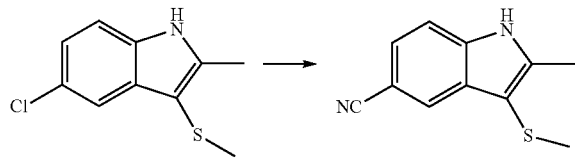

A stirring mixture of 5-chloro-2-methyl-3-(methylthio)-1H-indole (1.00 g, 4.70 mmol), Zn(CN)₂ (0.84 g, 7.10 mmol), Pd(PPh₃)₄ (543 mg, 0.47 mmol) and NMP (10 mL) was heated at 100° C. for 1 h under MW. The reaction mixture was diluted with water, extracted with ethyl acetate (50 ml×3), washed with brine, dried over Na₂SO₄ and concentrated in vacuo to afford 2-methyl-3-(methylthio)-1H-indole-5-carbonitrile (0.70 g), which was used directly in next step without further purification.

Procedure AAH: Preparation of 1-(2-methyl-3-(methylthio)-1H-indol-5-yl)ethan-1-one

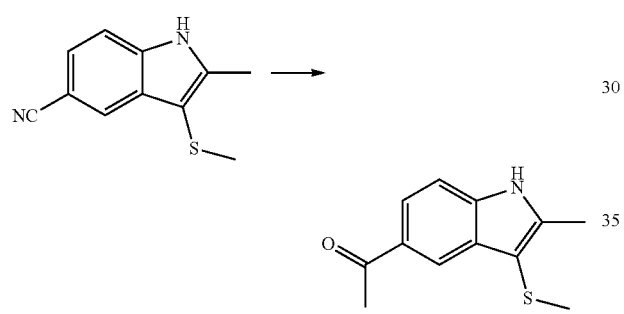

To a stirring solution of 2-methyl-3-(methylthio)-1H-indole-5-carbonitrile (2.8 g, 13.8 mmol) in dry THF (50 mL) under nitrogen was added methylmagnesium bromide (3 M in diethylether, 13.8 mL, 41.4 mmol) drop-wise at 0° C. The resulting mixture was stirred at rt overnight. The reaction mixture was poured into aqueous NH₄Cl, and stirring was continued for 30 min. The aqueous phase was extracted with ethyl acetate (100 mL×3), and the combined organic phases were dried over Na₂SO₄, concentrated in vacuo. The crude material was purified over silica gel ethyl acetate/hexane (5:1) to afford 1-(2-methyl-3-(methylthio)-1H-indol-5-yl)ethan-1-one (2.10 g, 69%) as a white solid. $^1$H-NMR (300 MHz, CDCl₃): δ ppm: 8.92 (s, 1H), 7.94-7.91 (m, 1H), 7.59-7.57 (m, 1H), 2.85 (s, 3H), 2.58 (s, 3H), 2.50 (s, 3H).

Procedure AAI: Preparation of tert-butyl 3-bromo-5-(1,1-difluoroethyl)-2-methyl-1H-indole-1-carboxylate

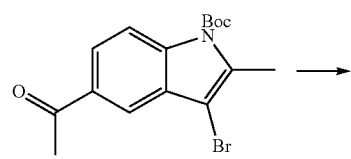

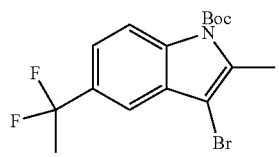

To tert-butyl 5-acetyl-3-bromo-2-methyl-1H-indole-1-carboxylate (1.30 g, 3.68 mmol) was added neat DAST (30 mL) and the mixture were heated at 50° C. overnight. After cooling to rt, the reaction mixture was quenched with cold sat.NaHCO₃, and the pH was adjusted to >8. The aqueous mixture was extracted with dichloromethane (50 mL×2), and the combined organics were dried over Na₂SO₄, and evaporated in vacuo. The crude material was purified over silica gel eluting with ethyl acetate/hexane (20:1) followed by ethyl acetate/hexane (10:1) to afford tert-butyl 3-bromo-5-(1,1-difluoroethyl)-2-methyl-1H-indole-1-carboxylate (0.90 g, 65% yield) as an off-white solid. $^1$H-NMR (300 MHz, CDCl₃): δ ppm: 8.42-8.39 (m, 1H), 7.62-7.59 (m, 1H), 2.73 (s, 3H), 2.19-2.06 (m, 3H), 1.70 (s, 9H).

(Z)-3-(1-(4-amino-2-fluorobut-2-en-1-yl)-5-(1,1-difluoroethyl)-2-methyl-1H-pyrrolo[3,2-b]pyridin-3-yl)-N,N-dimethylbenzenesulfonamide Dihydrochloride (Compound 111)

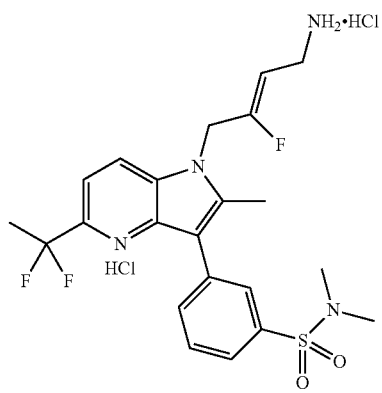

$^1$H NMR (300 MHz, DMSO-d₆) δ ppm: 8.25 (dd, J=1.8 Hz, 1H), 8.23 (s, 3H), 8.20 (d, J=8.6 Hz, 1H), 8.00 (dt, J=7.8, 1.5 Hz, 1H), 7.77 (dd, J=7.7 Hz, 1H), 7.68 (dt, J=7.9, 1.4 Hz, 1H), 7.55 (d, J=8.6 Hz, 1H), 5.32 (d, J=12.7 Hz, 2H), 5.14 (dt, J=36.1, 7.2 Hz, 1H), 3.45 (t, J=6.4 Hz, 2H), 2.70 (s, 6H), 2.69 (s, 3H), 2.04 (t, J=18.8 Hz, 3H).

Example 54

The following compound was prepared according to procedures AAJ, AAK, AAL, AAM, AAN and AAO.

(Z)-3-(1-(4-amino-2-fluorobut-2-en-1-yl)-5-hydroxy-2-methyl-1H-pyrrolo[3,2-b]pyridin-3-yl)-N,N-dimethylbenzenesulfonamide Hydrochloride (Compound 60)

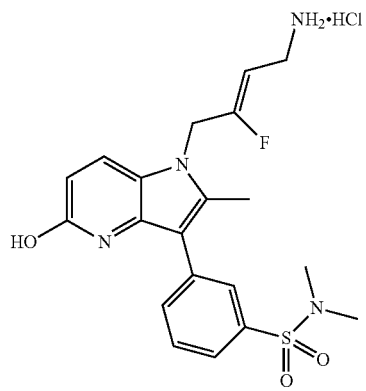

Procedure AAJ: Preparation of di-tert-butyl 1-(6-methoxypyridin-3-yl)hydrazine-1,2-dicarboxylate

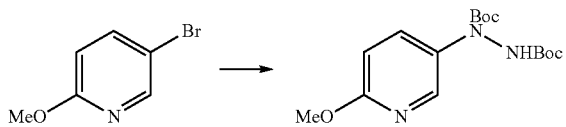 [SMILES: COc1ccc(Br)cn1 ; COc1ccc(N(NC(=O)OC(C)(C)C)C(=O)OC(C)(C)C)cn1]

To a stirring solution of 5-bromo-2-methoxy-pyridine (564 mg, 3.00 mmol) in THF (4 mL) at −40° C. under nitrogen was added n-butyllithium (2.06 mL, 3.30 mmol) dropwise. The resulting mixture was stirred for 10 mins at this temperature before addition of a solution of tert-butyl (NE)-N-tert-butoxycarbonyliminocarbamate (760 mg, 3.30 mmol) in THF (4 mL) dropwise. The reaction mixture was then allowed to warm slowly to rt and then poured onto ice water. The product was extracted with ethyl acetate (20 mL×2). The combined organic layers were washed with brine, dried over Na$_2$SO$_4$ and concentrated in vacuo. Purification was performed using a 40 g RediSep cartridge, eluting over a gradient of 10-30% ethyl acetate in hexane to afford the title compound di-tert-butyl 1-(6-methoxypyridin-3-yl)hydrazine-1,2-dicarboxylate (490 mg, 43%) as a yellow oil. $^1$H NMR (300 MHz, DMSO-d$_6$) δ ppm: 9.65 (s, 1H), 8.09 (d, J=2.7 Hz, 1H), 7.62 (d, J=8.9 Hz, 1H), 6.81 (dd, J=8.9, 0.7 Hz, 1H), 3.84 (d, J=2.2 Hz, 3H), 1.41 (s, 18H).

Procedure AAK: Preparation of 3-(2-hydroxypropyl)-N,N-dimethylbenzenesulfonamide

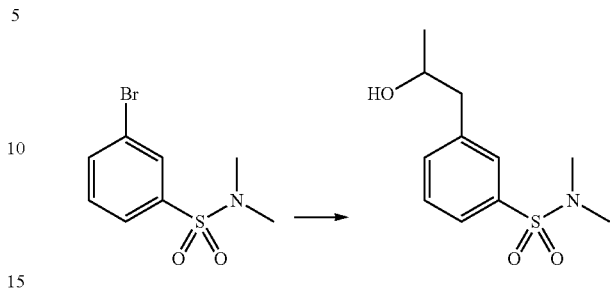

To a stirring solution of 3-bromo-N,N-dimethylbenzenesulfonamide (500 mg, 1.89 mmol) in THF (9 mL), at −78° C. was added n-butyllithium (1.04 mL, 2.08 mmol) dropwise. The mixture was stirred at this temperature for 15 mins. 2-Methyloxirane (332 uL, 4.73 mmol) was added, followed by boron trifluoride diethyl etherate (234 uL, 1.89 mmol). The resulting mixture was stirred at −78° C. for a further 20 mins and then warmed slowly to rt. Saturated aqueous NH$_4$Cl (20 mL) was added and the mixture was stirred at rt for 5 mins. The product was extracted with ethyl acetate and the organic layer was dried over Na$_2$SO$_4$ and concentrated in vacuo. The crude material was purified by reverse-phase chromatography using a 40 g C18 column, eluting with 40-60% acetonitrile/water over 30 mins to afford crude 3-(2-hydroxypropyl)-N,N-dimethylbenzenesulfonamide (200 mg, 29%) as a yellow oil. This material was progressed to the next step without further purification.

Procedure AAL: Preparation of N,N-dimethyl-3-(2-oxopropyl)benzenesulfonamide

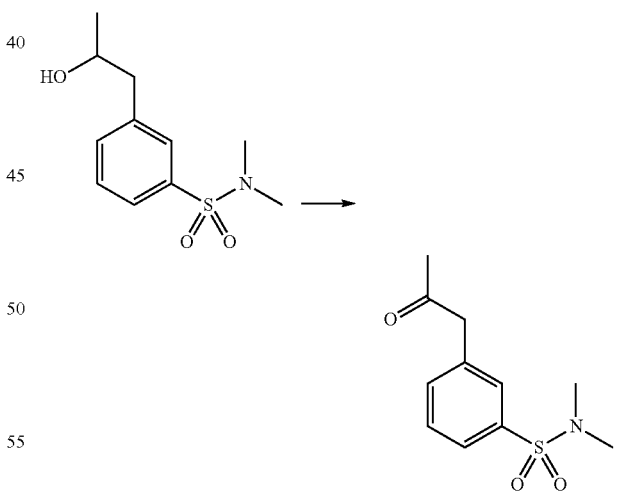

To a stirring solution of 3-(2-hydroxypropyl)-N,N-dimethyl-benzenesulfonamide (967 mg, 3.97 mmol) in dichloromethane (40 mL) under nitrogen at 0° C. was added Dess-Martin periodinane (2.02 g, 4.77 mmol) in three portions. The resulting mixture was stirred at this temperature for 1.5 h. The reaction mixture was poured into a mixture of 10% sat. aq. sodium thiosulphate (60 mL) and sat. aq. sodium bicarbonate (1:1) and the mixture was stirred for 5 mins at rt. The product was extracted with dichloromethane, and combined organics were dried over Na$_2$SO$_4$, and concentrated in vacuo to give N,N-dimethyl-3-(2-oxopropyl)benzenesulfonamide (790 mg, 82%) as a white solid. This material was progressed to the next step without further purification. $^1$H NMR (300 MHz, CDCl$_3$) δ ppm: 7.71 (dt, J=7.7, 1.6 Hz, 1H), 7.63 (dt, J=1.9, 0.9 Hz, 1H), 7.53 (dd, J=7.7 Hz, 1H), 7.44 (d, J=8.2 Hz, 1H), 3.84 (s, 2H), 2.74 (s, 6H), 2.25 (s, 3H).

Procedure AAM: Preparation of 3-(5-methoxy-2-methyl-1H-pyrrolo[3,2-b]pyridin-3-yl)-N,N-dimethylbenzenesulfonamide

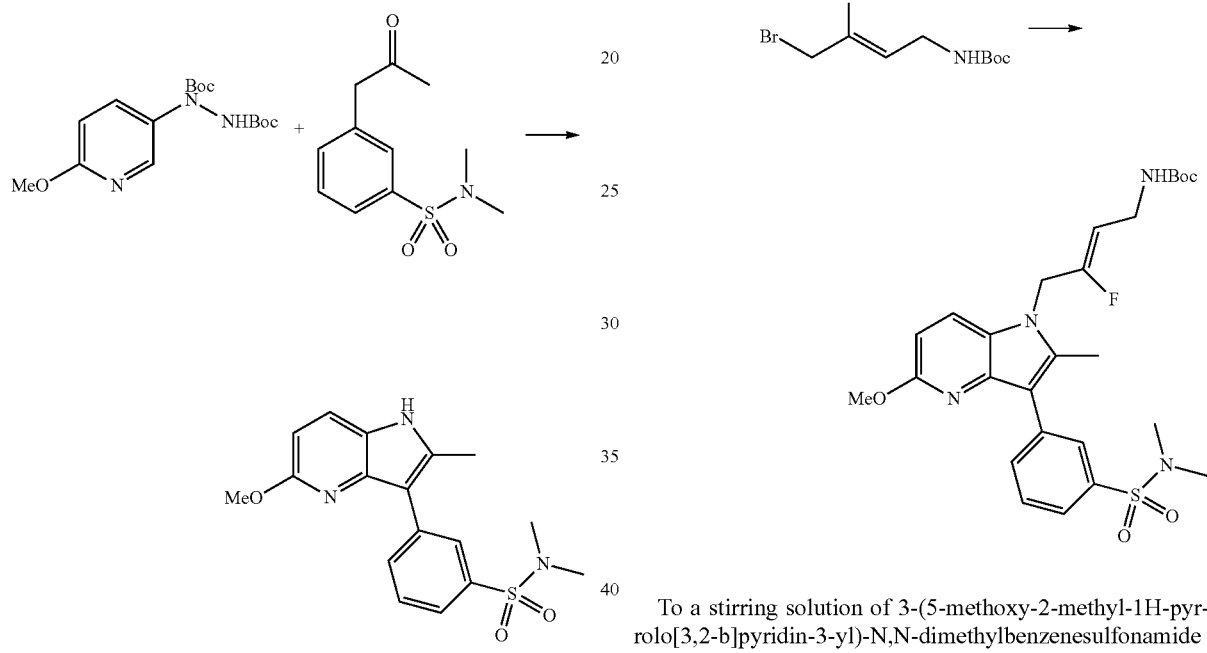

A stirring suspension of di-tert-butyl 1-(6-methoxypyridin-3-yl)hydrazine-1,2-dicarboxylate (307 mg, 0.90 mmol) and N,N-dimethyl-3-(2-oxopropyl)benzenesulfonamide (240 mg, 1.00 mmol) in 4% aqueous sulfuric acid (2 mL) was heated at a gentle reflux for 3 h. The reaction mixture was cooled to rt, and water (15 mL) and aq. HCl (1 M, 10 mL) were added. All unreacted ketone was extracted with diethyl ether (25 mL×3) and set aside. The aqueous layer was then neutralized by the addition of sat. aq. NaHCO$_3$. The desired product was extracted with ethyl acetate (25 mL×2) and the combined organics were washed with water and brine. After drying over Na$_2$SO$_4$, the solvent was removed in vacuo to afford 3-(5-methoxy-2-methyl-1H-pyrrolo[3,2-b]pyridin-3-yl)-N,N-dimethylbenzenesulfonamide (173 mg, 50%) as an orange oil. $^1$H NMR (300 MHz, CDCl$_3$) δ ppm: 8.43 (dt, J=1.9, 0.9 Hz, 1H), 8.23 (s, 1H), 8.06 (dt, J=7.4, 1.6 Hz, 1H), 7.67 (dt, J=7.8, 1.6 Hz, 1H), 7.62 (dd, J=7.5, 0.6 Hz, 1H), 7.53 (d, J=8.7 Hz, 1H), 6.60 (d, J=8.7 Hz, 1H), 3.99 (s, 3H), 2.80 (s, 6H), 2.63 (s, 3H).

Procedure AAN: Preparation of tert-butyl (Z)-(4-(3-(3-(N,N-dimethylsulfamoyl)phenyl)-5-methoxy-2-methyl-1H-pyrrolo[3,2-b]pyridin-1-yl)-3-fluorobut-2-en-1-yl)carbamate To a stirring solution of 3-(5-methoxy-2-methyl-1H-pyrrolo[3,2-b]pyridin-3-yl)-N,N-dimethylbenzenesulfonamide (50 mg, 0.14 mmol) and tert-butyl (Z)-(4-bromo-3-fluorobut-2-en-1-yl)carbamate (58.2 mg, 0.22 mmol) in DMSO (2.0 mL) at rt was added potassium hydroxide (16.2 mg, 0.23 mmol). The resulting mixture was stirred at rt for 2 h. HPLC analysis after this time showed approximately 50% conversion. A further amount of tert-butyl N—[(Z)-4-bromo-3-fluoro-but-2-enyl]carbamate (58.2 mg, 0.22 mmol) and potassium hydroxide (16.2 mg, 0.23 mmol) was added and stirring was continued for a further 1 h. The reaction mixture was poured onto a mixture of brine and water, and the product was extracted with ethyl acetate (30 mL). The organic layer was washed with further water and brine, dried over Na$_2$SO$_4$ and concentrated in vacuo. Purification was performed using a 12 g C-18 column, eluting over a gradient of 20-70% MeCN in water (+0.1% HCl) to afford tert-butyl (Z)-(4-(3-(3-(N,N-dimethylsulfamoyl)phenyl)-5-methoxy-2-methyl-1H-pyrrolo[3,2-b]pyridin-1-yl)-3-fluorobut-2-en-1-yl)carbamate (55 mg, 71%) as a brown foam. $^1$H NMR (300 MHz, CDCl$_3$) δ ppm: 8.30 (dt, J=1.8, 0.6 Hz, 1H), 7.98 (dt, J=7.5, 1.6 Hz, 1H), 7.70 (dt, J=7.9, 1.4 Hz, 1H), 7.64 (ddd, J=7.6, 7.6, 0.5 Hz, 1H), 7.54 (d, J=8.8 Hz, 1H), 6.65 (d, J=8.8 Hz, 1H), 4.80 (d, J=9.2 Hz, 3H), 4.66-4.83 (m, 1H), 4.57 (s, 1H), 3.97 (s, 3H), 3.81 (s, 2H), 2.80 (s, 6H), 2.60 (s, 3H), 1.43 (s, 9H).

Procedure AAO: Preparation of (Z)-3-(1-(4-amino-2-fluorobut-2-en-1-yl)-5-methoxy-2-methyl-1H-pyrrolo[3,2-b]pyridin-3-yl)-N,N-dimethylbenzenesulfonamide Dihydrochloride (Compound 60)

(Z)-3-(1-(4-amino-2-fluorobut-2-en-1-yl)-5-methoxy-2-methyl-1H-pyrrolo[3,2-b]pyridin-3-yl)-N,N-dimethylbenzenesulfonamide Dihydrochloride (Compound 61)

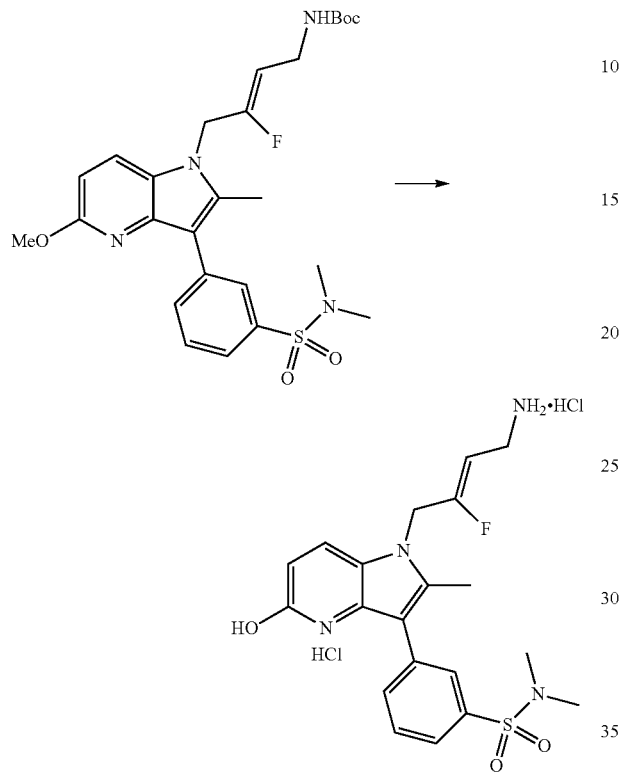

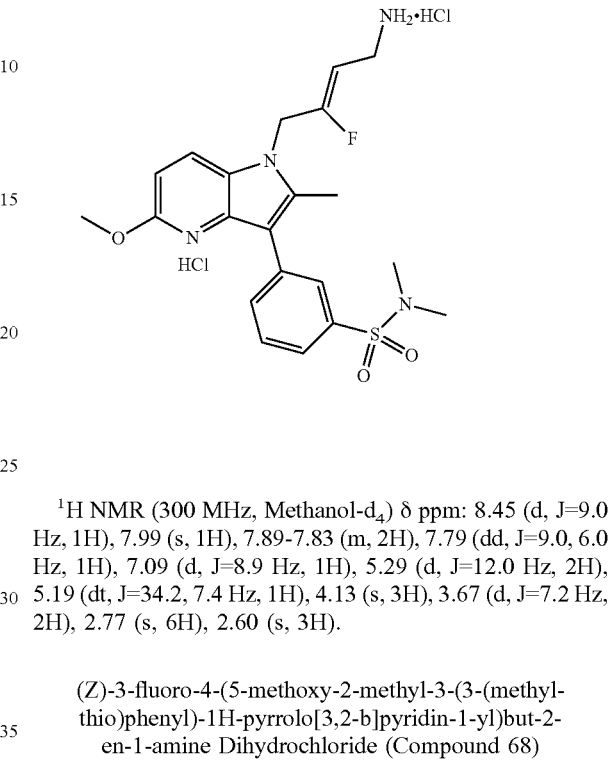

$^1$H NMR (300 MHz, Methanol-d$_4$) δ ppm: 8.45 (d, J=9.0 Hz, 1H), 7.99 (s, 1H), 7.89-7.83 (m, 2H), 7.79 (dd, J=9.0, 6.0 Hz, 1H), 7.09 (d, J=8.9 Hz, 1H), 5.29 (d, J=12.0 Hz, 2H), 5.19 (dt, J=34.2, 7.4 Hz, 1H), 4.13 (s, 3H), 3.67 (d, J=7.2 Hz, 2H), 2.77 (s, 6H), 2.60 (s, 3H).

(Z)-3-fluoro-4-(5-methoxy-2-methyl-3-(3-(methylthio)phenyl)-1H-pyrrolo[3,2-b]pyridin-1-yl)but-2-en-1-amine Dihydrochloride (Compound 68)

To a stirring solution of tert-butyl (Z)-(4-(3-(3-(N,N-dimethylsulfamoyl)phenyl)-5-methoxy-2-methyl-1H-pyrrolo[3,2-b]pyridin-1-yl)-3-fluorobut-2-en-1-yl)carbamate (55.0 mg, 0.10 mmol) in dichloromethane (4 mL) under nitrogen at −10° C. (ice-salt bath) was added boron tribromide (39 uL, 0.41 mmol). The resulting mixture was stirred at 0° C. for 1 h and then rt overnight. The reaction mixture was then poured onto ice in sat. NaHCO$_3$ (20 mL). The product was extracted with dichloromethane (30 mL), and the organic layer was washed with brine, dried over Na$_2$SO$_4$, and concentrated in vacuo. Purification was performed using a 12 g C-18 column, eluting over a gradient of 30-65% MeCN in water (+0.1% HCl) to afford the title compound (Z)-3-(1-(4-amino-2-fluorobut-2-en-1-yl)-5-methoxy-2-methyl-1H-pyrrolo[3,2-b]pyridin-3-yl)-N,N-dimethylbenzenesulfonamide dihydrochloride (3.9 mg, 9%) as a yellow film. $^1$H NMR (300 MHz, DMSO-d$_6$) δ ppm: 8.19-8.03 (m, 5H), 7.88-7.79 (m, 1H), 7.78-7.67 (m, 2H), 6.58 (d, J=9.0 Hz, 1H), 5.20 (d, J=13.3 Hz, 2H), 5.05-5.26 (m, 1H), 3.53-3.41 (m, 1H), 2.68 (s, 6H), 2.44 (s, 3H).

Example 55

The following compounds were prepared according to procedures AAJ, AAK, AAL, AAM, AAN and O.

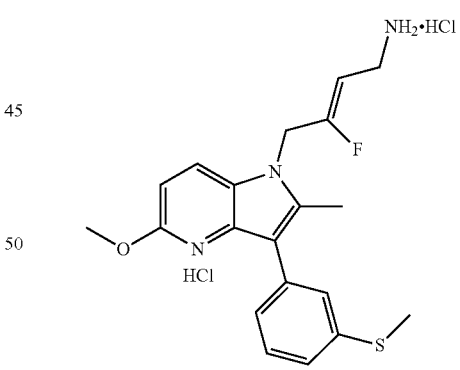

$^1$H NMR (300 MHz, Methanol-d$_4$) δ ppm: 8.73 (d, J=9.1 Hz, 1H), 7.50 (ddd, J=8.0, 7.4, 0.5 Hz, 1H), 7.39 (ddd, J=7.9, 1.9, 1.1 Hz, 1H), 7.34 (dq, J=2.3, 1.2 Hz, 1H), 7.25 (d, J=9.2 Hz, 1H), 7.23 (ddd, J=8.1, 1.6, 1.2 Hz, 1H), 7.21 (dd, J=1.6, 1.2 Hz, 1H), 5.39-5.32 (m, 2H), 5.35 (dt, J=34.9, 7.4 Hz, 1H), 4.22 (s, 3H), 3.73-3.64 (m, 2H), 3.36 (s, 3H), 2.58 (s, 3H).

209

(Z)-3-fluoro-4-(5-methoxy-2-methyl-3-(3-(methyl-sulfonyl)phenyl)-1H-pyrrolo[3,2-b]pyridin-1-yl)but-2-en-1-amine Dihydrochloride (Compound 69)

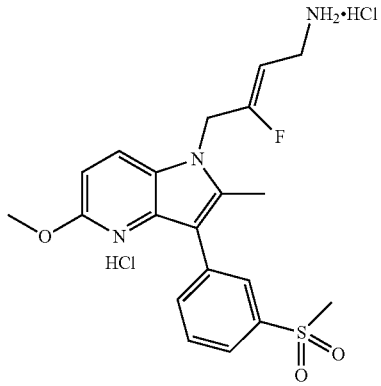

¹H NMR (300 MHz, Methanol-d₄) δ ppm: 8.68 (d, J=9.0 Hz, 1H), 8.14-8.04 (m, 2H), 7.90-7.80 (m, 2H), 7.25 (d, J=9.0 Hz, 1H), 5.36 (d, J=12.5 Hz, 2H), 5.31 (dt, J=35.4, 7.5 Hz, 1H), 4.21 (s, 3H), 3.72-3.64 (m, 2H), 3.23 (s, 3H), 2.59 (s, 3H).

(Z)-3-(1-(4-amino-2-fluorobut-2-en-1-yl)-5-(dimethylamino)-2-methyl-1H-pyrrolo[3,2-b]pyridin-3-yl)-N,N-dimethylbenzenesulfonamide Dihydrochloride (Compound 105)

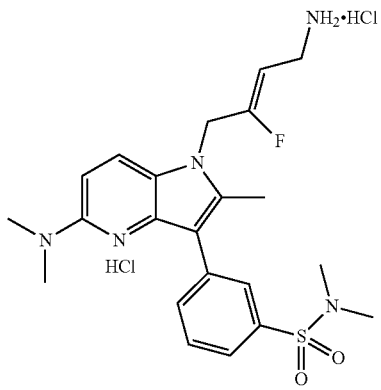

¹H NMR (300 MHz, Methanol-d₄) δ ppm: 8.34 (d, J=9.4 Hz, 1H), 7.92-7.78 (m, 4H), 6.96 (d, J=9.4 Hz, 1H), 5.27 (dt, J=35.2, 7.4 Hz, 1H), 3.68 (d, J=7.0 Hz, 2H), 3.32 (s, 6H), 2.78 (s, 6H), 2.54 (s, 3H).

Example 56

The following compound was prepared according to procedures E, F, AAP, AAQ, J, K, L, and O.

210

(Z)-3-(1-(4-amino-2-fluorobut-2-en-1-yl)-2,5-dimethyl-1H-pyrrolo[3,2-b]pyridin-3-yl)-N,N-dimethylbenzenesulfonamide Dihydrochloride (Compound 107)

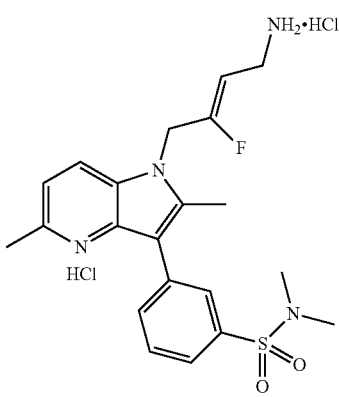

Procedure AAP: Preparation of N-(2,6-dimethylpyridin-3-yl)acetamide

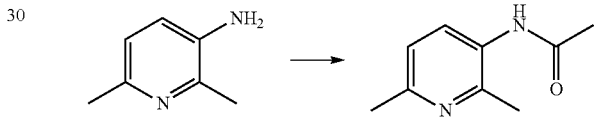

To a stirring solution of 2,6-dimethylpyridin-3-amine (25.0 g, 205 mmol) in dichloromethane (200 mL) was added Ac₂O (27.0 mL, 258 mmol) followed by triethylamine (35.1 mL, 226 mmol) and the mixture was stirred at rt for 2 h. The reaction mixture was then concentrated in vacuo. To the residue was added aqueous sodium carbonate, and the aqueous mixture was then extracted with dichloromethane (200 mL×6), dried over Na₂SO₄ and concentrated in vacuo to afford N-(2,6-dimethylpyridin-3-yl)acetamide (20.0 g, 60% yield), which was used directly in next step without further purification.

Procedure AAQ: Preparation of 2,5-dimethyl-1H-pyrrolo[3,2-b]pyridine

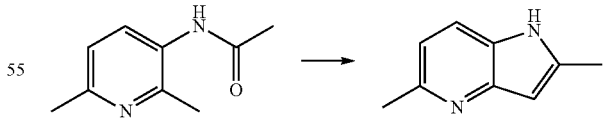

A stirring mixture of neat N-(2,6-dimethylpyridin-3-yl) acetamide (2.5 g, 15 mmol) and sodium ethoxide (2.50 g, 37.0 mmol) was heated to 320° C. under N₂ for 15 min. After cooling to rt, water (20 mL) was added, and the aqueous mixture was extracted with dichloromethane (25 mL×6), dried over Na₂SO₄ and concentrated in vacuo. A total of 15 batches of crude material were purified over silica gel eluting with ethyl acetate/hexane (1:5) followed by ethyl acetate (1:2) to afford 2,5-dimethyl-1H-pyrrolo[3,2-b]pyridine (10.0 g, 30% yield) as white solid. ¹H-NMR (300 MHz, CDCl₃): δ ppm: 9.24 (bs, 1H), 7.44-7.42 (m, 1H), 6.89-6.86 (m, 1H), 6.32 (s, 1H), 2.62 (s, 3H), 2.44 (s, 3H).

(Z)-3-(1-(4-amino-2-fluorobut-2-en-1-yl)-2,5-dimethyl-1H-pyrrolo[3,2-b]pyridin-3-yl)-N,N-dimethylbenzenesulfonamide Dihydrochloride (Compound 107)

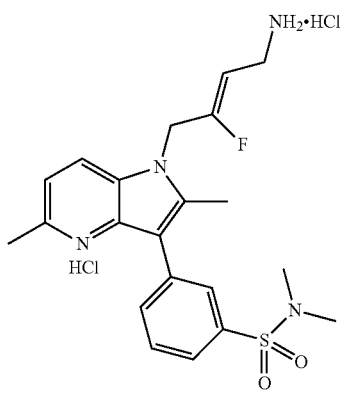

¹H NMR (300 MHz, Methanol-d₄) δ ppm: 8.66 (d, J=8.4 Hz, 1H), 7.99-7.93 (m, 1H), 7.93-7.83 (m, 3H), 7.58 (d, J=8.4 Hz, 1H), 5.38 (dt, J=35.3, 7.3 Hz, 1H), 3.68 (d, J=7.2 Hz, 2H), 2.81 (s, 3H), 2.78 (s, 6H), 2.62 (s, 3H).

Example 57

The following compound was prepared according to procedures E, F, AAR, AAS, AAT, J, K, L, and O.

(Z)-3-(1-(4-amino-2-fluorobut-2-en-1-yl)-2-methyl-1H-pyrrolo[3,2-b]pyridin-3-yl)-N,N-dimethylbenzenesulfonamide Dihydrochloride (Compound 25)

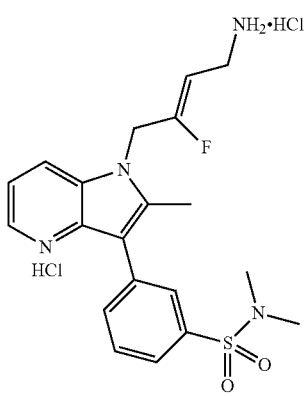

Procedure AAR: Preparation of Ethyl (2-chloropyridin-3-yl)carbamate

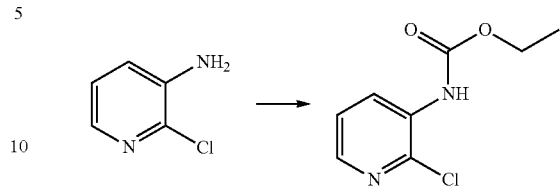

To a stirring solution of 2-chloropyridin-3-amine (5.00 g, 39.0 mmol) in 1,4-dioxane (50 mL) at 10° C. was added an aqueous solution of sodium hydroxide (1 M, 78.0 mL, 78.0 mmol). To this reaction mixture was added ethyl chloroformate (6.50 mL, 67.5 mmol), and the reaction was warmed to rt. Stirring was continued overnight. The reaction mixture was diluted in water (100 mL), extracted with ethyl acetate (100 mL×3), washed with brine (50 mL), dried over Na₂SO₄, filtered and concentrated in vacuo to afford a yellow oil. The crude material was purified over silica gel eluting with ethyl acetate in hexane (1:10) to afford ethyl (2-chloropyridin-3-yl)carbamate (4.42 g, 71%) as a white solid.

Procedure AAS: Preparation of Ethyl (2-(prop-1-yn-1-yl)pyridin-3-yl)carbamate

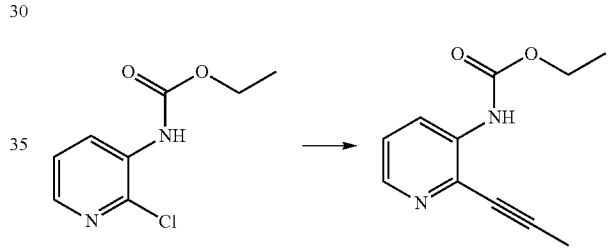

To a stirring suspension of lithium chloride (2.04 g, 48.30 mmol) in 1,4-dioxane (100 mL) was added ethyl (2-chloropyridin-3-yl)carbamate (3.96 g, 19.7 mmol), tributyl(prop-1-ynyl)stannane (19.7 mL, 19.7 mmol) and PdCl₂(dppf) (288 mg, 0.40 mmol). The mixture was the heated at reflux overnight. After cooling to rt, the reaction mixture was diluted with water, extracted with ethyl acetate (100 mL×3), washed with sat. aq. NaHCO₃ (50 mL×3), followed by brine (50 mL×3), dried over Na₂SO₄, filtered and concentrated in vacuo. Purification over silica gel, eluting with 10-60% ethyl acetate in hexane afforded ethyl (2-(prop-1-yn-1-yl)pyridin-3-yl)carbamate (2.52 g, 63%) as a brown oil.

Procedure AAT: Preparation of 2-methyl-1H-pyrrolo[3,2-b]pyridine

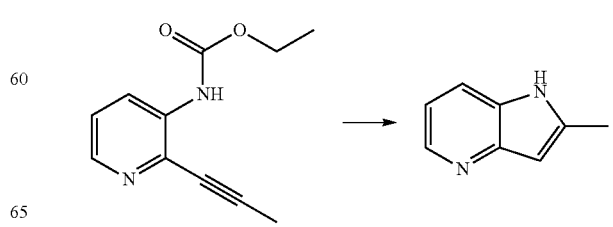

To a stirring solution of ethyl (2-(prop-1-yn-1-yl)pyridin-3-yl)carbamate (2.40 g, 11.76 mmol) in absolute ethanol (5 mL) was added solid sodium hydroxide (2.40 g, 35.3 mmol). The reaction was then heated at 80° C. for 1.5 h. The reaction mixture was cooled, diluted with water, extracted with dichloromethane (50 mL×3), dried over $Na_2SO_4$, filtered and concentrated in vacuo. The crude material was purified over silica gel, eluting with dichloromethane/MeOH=20/1) to afford of 2-methyl-1H-pyrrolo[3,2-b]pyridine (1.09 g, 70%) as a brown solid.

Z)-3-(1-(4-amino-2-fluorobut-2-en-1-yl)-2-methyl-1H-pyrrolo[3,2-b]pyridin-3-yl)-N,N-dimethyl-benzenesulfonamide Dihydrochloride (Compound 25)

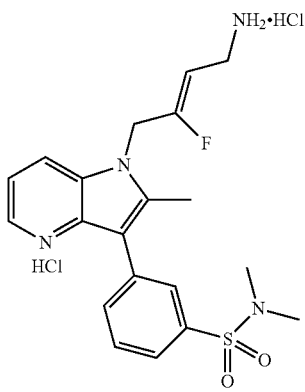

$^1$H NMR (300 MHz, Methanol-$d_4$) δ ppm 8.22 (d, J=1.6 Hz, 1H), 7.90 (dd, J=8.7, 1.7 Hz, 1H), 7.53 (d, J=8.7 Hz, 1H), 7.48 (dd, J=8.8, 5.4 Hz, 2H), 7.26 (dd, J=8.8 Hz, 2H), 5.20-5.09 (m, 2H), 4.85 (dt, J=34.1, 7.5 Hz, 1H), 4.36 (q, J=7.1 Hz, 2H), 3.67-3.57 (m, 2H), 2.52 (s, 3H), 1.39 (t, J=7.1 Hz, 3H).

Example 58

The following compound was prepared according to procedures E, F, AAR, AAU, AAT, J, K, L, and O.

(Z)-3-(1-(4-amino-2-fluorobut-2-en-1-yl)-2-methyl-1H-pyrrolo[3,2-c]pyridin-3-yl)-N,N-dimethylbenzenesulfonamide Dihydrochloride (Compound 26)

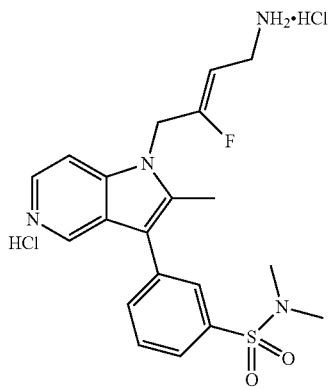

Procedure AAU: Preparation of Ethyl (3-(prop-1-yn-1-yl)pyridin-4-yl)carbamate

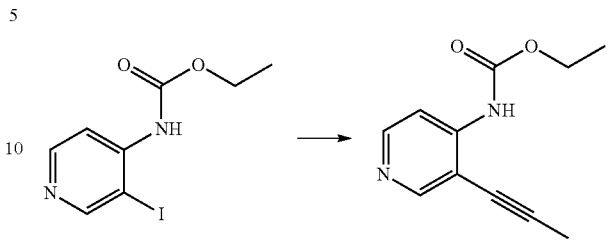

To a stirring solution of ethyl (3-iodopyridin-4-yl)carbamate (7.98 g, 24.9 mmol), propyne in hexanes (3%, 150 g, 112.5 mmol), triethylamine (60 mL, 430 mmol), $PdCl_2(PPh_3)_2$ (877 mg, 1.25 mmol), in DMF (15 mL), in a sealable tube was added CuI (472 mg, 2.49 mmol). The tube was sealed and stirred at room temperature overnight. Ethyl acetate (200 mL) and sat. aq. $NH_4Cl$ (100 mL) were added, the phases were separated and the aqueous layer was extracted with ethyl acetate (100 mL×3). The combined organic layers were dried over $Na_2SO_4$, filtered, and concentrated in vacuo. The residue was purified over silica gel eluting with ethyl acetate/hexane (1:10) to afford ethyl (3-(prop-1-yn-1-yl)pyridin-4-yl)carbamate (3.01 g, 59%) as a brown solid.

(Z)-3-(1-(4-amino-2-fluorobut-2-en-1-yl)-2-methyl-1H-pyrrolo[3,2-c]pyridin-3-yl)-N,N-dimethyl-benzenesulfonamide Dihydrochloride (Compound 26)

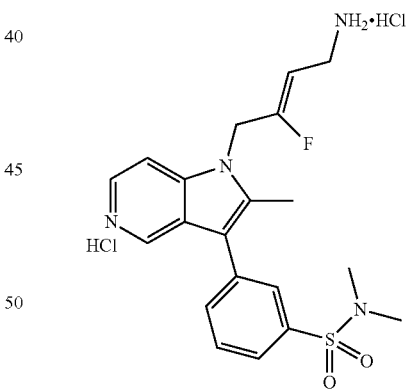

$^1$H NMR (300 MHz, DMSO-$d_6$) δ ppm: 9.07 (s, 1H), 8.60 (d, J=6.7 Hz, 1H), 8.30 (d, J=6.7 Hz, 1H), 8.15 (s, 3H), 8.00-7.93 (m, 1H), 7.91-7.79 (m, 3H), 5.51 (d, J=15.4 Hz, 2H), 5.39 (dt, J=36.0, 7.4 Hz, 1H), 3.55-3.44 (m, 2H), 2.71 (s, 6H), 2.64 (s, 3H).

Example 59

The following compound was prepared according to procedures E, F, AAV, AAW, AAX, AAR, AAU, AAT, J, K, L, and O.

(Z)-3-(1-(4-amino-2-fluorobut-2-en-1-yl)-2-methyl-1H-pyrrolo[2,3-c]pyridin-3-yl)-N,N-dimethylbenzenesulfonamide Dihydrochloride (Compound 32)

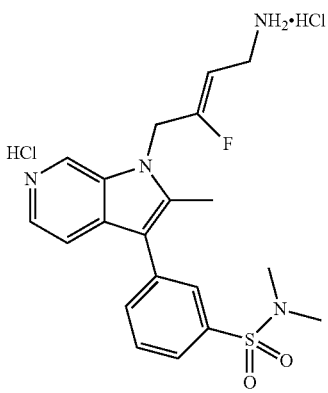

Procedure AAV: Preparation of N-(pyridin-3-yl)pivalamide

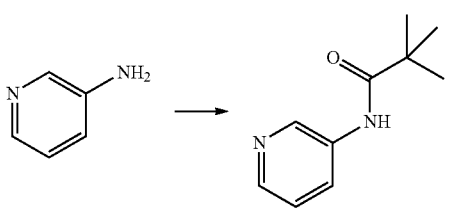

To a stirring solution of pyridin-3-amine (20.0 g, 212 mmol) in THF (100 mL) at was added, slowly, a solution of pivaloyl chloride (26.0 mL, 212 mmol) in THF (50 mL), followed by Et$_3$N (44.0 mL, 319 mmol). The resulting mixture was left to stir at 0° C. for 1 h. The reaction mixture was filtered, and the filtrate was evaporated in vacuo to yield the title N-(pyridin-3-yl)pivalamide (32.0 g, 85%) as white solid.

Procedure AAW: Preparation of N-(4-iodopyridin-3-yl)pivalamide

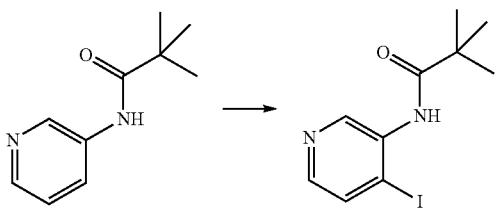

A stirring solution of N-(pyridin-3-yl)pivalamide (20 g, 112 mmol) in THF/Et$_2$O (200 mL: 500 mL) was cooled to −78° C. TMEDA (42.0 mL, 280 mmol) and t-butyl lithium (1.6 M in hexane, 176 mL, 280 mmol) were then added dropwise. The mixture was stirred for 15 minutes and then warmed to −10° C. Stirring was continued at this temperature for a further 2 h. The reaction mixture was again cooled to −78° C., and a solution of iodine (71.2 g, 280 mmol) in THF (200 mL) was added dropwise. The resulting slurry was stirred at −78° C. for 2 h. The mixture was warmed to 0° C., and was quenched with saturated aqueous sodium thiosulfate solution (1 L). The phases were separated and the aqueous phase was extracted with dichloromethane (500 mL×3). The combined organic phase was dried over Na$_2$SO$_4$ and concentrated in vacuo. The crude material was purified over silica gel, eluting with ethyl acetate/hexane (1:10) to afford N-(4-iodopyridin-3-yl)pivalamide (13.1 g, 38%) as a yellow solid.

Procedure AAX: Preparation of 4-iodopyridin-3-amine

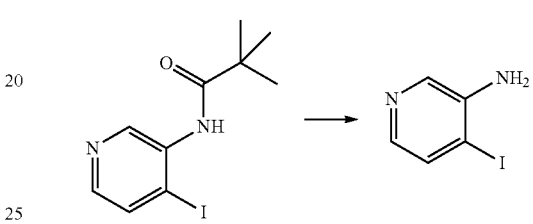

A stirring mixture of N-(4-iodopyridin-3-yl)pivalamide (13.1 g, 44.0 mmol) and 24% w/w sulfuric acid in water (400 mL) was heated to 100° C. for 4 hours. The mixture was allowed to cool to rt, and then carefully adjusted to pH 7-8 with 4 N NaOH. Saturated sodium bicarbonate was added to the mixture and the product extracted into dichloromethane (200 mL×3). The organic layers were combined, dried over Na$_2$SO$_4$ and concentrated to give 4-iodopyridin-3-amine (8.80 g, 92%).

(Z)-3-(1-(4-amino-2-fluorobut-2-en-1-yl)-2-methyl-1H-pyrrolo[2,3-c]pyridin-3-yl)-N,N-dimethyl-benzenesulfonamide Dihydrochloride (Compound 32)

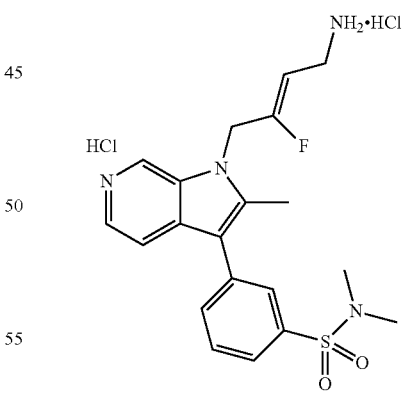

$^1$H NMR (300 MHz, Methanol-d$_4$) δ ppm: 9.37 (s, 1H), 8.34 (d, J=6.4 Hz, 1H), 8.02 (d, J=6.4 Hz, 1H), 7.96-7.82 (m, 4H), 5.50 (d, J=13.6 Hz, 2H), 5.39 (dt, J=35.4, 7.3 Hz, 1H), 3.69 (d, J=7.3 Hz, 2H), 2.79 (s, 6H), 2.76 (s, 3H).

Example 60

The following compound was prepared according to procedures AAY, F, G, H, I, J, K, L, M and U.

(Z)-1-(4-amino-2-fluorobut-2-en-1-yl)-3-(3-(dimethylcarbamoyl)phenyl)-2-methyl-1H-indole-5-carboxylic Acid Hydrochloride (Compound 16)

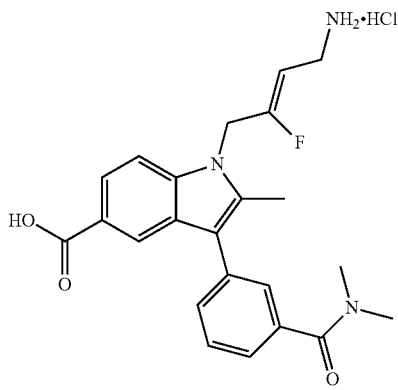

Procedure AAY: Preparation of 3-bromo-N,N-dimethylbenzamide

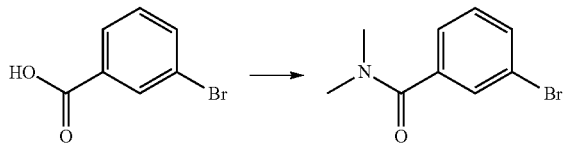

To a stirring mixture of dimethylamine hydrochloride (612 mg, 7.50 mmol) in DMF (10 mL) at rt was added and triethylamine (3.48 mL, 25.0 mmol). After Stirring for 10 mins, 3-bromobenzoic acid (1.00 g, 5.00 mmol) was added, followed by HATU (2.28 g, 6.00 mmol). The resulting mixture was stirred at rt for 2 h. The reaction mixture was poured onto water (100 mL), and the resulting slurry was stirred for 5 mins. The aqueous mixture was extracted with ethyl acetate (60 mL). The organics were then washed with aq. HCl (1 M, 30 mL), sat. aq. $NH_4Cl$ (30 mL), and brine (30 mL), dried over $MgSO_4$, and then concentrated in vacuo to afford the title compound 3-bromo-N,N-dimethylbenzamide (960 mg, 84%) as an orange oil. $^1$H NMR (300 MHz, $CDCl_3$) δ ppm: 7.36 (ddd, J=7.6, 1.4 Hz, 1H), 7.53-7.59 (m, 2H), 7.30 (ddd, J=7.6, 7.6, 0.7 Hz, 1H), 3.12 (s, 3H), 3.00 (s, 3H).

(Z)-1-(4-amino-2-fluorobut-2-en-1-yl)-3-(3-(dimethylcarbamoyl)phenyl)-2-methyl-1H-indole-5-carboxylic Acid Hydrochloride (Compound 16)

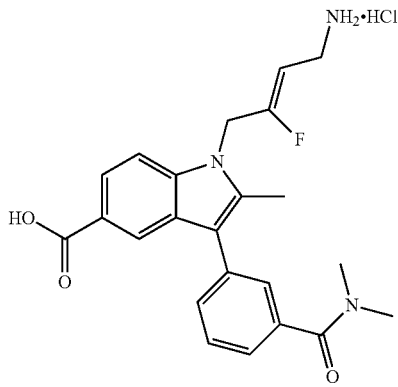

$^1$H NMR (300 MHz, Methanol-$d_4$) δ ppm: 8.29 (d, J=1.6 Hz, 1H), 7.92 (dd, J=8.6, 1.6 Hz, 1H), 7.67-7.57 (m, 2H), 7.57-7.49 (m, 2H), 7.44 (ddd, J=6.5, 2.4, 1.7 Hz, 1H), 5.16 (d, J=8.6 Hz, 2H), 4.84 (dt, J=35.4, 7.5 Hz, 1H), 3.63 (dd, J=7.7, 1.5 Hz, 2H), 3.15 (d, J=5.4 Hz, 6H), 2.56 (s, 3H).

Example 61

The following compound was prepared according to procedures AAY, F, G, H, I, J, K, L, and O.

(Z)-ethyl 1-(4-amino-2-fluorobut-2-en-1-yl)-3-(3-(dimethylcarbamoyl)phenyl)-2-methyl-1H-indole-5-carboxylate Hydrochloride (Compound 15)

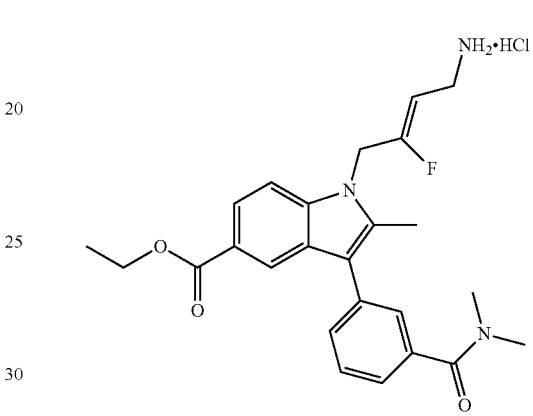

$^1$H NMR (300 MHz, Methanol-$d_4$) δ ppm: 8.26 (dd, J=1.6, 0.6 Hz, 1H), 7.92 (dd, J=8.7, 1.6 Hz, 1H), 7.67-7.48 (m, 4H), 7.45 (dt, J=7.0, 1.8 Hz, 1H), 5.22-5.12 (m, 2H), 4.87 (dt, J=35.2, 7.5 Hz, 1H), 4.36 (q, J=7.1 Hz, 2H), 3.68-3.58 (m, 2H), 3.15 (d, J=3.9 Hz, 6H), 2.56 (s, 3H), 1.39 (t, J=7.1 Hz, 3H).

Example 62

The following compounds were made according to procedures AAZ, AAAA, F, K, L and O.

Procedure AAZ: Preparation of 6-methyl-2-(prop-1-yn-1-yl)pyridin-3-amine

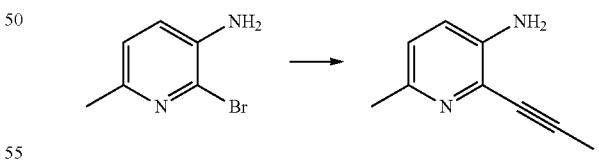

Into a 500 mL 3-necked round-bottom flask purged and maintained with an inert atmosphere of nitrogen, was placed 2-bromo-6-methylpyridin-3-amine (25.0 g, 134 mmol), acetonitrile (100 mL), triethylamine (100 mL), copper (I) iodide (1.30 g, 6.83 mmol), $Pd(PPh_3)_2Cl_2$ (1.40 g, 1.99 mmol). The resulting solution was stirred for 3 h at 80° C. with continued bubbling of propyne gas. The solids were filtered, and the filtrate was concentrated under vacuum. The residue was purified over silica gel, eluting with ethyl acetate/petroleum ether (1:3) to afford 6-methyl-2-(prop-1-yn-1-yl)pyridin-3-amine (18.0 g, 92%) as a yellow solid.

(300 MHz, DMSO-d$_6$) δ ppm: 6.96 (d, J=8.4 Hz, 1H), 6.88 (d, J=8.4 Hz, 1H), 5.16 (brs, 2H), 2.24 (s, 3H), 2.08 (s, 3H).

Procedure AAAA: Preparation of 2,5-dimethyl-1H-pyrrolo[3,2-b]pyridine

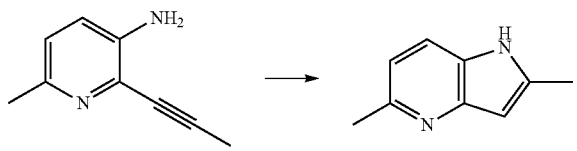

Into a 500 mL round-bottom flask, was placed a solution of 6-methyl-2-(prop-1-yn-1-yl)pyridin-3-amine (18.0 g, 123 mmol) in DMF (300 mL). To this was added KO$^t$Bu (28.0 g, 250 mmol), in portions at 0° C. The resulting solution was then stirred at rt for 3 h. The reaction was then quenched by the addition of water/ice (1.0 L). The resulting solution was extracted with of ethyl acetate (200 mL×6), and the combined were washed with of brine (1.0 L×2). The organics were dried over anhydrous sodium sulfate and concentrated under vacuum to afford 2,5-dimethyl-1H-pyrrolo[3,2-b]pyridine (16.0 g, 89%) as a yellow solid. (300 MHz, DMSO-d$_6$) δ ppm: 10.96 (brs, 1H), 7.50-7.42 (m, 1H), 6.84 (d, J=8.4 Hz, 1H), 6.14 (s, 1H), 2.51 (s, 3H), 2.40 (s, 3H).

(Z)-4-(2,5-dimethyl-3-(3-(methylsulfonyl)phenyl)-1H-pyrrolo[3,2-b]pyridin-1-yl)-3-fluorobut-2-en-1-amine Dihydrochloride (Compound 112)

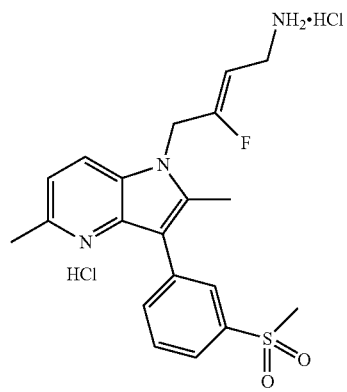

$^1$H-NMR (300 MHz, Methanol-d$_4$) δ ppm: 8.69 (s, 1H), 8.13 (d, J=7.1 Hz, 2H), 7.90 (s, 2H), 7.58 (s, 1H), 5.42 (d, J=11.8 Hz, 2H), 5.36-5.27 (m, 1H), 3.75-3.60 (m, 2H), 3.25 (s, 3H), 2.83 (s, 3H), 2.63 (s, 3H).

(Z)-4-(3-(3-(ethylsulfonyl)phenyl)-2-isopropyl-5-methyl-1H-pyrrolo[3,2-b]pyridin-1-yl)-3-fluorobut-2-en-1-amine Dihydrochloride (Compound 113)

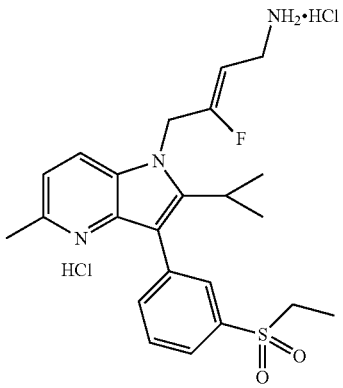

$^1$H-NMR (300 MHz, Methanol-d$_4$) δ ppm: 8.79 (d, J=8.2 Hz, 1H), 8.47 (d, J=5.6 Hz, 1H), 8.23-8.10 (m, 1H), 8.04 (s, 1H), 7.90 (d, J=4.4 Hz, 2H), 7.77 (dd, J=8.3, 5.9 Hz, 1H), 5.52 (d, J=11.7 Hz, 2H), 5.33 (dt, J=34.0, 7.4 Hz, 1H), 3.69 (d, J=7.2 Hz, 2H), 3.57 (p, J=14.5, 7.2 Hz, 1H), 3.33 (q, J=9.0 Hz, 2H), 1.35-1.23 (m, 9H).

(Z)-4-(3-(3-(ethylsulfonyl)phenyl)-2,5-dimethyl-1H-pyrrolo[3,2-b]pyridin-1-yl)-3-fluorobut-2-en-1-amine Dihydrochloride (Compound 114)

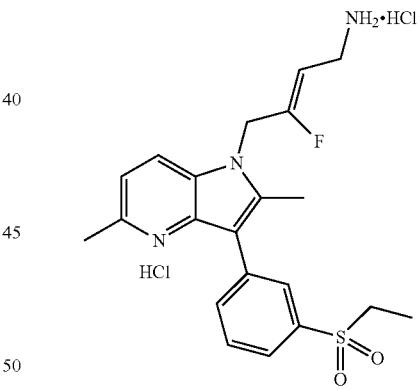

$^1$H-NMR (300 MHz, Methanol-d$_4$) δ ppm: 8.67 (d, J=8.5 Hz, 1H), 8.18-7.99 (m, 2H), 7.97-7.83 (m, 2H), 7.58 (d, J=8.5 Hz, 1H), 5.49-5.22 (m, 3H), 3.68 (d, J=7.3 Hz, 2H), 3.35 (q, J=6.7 Hz, 2H), 2.82 (s, 3H), 2.62 (s, 3H), 1.32 (t, J=7.4 Hz, 3H).

Example 63

The following compounds were prepared according to procedures AAAB, F, K, L and O.

Procedure AAAB: Preparation of 2-(2-methyl-1H-pyrrolo[3,2-b]pyridin-5-yl)propan-2-ol

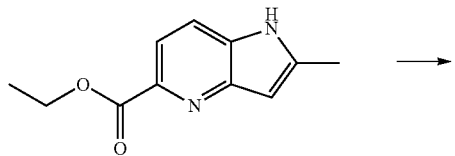

To a stirring solution of ethyl 2-methyl-1H-pyrrolo[3,2-b]pyridine-5-carboxylate (1.23 g, 6.00 mmol) in THF (20 mL) at rt was added methylmagnesium bromide (3 M in THF, 10.0 mL, 30.0 mmol) over 5 min. The mixture was stirred at rt for 30 min. Additional methylmagnesium bromide (3 M in THF, 6.00 mL, 18.0 mmol) was added and stirring was continued for 30 min at rt, and then at reflux for 1 h. The reaction mixture was quenched by addition of sat. aq. NH₄Cl (45 mL). The product was extracted with ethyl acetate (40 mL×3). The combined organic layer was dried over Na₂SO₄ and concentrated in vacuo. The crude material was purified over silica gel employing a Revelaris chromatography system to afford 2-(2-methyl-1H-pyrrolo[3,2-b]pyridin-5-yl)propan-2-ol (730 mg, 64%) as a pale yellow solid. $^1$H NMR (300 MHz, CDCl$_3$) δ ppm: 7.99 (s, 1H), 7.58 (dd, J=8.4, 0.9 Hz, 1H), 7.10 (d, J=8.4 Hz, 1H), 6.42 (dq, J=2.2, 1.1 Hz, 1H), 5.68 (s, 1H), 2.53 (d, J=0.9 Hz, 3H), 1.59 (d, J=2.2 Hz, 6H).

(Z)-2-(1-(4-amino-2-fluorobut-2-en-1-yl)-2-methyl-3-(3-(methylsulfonyl)phenyl)-1H-pyrrolo[3,2-b]pyridin-5-yl)propan-2-ol Dihydrochloride (Compound 116)

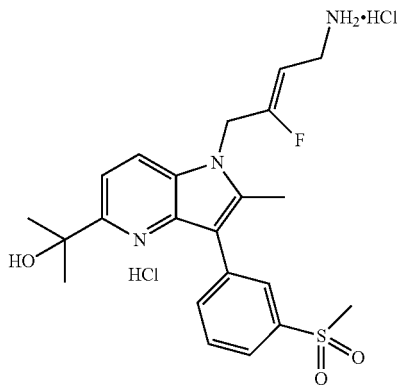

$^1$H-NMR (300 MHz, Methanol-d$_4$) δ 8.78 (d, J=8.6 Hz, 1H), 8.18-8.07 (m, 2H), 7.94 (dt, J=7.7, 1.7 Hz, 1H), 7.92-7.86 (m, 1H), 7.82 (d, J=8.6 Hz, 1H), 5.45 (d, J=13.2 Hz, 2H), 5.36 (dt, J=34.3, 7.0 Hz, 1H), 3.69 (d, J=8.0 Hz, 2H), 3.25 (s, 3H), 2.69 (s, 3H), 1.72 (s, 6H).

(Z)-2-(1-(4-amino-2-fluorobut-2-en-1-yl)-3-(3-(isopropylsulfonyl)phenyl)-2-methyl-1H-pyrrolo[3,2-b]pyridin-5-yl)propan-2-ol Dihydrochloride (Compound 117)

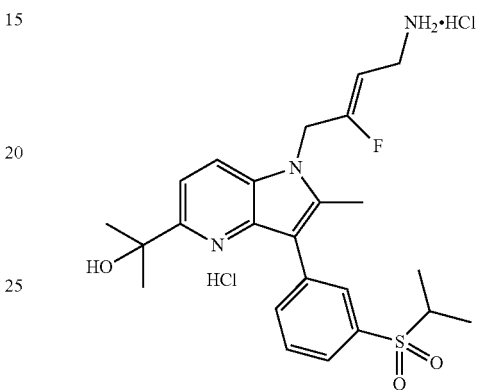

$^1$H-NMR (300 MHz, Methanol-d$_4$) δ ppm: 8.74 (d, J=8.6 Hz, 1H), 8.09-8.02 (m, 2H), 7.97-7.87 (m, 2H), 7.81 (d, J=8.6 Hz, 1H), 5.57-5.22 (m, 3H), 3.68 (d, J=7.3 Hz, 2H), 3.46 (p, J=6.8 Hz, 1H), 2.69 (s, 3H), 1.72 (s, 6H), 1.36 (d, J=6.8 Hz, 6H).

Example 64

The following compound was prepared according to procedures AAZ, AAAA, F, K, AQ, AAAC, L and O.

(Z)-3-fluoro-4-(5-(fluoromethyl)-2-methyl-3-(3-(methylsulfonyl)phenyl)-1H-pyrrolo[3,2-b]pyridin-1-yl)but-2-en-1-amine Dihydrochloride (Compound 115)

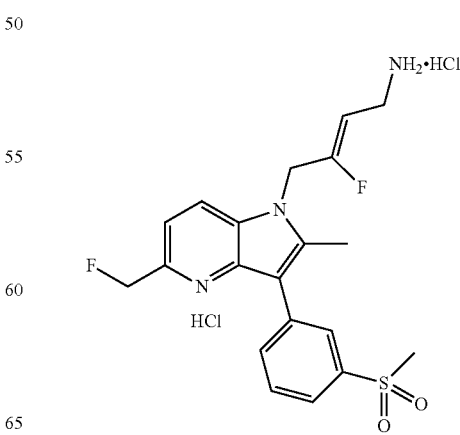

Procedure AAAC: Preparation of tert-butyl (Z)-(3-fluoro-4-(5-(fluoromethyl)-2-methyl-3-(3-(methylsulfonyl)phenyl)-1H-pyrrolo[3,2-b]pyridin-1-yl)but-2-en-1-yl)carbamate

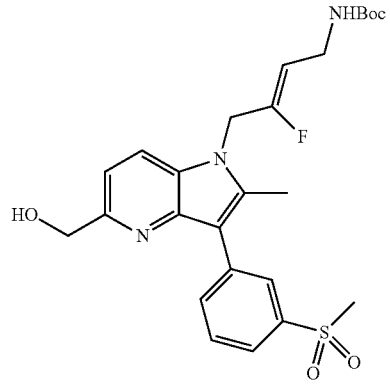

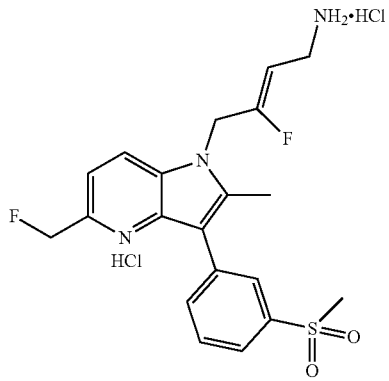

A solution of tert-butyl (Z)-(3-fluoro-4-(5-(hydroxymethyl)-2-methyl-3-(3-(methylsulfonyl)phenyl)-1H-pyrrolo[3,2-b]pyridin-1-yl)but-2-en-1-yl)carbamate (160 mg, 0.32 mmol) in CH$_2$Cl$_2$ (4 mL) was cooled to −10° C. under an argon atmosphere. Diethylaminosulfur trifluoride (0.05 mL, 0.36 mmol) was added in one lot. The reaction mixture was allowed to warm to rt and stirring was continued overnight. Water (10 mL) was added and the mixture was stirred at rt for 5 min. The organic layer was separated. The aqueous layer was extracted with CH$_2$Cl$_2$ (5 mL×3). The combined organics were dried over Na$_2$SO$_4$ and concentrated in vacuo. Purification over silica gel using CombiFlash™ afforded tert-butyl (Z)-(3-fluoro-4-(5-(fluoromethyl)-2-methyl-3-(3-(methylsulfonyl)phenyl)-1H-pyrrolo[3,2-b]pyridin-1-yl)but-2-en-1-yl)carbamate (35 mg, 22%) as a white foam. $^1$H NMR (300 MHz, CDCl$_3$) δ ppm: 8.23 (t, J=1.8 Hz, 1H), 8.04 (dt, J=7.9, 1.3 Hz, 1H), 7.84 (ddd, J=7.9, 1.9, 1.1 Hz, 1H), 7.6-7.60 (m, 2H), 7.30 (d, J=8.4 Hz, 1H), 5.27 (dd, J=29.9, 12.1 Hz, 2H), 4.84 (d, J=10.8 Hz, 2H), 4.70-4.92 (m, 3H), 3.80 (t, J=5.1 Hz, 2H), 3.09 (s, 3H), 2.60 (s, 3H), 1.42 (s, 9H).

tert-butyl (Z)-(3-fluoro-4-(5-(fluoromethyl)-2-methyl-3-(3-(methylsulfonyl)phenyl)-1H-pyrrolo[3,2-b]pyridin-1-yl)but-2-en-1-yl)carbamate (Compound 115)

$^1$H-NMR (300 MHz, Methanol-d$_4$) δ 8.73 (s, 1H), 8.20-8.07 (m, 2H), 7.95-7.84 (m, 2H), 7.82 (d, J=8.7 Hz, 1H), 5.74 (d, J=46.8 Hz, 2H), 5.57-5.17 (m, 3H), 3.69 (d, J=7.4 Hz, 2H), 3.24 (s, 3H), 2.67 (s, 3H).

Example 65

Method to Determine the Ability of Compounds of the Invention to Inhibit LOX and LOXL1-4 from Different Sources Lysyl oxidase (LOX) is an extracellular copper dependent enzyme which oxidizes peptidyl lysine and hydroxylysine residues in collagen and lysine residues in elastin to produce peptidyl alpha-aminoadipic-delta-semialdehydes. This catalytic reaction can be irreversibly inhibited by β-aminopropionitrile (BAPN) that binds to the active site of LOX (Tang S. S., Trackman P. C. and Kagan H. M., Reaction of aortic lysyl oxidase with beta-aminoproprionitrile. *J Biol Chem* 1983; 258: 4331-4338). There are five LOX family members; these are LOX, LOXL1, LOXL2, LOXL3 and LOXL4. LOX and LOXL family members can be acquired as recombinant active proteins from commercial sources, or extracted from animal tissues like bovine aorta, tendons, pig skin; or prepared from cell cultures. The inhibitory effects of the compounds of the present invention were tested against the given LOX-LOXL preparation using a high-throughput coupled colorimetric method (Holt A. and Palcic M., A peroxidase-coupled continuous absorbance plate-reader assay for flavin monoamine oxidases, copper-containing amine oxidases and related enzymes. *Nat. Protoc.* 2006; 1: 2498-2505). The assay was developed using either 384 or 96 well format. Briefly, in a standard 384 well plate assay 25 μL of a dilution of any of the isoenzymes and orthologues in 1.2 M urea, 50 mM sodium borate buffer (pH 8.2) were added into each well in the presence of 1 μM mofegiline and 0.5 mM pargyline (to inhibit SSAO and MAO-B and MAO-A, respectively). Test compounds were dissolved in DMSO and tested in a Concentration Response Curve (CRC) with 11 data points, typically in the micromolar or nanomolar range after incubation with the enzyme for 30 min at 37° C. Twenty five L of a reaction mixture containing twice the K$_M$ concentration of putrescine (Sigma Aldrich, e.g. 20 mM for LOX, or 10 mM for LOXL2 and LOXL3), 120 μM Amplex Red (Sigma Aldrich) and 1.5 U/mL horseradish peroxidase (Sigma Aldrich) prepared in 1.2 M urea, 50 mM sodium borate buffer (pH 8.2) were then added to the corresponding wells. The above volumes were doubled in the case of 96 wells plate. The fluorescence (RFU) was read every 2.5 min for 30 min at a range of temperatures from 37° to 45° C., excitation 565 nm and emission 590 (Optima; BMG labtech). The slope of the kinetics for each well was calculated using MARS data analysis software (BMG labtech) and this value was used to deduce the $IC_{50}$ value (Dotmatics). The ability of the inventive compounds to inhibit the amine oxidase activity LOX and other family members is shown in Table 2.

TABLE 2

LOX and LOXL2 inhibitory activities of examples of compounds of the invention

| Compound | Bovine LOX Activity $IC_{50}$ (nanomolar) | Human LOXL2 Activity $IC_{50}$ (nanomolar) |
| --- | --- | --- |
| BAPN | >1000 | <1000 |
| 1 | >300 | <300 |
| 2 | >300 | <300 |
| 3 | >300 | <300 |
| 4 | >300 | <300 |
| 5 | >300 | <300 |
| 6 | >300 | <300 |
| 7 | >300 | <300 |
| 8 | >300 | <300 |
| 9 | >300 | <300 |
| 10 | >300 | <300 |
| 11 | >300 | <300 |
| 12 | >300 | <300 |
| 13 | >300 | <300 |
| 14 | >300 | <300 |
| 15 | >300 | <300 |
| 16 | >300 | <300 |
| 17 | >300 | <300 |
| 18 | >300 | <300 |
| 19 | >300 | <300 |
| 20 | >300 | <300 |
| 21 | >300 | <300 |
| 22 | >300 | <300 |
| 23 | >300 | <300 |
| 24 | >300 | <300 |
| 25 | >300 | <300 |
| 26 | >300 | <300 |
| 27 | >300 | <300 |
| 28 | >300 | <300 |
| 29 | >300 | <300 |
| 30 | >300 | <300 |
| 31 | >300 | <300 |
| 32 | >300 | <300 |
| 33 | >300 | <300 |
| 34 | >300 | <300 |
| 35 | >300 | <300 |
| 36 | >300 | <300 |
| 37 | >300 | <300 |
| 38 | >300 | <300 |
| 39 | >300 | <300 |
| 40 | >300 | <300 |
| 41 | >300 | <300 |
| 42 | >300 | <300 |
| 43 | >300 | <300 |
| 44 | >300 | <300 |
| 45 | >300 | <300 |
| 46 | >300 | <300 |
| 47 | >300 | <300 |
| 48 | >300 | <300 |
| 49 | >300 | <300 |
| 50 | >300 | <300 |
| 51 | >300 | <300 |
| 52 | >300 | <300 |
| 53 | >300 | <300 |
| 54 | >300 | <300 |
| 55 | >300 | <300 |
| 56 | >300 | <300 |
| 57 | >300 | <300 |
| 58 | >300 | <300 |
| 59 | >300 | <300 |
| 60 | >300 | <300 |
| 61 | >300 | <300 |
| 62 | >300 | <300 |
| 63 | >300 | <300 |
| 64 | >300 | <300 |
| 65 | >300 | <300 |
| 66 | >300 | <300 |
| 67 | >300 | <300 |
| 68 | >300 | <300 |
| 69 | >300 | <300 |
| 70 | >300 | <300 |
| 71 | >300 | <300 |
| 72 | >300 | <300 |
| 73 | >300 | <300 |
| 74 | >300 | <300 |
| 75 | >300 | <300 |
| 76 | >300 | <300 |
| 77 | >300 | <300 |
| 78 | >300 | <300 |
| 79 | >300 | <300 |
| 80 | >300 | <300 |
| 81 | >300 | <300 |
| 82 | >300 | <300 |
| 83 | >300 | <300 |
| 84 | >300 | <300 |
| 85 | >300 | <300 |
| 86 | >300 | <300 |
| 87 | >300 | <300 |
| 88 | >300 | <300 |
| 89 | >300 | <300 |
| 90 | >300 | <300 |
| 91 | >300 | <300 |
| 92 | >300 | <300 |
| 93 | >300 | <300 |
| 94 | >300 | <300 |
| 95 | >300 | <300 |
| 96 | >300 | <300 |
| 97 | >300 | <300 |
| 98 | >300 | <300 |
| 99 | >300 | <300 |
| 100 | >300 | <300 |
| 101 | >300 | <300 |
| 102 | >300 | <300 |
| 103 | >300 | <300 |
| 104 | >300 | <300 |
| 105 | >300 | <300 |
| 106 | >300 | <300 |
| 107 | >300 | <300 |
| 108 | >300 | <300 |
| 109 | >300 | <300 |
| 110 | >300 | <300 |
| 111 | >300 | <300 |
| 112 | >300 | <300 |
| 113 | >300 | <300 |
| 114 | >300 | <300 |
| 115 | >300 | <300 |
| 116 | >300 | <300 |
| 117 | >300 | <300 |

Example 66

Method to Determine the Ability of Compounds of Formula I to Inhibit Human Recombinant SSAO/VAP-1

Human recombinant SSAO/VAP-1 amine oxidase activity was determined using the coupled colorimetric method as described for monoamine oxidase, copper-containing amine oxidases and related enzymes (Holt A. and Palcic M., A peroxidase-coupled continuous absorbance plate-reader assay for flavin monoamine oxidases, copper-containing amine oxidases and related enzymes. *Nat Protoc* 2006; 1: 2498-2505). Briefly, a cloned cDNA template corresponding to residues 34-763 of human SSAO/VAP-1, and incorporating a mouse Ig kappa (κ) signal sequence, N-terminal flag epitope tag and tobacco etch virus (TEV) cleavage site, was assembled in a mammalian expression vector (pLO-CMV) by Geneart AG. This vector containing human SSAO/VAP-1 residues was transfected into CHO-K1 glycosylation mutant cell line, Lec 8. A clone stably expressing human SSAO/VAP-1 was isolated and cultured in large scale. Active human SSAO/VAP-1 was purified and recovered using immunoaffinity chromatography. This was used as the source for SSAO/VAP-1 activity. A high-throughput colorimetric assay was developed using either 96 or 384 well format. Briefly, in a standard 96 well plate assay 50 µL of purified human SSAO/VAP-1 (0.25 µg/mL) in 0.1 M sodium phosphate buffer (pH 7.4) was added into each well. Test compounds were dissolved in DMSO and tested in a Concentration Response Curve (CRC) with 4-11 data points, typically in the micromolar or nanomolar range after incubation with human SSAO/VAP-1 for 30 min at 37° C. After 30 min incubation, 50 µL of the reaction mixture containing 600 µM benzylamine (Sigma Aldrich), 120 µM Amplex Red (Sigma Aldrich) and 1.5 U/mL horseradish peroxidase (Sigma Aldrich) prepared in 0.1 M sodium phosphate buffer (pH 7.4) were added to the corresponding well. The fluorescence unit (RFU) was read every 2.5 min for 30 min at 37° C. excitation 565 nm and emission 590 (Optima; BMG labtech). The slope of the kinetics for each well was calculated using MARS data analysis software (BMG labtech) and this value was used to deduce the $IC_{50}$ value (Dotmatics). The ability of the compounds of Formula I to inhibit SSAO/VAP-1 is shown in Table 3.

Example 67

Method to Determine the Ability of Compounds of Formula I to Inhibit Human Recombinant MAO-B The specificity of the compounds of this invention was tested by determining their ability to inhibit MAO-B activities in vitro. Recombinant human MAO-B (0.06 mg/mL; Sigma Aldrich) was used as source of MAO-B enzyme activities. The assay was performed in a similar way as for human SSAO/VAP-1 (Example 66) except, the substrate benzylamine was used at 100 µM. The ability of compounds of Formula I to inhibit MAO-B is shown in Table 3.

TABLE 3

Selectivity of Compounds of Formula I for LOX and LOXL2 compared to SSAO/VAP-1 and MAO-B

| Compound | SSAO/VAP-1 Activity $IC_{50}$ (micromolar) | MAO-B Activity $IC_{50}$ (micromolar) |
| --- | --- | --- |
| BAPN | >3 | >3 |
| 1 | >3 | >3 |
| 2 | >3 | >3 |
| 3 | >3 | >3 |
| 4 | >3 | >3 |
| 5 | >3 | >3 |
| 6 | >3 | >3 |
| 7 | >3 | >3 |
| 8 | >3 | >3 |
| 9 | >3 | >3 |
| 10 | >3 | >3 |
| 11 | >3 | >3 |

TABLE 3-continued

Selectivity of Compounds of Formula I for LOX and LOXL2 compared to SSAO/VAP-1 and MAO-B

| Compound | SSAO/VAP-1 Activity $IC_{50}$ (micromolar) | MAO-B Activity $IC_{50}$ (micromolar) |
| --- | --- | --- |
| 12 | >3 | >3 |
| 13 | >3 | >3 |
| 14 | >3 | >3 |
| 15 | >3 | >3 |
| 16 | >3 | >3 |
| 17 | >3 | >3 |
| 18 | >3 | >3 |
| 19 | >3 | >3 |
| 20 | >3 | >3 |
| 21 | >3 | >3 |
| 22 | >3 | >3 |
| 23 | >3 | >3 |
| 24 | >3 | >3 |
| 25 | >3 | >3 |
| 26 | >3 | >3 |
| 27 | >3 | >3 |
| 28 | >3 | >3 |
| 29 | >3 | >3 |
| 30 | >3 | >3 |
| 31 | >3 | >3 |
| 32 | >3 | >3 |
| 33 | >3 | >3 |
| 34 | >3 | >3 |
| 35 | >3 | >3 |
| 36 | >3 | >3 |
| 37 | >3 | >3 |
| 38 | >3 | >3 |
| 39 | >3 | >3 |
| 40 | >3 | >3 |
| 41 | >3 | >3 |
| 42 | >3 | >3 |
| 43 | >3 | >3 |
| 44 | >3 | >3 |
| 45 | >3 | >3 |
| 46 | >3 | >3 |
| 47 | >3 | >3 |
| 48 | >3 | >3 |
| 49 | >3 | >3 |
| 50 | >3 | >3 |
| 51 | >3 | >3 |
| 52 | >3 | >3 |
| 53 | >3 | >3 |
| 54 | >3 | >3 |
| 55 | >3 | >3 |
| 56 | >3 | >3 |
| 57 | >3 | >3 |
| 58 | >3 | >3 |
| 59 | >3 | >3 |
| 60 | >3 | >3 |
| 61 | >3 | >3 |
| 62 | >3 | >3 |
| 63 | >3 | >3 |
| 64 | >3 | >3 |
| 65 | >3 | >3 |
| 66 | >3 | >3 |
| 67 | >3 | >3 |
| 68 | >3 | >3 |
| 69 | >3 | >3 |
| 70 | >3 | >3 |
| 71 | >3 | >3 |
| 72 | >3 | >3 |
| 73 | >3 | >3 |
| 74 | >3 | >3 |
| 75 | >3 | >3 |
| 76 | >3 | >3 |
| 77 | >3 | >3 |
| 78 | >3 | >3 |
| 79 | >3 | >3 |
| 80 | >3 | >3 |
| 81 | >3 | >3 |
| 82 | >3 | >3 |
| 83 | >3 | >3 |
| 84 | >3 | >3 |

TABLE 3-continued

Selectivity of Compounds of Formula I for LOX
and LOXL2 compared to SSAO/VAP-1 and MAO-B

| Compound | SSAO/VAP-1 Activity IC$_{50}$ (micromolar) | MAO-B Activity IC$_{50}$ (micromolar) |
|---|---|---|
| 85 | >3 | >3 |
| 86 | >3 | >3 |
| 87 | >3 | >3 |
| 88 | >3 | >3 |
| 89 | >3 | >3 |
| 90 | >3 | >3 |
| 91 | >3 | >3 |
| 92 | >3 | >3 |
| 93 | >3 | >3 |
| 94 | >3 | >3 |
| 95 | >3 | >3 |
| 96 | >3 | >3 |
| 97 | >3 | >3 |
| 98 | >3 | >3 |
| 99 | >3 | >3 |
| 100 | >3 | >3 |
| 101 | >3 | >3 |
| 102 | >3 | >3 |
| 103 | >3 | >3 |
| 104 | >3 | >3 |
| 105 | >3 | >3 |
| 106 | >3 | >3 |
| 107 | >3 | >3 |
| 108 | >3 | >3 |
| 109 | >3 | >3 |
| 110 | >3 | >3 |
| 111 | >3 | >3 |
| 112 | >3 | >3 |
| 113 | nt | nt |
| 114 | nt | nt |
| 115 | nt | nt |
| 116 | nt | nt |
| 117 | nt | nt |

LOX and LOXL1-4 enzymes are members of a large family of flavin-dependent and copper-dependent amine oxidases, which includes SSAO/VAP-1 and monoamine oxidase-B (MAO-B). Compounds of the present invention selectively inhibit members of the LOX family of enzymes with respect to SSAO/VAP-1, MAO-B and other family member amine oxidases. Examples of the magnitude of selectivity can be seen in Table 3.

Example 68

Inhibition of CCl$_4$ Induced Liver Fibrosis

An analysis of the use of LOXL2 inhibitors to treat inflammatory/fibrotic diseases is performed through the use of a CCl$_4$ induced liver fibrosis model. Liver injury is frequently followed by complete parenchymal regeneration due to regenerative potency of hepatocytes. Continuous liver injury due to the administration of CCl$_4$ leads to extracellular matrix accumulation, accompanied by recurrent hepatocyte necrosis, inflammation, and regenerative processes, causing liver fibrosis and consequently liver cirrhosis (see Natsume, M., et al., *Attenuated liver fibrosis and depressed serum albumin levels in carbon tetrachloride-treated IL-6-deficient mice. J. Leukoc. Biol.,* 1999, 66, 601-608 also See Yao, Q, Y., et al. *Inhibition by curcumin of multiple sites of the transforming growth factor-beta1 signalling pathway ameliorates the progression of liver fibrosis induced by carbon tetrachloride in rats. BMC Complement Altern Med.* 2012 Sep. 16; 12(1):156.)

Rats are administered orally with CCl$_4$ at a concentration of 0.25 μL/g in olive oil, 3 times per week for 6 weeks. Compound 25 is given 0.1-100 mg/Kg throughout the period of the experimental procedure or only 3 weeks after CCl$_4$ administration and then throughout the entire study. Compared with the vehicle-treated group that show increases in fibrosis in the liver, Compound 25 administration shows up to 50% reduction as demonstrated by liver sirius red staining with quantification (See FIG. 1). In addition, Compound 25 treated mice results in a statistically significant reduction in the liver collagen with inhibition of >30% of collagen by hydroxyproline analysis.

Example 69

Inhibition of Bleomycin Induced Lung Fibrosis

Bleomycin induced lung fibrosis in rodents is a widely accepted experimental model to determine the anti-fibrotic activity of therapeutic agents.

Fibrosis is induced by intranasal administered of bleomycin sulphate at a dose of 0.05 U/mouse in a total volume of 50 uL PBS (see Corbel, M., et al *Inhibition of bleomycin-induced pulmonary fibrosis in mice by the matrix metalloproteinase inhibitor batimastat J Pathol.* 2001 April; 193 (4):538-45.) Compound 12 is given 0.1-100 mg/Kg throughout the period of the experimental procedure or 7 days after bleomycin administration and then throughout the entire study.

Figure 2:
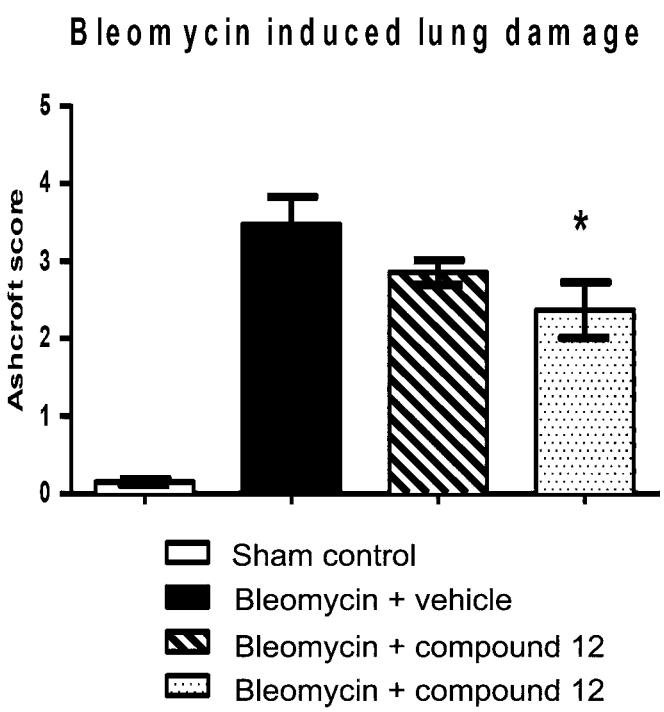
FIG. 2 shows the ability of Compound 12 to reduce fibrosis in a mouse model of lung fibrosis.

Formalin fixed lungs sections stained with haematoxylin and eosin are assessed for fibrosis as per the scale outlined by Ashcroft et al (*Simple method of estimating severity of pulmonary fibrosis on a numerical scale J Clin Pathol* 1988; 41:467-470). Bleomycin administration increases the Ashcroft score, while 15 mg/kg of Compound 12 significantly reduced this score in the lungs (See FIG. 2).

Example 70

Inhibition of Streptozotocin Induced Diabetic Nephropathy

Streptozotocin (STZ)-induced diabetic nephropathy is commonly used for creating rodent models of type 1 diabetes which develop renal injury, due to pancreatic cell damage with similarities to human diabetic nephropathy.

This model can be established for investigating anti-fibrotic effects of compounds in the development of kidney fibrosis.

Diabetes is induced in eNOS knockout mice on C57BL/6 background by intraperitoneal STZ injection (55 mg/kg in 0.1 M citrate buffer) in mice of 6-9 weeks of age (see Huang C et al, *Blockade of KCa3.1 ameliorates renal fibrosis through a TGF-bl/Smad pathway in diabetic mice. Diabetes,* 2013 62(8):2923-2934).

Figure 3:
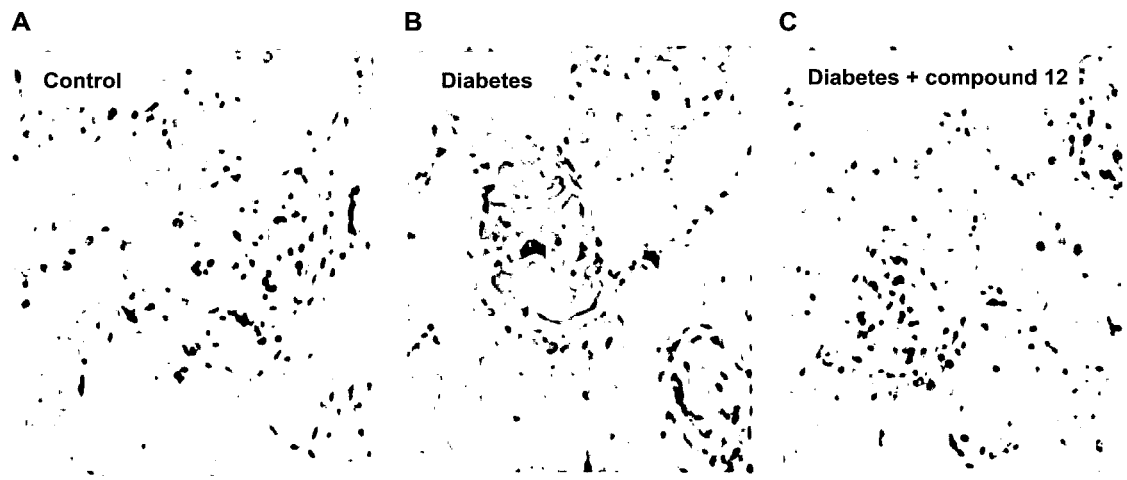
FIG. 3A-3C shows the ability of Compound 12 to reduce fibrosis and to improve kidney function in a mouse model of kidney fibrosis.
Figure 4:
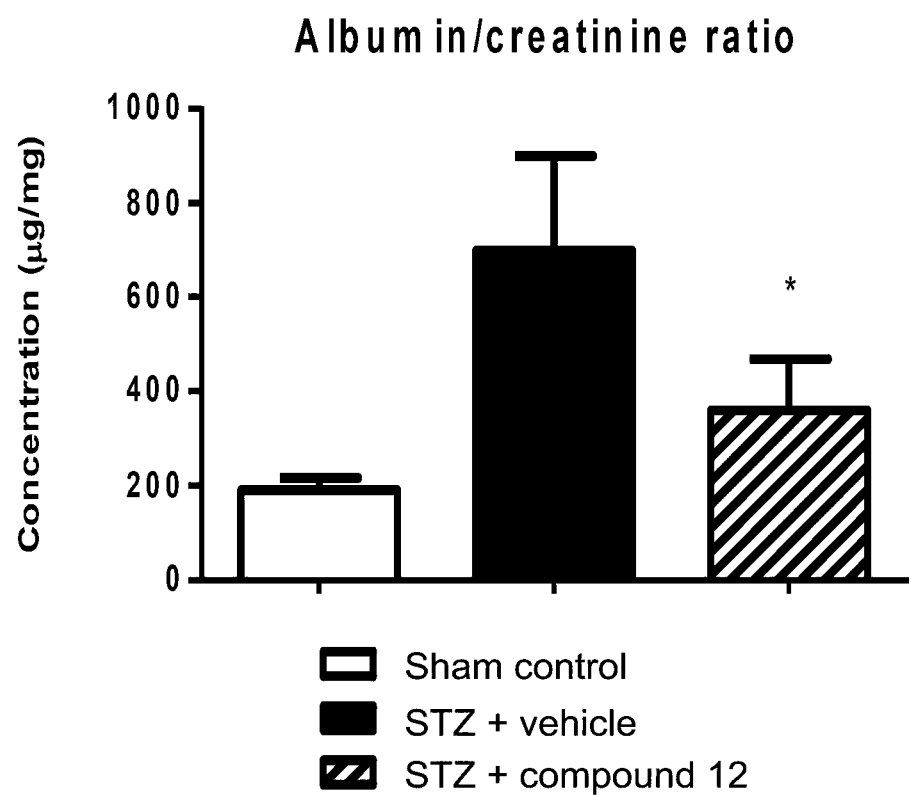
FIG. 4 shows the ability of Compound 12 to improve kidney function in a mouse model of kidney fibrosis.

Blood sugar level (BSL) is determined by tail vein blood. Mice with BSL>16 mmol/L two weeks post STZ injection are considered diabetic. Treatment with Compound 12 is carried out for 24 weeks from diagnosis of diabetes at a dose of 0.1-100 mg/Kg. Compared with the vehicle-treated group that show increases in fibrosis and decline in kidney function, Compound 12 administration shows up to 50% reduction of fibrosis (by Masson's Trichrome staining showing collagen expression and glomerular damage) (See FIG. 3A-3C) and a significant improvement in kidney function as demonstrated by albumin/creatinine ratio quantification (see FIG. 4).

Example 71

Inhibition of Myocardial Infarction Induced Fibrosis

Carotic ligation is a widely accepted experimental model to induce cardiac fibrosis and to determine the anti-fibrotic activity of therapeutic agents.

In mice, the chest is opened via a left thoracotomy. The left coronary artery is identified visually using a stereo microscope, and a 7-0 suture is placed around the artery 1-2 mm below the left auricle. Permanent occlusion of the left coronary artery resulted from its ligation with the suture. Myocardial ischemia was confirmed by pallor in heart color and ST-segment elevation. (see Parajuli et al. *Phosphatase PTEN is critically involved in post-myocardial infarction remodeling through the Akt/interleukin-10 signaling pathway Basic Res Cardiol* (2012) 107:248).

Figure 5:
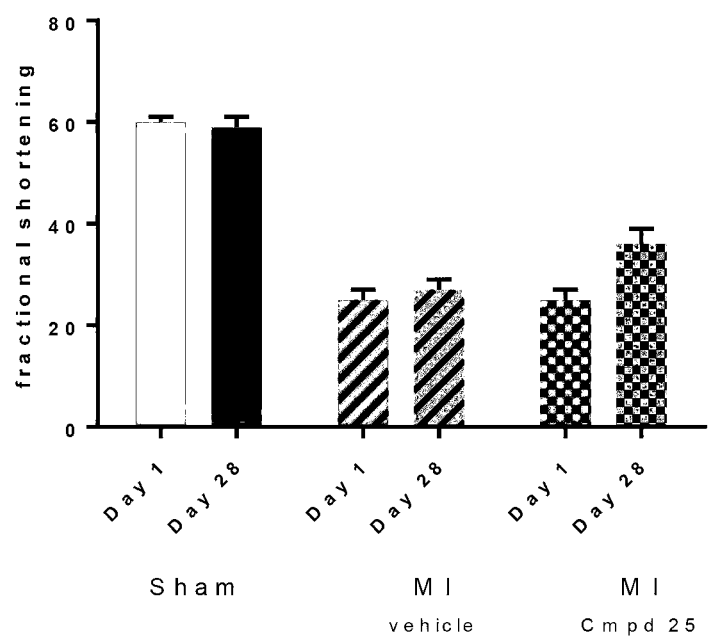
FIG. 5 shows the ability of Compound 25 to reduce fibrosis after carotic ligation in a mouse model of myocardial infarction.

Mice were subjected to sham or carotic ligation surgery. At 24 hrs post-surgery, echocardiography was performed on the mice. Mice were treated with compound 25 0.1-100 mg/Kg once a day for 21 (7 days after carotic ligation) or 28 days or saline as vehicle controls by oral gavage. At the end of the experiment, echocardiography was repeated to assess left ventricular function and remodeling. Then mice were euthanized for heart collection. Each heart was photographed and fixed with 10% formalin. Hearts were sectioned for Masson's trichrome stain to measure fibrosis (See FIG. 5).

Example 72

Streptozotocin and High Fat Diet Induced Liver Fibrosis

High fat/carbohydrate diet induced liver fibrosis is the most common reason for liver dysfunction and ultimately liver failure. NASH is induced in male mice by a single subcutaneous injection of 200 μg streptozotocin solution 2 days after birth and feeding with high fat diet after 4 weeks of age (STAM™ model). The STAM™ model demonstrates NASH progression that resembles the disease in humans: STAM™ mice manifest NASH at 8 weeks, which progresses to fibrosis at 12 weeks (K. Saito et al. *Characterization of hepatic lipid profiles in a mouse model with nonalcoholic steatohepatitis and subsequent fibrosis Sci Rep.* 2015 Aug. 20; 5:12466).

Figure 6:
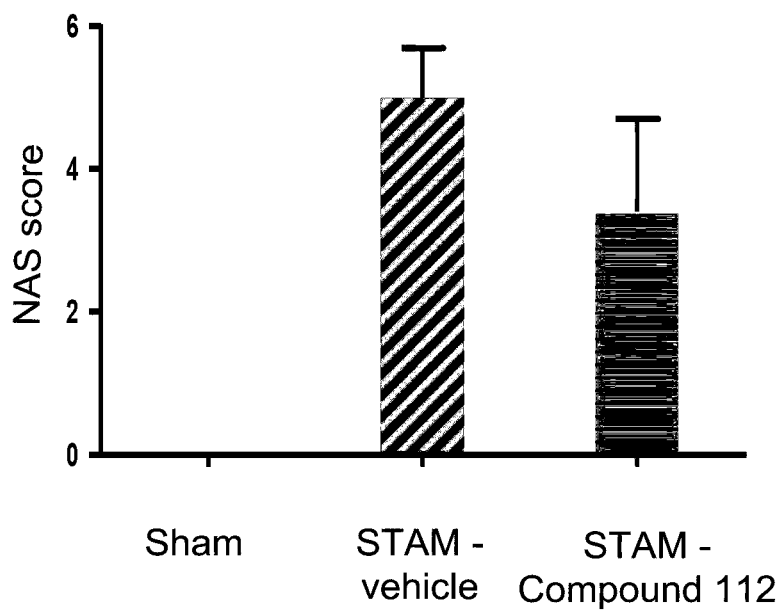
FIG. 6 shows the ability of Compound 112 to reduce lilver fibrosis in a STAM™ mice model.

LOXL2 inhibitor compound 112 was administered by daily oral gavage at doses between 10-30 mg/kg 8 weeks after streptozotocin application. Mice were sacrificed after NASH had been established and whole blood samples were taken via cardiac puncture. Liver samples were collected and washed with cold saline. Liver weight was measured. The left lateral, right and caudate lobes of livers were snap frozen in liquid nitrogen and stored at −80° C. For HE staining, sections were cut from paraffin blocks of liver tissue prefixed in Bouin's solution and stained with Lillie-Mayer's Hematoxylin and eosin solution. NAFLD Activity score (NAS) was calculated according to the criteria of Kleiner (Kleiner D E. et al., *Design and validation of a histological scoring system for nonalcoholic fatty liver disease. Hepatology*, 2005; 41:1313). To visualize collagen deposition, Bouin's fixed liver sections were stained using picro-Sirius red solution and the area of fibrosis was quantified (See FIG. 6).

Example 73

Reduction of Collagen Cross-Link Formation in an In Vitro Fibroblastic Foci Model of IPF The lung tissue of patients with idiopathic pulmonary fibrosis (IPF) is characterised by dense collections of myofibroblasts and extracellular matrix (ECM) termed 'fibroblastic foci'. Using a novel in vitro model of fibroblastic foci (Jones et al., AJRCCM 191; 2015:A4912) the formation of lysyl oxidase (LOX) mediated collagen cross-links and the effects of the nonselective LOX inhibitor β-aminopropionitrile (BAPN) as well lysyl oxidase like-2 (LOXL2)-selective inhibitors were investigated.

Cultures of primary fibroblasts were grown out from clinical diagnostic biopsies of fibrotic lung and stored in liquid nitrogen. Fibroblasts from confirmed cases of IPF were subsequently expanded and seeded onto transwell membranes under optimised conditions for mature collagen matrix deposition in the presence of BAPN or a LOXL2-selective inhibitor (Compound 112). Following stimulation with transforming growth factor β1 (TGF-β1) multicellular foci formed which were histochemically similar in organisation to fibroblastic foci in vivo. The foci were cultured for a further six weeks in the presence of TGF-β1 and the inhibitors. Cultures were then harvested and snap frozen in liquid nitrogen.

To quantify collagen cross-links (Robins Biochem Soc Trans 2007; 35(5): 849-852; Saito et al Anal. Biochem. 1997; 253: 26-32; Sims, Avery & Bailey Methods in Molecular Biology 2000; vol 139: 11-26), cultures were treated with potassium borohydride to stabilise the reducible immature cross-links, and hydrolysed in 6N HCl at 100° C. for 16 hr. Total collagen content was assessed by hydroxyproline assay. Immature cross-links were assessed by LC/MS/MS and mature pyridinoline cross-links by ELISA. Cross-link data is expressed as moles of cross-link per mole collagen.

Figure 7A:
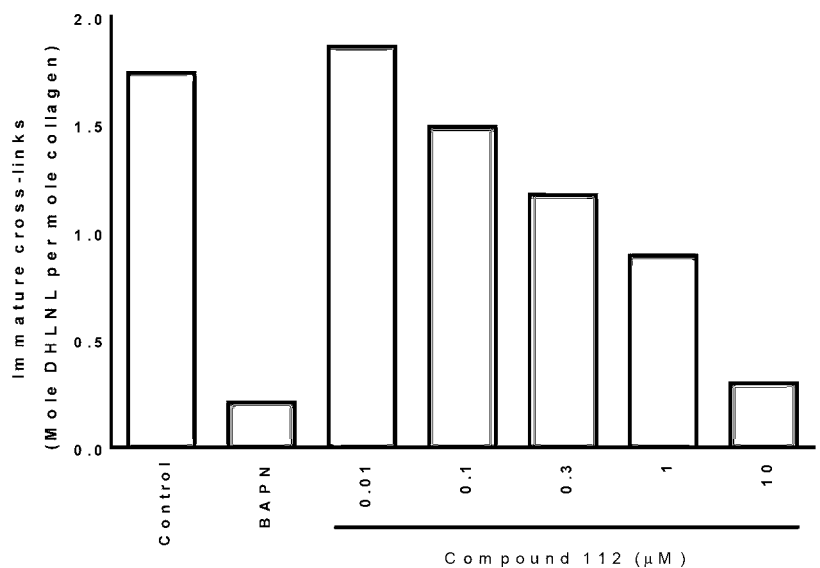
FIGS. 7a and 7b show the ability of Compound 112 to reduce collagen cross-link formation in an in vitro fibroblastic foci model of idiopathic pulmonary fibrosis (IPF).
Figure 7B:
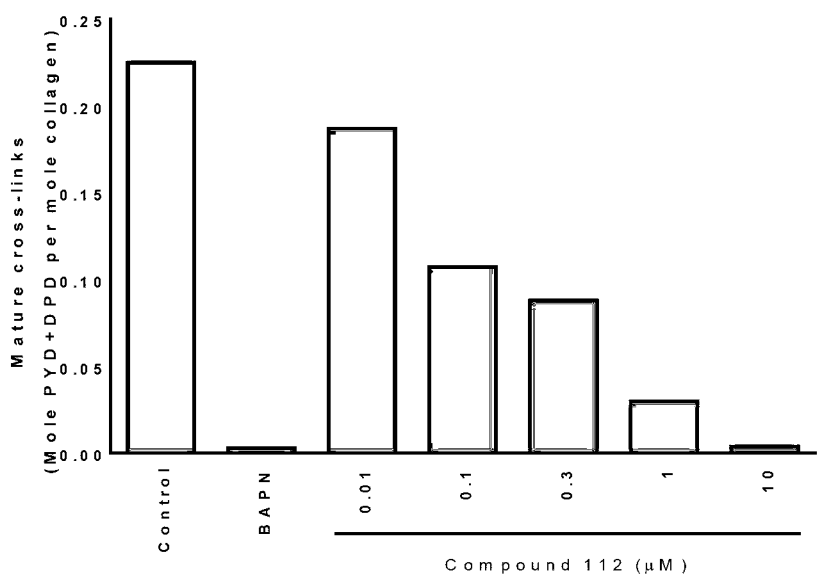

The number of immature and mature LOX family-mediated collagen crosslinks increased over the 6 week duration of the model. Both BAPN and the LOXL2-selective inhibitor (Compound 112) reduced cross-link formation in a concentration dependent manner (see FIGS. 7a and 7b).

The invention claimed is:
1. A compound of Formula I:

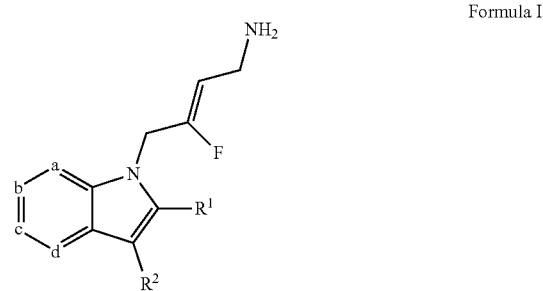

Formula I or a stereoisomer, pharmaceutically acceptable salt, or tautomeric form thereof; wherein:
a is N or $CR^3$;
b is N or $CR^4$;
c is N or $CR^5$;
d is N or $CR^6$;
and from 0 to 2 of a, b, c and d are N;
$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9C(O)R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^{2'}$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

2. A compound according to claim 1, of Formula Ia:

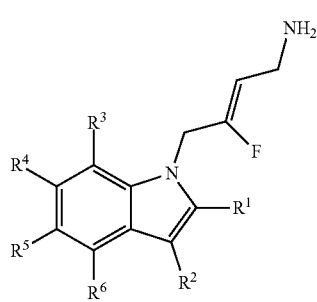

Formula Ia or a pharmaceutically acceptable salt thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)$OR^8$, —C(O)$NR^9R^{10}$ and —$NR^9$C(O)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —$NO_2$, —$NR^9R^{10}$, —C(O) $OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$, —S($O_2$)$R^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)$OR^8$, —C(O)$NR^9R^{10}$, —$NR^9$C(O)$R^{11}$, —S($O_2$)$NR^9R^{10}$, —$NR^9$S($O_2$)$R^{11}$, —S(O)$R^{11}$ and —S($O_2$)$R^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

3. A compound according to claim 1, of Formula Ib:

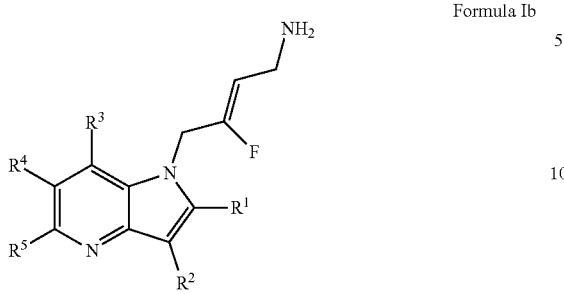

Formula Ib or a pharmaceutically acceptable salt thereof; wherein:
R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^2$ is aryl or heteroaryl; wherein each R$^2$ is optionally substituted by one or more R$^{12}$;
R$^3$, R$^4$ and R$^5$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or
R$^9$ and R$^{10}$ when attached to the same nitrogen atom are combined to form a 3- to 7-membered ring having from 0 to 2 additional heteroatoms as ring members;
R$^{11}$ is selected from the group consisting of C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; and
R$^{12}$ is selected from the group consisting of halogen, C$_{1-6}$alkyl, —O—C$_{1-6}$alkyl, —S—C$_{1-6}$alkyl, C$_{3-7}$cycloalkyl, —O—C$_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —C$_{1-3}$alkyl, —O—C$_{1-3}$alkyl, —CF$_3$, —CH$_2$CF$_3$, and —O—CF$_3$.

4. A compound according to claim 1, of Formula Ic:

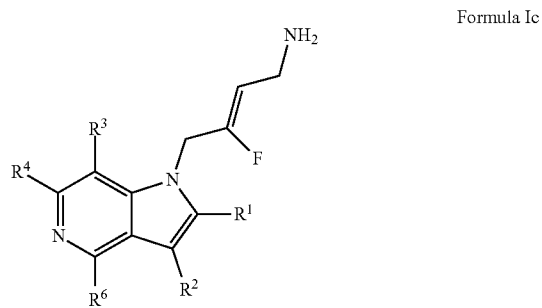

Formula Ic or a pharmaceutically acceptable salt thereof; wherein:
R$^1$ is selected from the group consisting of hydrogen, halogen, C$_{1-6}$alkyl, C$_{3-7}$cycloalkyl, —O—C$_{1-6}$alkyl, —O—C$_{3-7}$cycloalkyl, —C(O)OR$^8$, —C(O)NR$^9$R$^{10}$ and —NR$^9$C(O)R$^{11}$; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^2$ is aryl or heteroaryl; wherein each R$^2$ is optionally substituted by one or more R$^{12}$;
R$^3$, R$^4$ and R$^6$ are each independently selected from the group consisting of hydrogen, halogen, hydroxyl, C$_{1-6}$alkyl, C$_{3-7}$cycloalkyl, —O—C$_{1-6}$alkyl, —O—C$_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^8$ is selected from the group consisting of hydrogen, C$_{1-6}$alkyl, and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$;
R$^9$ and R$^{10}$ are independently selected from the group consisting of hydrogen, C$_{1-6}$alkyl and C$_{3-7}$cycloalkyl; wherein each C$_{1-6}$alkyl is a straight or branched chain alkyl; and wherein each C$_{1-6}$alkyl and C$_{3-7}$cycloalkyl is optionally substituted by one or more substituents selected from the group consisting of halogen, —OH, —SH, —C$_{1-3}$alkyl, —O—C$_{1-3}$alkyl, —CF$_3$, —CH$_2$CF$_3$, and —O—CF$_3$; or
R$^9$ and R$^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

5. A compound according to claim 1, of Formula Id:

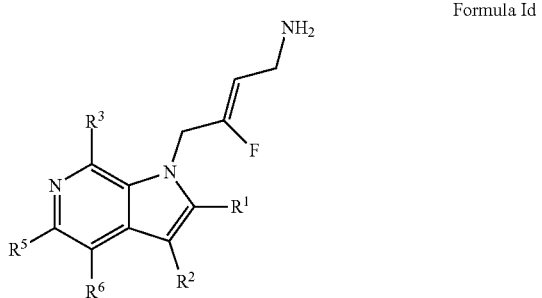

Formula Id or a pharmaceutically acceptable salt thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^3$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

6. A compound according to claim 1, of Formula Ie:

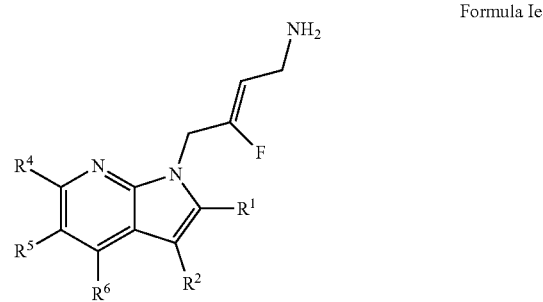

Formula Ie or a pharmaceutically acceptable salt thereof; wherein:

$R^1$ is selected from the group consisting of hydrogen, halogen, $C_{1-6}$alkyl, $C_{3-7}$cycloalkyl, —O—$C_{1-6}$alkyl, —O—$C_{3-7}$cycloalkyl, —C(O)OR$^8$, —C(O)NR$^9$R$^{10}$ and —NR$^9$C(O)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^2$ is aryl or heteroaryl; wherein each $R^2$ is optionally substituted by one or more $R^{12}$;

$R^4$, $R^5$ and $R^6$ are each independently selected from the group consisting of hydrogen, halogen, hydroxyl, $C_{1-6}$alkyl, $C_{3-7}$cycloalkyl, —O—$C_{1-6}$alkyl, —O—$C_{3-7}$cycloalkyl, —CN, —NO$_2$, —NR$^9$R$^{10}$, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$, —S(O$_2$)R$^{11}$, tetrazole and oxadiazole; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^8$ is selected from the group consisting of hydrogen, $C_{1-6}$alkyl, and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$;

$R^9$ and $R^{10}$ are independently selected from the group consisting of hydrogen, $C_{1-6}$alkyl and $C_{3-7}$cycloalkyl; wherein each $C_{3-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; or $R^9$ and $R^{10}$ when attached to the same nitrogen atom are combined to form a 3- to 7-membered ring having from 0 to 2 additional heteroatoms as ring members;

$R^{11}$ is selected from the group consisting of $C_{1-6}$alkyl and $C_{3-7}$cycloalkyl; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —SH, —$C_{1-3}$alkyl, —O—$C_{1-3}$alkyl, —$CF_3$, —$CH_2CF_3$, and —O—$CF_3$; and $R^{12}$ is selected from the group consisting of halogen, $C_{1-6}$alkyl, —O—$C_{1-6}$alkyl, —S—$C_{1-6}$alkyl, $C_{3-7}$cycloalkyl, —O—$C_{3-7}$cycloalkyl, —C(O)OR$^8$, —C(O)NR$^9$R$^{10}$, —NR$^9$C(O)R$^{11}$, —S(O$_2$)NR$^9$R$^{10}$, —NR$^9$S(O$_2$)R$^{11}$, —S(O)R$^{11}$ and —S(O$_2$)R$^{11}$; wherein each $C_{1-6}$alkyl is a straight or branched chain alkyl; and wherein each $C_{1-6}$alkyl and $C_{3-7}$cycloalkyl is optionally substituted by one or more substituents selected from the group consisting of halogen, —OH, —$C_{1-3}$alkyl, —O—$C_{1-3}$alkyl, —$CF_3$, —$CH_2CF_3$, and —O—$CF_3$.

7. A compound according to claim 1, wherein $R^2$ is selected from the group consisting of phenyl

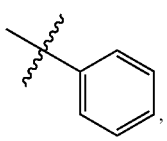

1,3-benzodioxolyl

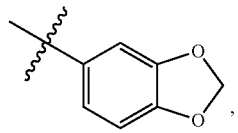 [SMILES: *c1ccc2c(c1)OCO2]

2-pyridinyl

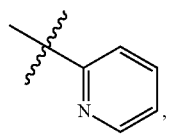 [SMILES: *c1ccccn1]

3-pyridinyl

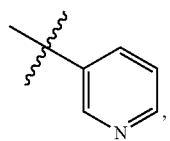 [SMILES: *c1cccnc1]

4-pyridinyl

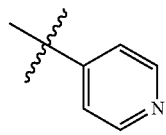 [SMILES: *c1ccncc1]

and 5-pyrimidinyl

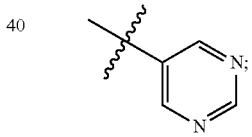

wherein each $R^2$ is optionally substitute by n or more $R^{12}$.

8. A compound according to claim 1, selected from the group consisting of:

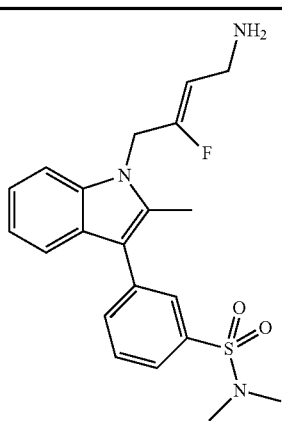

(Z)-3-(1-(4-amino-2-fluorobut-2-en-1-yl)-2-methyl-1H-indol-3-yl)-N,N-dimethylbenzenesulfonamide

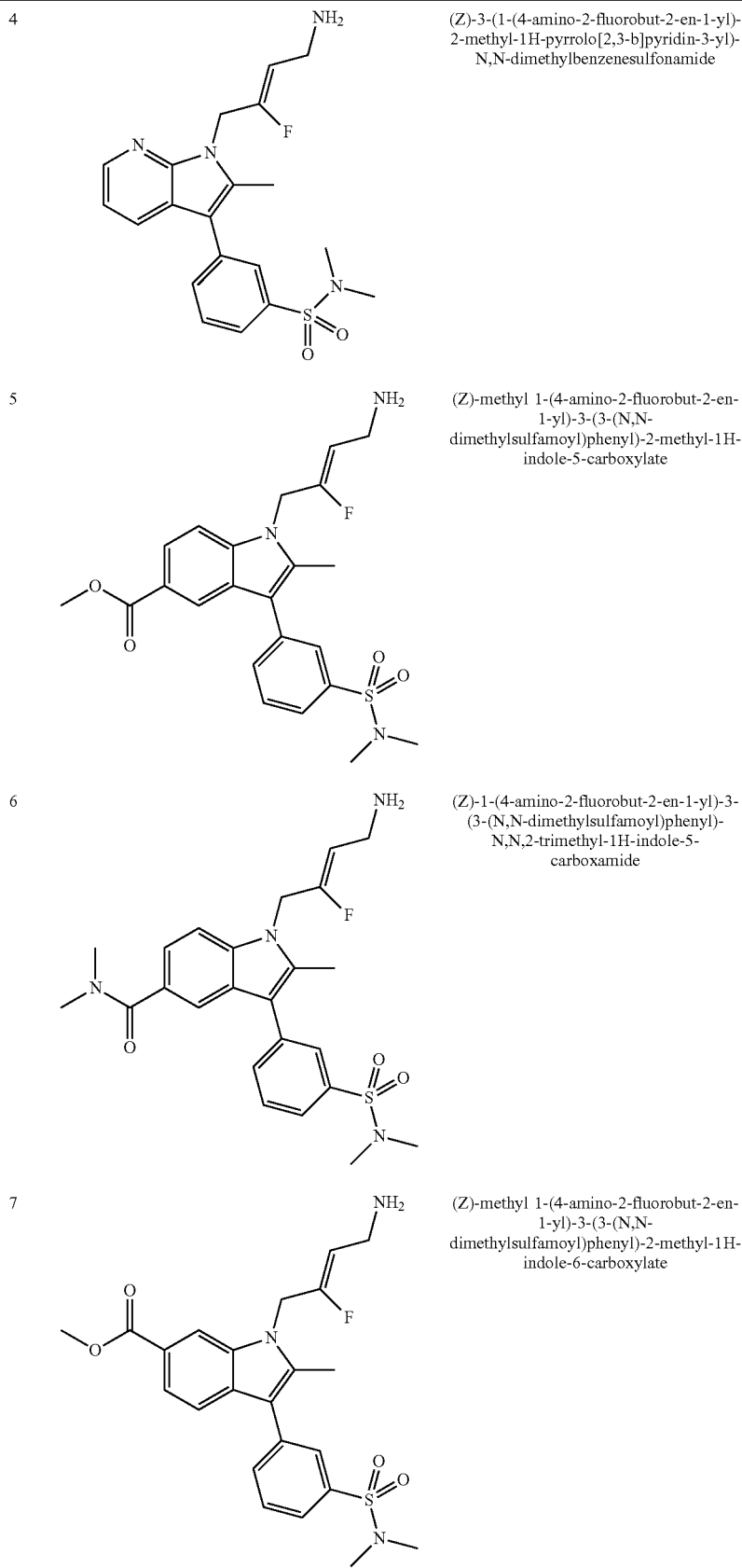
| | | |
|---|---|---|
| 4 | | (Z)-3-(1-(4-amino-2-fluorobut-2-en-1-yl)-2-methyl-1H-pyrrolo[2,3-b]pyridin-3-yl)-N,N-dimethylbenzenesulfonamide |
| 5 | | (Z)-methyl 1-(4-amino-2-fluorobut-2-en-1-yl)-3-(3-(N,N-dimethylsulfamoyl)phenyl)-2-methyl-1H-indole-5-carboxylate |
| 6 | | (Z)-1-(4-amino-2-fluorobut-2-en-1-yl)-3-(3-(N,N-dimethylsulfamoyl)phenyl)-N,N,2-trimethyl-1H-indole-5-carboxamide |
| 7 | | (Z)-methyl 1-(4-amino-2-fluorobut-2-en-1-yl)-3-(3-(N,N-dimethylsulfamoyl)phenyl)-2-methyl-1H-indole-6-carboxylate |

| | | |
|---|---|---|
| 8 | 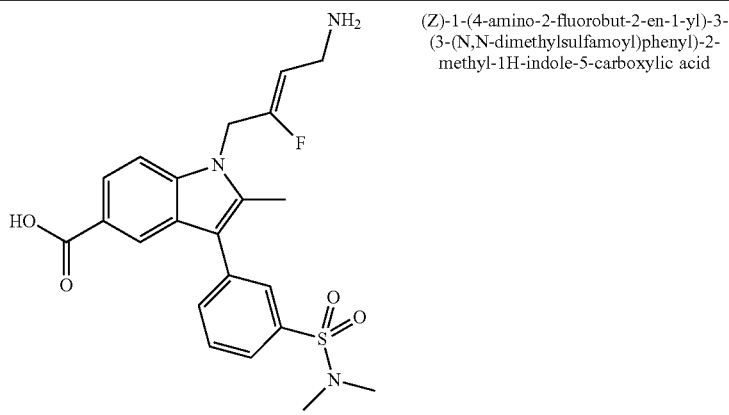 | (Z)-1-(4-amino-2-fluorobut-2-en-1-yl)-3-(3-(N,N-dimethylsulfamoyl)phenyl)-2-methyl-1H-indole-5-carboxylic acid |
| 10 | 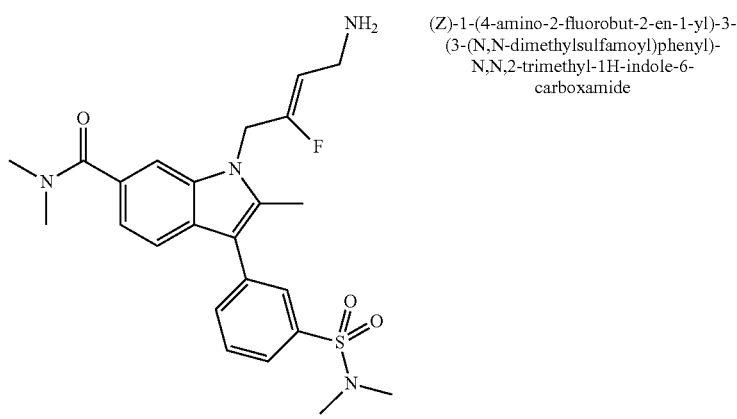 | (Z)-1-(4-amino-2-fluorobut-2-en-1-yl)-3-(3-(N,N-dimethylsulfamoyl)phenyl)-N,N,2-trimethyl-1H-indole-6-carboxamide |
| 11 | 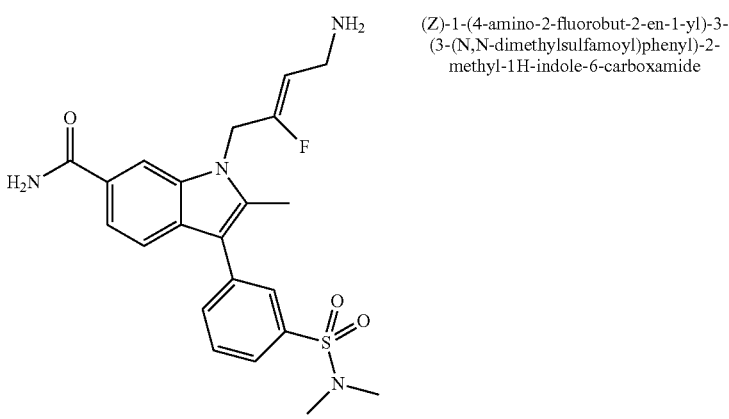 | (Z)-1-(4-amino-2-fluorobut-2-en-1-yl)-3-(3-(N,N-dimethylsulfamoyl)phenyl)-2-methyl-1H-indole-6-carboxamide |
| 12 | 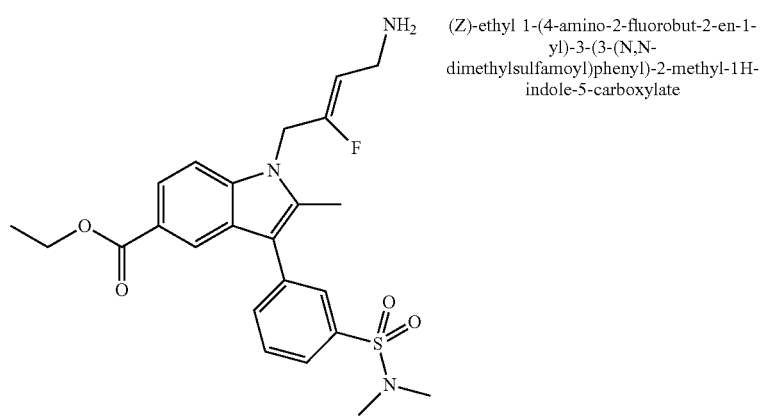 | (Z)-ethyl 1-(4-amino-2-fluorobut-2-en-1-yl)-3-(3-(N,N-dimethylsulfamoyl)phenyl)-2-methyl-1H-indole-5-carboxylate |

| | | |
|---|---|---|
| 13 | 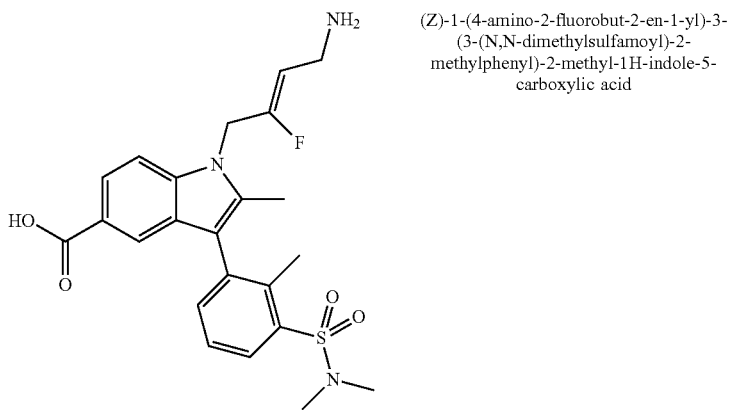 | (Z)-1-(4-amino-2-fluorobut-2-en-1-yl)-3-(3-(N,N-dimethylsulfamoyl)-2-methylphenyl)-2-methyl-1H-indole-5-carboxylic acid |
| 14 | 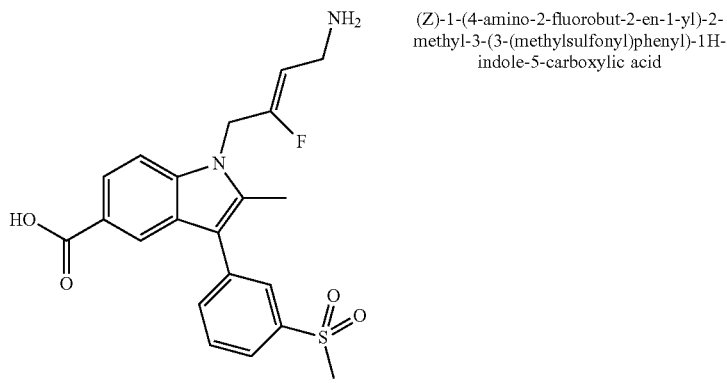 | (Z)-1-(4-amino-2-fluorobut-2-en-1-yl)-2-methyl-3-(3-(methylsulfonyl)phenyl)-1H-indole-5-carboxylic acid |
| 15 | 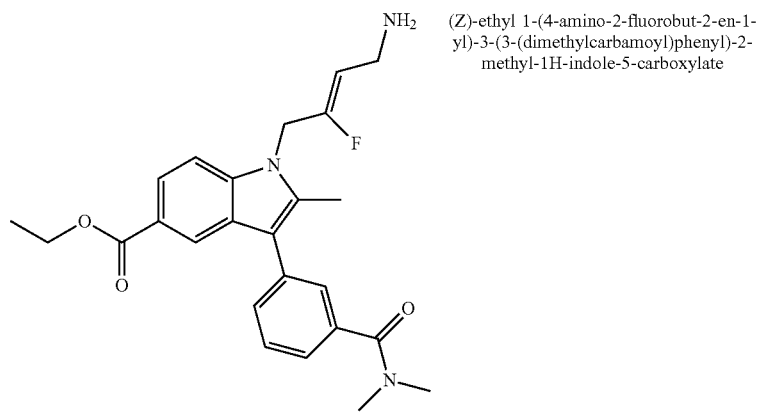 | (Z)-ethyl 1-(4-amino-2-fluorobut-2-en-1-yl)-3-(3-(dimethylcarbamoyl)phenyl)-2-methyl-1H-indole-5-carboxylate |
| 16 | 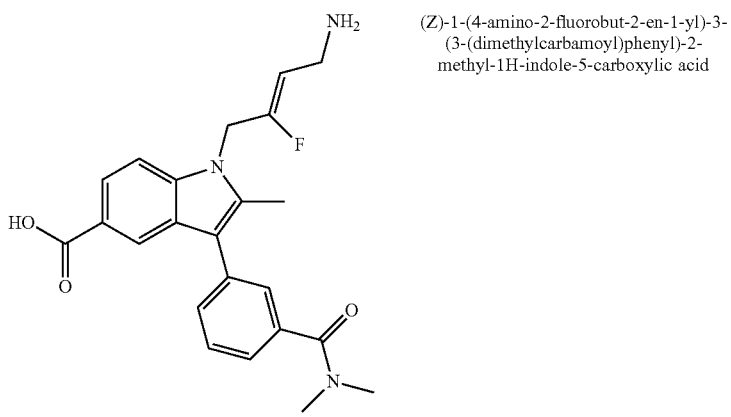 | (Z)-1-(4-amino-2-fluorobut-2-en-1-yl)-3-(3-(dimethylcarbamoyl)phenyl)-2-methyl-1H-indole-5-carboxylic acid |

| | | |
|---|---|---|
| 17 | 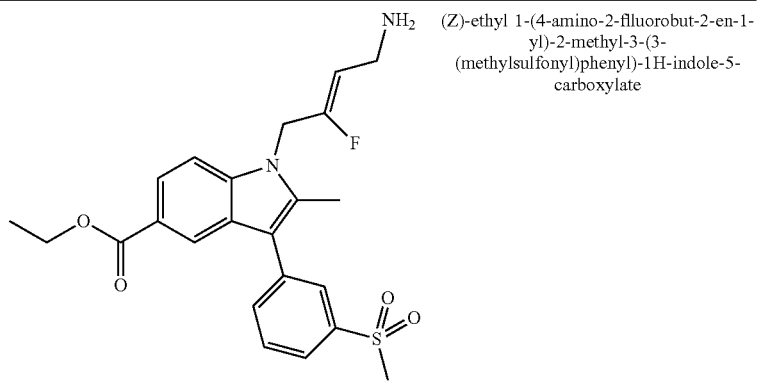 | (Z)-ethyl 1-(4-amino-2-flluorobut-2-en-1-yl)-2-methyl-3-(3-(methylsulfonyl)phenyl)-1H-indole-5-carboxylate |
| 18 | 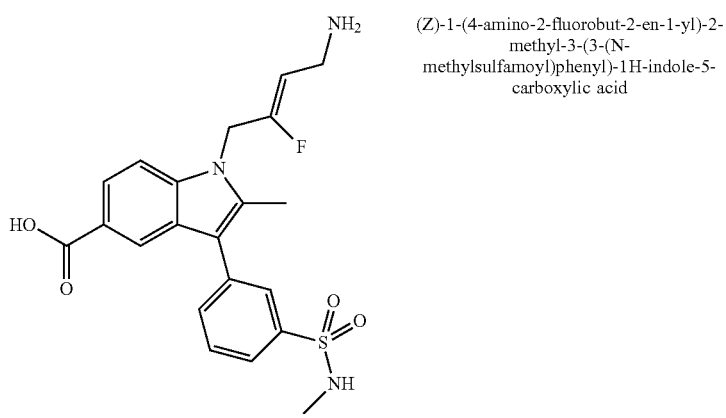 | (Z)-1-(4-amino-2-fluorobut-2-en-1-yl)-2-methyl-3-(3-(N-methylsulfamoyl)phenyl)-1H-indole-5-carboxylic acid |
| 19 | 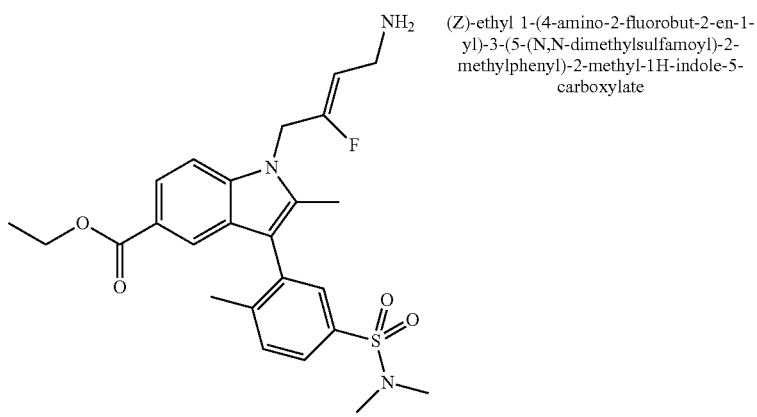 | (Z)-ethyl 1-(4-amino-2-fluorobut-2-en-1-yl)-3-(5-(N,N-dimethylsulfamoyl)-2-methylphenyl)-2-methyl-1H-indole-5-carboxylate |
| 20 | 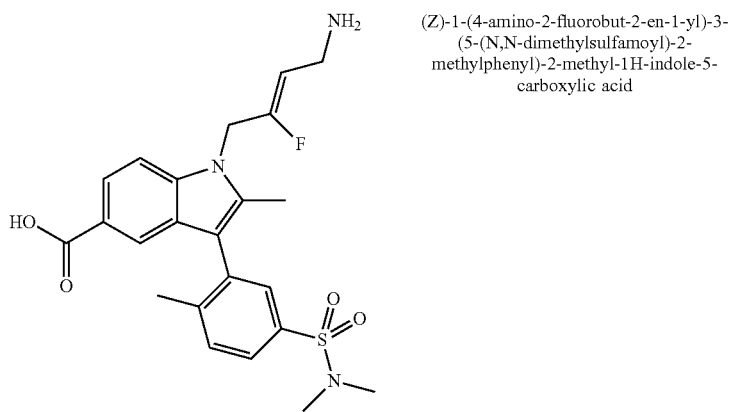 | (Z)-1-(4-amino-2-fluorobut-2-en-1-yl)-3-(5-(N,N-dimethylsulfamoyl)-2-methylphenyl)-2-methyl-1H-indole-5-carboxylic acid |

| | | |
|---|---|---|
| 21 | 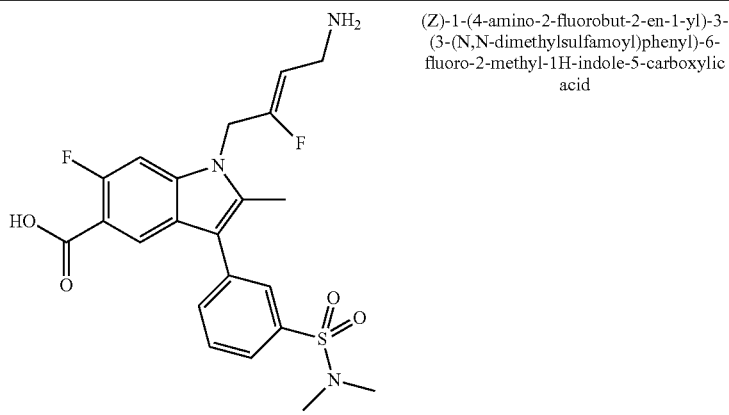 | (Z)-1-(4-amino-2-fluorobut-2-en-1-yl)-3-(3-(N,N-dimethylsulfamoyl)phenyl)-6-fluoro-2-methyl-1H-indole-5-carboxylic acid |
| 22 | 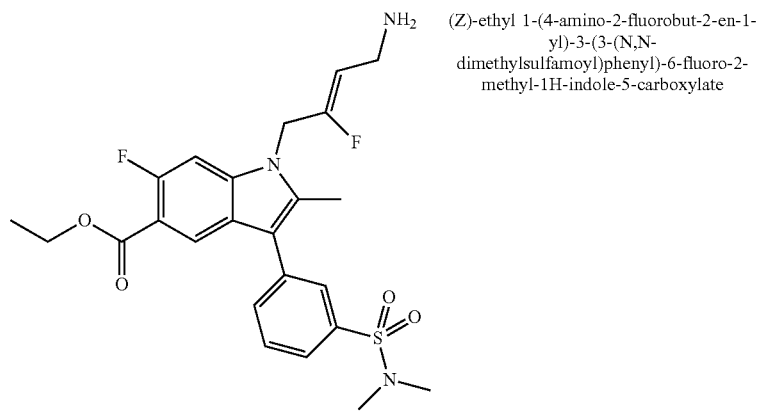 | (Z)-ethyl 1-(4-amino-2-fluorobut-2-en-1-yl)-3-(3-(N,N-dimethylsulfamoyl)phenyl)-6-fluoro-2-methyl-1H-indole-5-carboxylate |
| 25 | 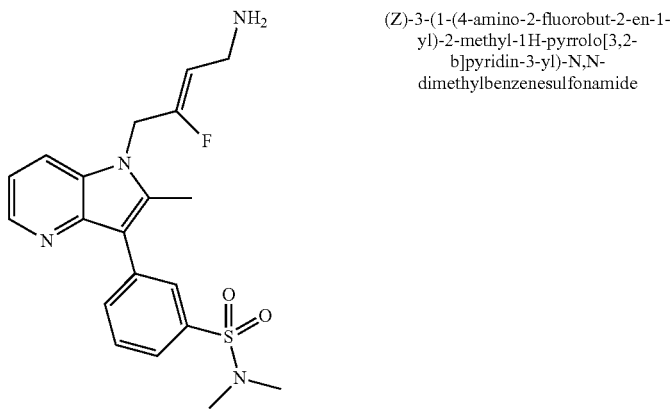 | (Z)-3-(1-(4-amino-2-fluorobut-2-en-1-yl)-2-methyl-1H-pyrrolo[3,2-b]pyridin-3-yl)-N,N-dimethylbenzenesulfonamide |
| 26 | 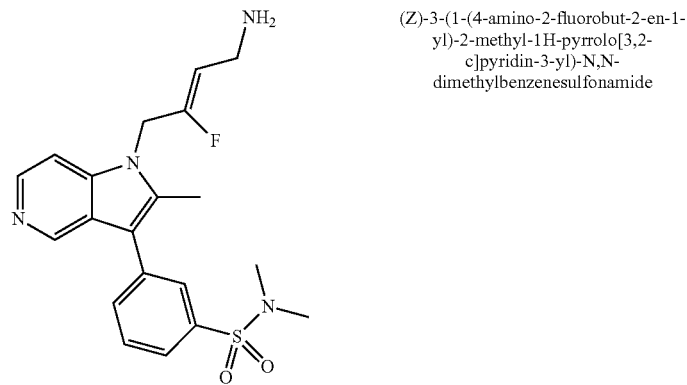 | (Z)-3-(1-(4-amino-2-fluorobut-2-en-1-yl)-2-methyl-1H-pyrrolo[3,2-c]pyridin-3-yl)-N,N-dimethylbenzenesulfonamide |

| | | -continued |
|---|---|---|
| 29 | 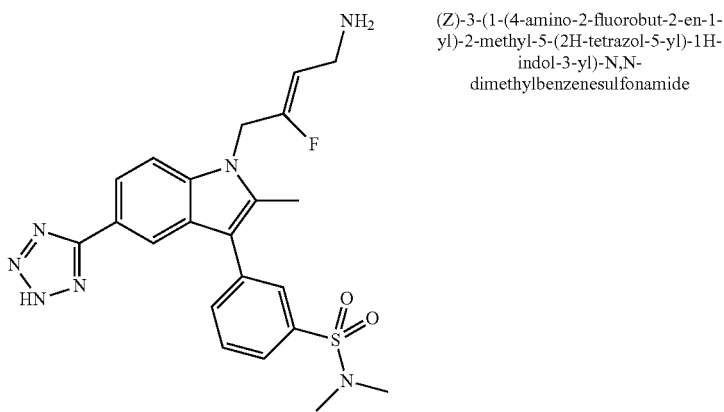 | (Z)-3-(1-(4-amino-2-fluorobut-2-en-1-yl)-2-methyl-5-(2H-tetrazol-5-yl)-1H-indol-3-yl)-N,N-dimethylbenzenesulfonamide |
| 32 | 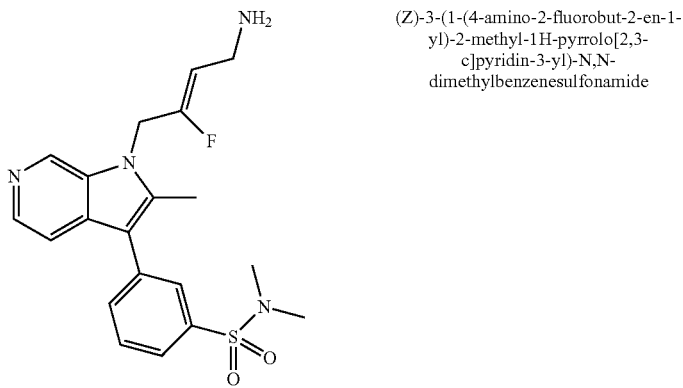 | (Z)-3-(1-(4-amino-2-fluorobut-2-en-1-yl)-2-methyl-1H-pyrrolo[2,3-c]pyridin-3-yl)-N,N-dimethylbenzenesulfonamide |
| 35 | 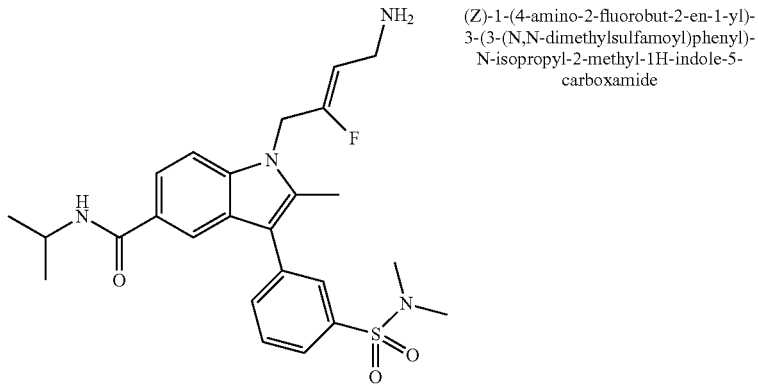 | (Z)-1-(4-amino-2-fluorobut-2-en-1-yl)-3-(3-(N,N-dimethylsulfamoyl)phenyl)-N-isopropyl-2-methyl-1H-indole-5-carboxamide |
| 36 | 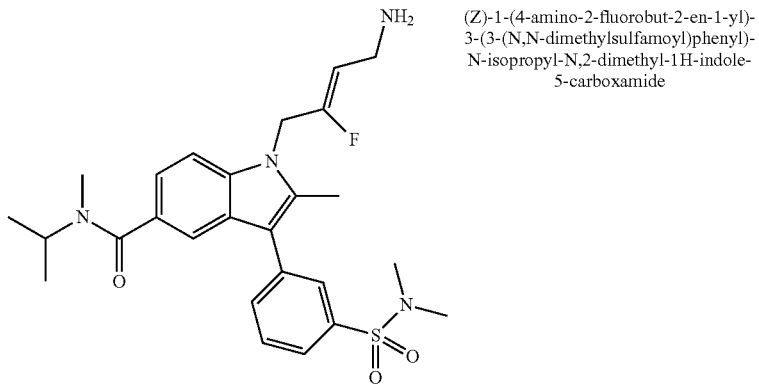 | (Z)-1-(4-amino-2-fluorobut-2-en-1-yl)-3-(3-(N,N-dimethylsulfamoyl)phenyl)-N-isopropyl-N,2-dimethyl-1H-indole-5-carboxamide |

| | | |
|---|---|---|
| 37 | 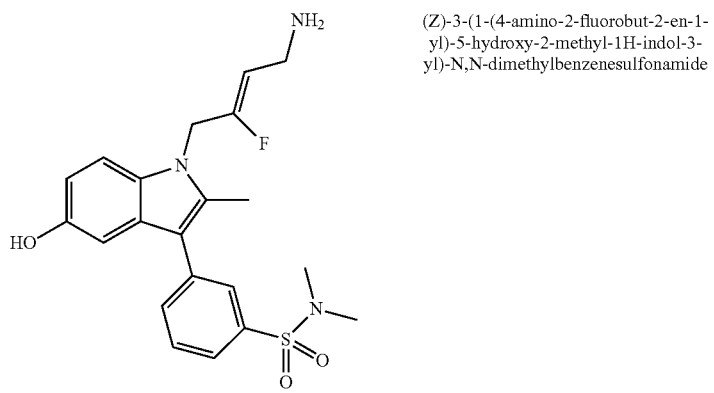 | (Z)-3-(1-(4-amino-2-fluorobut-2-en-1-yl)-5-hydroxy-2-methyl-1H-indol-3-yl)-N,N-dimethylbenzenesulfonamide |
| 38 | 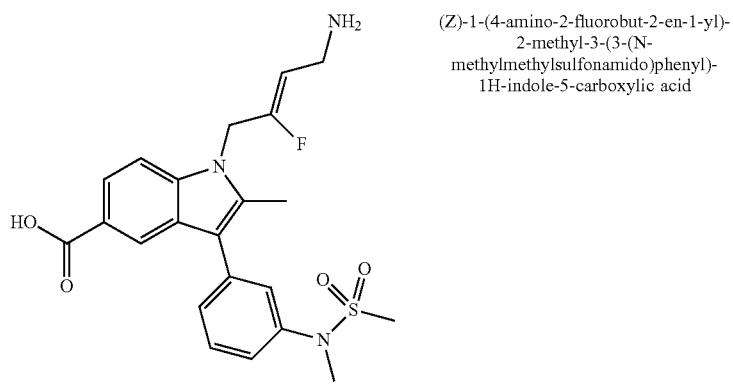 | (Z)-1-(4-amino-2-fluorobut-2-en-1-yl)-2-methyl-3-(3-(N-methylmethylsulfonamido)phenyl)-1H-indole-5-carboxylic acid |
| 39 | 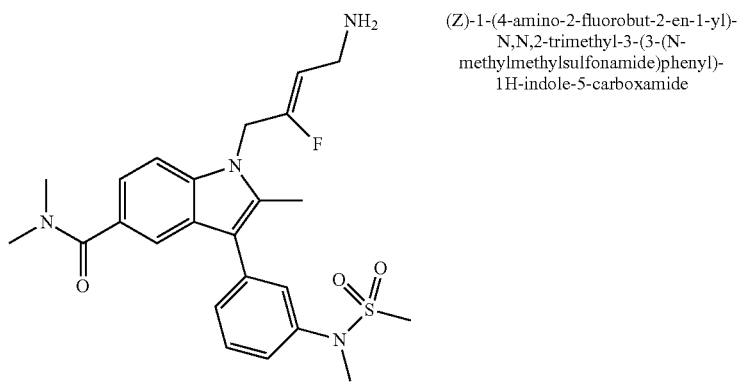 | (Z)-1-(4-amino-2-fluorobut-2-en-1-yl)-N,N,2-trimethyl-3-(3-(N-methylmethylsulfonamide)phenyl)-1H-indole-5-carboxamide |
| 40 | 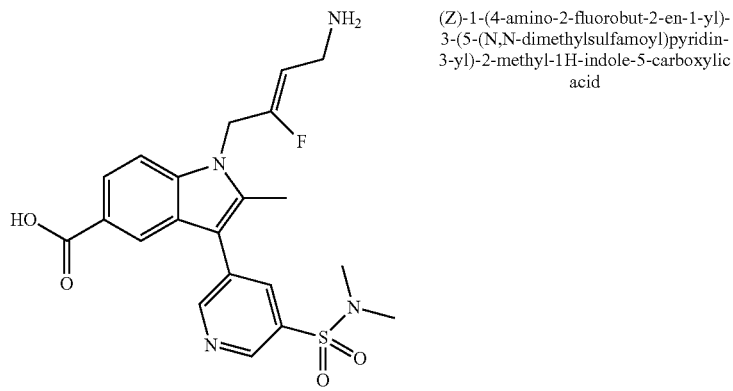 | (Z)-1-(4-amino-2-fluorobut-2-en-1-yl)-3-(5-(N,N-dimethylsulfamoyl)pyridin-3-yl)-2-methyl-1H-indole-5-carboxylic acid |

| | | |
|---|---|---|
| 41 | 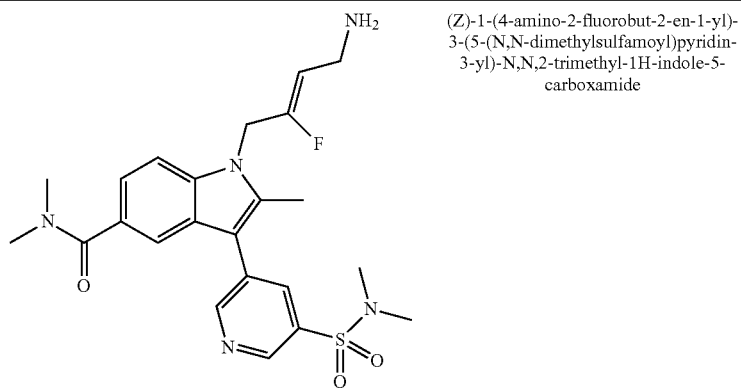 | (Z)-1-(4-amino-2-fluorobut-2-en-1-yl)-3-(5-(N,N-dimethylsulfamoyl)pyridin-3-yl)-N,N,2-trimethyl-1H-indole-5-carboxamide |
| 42 | 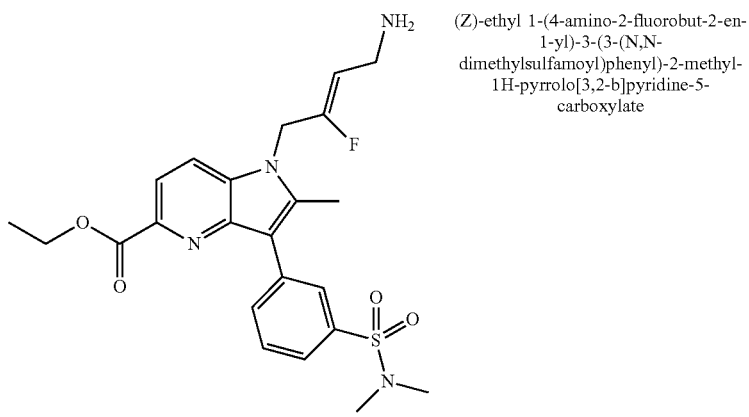 | (Z)-ethyl 1-(4-amino-2-fluorobut-2-en-1-yl)-3-(3-(N,N-dimethylsulfamoyl)phenyl)-2-methyl-1H-pyrrolo[3,2-b]pyridine-5-carboxylate |
| 43 | 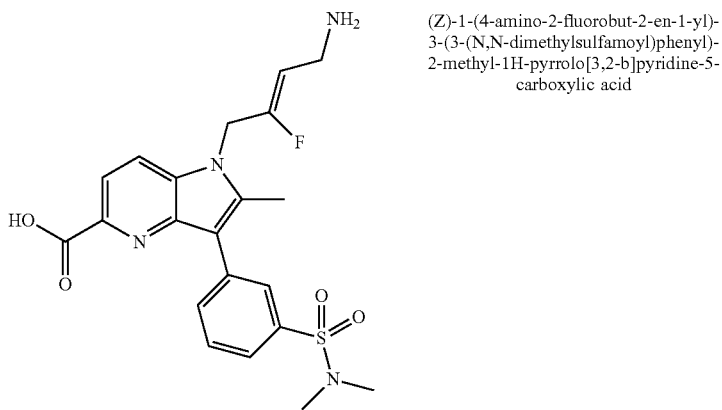 | (Z)-1-(4-amino-2-fluorobut-2-en-1-yl)-3-(3-(N,N-dimethylsulfamoyl)phenyl)-2-methyl-1H-pyrrolo[3,2-b]pyridine-5-carboxylic acid |
| 44 | 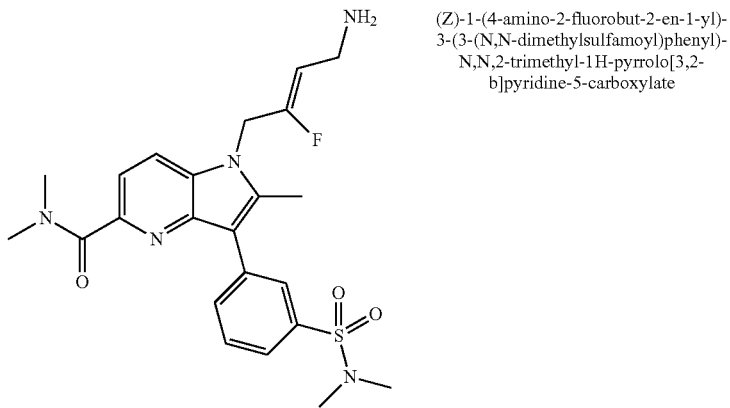 | (Z)-1-(4-amino-2-fluorobut-2-en-1-yl)-3-(3-(N,N-dimethylsulfamoyl)phenyl)-N,N,2-trimethyl-1H-pyrrolo[3,2-b]pyridine-5-carboxylate |

| | | |
|---|---|---|
| 45 | 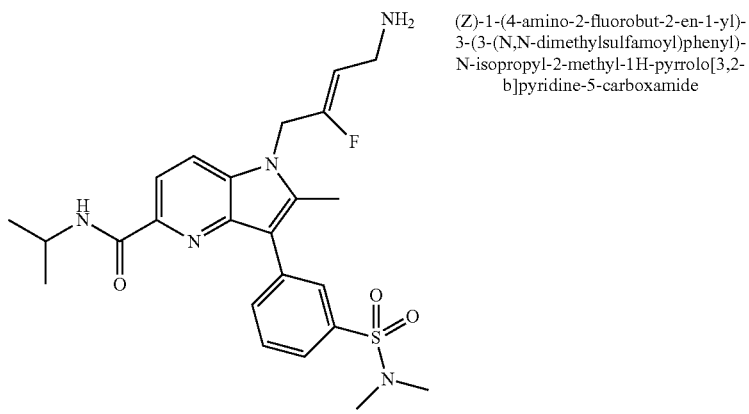 | (Z)-1-(4-amino-2-fluorobut-2-en-1-yl)-3-(3-(N,N-dimethylsulfamoyl)phenyl)-N-isopropyl-2-methyl-1H-pyrrolo[3,2-b]pyridine-5-carboxamide |
| 46 | 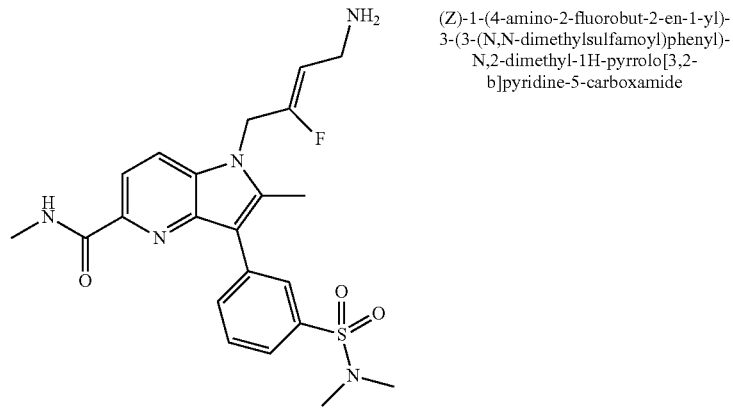 | (Z)-1-(4-amino-2-fluorobut-2-en-1-yl)-3-(3-(N,N-dimethylsulfamoyl)phenyl)-N,2-dimethyl-1H-pyrrolo[3,2-b]pyridine-5-carboxamide |
| 49 | 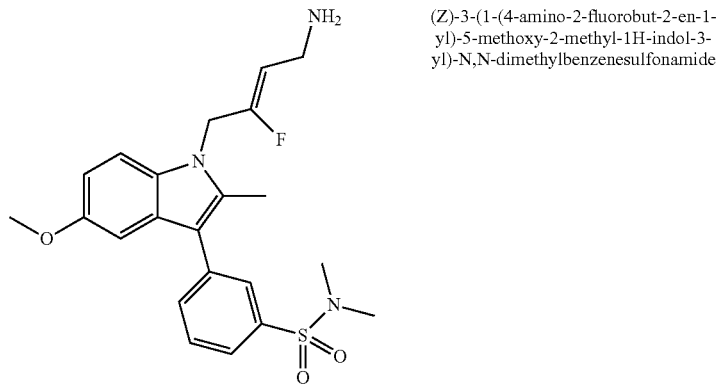 | (Z)-3-(1-(4-amino-2-fluorobut-2-en-1-yl)-5-methoxy-2-methyl-1H-indol-3-yl)-N,N-dimethylbenzenesulfonamide |
| 50 | 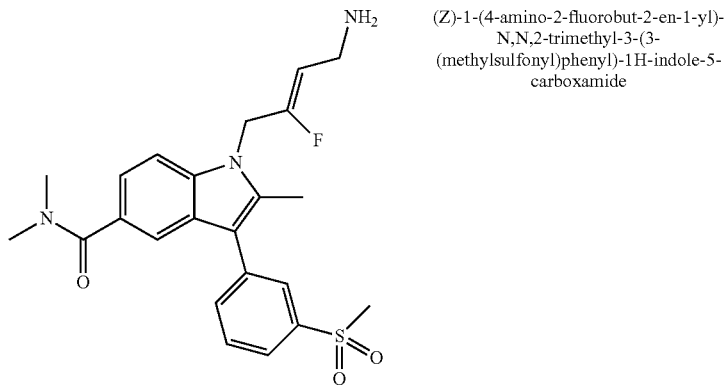 | (Z)-1-(4-amino-2-fluorobut-2-en-1-yl)-N,N,2-trimethyl-3-(3-(methylsulfonyl)phenyl)-1H-indole-5-carboxamide |

| | | |
|---|---|---|
| 51 | 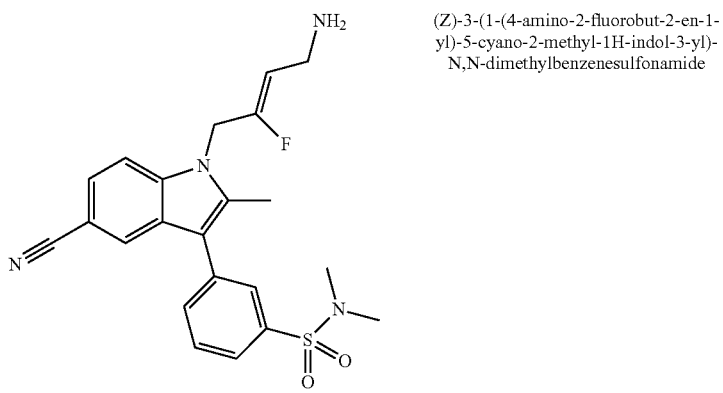 | (Z)-3-(1-(4-amino-2-fluorobut-2-en-1-yl)-5-cyano-2-methyl-1H-indol-3-yl)-N,N-dimethylbenzenesulfonamide |
| 52 | 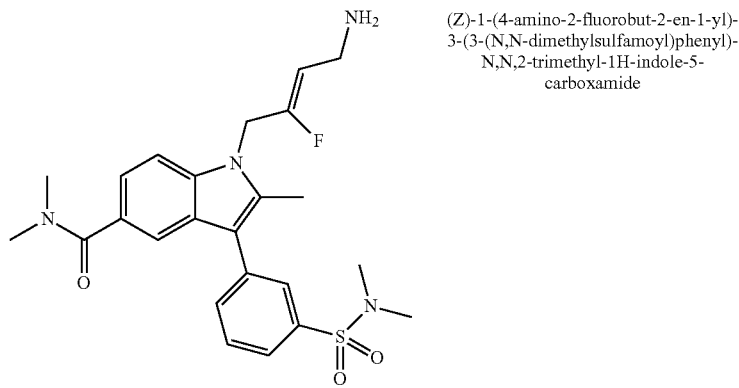 | (Z)-1-(4-amino-2-fluorobut-2-en-1-yl)-3-(3-(N,N-dimethylsulfamoyl)phenyl)-N,N,2-trimethyl-1H-indole-5-carboxamide |
| 53 | 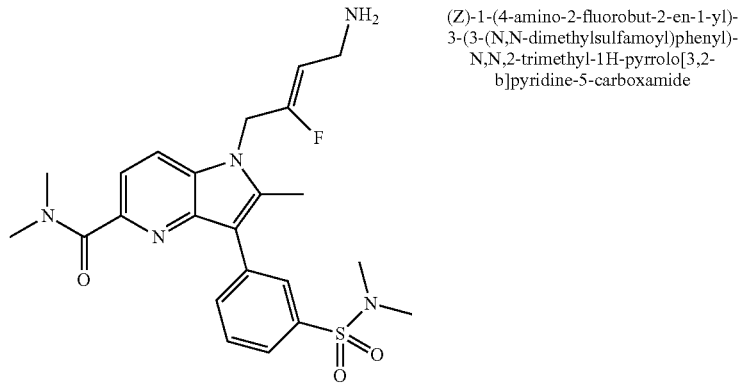 | (Z)-1-(4-amino-2-fluorobut-2-en-1-yl)-3-(3-(N,N-dimethylsulfamoyl)phenyl)-N,N,2-trimethyl-1H-pyrrolo[3,2-b]pyridine-5-carboxamide |
| 54 | 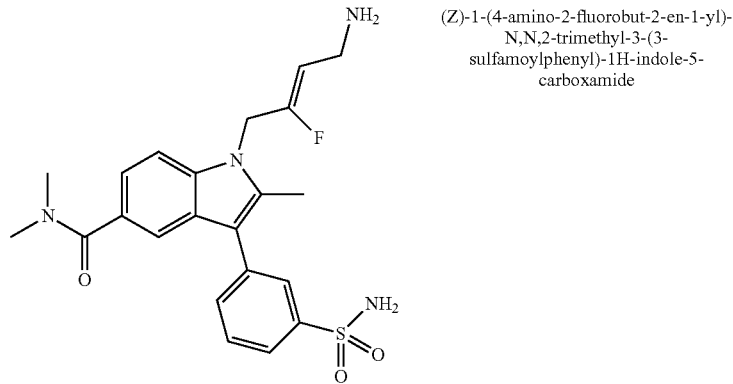 | (Z)-1-(4-amino-2-fluorobut-2-en-1-yl)-N,N,2-trimethyl-3-(3-sulfamoylphenyl)-1H-indole-5-carboxamide |

| | | |
|---|---|---|
| 55 | 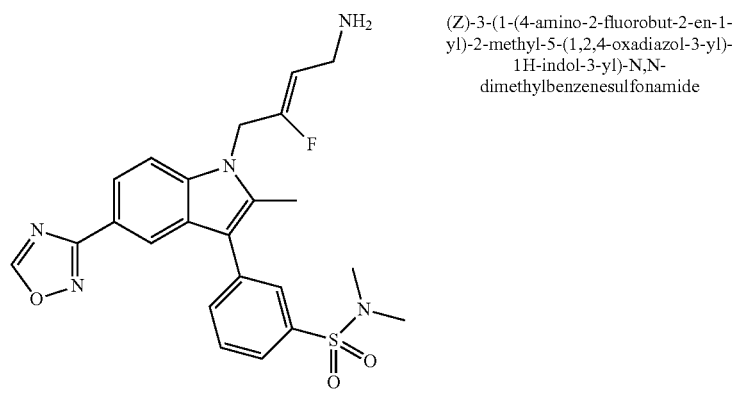 | (Z)-3-(1-(4-amino-2-fluorobut-2-en-1-yl)-2-methyl-5-(1,2,4-oxadiazol-3-yl)-1H-indol-3-yl)-N,N-dimethylbenzenesulfonamide |
| 57 | 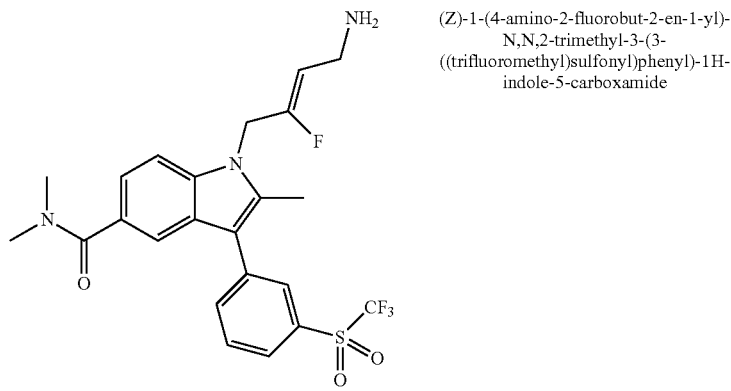 | (Z)-1-(4-amino-2-fluorobut-2-en-1-yl)-N,N,2-trimethyl-3-(3-((trifluoromethyl)sulfonyl)phenyl)-1H-indole-5-carboxamide |
| 58 | 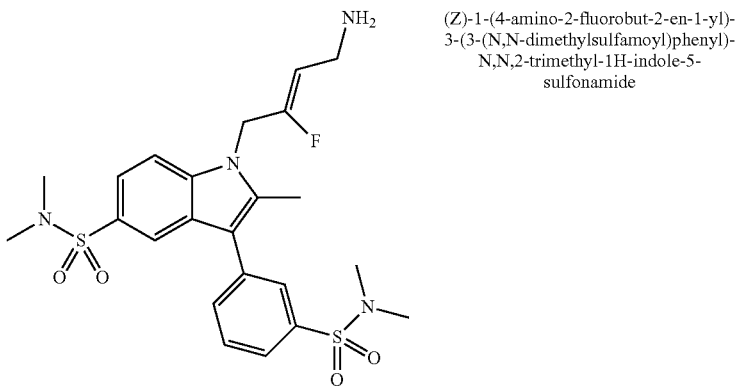 | (Z)-1-(4-amino-2-fluorobut-2-en-1-yl)-3-(3-(N,N-dimethylsulfamoyl)phenyl)-N,N,2-trimethyl-1H-indole-5-sulfonamide |
| 59 | 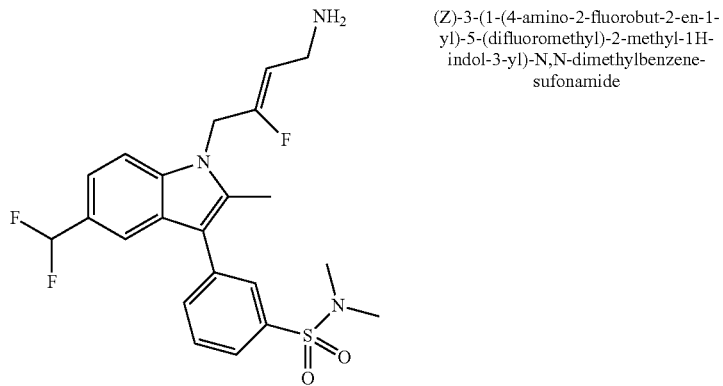 | (Z)-3-(1-(4-amino-2-fluorobut-2-en-1-yl)-5-(difluoromethyl)-2-methyl-1H-indol-3-yl)-N,N-dimethylbenzenesufonamide |

| | | |
|---|---|---|
| 60 | 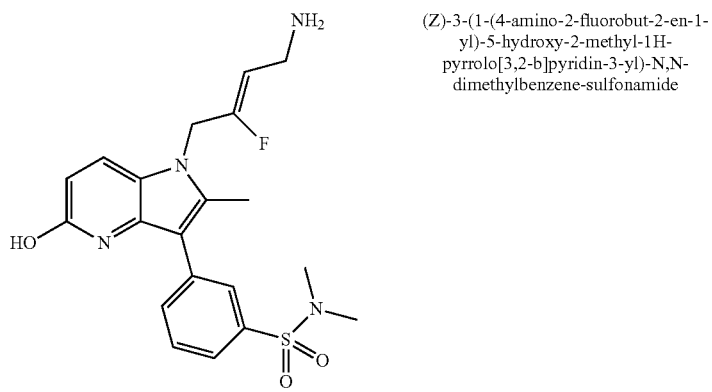 | (Z)-3-(1-(4-amino-2-fluorobut-2-en-1-yl)-5-hydroxy-2-methyl-1H-pyrrolo[3,2-b]pyridin-3-yl)-N,N-dimethylbenzene-sulfonamide |
| 61 | 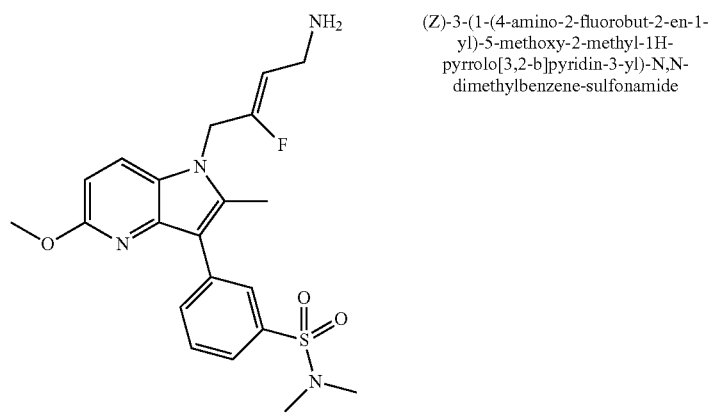 | (Z)-3-(1-(4-amino-2-fluorobut-2-en-1-yl)-5-methoxy-2-methyl-1H-pyrrolo[3,2-b]pyridin-3-yl)-N,N-dimethylbenzene-sulfonamide |
| 62 | 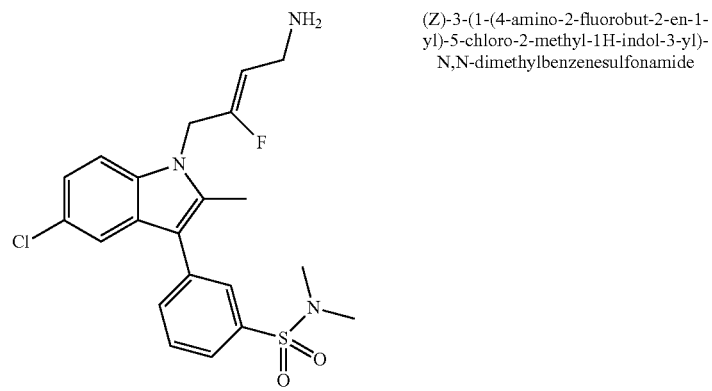 | (Z)-3-(1-(4-amino-2-fluorobut-2-en-1-yl)-5-chloro-2-methyl-1H-indol-3-yl)-N,N-dimethylbenzenesulfonamide |
| 63 | 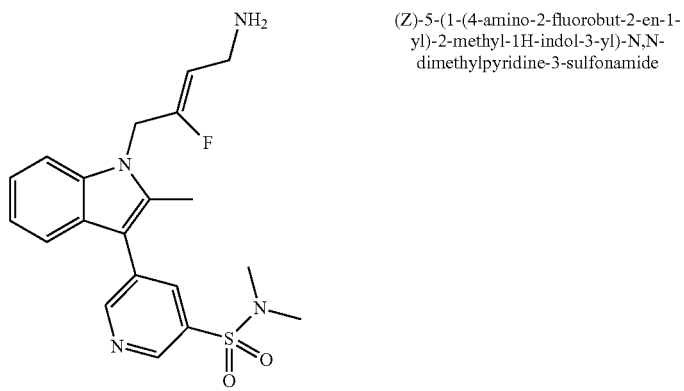 | (Z)-5-(1-(4-amino-2-fluorobut-2-en-1-yl)-2-methyl-1H-indol-3-yl)-N,N-dimethylpyridine-3-sulfonamide |

-continued
| | | |
|---|---|---|
| 64 | 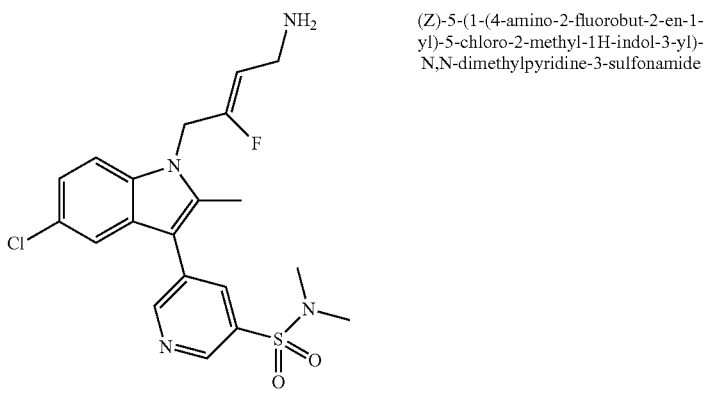 | (Z)-5-(1-(4-amino-2-fluorobut-2-en-1-yl)-5-chloro-2-methyl-1H-indol-3-yl)-N,N-dimethylpyridine-3-sulfonamide |
| 65 | 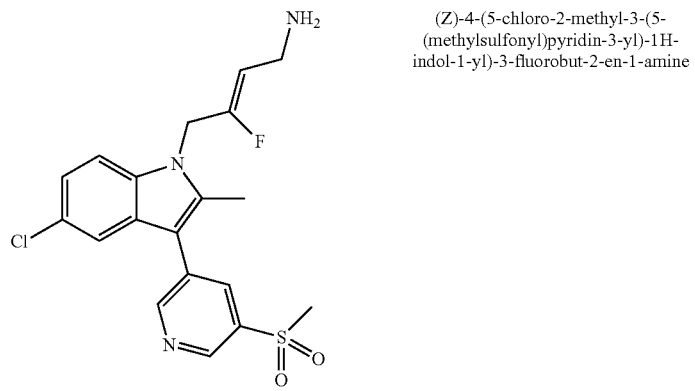 | (Z)-4-(5-chloro-2-methyl-3-(5-(methylsulfonyl)pyridin-3-yl)-1H-indol-1-yl)-3-fluorobut-2-en-1-amine |
| 66 | 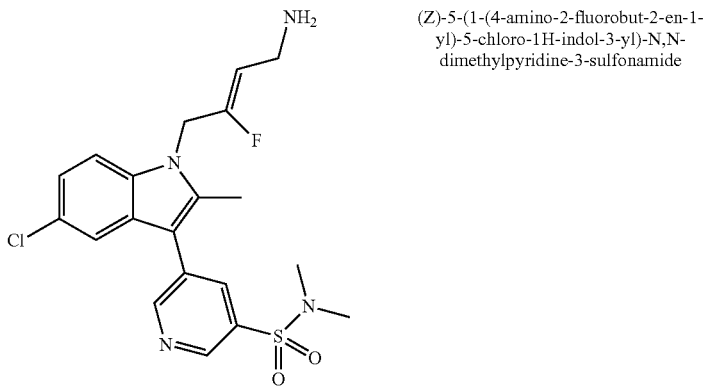 | (Z)-5-(1-(4-amino-2-fluorobut-2-en-1-yl)-5-chloro-1H-indol-3-yl)-N,N-dimethylpyridine-3-sulfonamide |
| 67 | 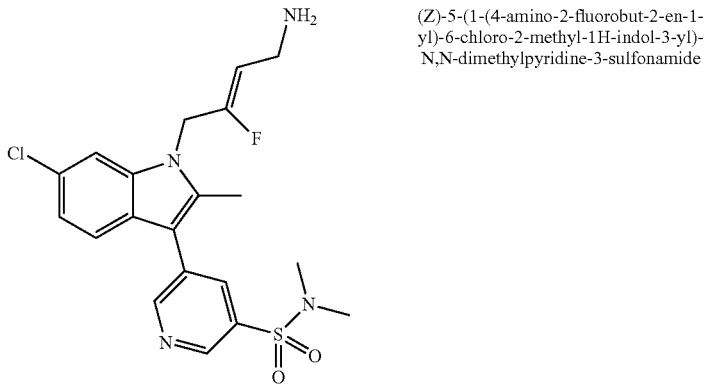 | (Z)-5-(1-(4-amino-2-fluorobut-2-en-1-yl)-6-chloro-2-methyl-1H-indol-3-yl)-N,N-dimethylpyridine-3-sulfonamide |

| | | |
|---|---|---|
| 69 | 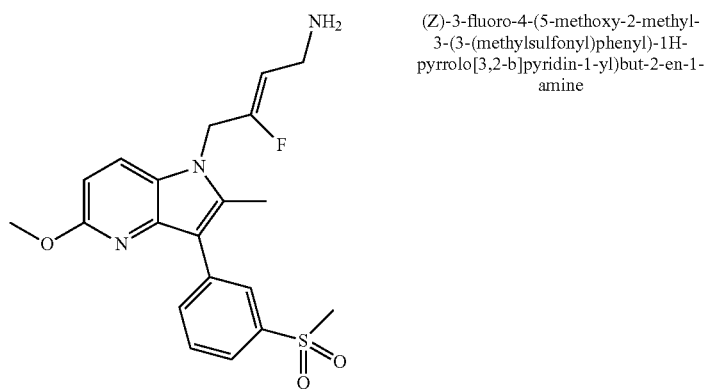 | (Z)-3-fluoro-4-(5-methoxy-2-methyl-3-(3-(methylsulfonyl)phenyl)-1H-pyrrolo[3,2-b]pyridin-1-yl)but-2-en-1-amine |
| 70 | 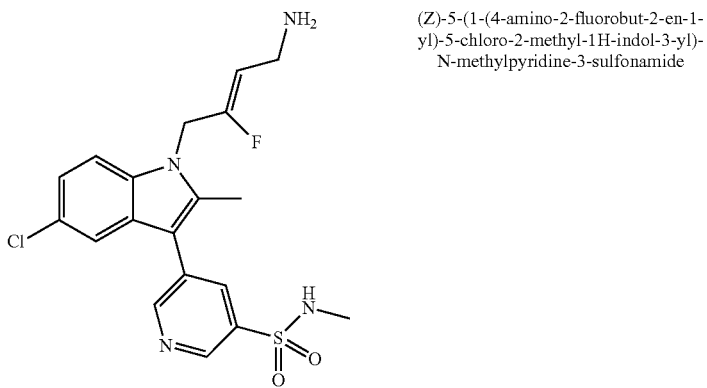 | (Z)-5-(1-(4-amino-2-fluorobut-2-en-1-yl)-5-chloro-2-methyl-1H-indol-3-yl)-N-methylpyridine-3-sulfonamide |
| 71 | 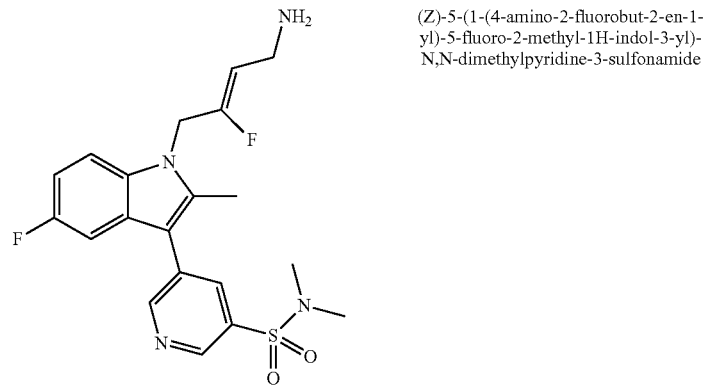 | (Z)-5-(1-(4-amino-2-fluorobut-2-en-1-yl)-5-fluoro-2-methyl-1H-indol-3-yl)-N,N-dimethylpyridine-3-sulfonamide |
| 72 | 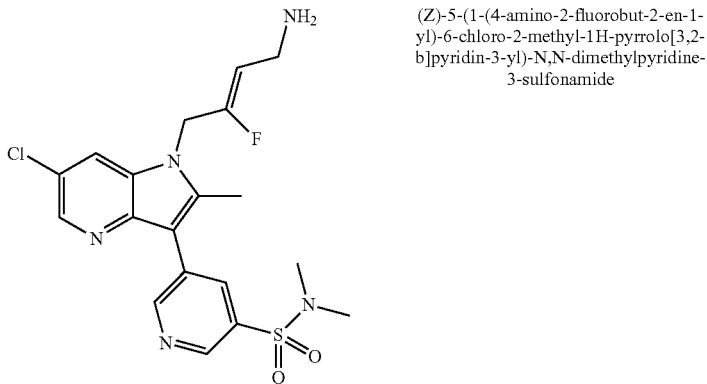 | (Z)-5-(1-(4-amino-2-fluorobut-2-en-1-yl)-6-chloro-2-methyl-1H-pyrrolo[3,2-b]pyridin-3-yl)-N,N-dimethylpyridine-3-sulfonamide |

-continued
| | | |
|---|---|---|
| 73 | 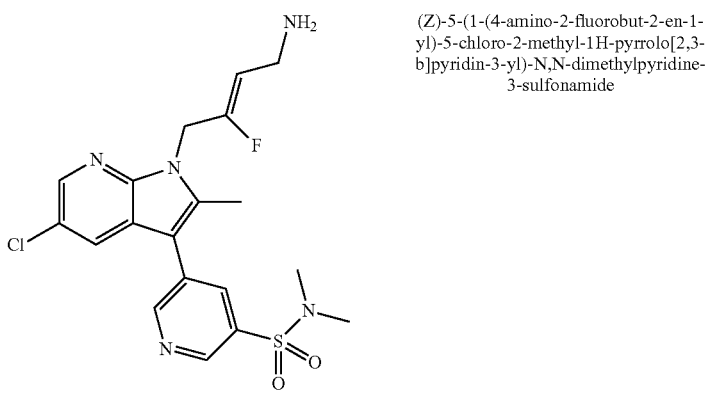 | (Z)-5-(1-(4-amino-2-fluorobut-2-en-1-yl)-5-chloro-2-methyl-1H-pyrrolo[2,3-b]pyridin-3-yl)-N,N-dimethylpyridine-3-sulfonamide |
| 75 | 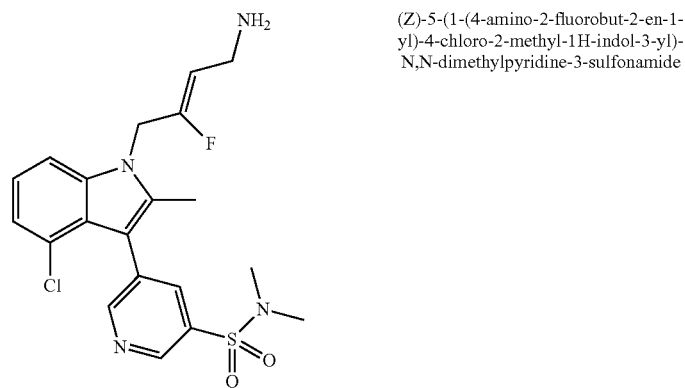 | (Z)-5-(1-(4-amino-2-fluorobut-2-en-1-yl)-4-chloro-2-methyl-1H-indol-3-yl)-N,N-dimethylpyridine-3-sulfonamide |
| 76 | 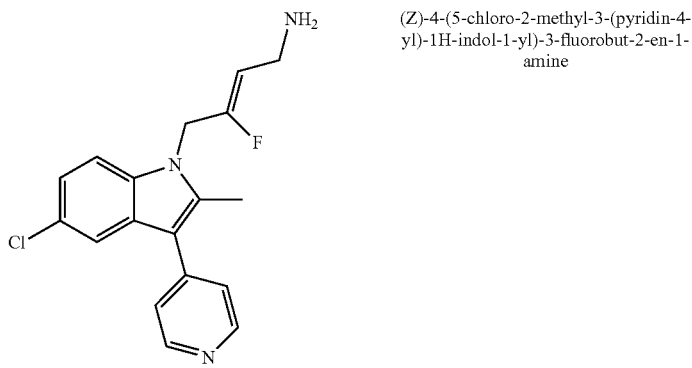 | (Z)-4-(5-chloro-2-methyl-3-(pyridin-4-yl)-1H-indol-1-yl)-3-fluorobut-2-en-1-amine |
| 77 | 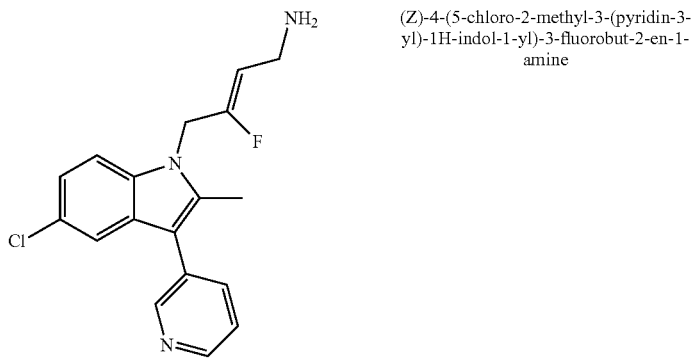 | (Z)-4-(5-chloro-2-methyl-3-(pyridin-3-yl)-1H-indol-1-yl)-3-fluorobut-2-en-1-amine |

-continued
| | | |
|---|---|---|
| 78 | 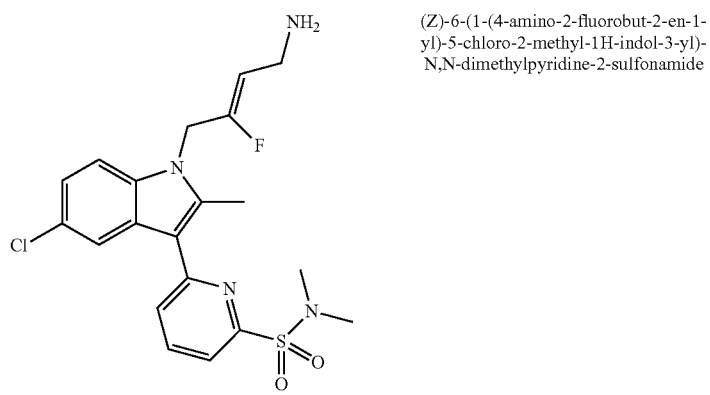 | (Z)-6-(1-(4-amino-2-fluorobut-2-en-1-yl)-5-chloro-2-methyl-1H-indol-3-yl)-N,N-dimethylpyridine-2-sulfonamide |
| 79 | 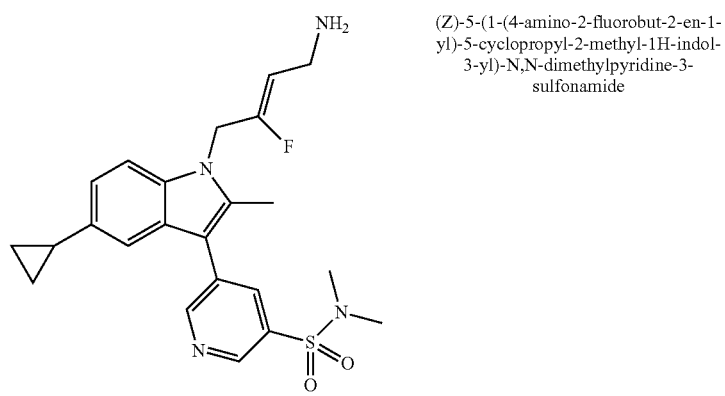 | (Z)-5-(1-(4-amino-2-fluorobut-2-en-1-yl)-5-cyclopropyl-2-methyl-1H-indol-3-yl)-N,N-dimethylpyridine-3-sulfonamide |
| 80 | 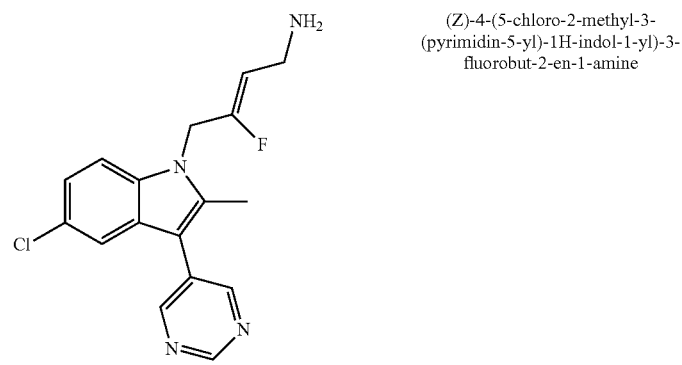 | (Z)-4-(5-chloro-2-methyl-3-(pyrimidin-5-yl)-1H-indol-1-yl)-3-fluorobut-2-en-1-amine |
| 81 | 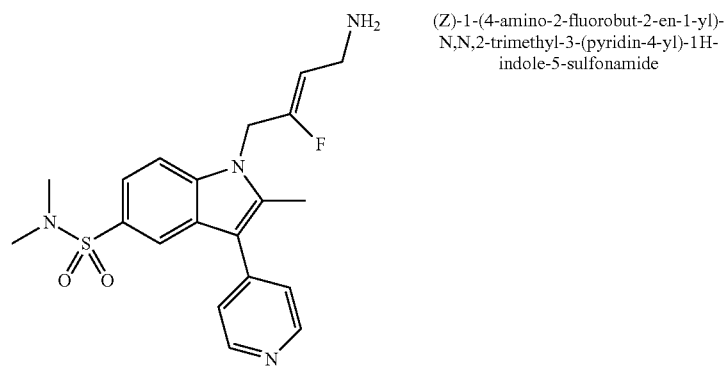 | (Z)-1-(4-amino-2-fluorobut-2-en-1-yl)-N,N,2-trimethyl-3-(pyridin-4-yl)-1H-indole-5-sulfonamide |

-continued
| | | |
|---|---|---|
| 83 | 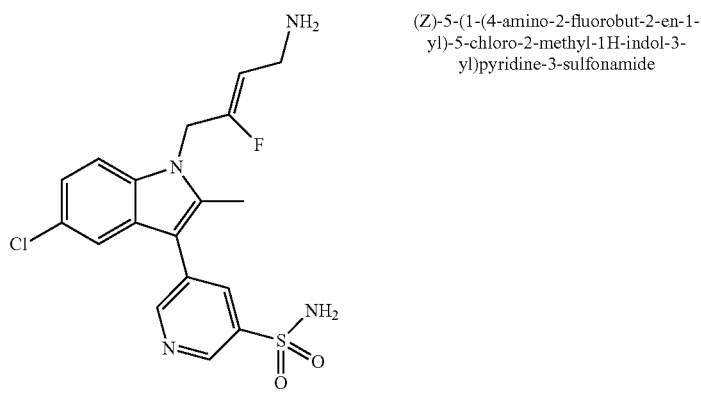 | (Z)-5-(1-(4-amino-2-fluorobut-2-en-1-yl)-5-chloro-2-methyl-1H-indol-3-yl)pyridine-3-sulfonamide |
| 84 | 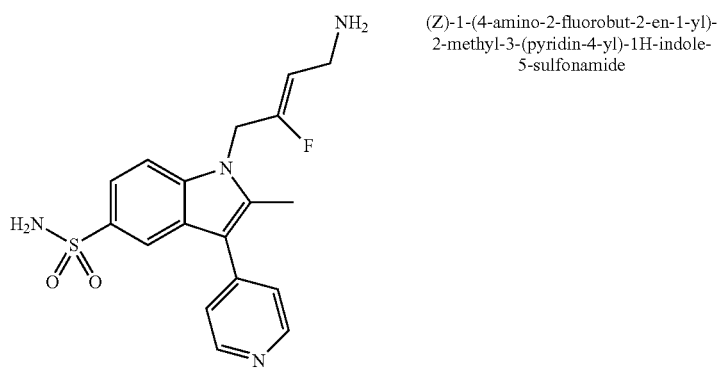 | (Z)-1-(4-amino-2-fluorobut-2-en-1-yl)-2-methyl-3-(pyridin-4-yl)-1H-indole-5-sulfonamide |
| 85 | 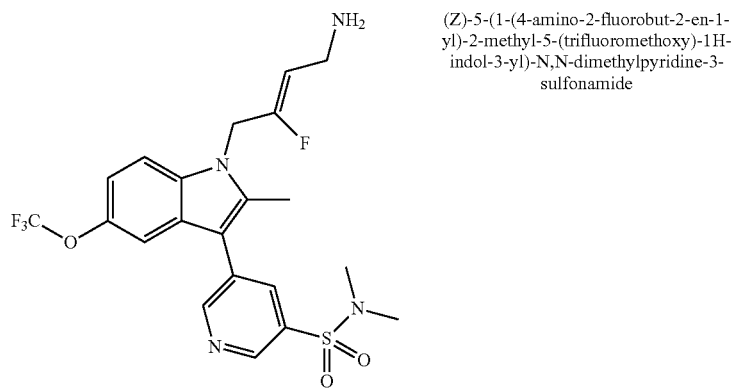 | (Z)-5-(1-(4-amino-2-fluorobut-2-en-1-yl)-2-methyl-5-(trifluoromethoxy)-1H-indol-3-yl)-N,N-dimethylpyridine-3-sulfonamide |
| 86 | 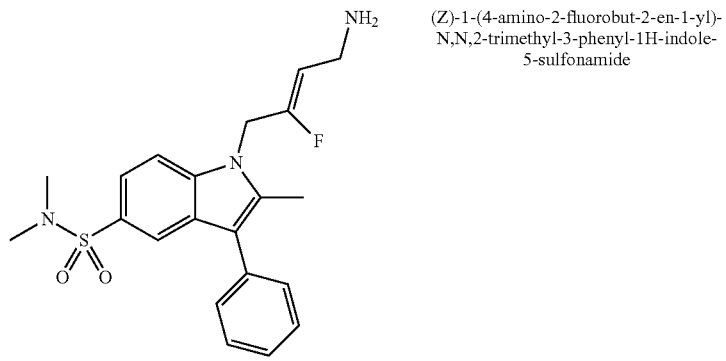 | (Z)-1-(4-amino-2-fluorobut-2-en-1-yl)-N,N,2-trimethyl-3-phenyl-1H-indole-5-sulfonamide |

| | | |
|---|---|---|
| 87 | 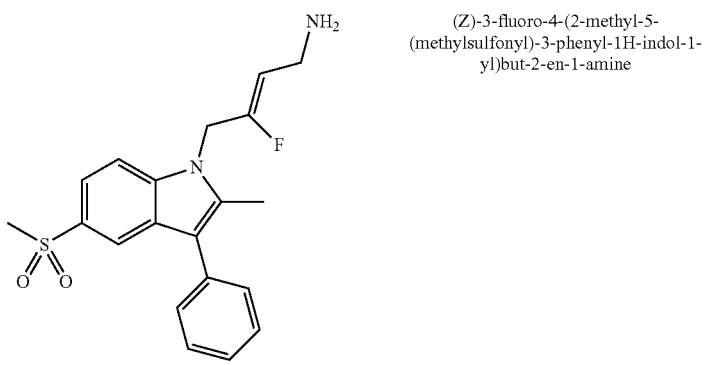 | (Z)-3-fluoro-4-(2-methyl-5-(methylsulfonyl)-3-phenyl-1H-indol-1-yl)but-2-en-1-amine |
| 88 | 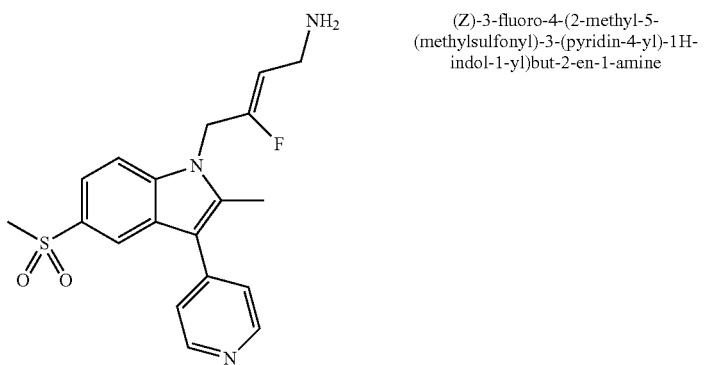 | (Z)-3-fluoro-4-(2-methyl-5-(methylsulfonyl)-3-(pyridin-4-yl)-1H-indol-1-yl)but-2-en-1-amine |
| 92 | 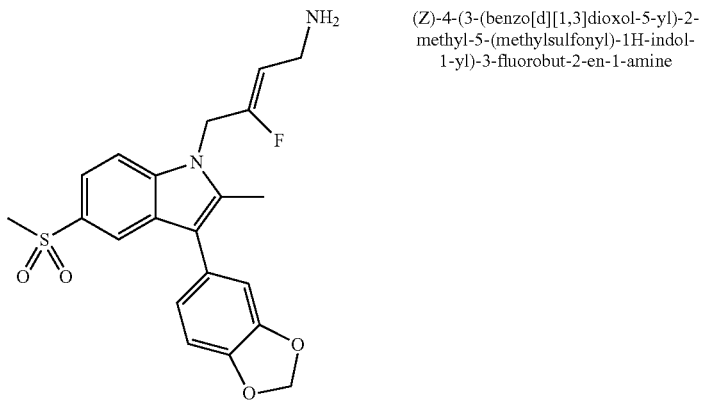 | (Z)-4-(3-(benzo[d][1,3]dioxol-5-yl)-2-methyl-5-(methylsulfonyl)-1H-indol-1-yl)-3-fluorobut-2-en-1-amine |
| 93 | 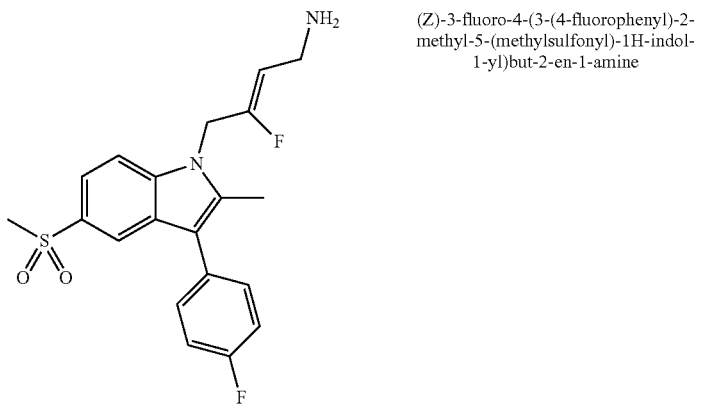 | (Z)-3-fluoro-4-(3-(4-fluorophenyl)-2-methyl-5-(methylsulfonyl)-1H-indol-1-yl)but-2-en-1-amine |

| | | |
|---|---|---|
| 94 | 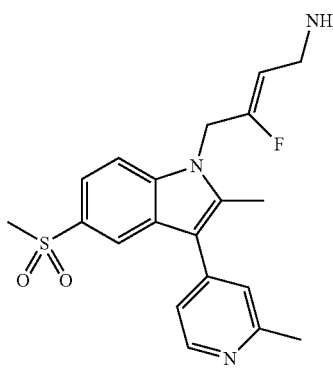 | (Z)-3-fluoro-4-(2-methyl-3-(2-methylpyridin-4-yl)-5-(methylsulfonyl)-1H-indol-1-yl)but-2-en-1-amine |
| 95 | 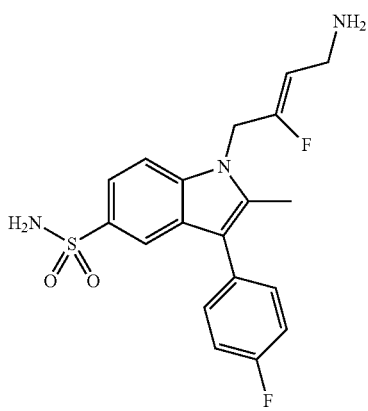 [SMILES: Cc1c(-c2ccc(F)cc2)c2cc(S(N)(=O)=O)ccc2n1C/C(F)=C/CN] | (Z)-1-(4-amino-2-fluorobut-2-en-1-yl)-3-(4-fluorophenyl)-2-methyl-1H-indole-5-sulfonamide |
| 96 | 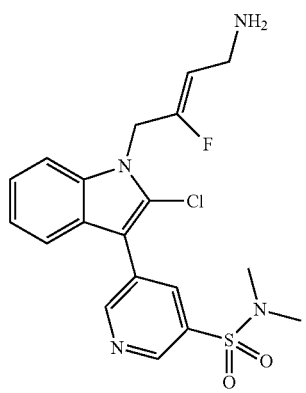 | (Z)-5-(1-(4-amino-2-fluorobut-2-en-1-yl)-2-chloro-1H-indol-3-yl)-N,N-dimethylpyridine-3-sulfonamide |
| 97 | 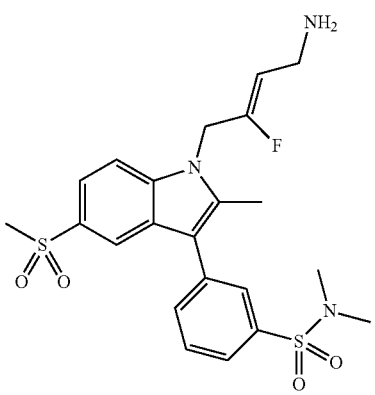 | (Z)-3-(1-(4-amino-2-fluorobut-2-en-1-yl)-2-methyl-5-(methylsulfonyl)-1H-indol-3-yl)-N,N-dimethylbenzenesulfonamide |

-continued
| | | |
|---|---|---|
| 98 | 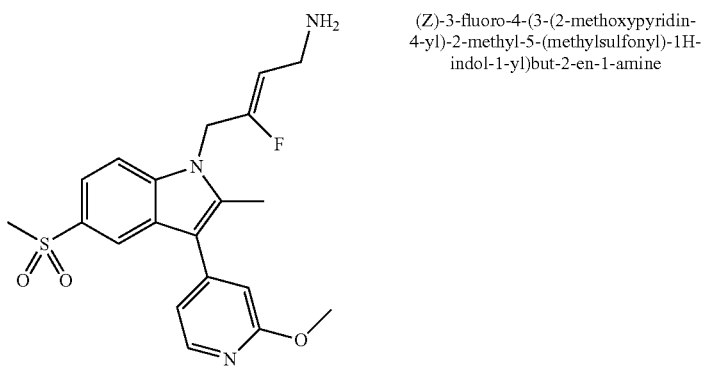 | (Z)-3-fluoro-4-(3-(2-methoxypyridin-4-yl)-2-methyl-5-(methylsulfonyl)-1H-indol-1-yl)but-2-en-1-amine |
| 99 | 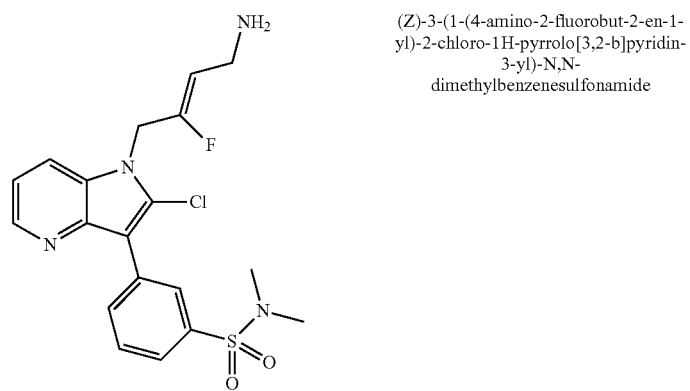 | (Z)-3-(1-(4-amino-2-fluorobut-2-en-1-yl)-2-chloro-1H-pyrrolo[3,2-b]pyridin-3-yl)-N,N-dimethylbenzenesulfonamide |
| 100 | 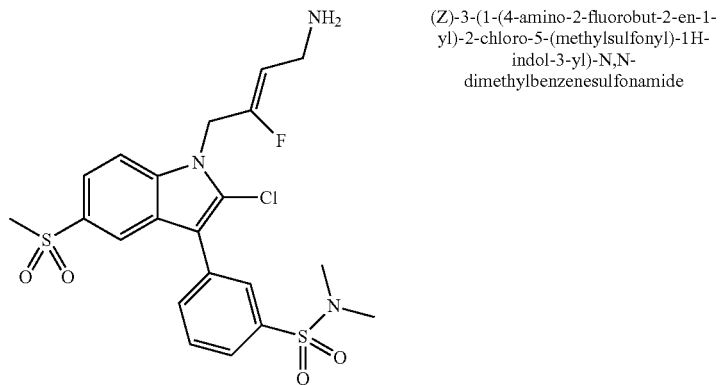 | (Z)-3-(1-(4-amino-2-fluorobut-2-en-1-yl)-2-chloro-5-(methylsulfonyl)-1H-indol-3-yl)-N,N-dimethylbenzenesulfonamide |
| 101 | 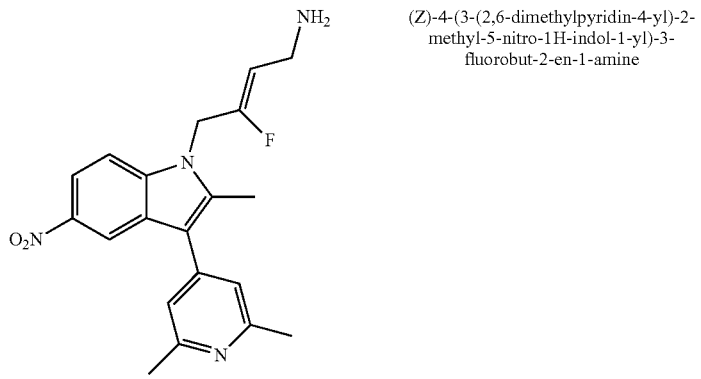 | (Z)-4-(3-(2,6-dimethylpyridin-4-yl)-2-methyl-5-nitro-1H-indol-1-yl)-3-fluorobut-2-en-1-amine |

| | | |
|---|---|---|
| 102 | 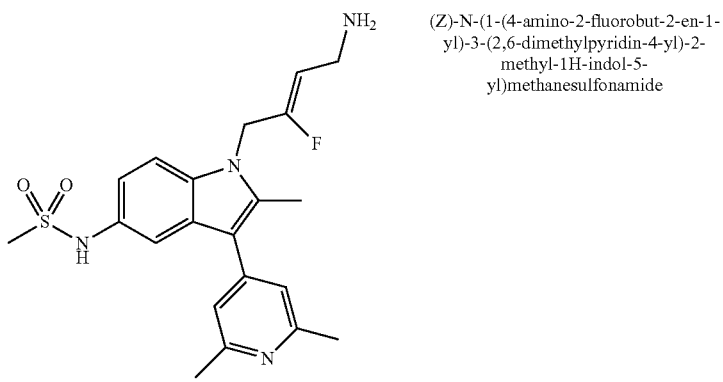 | (Z)-N-(1-(4-amino-2-fluorobut-2-en-1-yl)-3-(2,6-dimethylpyridin-4-yl)-2-methyl-1H-indol-5-yl)methanesulfonamide |
| 103 | 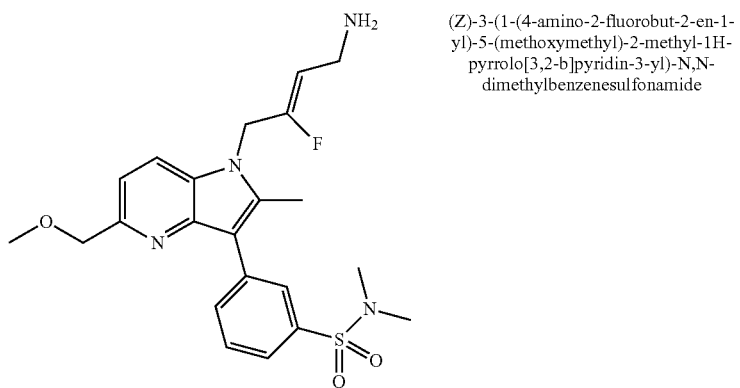 | (Z)-3-(1-(4-amino-2-fluorobut-2-en-1-yl)-5-(methoxymethyl)-2-methyl-1H-pyrrolo[3,2-b]pyridin-3-yl)-N,N-dimethylbenzenesulfonamide |
| 104 | 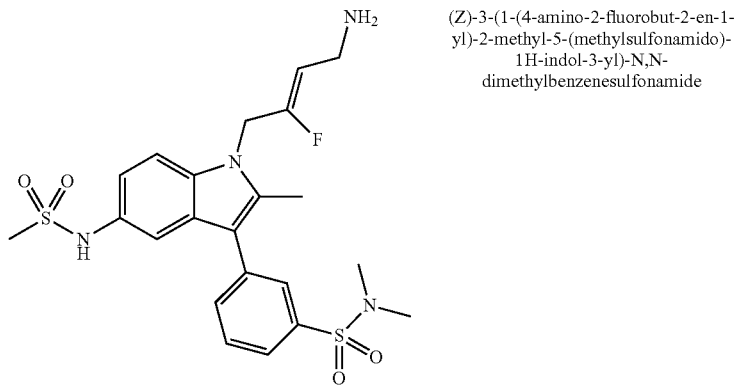 | (Z)-3-(1-(4-amino-2-fluorobut-2-en-1-yl)-2-methyl-5-(methylsulfonamido)-1H-indol-3-yl)-N,N-dimethylbenzenesulfonamide |
| 105 | 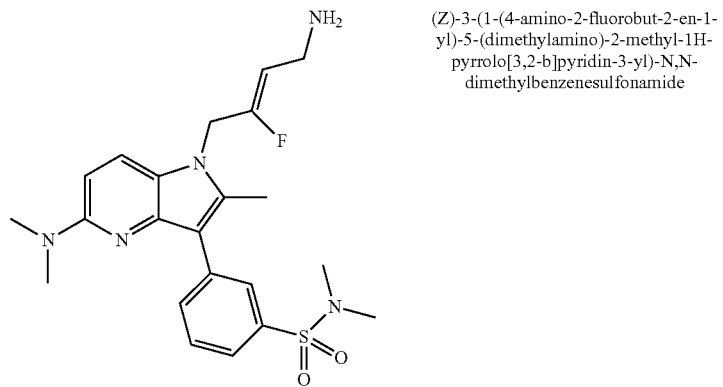 | (Z)-3-(1-(4-amino-2-fluorobut-2-en-1-yl)-5-(dimethylamino)-2-methyl-1H-pyrrolo[3,2-b]pyridin-3-yl)-N,N-dimethylbenzenesulfonamide |

| | | |
|---|---|---|
| 106 | 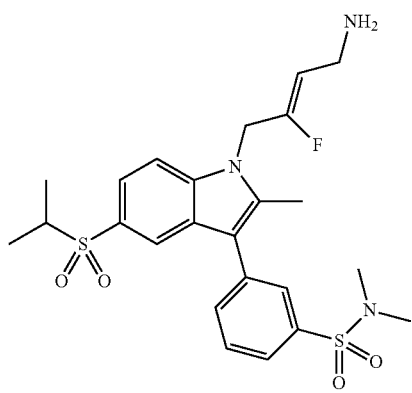 [SMILES: Cc1c(-c2cccc(S(=O)(=O)N(C)C)c2)c2cc(S(=O)(=O)C(C)C)ccc2n1C/C(F)=C/CN] | (Z)-3-(1-(4-amino-2-fluorobut-2-en-1-yl)-5-(isopropylsulfonyl)-2-methyl-1H-indol-3-yl)-N,N-dimethylbenzenesulfonamide |
| 107 | 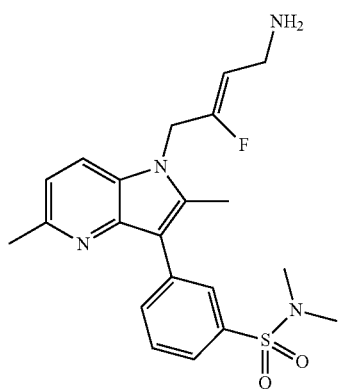 | (Z)-3-(1-(4-amino-2-fluorobut-2-en-1-yl)-2,5-dimethyl-1H-pyrrolo[3,2-b]pyridin-3-yl)-N,N-dimethylbenzenesulfonamide |
| 108 | 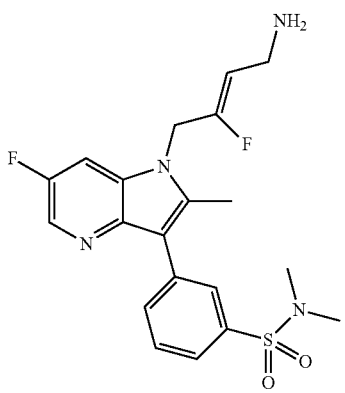 [SMILES: Cc1c(-c2cccc(S(=O)(=O)N(C)C)c2)c2ncc(F)cc2n1C/C(F)=C/CN] | (Z)-3-(1-(4-amino-2-fluorobut-2-en-1-yl)-6-fluoro-2-methyl-1H-pyrrolo[3,2-b]pyridin-3-yl)-N,N-dimethylbenzenesulfonamide |
| 109 | 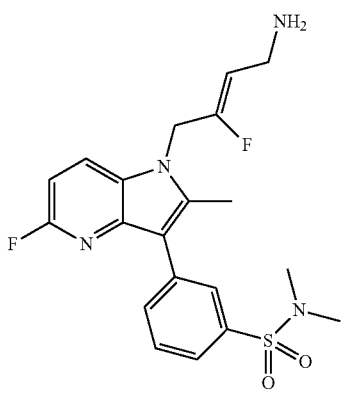 | (Z)-3-(1-(4-amino-2-fluorobut-2-en-1-yl)-5-fluoro-2-methyl-1H-pyrrolo[3,2-b]pyridin-3-yl)-N,N-dimethylbenzenesulfonamide |

-continued

| | | |
|---|---|---|
| 110 | 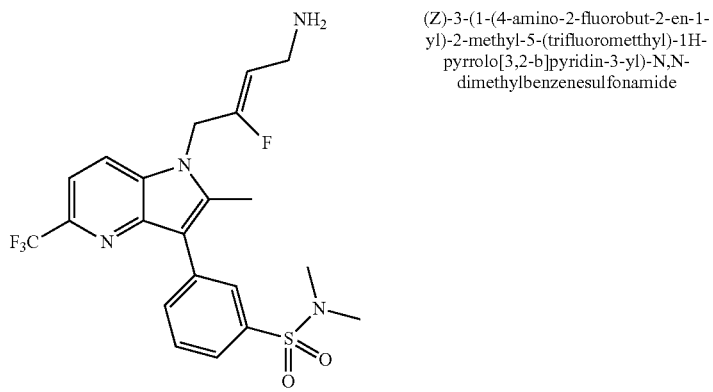 | (Z)-3-(1-(4-amino-2-fluorobut-2-en-1-yl)-2-methyl-5-(trifluorometthyl)-1H-pyrrolo[3,2-b]pyridin-3-yl)-N,N-dimethylbenzenesulfonamide |
| 111 | 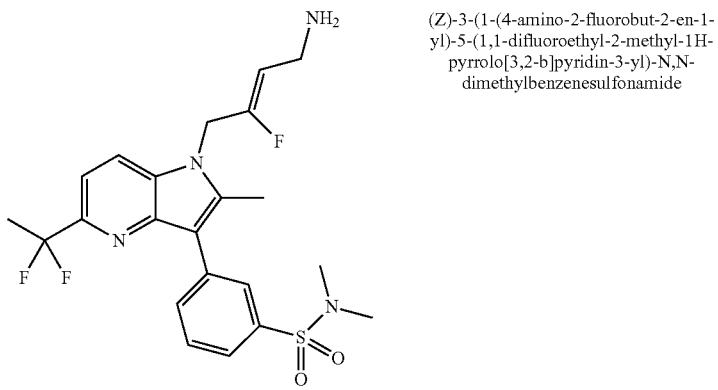 | (Z)-3-(1-(4-amino-2-fluorobut-2-en-1-yl)-5-(1,1-difluoroethyl-2-methyl-1H-pyrrolo[3,2-b]pyridin-3-yl)-N,N-dimethylbenzenesulfonamide |
| 112 | 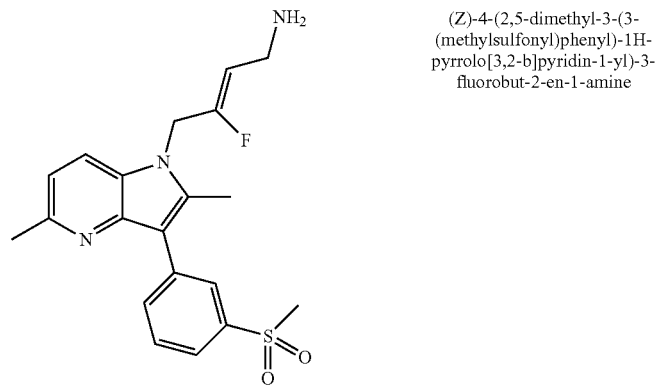 | (Z)-4-(2,5-dimethyl-3-(3-(methylsulfonyl)phenyl)-1H-pyrrolo[3,2-b]pyridin-1-yl)-3-fluorobut-2-en-1-amine |
| 113 | 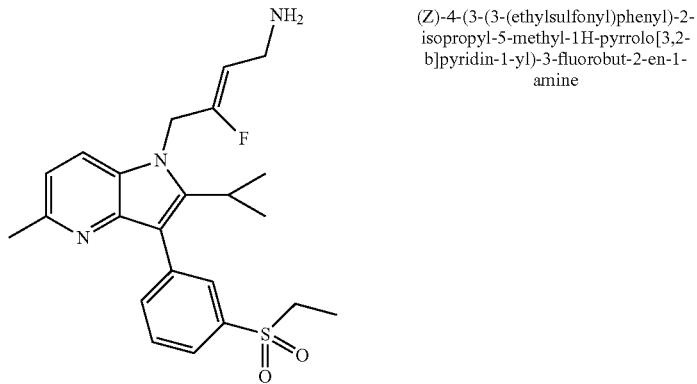 | (Z)-4-(3-(3-(ethylsulfonyl)phenyl)-2-isopropyl-5-methyl-1H-pyrrolo[3,2-b]pyridin-1-yl)-3-fluorobut-2-en-1-amine |

-continued

| | | |
|---|---|---|
| 114 | 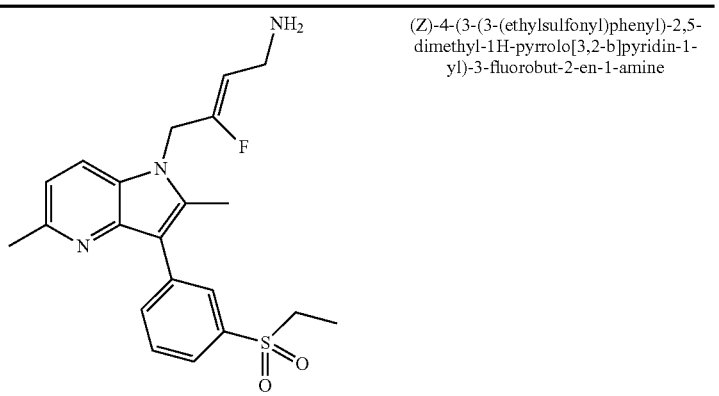 | (Z)-4-(3-(3-(ethylsulfonyl)phenyl)-2,5-dimethyl-1H-pyrrolo[3,2-b]pyridin-1-yl)-3-fluorobut-2-en-1-amine |
| 115 | 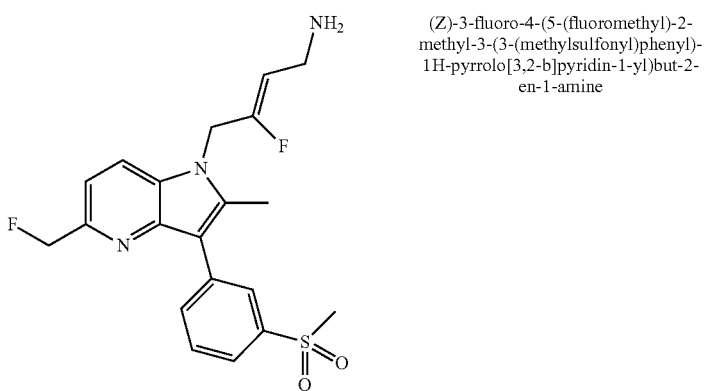 | (Z)-3-fluoro-4-(5-(fluoromethyl)-2-methyl-3-(3-(methylsulfonyl)phenyl)-1H-pyrrolo[3,2-b]pyridin-1-yl)but-2-en-1-amine |
| 116 | 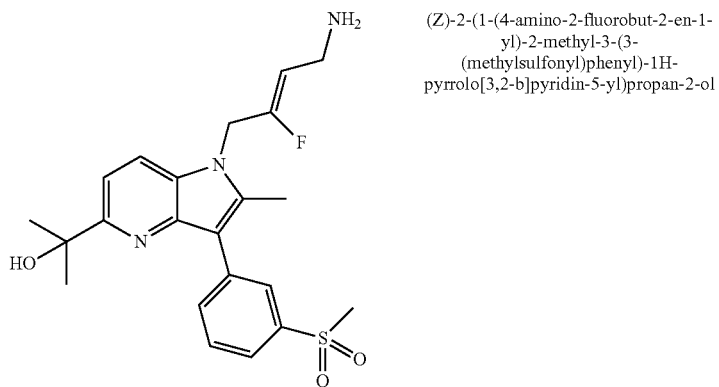 | (Z)-2-(1-(4-amino-2-fluorobut-2-en-1-yl)-2-methyl-3-(3-(methylsulfonyl)phenyl)-1H-pyrrolo[3,2-b]pyridin-5-yl)propan-2-ol |
| 117 | 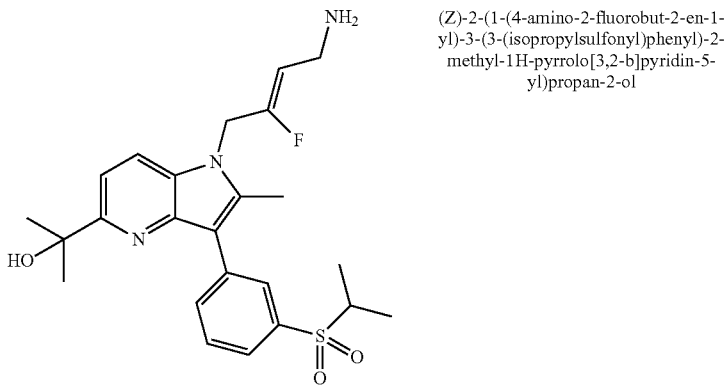 | (Z)-2-(1-(4-amino-2-fluorobut-2-en-1-yl)-3-(3-(isopropylsulfonyl)phenyl)-2-methyl-1H-pyrrolo[3,2-b]pyridin-5-yl)propan-2-ol | or a pharmaceutically acceptable salt thereof.

9. A pharmaceutical composition comprising a compound according to claim 1, or a pharmaceutically acceptable salt thereof and at least one pharmaceutically acceptable excipient, carrier or diluent.

10. A method of inhibiting the amine oxidase activity of LOX, LOXL1, LOXL2, LOXL3 and LOXL4 in a subject in need thereof, comprising administering to the subject an effective amount of a compound according to claim 1, or a pharmaceutically acceptable salt thereof.

11. A compound according to claim 1 of Formula I:

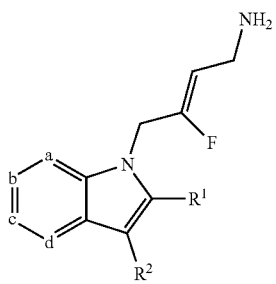

Formula I or a stereoisomer or pharmaceutically acceptable salt thereof; wherein:
a is N or CH;
b is N or $CR^4$;
c is N or $CR^5$;
d is N or $CR^6$;
and from 0 to 1 of a, b, c and d are N;
$R^1$ is selected from the group consisting of hydrogen, halogen and $C_{1-6}$alkyl: wherein each $C_{3-6}$alkyl is a straight or branched chain alkyl;
$R^2$ is selected from the group consisting of phenyl, pyridinyl and pyrimidinyl; wherein each $R^1$ is optionally substituted by one or more $R^{12}$;
$R^4$ is selected from the group consisting of hydrogen, halogen, —C(O)$OR^8$ and —C(O)$NR^9R^{10}$;
$R^5$ is selected from the group consisting of hydrogen, halogen, hydroxyl, $C_{1-6}$alkyl, $C_{3-7}$cycloalkyl, —O—$C_{1-6}$alkyl, —CN, —$NO_2$, —$NR^9R^{10}$, —C(O)$OR^8$, —C(O)$NR^9R^{10}$, —$S(O_2)NR^9R^{10}$, —$NR^9S(O_2)R^{11}$, —$S(O_2)R^{11}$, tetrazole and oxadiazole; wherein each $C_{1-6}$alkyl is a straight or branched chain alkyl; and wherein each $C_{1-6}$alkyl is optionally substituted by one or more substituents selected from the group consisting of halogen, —OH and O—$C_{1-3}$alkyl;
$R^6$ is selected from the group consisting of hydrogen and halogen;
$R^8$ is selected from the group consisting of hydrogen and $C_{1-6}$alkyl;
$R^9$ and $R^{10}$ are independently selected from the group consisting of hydrogen and $C_{1-6}$alkyl; wherein each $C_{1-6}$alkyl is a straight or branched chain alkyl;
$R^{11}$ is $C_{1-6}$alkyl; wherein each $C_{1-6}$alkyl is a straight or branched chain alkyl; and wherein each $C_{1-6}$alkyl is optionally substituted by one or more halogen; and
$R^{12}$ is selected from the group consisting of halogen, $C_{1-6}$alkyl, —O—$C_{1-6}$alkyl, —S—$C_{1-6}$alkyl, —C(O)$OR^8$, —C(O)$NR^9R^{10}$, —$S(O_2)NR^9R^{10}$, and —$S(O_2)R^{11}$; wherein each $C_{1-6}$alkyl is a straight or branched chain alkyl; and wherein each $C_{1-6}$alkyl is optionally substituted by one or more halogen.

12. A compound according to claim 1 of Formula I:

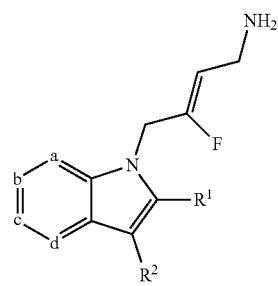

Formula I or a stereoisomer or pharmaceutically acceptable salt thereof; wherein:
a is $CR^3$, b is $CR^4$, c is $CR^5$ and d is $CR^6$; or
a is $CR^3$, b is $CR^4$, c is $CR^5$ and d is N; or
a is $CR^3$, b is $CR^4$, c is N and d is $CR^6$; or
a is $CR^3$, b is N, c is $CR^5$ and d is $CR^6$; or
a is N, b is $CR^4$, c is $CR^5$ and d is $CR^6$;
$R^1$ is selected from the group consisting of hydrogen and $C_{1-3}$alkyl; wherein each $C_{1-3}$alkyl is a straight or branched chain alkyl;
$R^2$ is selected from the group consisting of phenyl

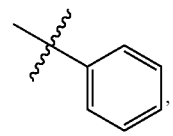 [SMILES: *c1ccccc1], 2-pyridinyl

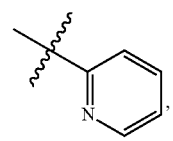 [SMILES: *c1ccccn1], 3-pyridinyl

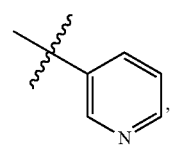 [SMILES: *c1cccnc1], 4-pyridinyl

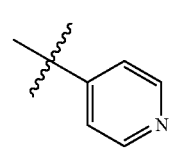 [SMILES: *c1ccncc1]

and 5-pyrimidinyl

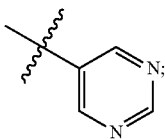

wherein each R² is unsubstituted or substituted by one or more R¹²;
R³ is hydrogen;
R⁴ is selected from the group consisting of hydrogen, halogen, C(O)OH, C(O)OCH₃, C(O)NH₂ and C(O)N(CH₃)₂;
R⁵ is selected from the group consisting of hydrogen, halogen, hydroxyl, $C_{1-4}$alkyl, cyclopropyl, —O—$C_{1-4}$alkyl, —CN, —NO₂, —NR⁹R¹⁰, —C(O)OR⁸, —C(O)NR⁹R¹⁰, —S(O₂)NR⁹R¹⁰, —NR⁹S(O₂)R¹¹, —S(O₂)R¹¹, tetrazole and oxadiazole; wherein each $C_{1-4}$alkyl is a straight or branched chain alkyl; and wherein each $C_{1-4}$alkyl is unsubstituted or substituted by one or more substituents selected from the group consisting of halogen, —OH and O—$C_{1-3}$alkyl;
R⁶ is selected from the group consisting of hydrogen and chlorine;
R⁸ is selected from the group consisting of hydrogen, methyl and ethyl;
R⁹ and R¹⁰ are independently selected from the group consisting of hydrogen and $C_{1-4}$alkyl; wherein each $C_{1-4}$alkyl is a straight or branched chain alkyl;
R¹¹ is $C_{1-3}$alkyl; wherein each $C_{1-3}$alkyl is a straight or branched chain alkyl; and wherein each $C_{1-3}$alkyl is unsubstituted or substituted by one or more halogen; and
R¹² is selected from the group consisting of halogen, $C_{1-4}$alkyl, —O—$C_{1-4}$alkyl, —C(O)OR⁸, —C(O)NR⁹R¹⁰, —S(O₂)NR⁹R¹⁰, —SCH₃, and —S(O₂)R¹¹; wherein each $C_{1-4}$alkyl is a straight or branched chain alkyl; and wherein each $C_{1-4}$alkyl is unsubstituted or substituted by one or more halogen.

13. A compound according to claim 1 of Formula I, wherein:
R¹ is selected from the group consisting of hydrogen, methyl and isopropyl;
R² is selected from the group consisting of phenyl

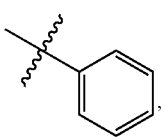

2-pyridinyl

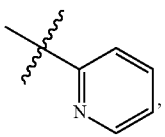 [SMILES: *c1ccccn1]

3-pyridinyl

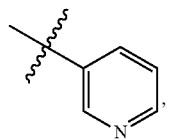 [SMILES: *c1cccnc1]

4-pyridinyl

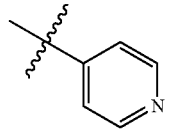 [SMILES: *c1ccncc1]

and 5-pyrimidinyl

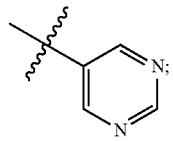

wherein each R² is unsubstituted or substituted by one or more R¹²;
R³ is hydrogen;
R⁴ is selected from the group consisting of hydrogen, fluorine, chlorine, C(O)OH, C(O)OCH₃, C(O)NH₂ and C(O)N(CH₃)₂;
R⁵ is selected from the group consisting of hydrogen, fluorine, chlorine, hydroxyl, —CH₃, —CH₂F, —CHF₂, —CF₃, —CF₂CH₃, cyclopropyl, —C(CH₃)₂OH, —CH₂OCH₃, —OCH₃, —OCF₃, —CN, —NO₂, —N(CH₃)₂, —C(O)OH, —C(O)OCH₃, —C(O)OEt, —C(O)N(CH₃)₂, —C(O)NHCH₃, —C(O)NHⁱPr, —C(O)NCH₃ⁱPr, —C(O)NHᵗBu, —S(O₂)N(CH₃)₂, —S(O₂)NH₂, —NHS(O₂)CH₃, —S(O₂)CH₃, —S(O₂)ⁱPr, tetrazole and oxadiazole;
R⁶ is selected from the group consisting of hydrogen and chlorine; and
R¹² is selected from the group consisting of fluorine, chlorine, —CH₃, —ᵗBu, CF₃, —O—CH₃, —C(O)OH, —C(O)OEt, —C(O)N(CH₃)₂, —S(O₂)N(CH₃)₂, S(O₂)NHCH₃, —S(O₂)NH₂, —S(O₂)CH₃, —S(O₂)Et, —S(O₂)ⁱPr, and —S(O₂)CF₃.

14. A compound according to claim 1, of Formula Ib:

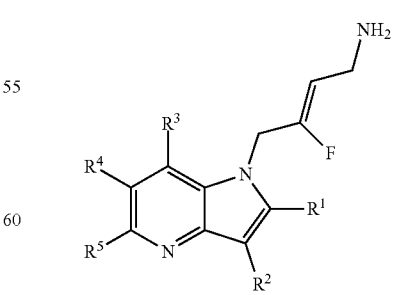

Formula Ib or a pharmaceutically acceptable salt thereof; wherein:
R¹ is selected from the group consisting of hydrogen, halogen and $C_{1-6}$alkyl; wherein each $C_{1-6}$alkyl is a straight or branched chain alkyl;

R² is phenyl substituted by one or more R¹²;
R³ is hydrogen;
R⁴ is selected from the group consisting of hydrogen and halogen;
R⁵ is selected from the group consisting of hydrogen, halogen, hydroxyl, $C_{1-6}$alkyl, —O—$C_{1-6}$alkyl, —NR⁹R¹⁰, —C(O)OR⁸, and —C(O)NR⁹R¹⁰; wherein each $C_{1-6}$alkyl is a straight or branched chain alkyl; and wherein each $C_{1-6}$alkyl is optionally substituted by one or more substituents selected from the group consisting of halogen, —OH and O—$C_{1-3}$alkyl;
R⁶ is selected from the group consisting of hydrogen and, $C_{1-6}$alkyl;
R⁹ and R¹⁰ are independently selected from the group consisting of hydrogen and $C_{1-6}$alkyl; wherein each $C_{1-6}$alkyl is a straight or branched chain alkyl;
R¹¹ is $C_{1-6}$alkyl; wherein each $C_{1-6}$alkyl is a straight or branched chain alkyl; and
R¹² is selected from the group consisting of —S(O₂)NR⁹R¹⁰ and —S(O₂)R¹¹.

15. A compound according to claim 14 of Formula Ib, wherein:
R¹ is selected from the group consisting of hydrogen, methyl and isopropyl;
R² is phenyl substituted by one or more R¹²;
R³ is hydrogen;
R⁴ is selected from the group consisting of hydrogen, fluorine and chlorine;
R⁵ is selected from the group consisting of hydrogen, fluorine, hydroxyl, —CH₃, —CH₂F, —CHF₂, —CF₃, —CF₂CH₃, —C(CH₃)₂OH, —CH₂OCH₃, —OCH₃, —C(O)OH, —N(CH₃)₂, —C(O)OEt, —C(O)N(CH₃)₂, —C(O)NHCH₃ and —C(O)NHⁱPr; and
R¹² is selected from the group consisting of —S(O₂)N(CH₃)₂, —S(O₂)NH₂, —S(O₂)CH₃, —S(O₂)Et and —S(O₂)ⁱPr.

16. The compound of claim 1 having the structure:

or a pharmaceutically acceptable salt thereof.

17. The compound of claim 1 having the structure:

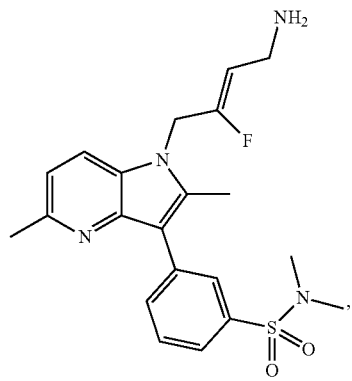

or a pharmaceutically acceptable salt thereof.

18. The compound of claim 1 having the structure:

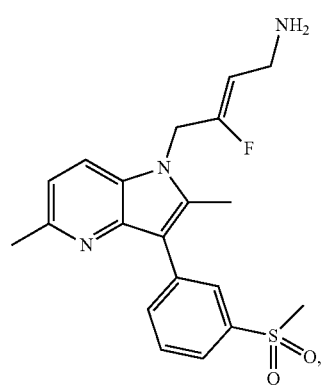 [SMILES: Cc1ccc2c(n1)c(-c1cccc(S(C)(=O)=O)c1)c(C)n2C/C(F)=C/CN]

or a pharmaceutically acceptable salt thereof.

* * * * *

UNITED STATES PATENT AND TRADEMARK OFFICE
CERTIFICATE OF CORRECTION

Page 1 of 2

PATENT NO. : 10,717,733 B2
APPLICATION NO. : 16/076979
DATED : July 21, 2020
INVENTOR(S) : Alison Dorothy Findlay et al.

It is certified that error appears in the above-identified patent and that said Letters Patent is hereby corrected as shown below:

In the Drawings

On sheet 1 of 4, Figure (1):

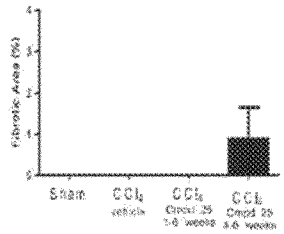

Should read:

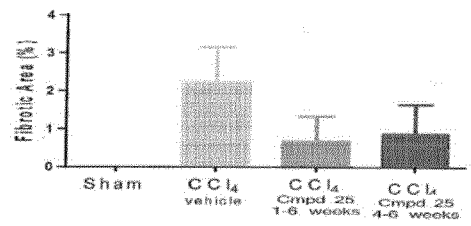

In the Claims

Column 218, Example (62):
The following compounds were made according to procedures AAZ, AAAA, F, K, L and O.
Should read:
-The following compounds were made according to procedures AAZ, AAAA. F, J, K, L and O.-

Column 220, Example (63):
The following compounds were prepared according to procedures AAAB, F, K, L and O.

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,717,733

Should read:
-The following compounds were prepared according to procedures AAAB, F, J, K, L and O.-